US008759009B2

(12) United States Patent
Lazarides et al.

(10) Patent No.: US 8,759,009 B2
(45) Date of Patent: *Jun. 24, 2014

(54) ANTI-ALPHA2 INTEGRIN ANTIBODIES AND THEIR USES

(75) Inventors: Elias Lazarides, La Jolla, CA (US); Catherine Mary Woods, La Jolla, CA (US); Mark Bernard, Walnut Creek, CA (US)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/858,174

(22) Filed: Aug. 17, 2010

(65) Prior Publication Data
US 2011/0135635 A1 Jun. 9, 2011

Related U.S. Application Data

(63) Continuation of application No. 11/601,595, filed on Nov. 17, 2006, now Pat. No. 7,807,794.

(60) Provisional application No. 60/738,303, filed on Nov. 18, 2005.

(51) Int. Cl.
*C07K 16/00* (2006.01)
*C07K 16/46* (2006.01)
*C07K 16/28* (2006.01)
*G01N 33/53* (2006.01)

(52) U.S. Cl.
USPC .. 435/7.1; 530/387.1; 530/387.3; 530/388.22

(58) Field of Classification Search
None
See application file for complete search history.

(56) References Cited

U.S. PATENT DOCUMENTS

| | | | |
|---|---|---|---|
| 5,196,511 A | 3/1993 | Plow et al. | |
| 5,262,520 A | 11/1993 | Plow et al. | |
| 5,523,209 A | 6/1996 | Ginsberg et al. | |
| 5,530,101 A * | 6/1996 | Queen et al. | 530/387.3 |
| 5,618,920 A * | 4/1997 | Robinson et al. | 530/387.1 |
| 5,855,888 A | 1/1999 | Nishida et al. | |
| 5,932,421 A | 8/1999 | Ginsberg et al. | |
| 6,291,196 B1 | 9/2001 | Vielkind | |
| 6,596,276 B1 | 7/2003 | Senger et al. | |
| 6,780,603 B1 | 8/2004 | Tsilibary et al. | |
| 6,933,368 B2 * | 8/2005 | Co et al. | 530/387.3 |
| 7,517,525 B2 | 4/2009 | Prenner et al. | |
| 7,807,794 B2 * | 10/2010 | Lazarides et al. | 530/387.3 |
| 7,829,027 B2 | 11/2010 | Osterloh et al. | |
| 7,901,683 B2 | 3/2011 | Griswold-Prenner et al. | |
| 2003/0109435 A1 * | 6/2003 | Prenner et al. | 514/12 |
| 2004/0162413 A1 | 8/2004 | Watkins et al. | |
| 2007/0128190 A1 | 6/2007 | Lazarides et al. | |
| 2008/0181888 A1 * | 7/2008 | Ambrose et al. | 424/133.1 |
| 2008/0267978 A1 | 10/2008 | Zutter et al. | |
| 2011/0150859 A1 | 6/2011 | Marjamaki et al. | |

FOREIGN PATENT DOCUMENTS

| | | |
|---|---|---|
| EP | 0 759 302 A1 | 2/1997 |
| EP | 0 879 602 A1 | 11/1998 |
| EP | 1 121 151 B1 | 8/2001 |
| EP | 1 414 491 A2 | 5/2004 |
| WO | WO 92/08739 | 5/1992 |
| WO | WO 98/22500 | 5/1998 |
| WO | WO 2006/022682 A2 | 3/2006 |
| WO | WO 2007/024921 A2 | 3/2007 |

OTHER PUBLICATIONS

Ho et al. Modulation of in vivo migratory function of alpha 2 beta 1 integrin in mouse liver. Mol Biol Cell. Oct. 1997;8(10):1863-75.*
Lerner R. Tapping the immunological repertoire to produce antibodies of predetermined specificity. Nature 1982; 299:592-596.*
Fundamental Immunology, William E. Paul, ed., 3rd Ed., pp. 292-295, 1993.*
Van Regenmortel MHV. Mapping Epitope Structure and Activity: From One-Dimensional Prediction to Four-Dimensional Description of Antigenic Specificity Methods. 9(3):465-72, 1996.*
Casset et al. A peptide mimetic of an anti-CD4 monoclonal antibody by rational desig. Biochem Biophys Res Commun. Jul. 18, 2003;307(1):198-205.*
MacCallum et al Antibody-antigen interactions: contact analysis and binding site topography. J Mol Biol. Oct. 11, 1996;262(5):732-45.*
Bendig M. M. Humanization of Rodent Monoclonal Antibodies ,by CDR Grafting. Methods: A Companion to Methods in Enzymology, 1995; 8:83-93.*
Colman PM. Effects of amino acid sequence changes on antibody-antigen interactions. Res Immunol. 145(1):33-36, 1994.*
Rudikoff et al Single amino acid substitution altering antigen-binding specificity. Proc Natl Acad Sci U S A. Mar. 1982;79(6):1979-83.*
The Miura et al. Chemokine receptor CXCR4-beta1 integrin axis mediates tumorigenesis of osteosarcoma HOS cells. Biochem Cell Biol. Feb. 2005;83(1):36-48.*
Ho et al., Mol Biol Cell, Modulation of in vivo migratory function of alpha 2 beta 1 integrin in mouse liver. 8: 1863-75 (1997).
Lerner R., Nature, Tapping the immunological repertoire to produce antibodies of predetermined specificity. 299: 592-596 (1982).
Fundamental Immunology, William E. Paul, ed., 3rd Ed., pp. 292-295, (1993).
Van Regenmortel MHV, Methods, Mapping Epitope Structure and Activity: From One-Dimensional Prediction to Four-Dimensional Description of Antigenic Specificity. 9: 465-72 (1996).
Casset et al., Biochem Biophys Res Commun., A peptide mimetic of an anti-CD4 monoclonal antibody by rational design. 307: 198-205 (2003).

(Continued)

Primary Examiner — Maher Haddad
(74) Attorney, Agent, or Firm — Sterne, Kessler, Goldstein & Fox, P.L.L.C.

(57) ABSTRACT

The invention relates to anti-α2 integrin antibodies and their uses. Humanized antibodies are disclosed that bind to the I domain of α2 integrin and inhibit the interaction of α2β1 integrin with collagen. Also disclosed are therapeutic uses of anti-α2 integrin antibodies in treating α2β1-mediated disorders, including anti-α2 integrin antibodies that bind to α2 integrin without activating platelets.

36 Claims, 2 Drawing Sheets

(56) References Cited

OTHER PUBLICATIONS

MacCallum et al, J Mol Biol., Antibody-antigen interactions: contact analysis and binding site topography. 262:732-45 (1996).
Bendig M. M. Humanization of Rodent Monoclonal Antibodies by CDR Grafting. Methods: A Companion to Methods in Enzymology. 8:83-93 (1995).
Colman PM., Res Immunol., Effects of amino acid sequence changes on antibody-antigen interactions. 145:33-36 (1994).
Rudikoff et al, Proc Natl Acad Sci U S A., Single amino acid substitution altering antigen-binding specificity. 79: 1979-83 (1982).
Estavillo, D. et al., The Journal of Biological Chemistry, Functional Analysis of a Recombinant Glycoprotein Ia/IIa (Integrin a2b1) I Domain That Inhibits Platelet Adhesion to Collagen and Endothelial Matrix under Flow Conditions, 274: 35921-35926 (1999).
Schoolmeester, A. et al., Hemostasis, Thrombosis, and Vascular Biology, Monoclonal antibody IAC-1 is specific for activated a2Pi and binds to amino acids 199 to 201 of the integrin a2 I-domain. 104: 390-396 (Jul. 2004).
Smith, C. et al., J. Biol. Chem., Mapping the Collagen-binding Site in the I Domain of the Glycoprotein Ia/IIa (Integrin a2b1). 275: 4206-4209 (2000).
Tuckwell, D. et al., Biochem. J., Monoclonal antibodies identify residues 199-216 of the integrin a2 vWFA domain as a functionally important region within a2b1. 350: 485-493 (2000).
Al-Lazikani et al, J. Mol. Biol., Standard conformations for the canonical structures of immunoglobulins. 273: 927-48 (1997).
Andreasen S.O. et al., J. Immunol., Expression and functional importance of collagen-binding integrins, alpha 1 beta 1 and alpha 2 beta 1, on virus-activated T cells. 171:2804-2811 (2003).
Aquilina A, et al., Eur. J. Biochem, A novel gain-of-function mutation of the integrin alpha2 VWFA domain. 269:1136-44 (2002).
Argraves, W.S, J. Cell. Biol., Amino acid sequence of the human fibronectin receptor. 105:1183-90 (1987).
Bahou W.F., et al., Blood. The VLA-2 (alpha 2 beta 1) I domain functions as a ligand-specific recognition sequence for endothelial cell attachment and spreading: molecular and functional characterization. 84:3734-3741 (1994).
Bergelson J.M., et al., Cell Adhes. Commun., The I domain is essential for echovirus 1 interaction with VLA-2. 2: 455-64 (1994).
Bhatt, D.L. and Topol, E.J., Nat. Rev. Drug Discov., Scientific and therapeutic advances in antiplatelet therapy. 2:15-28 (2003).
Champe, M., et al., J. Biol. Chem., Monoclonal antibodies that block the activity of leukocyte function-associated antigen 1 recognize three discrete epitopes in the inserted domain of CD11a. 270: 1388-94 (1995).
Chan, et. al., J. Immunol., T cell receptor-dependent, antigen-specific stimulation of a murine T cell clone induces a transient, VLA protein-mediated binding to extracellular matrix. 147:398-404 (1991).
Chen, J., et al., Am. J. Pathol., The Integrin Subunit-Deficient Mouse: A Multifaceted Phenotype Including Defects of Branching Morphogenesis and Hemostasis. 161: 337-344 (2002).
Cheng, Y. and Prusoff, W.H., Biochem. Pharmacol., Relationship between the inhibition constant (K1) and the concentration of inhibitor which causes 50 per cent inhibition (I50) of an enzymatic reaction. 22: 3099-108 (1973).
Clackson, T., et al., Nature, Making antibody fragments using phage display libraries. 352:624-628 (1991).
Colombatti, A. and Bonaldo, P., Blood, The superfamily of proteins with von Willebrand factor type A-like domains: one theme common to components of extracellular matrix, hemostasis, cellular adhesion, and defense mechanisms. 77: 2305-15 (1991).
Cunningham, B.C. and Wells, J.A., Science, High-resolution epitope mapping of hGH-receptor interactions by alanine-scanning mutagenesis. 244: 1081-1085 (1989).
De Fougerolles, A., et al., J. Clin. Invest, Regulation of inflammation by collagen-binding integrins alpha1beta1 and alpha2beta1 in models of hypersensitivity and arthritis. 105: 721-720 (2000).
Kamata, T., et. al., J Biol.Chem., Interaction between collagen and the alpha(2) I-domain of integrin alpha(2)beta(1). Critical role of conserved residues in the metal ion-dependent adhesion site (MIDAS) region 274: 32108-32111 (1999).
Dickeson, S.K., et al., Cell Adhesion and Communications, Binding of the alpha 2 integrin I domain to extracellular matrix ligands: structural and mechanistic differences between collagen and laminin binding. 5: 273-281 (1998).
Dickeson, S.K., et al., J Biol. Chem., Contributions of the I and EF hand domains to the divalent cation-dependent collagen binding activity of the alpha2beta1 integrin. 272: 7661-7668 (1997).
Dustin, M.L. and de Fougerolles, A., Curr Opin Immunol, Reprogramming T cells: the role of extracellular matrix in coordination of T cell activation and migration. 13:286-290 (2001).
Eble, J.A., Curr. Pharm. Des., Collagen-binding integrins as pharmaceutical targets. 11: 867-880 (2005).
Edelson, B.T., et al., Blood, Mast cell-mediated inflammatory responses require the alpha 2 beta 1 integrin. 103: 2214-2220 (Mar. 2004).
Edelson, B.T., et al., Blood, Novel collectin/C1q receptor mediates mast cell activation and innate immunity. 107: 143-50 (Jan. 2006).
Emsley, J., et al., Cell, Structural basis of collagen recognition by integrin alpha2beta1 . 101: 47-56 (2000).
Emsley, J., et al., J. Biol. Chem., Crystal structure of the I domain from integrin alpha2beta1 272: 28512 (1997).
Feuston, B.P., et al., J. Med. Chem., Molecular model of the alpha(IIb)beta(3) integrin. 46: 5316-5325 (2003).
Foote, J. and Winter, G., J. Mol. Biol., Antibody framework residues affecting the conformation of the hypervariable loops. 224: 487-99 (1992).
Gadek, T.R., et al., Science, Generation of an LFA-1 antagonist by the transfer of the ICAM-1 immunoregulatory epitope to a small molecule. 295: 1086-1089 (2002).
Giltay, J.C., et al., Blood, Human vascular endothelial cells express a membrane protein complex immunochemically indistinguishable front the platelet VLA-2. 73: 1235-1241 (1989).
Gruner, S., et al., Blood, Multiple integrin-ligand interactions synergize in shear-resistant platelet adhesion at sites of arterial injury in vivo. 102:4021-4027 (2003).
Gurrath, M., et al., Eur. J. Biochem., Conformation/activity studies of rationally designed potent anti-adhesive RGD peptides. 210: 911-921 (1992).
Haas, T.A. and Plow, E.A., Curr. Opin. Cell. Bio., Integrin-ligand interactions: a year in review. 6: 656-62 (1994).
Hangan, D., et al., Cancer Res., Integrin VLA-2 (alpha2beta1) function in postextravasation movement of human rhabdomyosarcoma RD cells in the liver. 56: 3142-9 (1996).
Hemler, M., Annu Rev Immunol., VLA Proteins in the Integrin Family: Structures, Functions, and Their Role on Leukocytes. 8: 365-400 (1990).
Holtkotter; O., et al., J. Biol. Chem., Integrin alpha 2-deficient mice develop normally, are fertile, but display partially defective platelet interaction with collagen. 277: 10789-94 (2002).
Hynes, R., Cell., Integrins: bidirectional, allosteric signaling machines. 110: 673-87 (2002).
Jackson, D.Y., et al., J. Med. Chem., Potent alpha 4 beta 1 peptide antagonists as potential anti-inflammatory agents. 40:3359-3368 (1997).
Johnson, G. and Wu, T.T., Nucleic Acids Res., Kabat Database and its applications: future directions. 29: 205-206 (2001).
Jones, P., et al., Nature, Replacing the complementarity-determining regions in a human antibody with those from a mouse. 321: 522-5 (1986).
Kabat, E.A., et al., J. Biol. Chem., Unusual distribution of amino acids in complementarity-determining (hypervariable) segments of heavy and light chains of immunoglobulins and their possible roles in specificity of anitbody-combining sites. 252: 6609-6616 (1977).
Kamata, T., et al., J Biol. Chem., Direct binding of collagen to the I domain of integrin alpha 2 beta 1 (VLA-2, CD49b/ CD29) in a divalent cation-independent manner. 269: 9659-9663 (1994).
Kapyla J., et al., J Biol Chem., Integrin alpha(2)I domain recognizes type I and type IV collagens by different mechanisms. 275: 3348-3354 (2000).

(56) References Cited

OTHER PUBLICATIONS

Karpusas, M., et al., J. Mol. Biol., Crystal structure of the alpha1beta1 integrin I domain in complex with an antibody Fab fragment. 327: 1031-41 (2003).
Keely, P.J., et. al., J. Cell Sci., Alteration of collagen-dependent adhesion, motility, and morphogenesis by the expression of antisense alpha 2 integrin mRNA in mammary cells. 108: 595-607 (1995).
Krieglstein, C.F., et al., J Clin Invest., Collagen-binding integrin alpha1beta1 regulates intestinal inflammation in experimental colitis. 110: 1773-82 (2002).
Kurz, K.D., et al., Thromb Res., Rat model of arterial thrombosis induced by ferric chloride. 60: 269-80 (1990).
Languino, L.R., et al., J Cell Bio., Endothelial cells use alpha 2 beta 1 integrin as a laminin receptor. 109: 2455-2462 (1989).
Larson, R.S., et al., J Cell Biol., Primary structure of the leukocyte function-associated molecule-1 alpha subunit: an integrin with an embedded domain defining a protein superfamily. 108: 703-712 (1989).
Lee, et al., J Biol Chem., O-glycosylation in hinge region of mouse immunoglobulin G2b. 269: 12395-12398 (1994).
Martin, et al., Proc. Natl Acad. Sci USA, Modeling antibody hypervariable loops: a combined algorithm. 86: 9268-9272 (1989).
Merlini, et al., Circulation, Thrombocytopenia caused by abciximab or tirofiban and its association with clinical outcome in patients undergoing coronary stenting. 109: 2203-2206 (May 2004).
Miller, et al., N. Engl. J. Med., A controlled trial of natalizumab for relapsing multiple sclerosis. 348: 15-23 (2003).
Miyake, et al., Eur. J. Immunol., Identification of collagen and laminin receptor integrins on murine T lymphocytes. 24: 2000-2005 (1994).
Nieswandt, B. and Watson S.P., Blood, Platelet-collagen interaction: is GPVI the central receptor? 102: 449-461 (2003).
Nolte, M. et al.; FEBS Letters, Crystal structure of the aipha1beta1 integrin I-domain: insights into integrin I-domain function. 452: 379-385 (1999).
Pascual, V. and Capra, J.D., Adv. Immunol., Human immunoglobulin heavy-chain variable region genes: organization, polymorphism, and expression. 49: 1-74 (1991).
Pedersen, et al., Immunomethods, Antibody modeling: Beyond homology. 1: 126-136 (1992).
Pozzi, A. & Zent, R., Exp Nephrol., Integrins: sensors of extracellular matrix and modulators of cell function. 94: 77-84 (2003).
Queen, C., et al., Proc. Natl. Acad. Sci. USA, A humanized antibody that binds to the interleukin 2 receptor. 86: 10029 (1989).
Randi, A.M. and Hogg, N., J Biol Chem., I domain of beta 2 integrin lymphocyte function-associated antigen-1 contains a binding site for ligand intercellular adhesion molecule-1. 269: 12395-12398 (1994).
Rao, W.H., et al., J. Immunol., Potent costimulation of effector T lymphocytes by human collagen type I. 165: 4935-40 (2000).
Riechmann, L., et al., Nature, Expression of an antibody Fv fragment in myeloma cells. 332: 323-327 (1988).
Schell, D.A., et al., Ann. Hematol., Thrombocytopenia associated with c7E3 Fab (abciximab). 81: 76-79 (2002).
Senger, D.R., et al., Am. J. Pathol., The alpha(1)beta(1) and alpha(2)beta(1) integrins provide critical support for vascular endothelial growth factor signaling, endothelial cell migration, and tumor angiogenesis. 160: 195-204 (2002).
Senger, D.R., et al., PNAS, Angiogenesis promoted by vascular endothelial growth factor: regulation through alpha1beta1 and alpha2beta1 integrins. 94: 13612-7 (1997).
Shalaby, M.R., et al., J. Exp. Med., Development of humanized bispecific antibodies reactive with cytotoxic lymphocytes and tumor cells overexpressing the HER2 protooncogene. 175: 217-225 (1992).
Shopes, B., J. Immunol., A genetically engineered human IgG mutant with enhanced cytolytic activity. 148: 2918-2922 (1992).
Siljander, P.R., et al., Blood, Platelet receptor interplay regulates collagen-induced thrombus formation in flowing human blood. 103: 1333-1341 (Feb. 2004).

Sircar, I., et al., Bioorg. Med. Chem., Synthesis and SAR of N-benzoyl-L-biphenylalanien derivatives: discovery of TR-14035, a dual alpha(4)beta(7)/alpha(4)beta(1) integrin antagonist. 10: 2051-2066 (2002).
Staatz, W. D., et. al., Cell Biol., The membrane glycoprotein la-IIa (VLA-2) complex mediates the Mg++-dependent adhesion of platelets to collagen. 108: 1917-24 (1989).
Symington, B.E., et al, J Cell Biol., Interaction of integrins alpha 3 beta 1 and alpha 2 beta 1: potential role in keratinocyte intercellular adhesion. 120: 523-35 (1993).
Takada, Y. and Hemler, M., J. Cell Biol., The primary structure of the VLA-2/collagen receptor alpha 2 subunit (platelet GPIa): homology to other integrins and the presence of a possible collagen-binding domain. 109: 397-407 (1989).
Tempest, P.R., et al., Biotechnology (NY), Reshaping a human monoclonal antibody to inhibit human respiratory syncytial virus infection in vivo. 9: 266-271 (1991).
Theien, B.E., et al., J. Clin. Invest., Discordant effects of anti-VLA-4 treatment before and after onset of relapsing experimental autoimmune encephalomyelitis. 107: 995-1006 (2001).
Tuckwell, D., et al., J Cell Sci., Integrin alpha 2 I-domain is a binding site for collagens. 108: 1629-37 (1995).
Tutt, A., et al., J. Immunol., Trispecific F(ab')3 derivatives that use cooperative signaling via the TCR/CD3 complex and CD2 to activate and redirect resting cytotoxic T cells. 147: 60 (1991).
Verhoeyen, M., et al., Science, Reshaping human antibodies: grafting an antilysozyme activity. 239: 1534-1536 (1988).
Vitetta, E.S., et al., Science, Redesigning nature's poisons to create anti-tumor reagents. 238: 1098-1104 (1987).
Watanabe, C., et al., Am J Physiol Gastrointest Liver Physiol., Spatial heterogeneity of TNF-alpha-induced T cell migration to colonic mucosa is mediated by MAdCAM-1 and VCAM-1. 283: G1379-G1387 (2002).
Werr, J., et al., Blood, Integrin alpha(2)beta(1) (VLA-2) is a principal receptor used by neutrophils for locomotion in extravascular tissue. 95: 1804-1809 (2000).
Yednock, T.A., et al., Nature, Precvention of experimental autoimmune encephalomyelitis by antibodies against alpha 4 beta 1 integrin. 356: 63-66 (1992).
Zutter, M., et al., processes, Am. J. Pathol., Collagen Receptor Control of Epithelial Morphogenesis and Cell Cycle Progression. 155: 927-940 (1999).
Cramer, E.M., "Platelets and megakaryocytes: anatomy amd structural organization" in Hemostatis and Thrombosis, basic principles & clinical practice, 4th edition, pp. 411-428 (2002).
Gendron, J., et al., J. Biol. Chem., Integrin alpha2beta1 inhibits Fas-mediated apoptosis in T lymphocytes by protein phosphatase 2A-dependent activation of the MAPK/ERK pathway. 278: 48633-48643 (2003).
Kabat, E.A., Adv. Protein Chem., The structural basis of antibody complementarity. 32: 1-75 (1978).
Kohler, G. and Milstein, C., Nature, Continuous cultures of fused cells secreting antibody of predefined specificity 256: 495 (1975).
Martin, A.C.R., et al., Methods Enzymol., Molecular modeling of antibody combining sites. 203: 121-153 (1991).
Mendrick, D.L. and Kelly, D.M., Lab Invest., Temporal expression of VLA-2 and modulation of its ligand specificity by rat glomerular epithelial cells in vitro. 69: 690-702 (1993).
Rees, M., et al., Antibody combining sites: structure and prediction, Oxford Univ. Press, 141-172 (1996).
Santoro, S.A. and Zutter, M.M., Thromb. Haemost, The alpha 2 beta 1 integrin: a collagen receptor on platelets and other cells. 74: 813-821. (1995).
Stevenson, G.T., et al., Anti-Cancer Drug Design, A chimeric antibody with dual Fc regions (bisFabFc) prepared by manipulations at the IgG hinge. 3: 219-230 (1989).
Thotakura, Nageswara R. and Bahl, Om P., Meth Enzymol. Enzymatic deglycosylation of glycoproteins. 138: 350 (1987).
Wu, J.E. and Santoro, S.A., Dev. Dyn., Differential Expression of Integrin Alpha Subunits Supports Distinct Roles During Lung Branching Morphogenesis. 206: 169-171 (1994).
Co, Man Sung, et al., Nature, Humanzied Antibodies For Therapy. 351: 501-502 (1991).

(56) References Cited

OTHER PUBLICATIONS

Davies, J. et al., Immunotechnology, Affinity Improvement of Single Antibody VH Domains: Residues in All Three Hypervariable Regions Affect Antigen Binding. 2: 169-179 (1996).
Holt L. J. et al., Trends in Biotechnology, Domain Antibodies: Proteins for Therapy.21: 484-490 (2003).
Kohichioro, Yoshino et al. "Suppression of Murine Collagen-Induced Arthritis With Monoclonal Antibody Against Alpha2beta1 Integrin" Arthritis and Rheumatism, Lippincott, Philadelphia, US, vol. 40, No. 9, Suppl, pp. S97- ISSN: 0004-3591 (Nov. 12, 1997).
Little M. et al., Immunoloogy Today, Of Mice and Men: Hybridoma and Recombinant Antibodies. 21: 364-370 (2000).
PCT International Preliminary Report on Patentability, PCT/CA2006/001876, one page, May 20, 2008.
PCT Written Opinion of the International Searching Authority, PCT/CA2006/001876, nine pages, Mar. 13, 2007.
Supplementary European Search Report with the European Search Opinion and Annex for European Patent Application No. EP 06804739.8, dated Jan. 22, 2010, by the European Patent Office, Munich.
Notice of Allowance mailed May 17, 2010 in U.S. Appl. No. 11/601,595, filed Nov. 17, 2006, inventors Lazarides, E., et al.
Final Office Action mailed Jan. 22, 2010 in U.S. Appl. No. 11/601,595, filed Nov. 17, 2006, inventors Lazarides, E., et al.
Non-Final Office Action mailed Jul. 30, 2009 in U.S. Appl. No. 11/601,595, filed Nov. 17, 2006, inventors Lazarides, E., et al.

* cited by examiner

ANTI-ALPHA2 INTEGRIN ANTIBODIES AND THEIR USES

CROSS REFERENCE TO RELATED APPLICATIONS

This application is a continuation of U.S. application Ser. No. 11/601,595, filed on Nov. 17, 2006 (now U.S. Pat. No. 7,807,794), and U.S. provisional Application Ser. No. 60/738,303, filed on Nov. 18, 2005, the disclosures of which are incorporated herein by reference in their entirety.

TECHNICAL FIELD

The present invention generally relates to antibodies directed to α2β1 integrin and their uses, including humanized anti-alpha 2 (α2) integrin antibodies and methods of treatment with anti-α2 integrin antibodies.

BACKGROUND OF THE INVENTION

The integrin α2β1 (Very late antigen 2; VLA-2) is expressed on a variety of cell types including platelets, vascular endothelial cells, epithelial cells, activated monocytes/macrophages, fibroblasts, leukocytes, lymphocytes, activated neutrophils and mast cells. (Hemler, Annu Rev Immunol 8:365:365-400 (1999); Wu and Santoro, Dev. Dyn. 206:169-171 (1994); Edelson et. al., Blood. 103(6):2214-20 (2004); Dickeson et al, Cell Adhesion and Communication. 5: 273-281 (1998)). The most typical ligands for α2β1 include collagen and laminin, both of which are found in extracellular matrix. Typically the I-domain of the α2 integrin binds to collagen in a divalent-cation dependent manner whereas the same domain binds to laminin through both divalent-cation dependent and independent mechanisms. (Dickeson et al, Cell Adhesion and Communication. 5: 273-281 (1998)) The specificity of the α2β1 integrin varies with cell type and serves as a collagen and/or laminin receptor for particular cell types, for example α2β1 integrin is known as a collagen receptor for platelets and a laminin receptor for endothelial cells. (Dickeson et al, J Biol. Chem. 272: 7661-7668 (1997)) Echovirus-1, decorin, E-cadherin, matrix metalloproteinase I (MMP-I), endorepellin and multiple collectins and the C1q complement protein are also ligands for α2β1 integrin. (Edelson et al., Blood 107(1): 143-50 (2006)) The α2β1 integrin has been implicated in several biological and pathological processes including collagen-induced platelet aggregation, cell migration on collagen, cell-dependent reorganization of collagen fibers as well as collagen-dependent cellular responses that result in increases in cytokine expression and proliferation, (Gendron, J. Biol. Chem. 278:48633-48643 (2003); Andreasen et al., J. Immunol. 171:2804-2811 (2003); Rao et al., J. Immunol. 165(9):4935-40 (2000)), aspects of T-cell, mast cell, and neutrophil function (Chan et. al., J. Immunol. 147:398-404 (1991); Dustin and de Fougerolles, Curr Opin Immunol 13:286-290 (2001), Edelson et. al., Blood. 103(6):2214-20 (2004), Werr et al., Blood 95:1804-1809 (2000), aspects of delayed type hypersensitivity contact hypersensitivity and collagen-induced arthritis (de Fougerolles et. al., J. Clin. Invest. 105:721-720 (2000); Kriegelstein et al., J. Clin. Invest. 110(12):1773-82 (2002)), mammary gland ductal morphogenesis (Keely et. al., J. Cell Sci. 108:595-607 (1995); Zutter et al., Am. J. Pathol. 155(3):927-940 (1995)), epidermal wound healing (Pilcher et. al., J. Biol. Chem. 272:181457-54 (1997)), and processes associated with VEGF-induced angiogenesis (Senger et al., Am. J. Pathol. 160(1):195-204 (2002)).

Integrins are heterodimers comprised of one α and one β subunit, and comprise a large family of cell surface proteins that mediate cell adhesion to extracellular matrix (ECM) as well as plasma proteins and are central to some types of cell-cell interactions. Integrins interact with ECM components through their extracellular domains. (Pozzi & Zent, Exp Nephrol. 94:77-84 (2003)) Upon binding to ligands, integrins transduce intracellular signals to the cytoskeleton that modify cellular activity in response to these cellular adhesion events, referred to as outside-in signaling (see, e.g., Hemler, Annu Rev Immunol 8:365:365-400 (1999); Hynes, Cell. 110(6): 673-87 (2002)). Such signaling can also activate other integrin subtypes expressed on the same cell, referred to as inside-out signaling. Inside-out signaling further occurs via regulatory signals that originate within cell cytoplasm such as a disruption of the clasp between an α and β subunit, which are then transmitted to the external ligand-binding domain of the receptor. Integrins can play important roles in the cell adhesion events that control development, organ morphogenesis, physiology and pathology as well as normal tissue homeostasis and immune and thrombotic responses, and in addition, they serve as environmental sensors for the cell. These proteins are characterized as being in a closed conformation under normal conditions that, upon activation undergo rapid conformational change that exposes the ligand binding site. X-ray crystal structure is a recent tool that has been used in the study of integrin structure and mechanisms of activation. The understanding of integrin structural features facilitates the better understanding of binding sites, differentiated states and their active and inactive formations. In general, the binding site for ligand/counter-receptor for all integrins lies within the α domain and is comprised of a metal ion dependent binding site, referred to as the MIDAS domain (Dembo et al, J Biol. Chem. 274, 32108-32111 (1988); Feuston at al., J. Med. Chem. 46:5316-5325 (2003); Gadek at al., Science 295(5557):1086-9 (2002)); Gurrath at al., Eur. J. Biochem. 210:911-921 (1992)). In the α subunits of the collagen-binding integrins, which include α1, α2, α10 and α11 integrins, the MIDAS site is located within an extra inserted domain at the N-terminus known as the I, A or I/A domain, a feature they share with the α subunits of the leukocyte β2 family of integrins (Randi and Hogg, J Biol Chem. 269: 12395-8 (1994), Larson et al, J Cell Biol. 108(2):703-12 (1989), Lee et al., J Biol Chem. 269: 12395-8 (1995); Emsley et al, J. Biol. Chem. 272:28512-28517 (1997) and Cell 100: 47-56 (2000)). The I domains are structurally homologous to the A1 domain of von Willebrandt factor, with a Rossman-fold topology of six β-sheet strands surrounded by seven α-helices (Colombatti and Bonaldo, Blood 77(11):2305-15 (1991); Larson et al, J Cell Biol. 108(2):703-712 (1989); Emsley et al, J. Biol. Chem. 272:28512-28517 (1997); Nolte et al; FEBS Letters, 452(3):379-385 (1999)). The collagen-binding integrins have an additional α-helix known as the αC helix (Emsley et al, J. Biol. Chem. 272:28512-28517 (1997) and Cell 100:47-56 (2000); Nolte et al; FEBS Letters, 452(3): 379-385 (1999)).

Integrin/ligand interactions can facilitate leukocyte extravasation into inflamed tissues (Jackson et al., J. Med. Chem. 40:3359-3368 (1997); Gadek et al., Science 295(5557):1086-9 (2002), Sircar et al., Bioorg. Med. Chem. 10:2051-2066 (2002)), and play a role in downstream events following the initial extravasation of leukocytes from the circulation into tissues in response to inflammatory stimuli, including migration, recruitment and activation of pro-inflammatory cells at the site of inflammation (Eble J. A., Curr. Phar. Des. 11(7):867-880 (2005)). Some antibodies that block α2β1 integrin were reported to show impact on delayed hypersensitivity responses and efficacy in a murine model of rheumatoid arthritis and a model of inflammatory bowel disease (Kriegelstein et al., J. Clin. Invest. 110(12):1773-82 (2002); de Fougerolles et. al., J. Clin. Invest. 105:721-720 (2000) and were reported to attenuate endothelial cell proliferation and migration in vitro (Senger et al., Am. J. Pathol. 160(1):195-204 (2002), suggesting that the blocking of α2β1 integrin might prevent/inhibit abnormal or higher than normal angiogenesis, as observed in various cancers.

Platelets normally circulate in the blood in an inactive resting state, however, they are primed to respond rapidly at sites of injury to a wide variety of agonists. Upon stimulation, they undergo shape changes and become highly reactive with plasma proteins, such as fibrinogen and von Willebrand factor (vWf), other platelets, and the endothelial lining of the vessel wall. These interactions all cooperate to facilitate the rapid formation of a hemostatic fibrin platelet plug (Cramer, 2002 in Hemostasis and Thrombosis, $4^{th}$ edition). Upon binding ligand, platelet receptors transduce outside-in signal pathways which in turn, trigger inside-out signaling that results in activation of secondary receptors such as the platelet fibrinogen receptor, αIIbβ3 integrin, leading to platelet aggregation. Antibodies or peptide ligand mimetics that bind to or interact with platelet receptors are anticipated to induce a similar signaling cascade leading to platelet activation. Even minor activation of platelets can result in platelet thrombotic responses, thrombocytopenia and bleeding complications.

α2β1 integrin is the only collagen-binding integrin expressed on platelets and has been implicated to play some role in platelet adhesion to collagen and hemostasis (Gruner et al., Blood 102:4021-4027 (2003); Nieswandt and Watson, Blood 102(2):449-461 (2003); Santoro et al., Thromb. Haemost. 74:813-821 (1995); Siljander et al., Blood 15:1333-1341 (2004); Vanhoorelbeke et al., Curr. Drug Targets Cardiovasc. Haemool. Disord. 3(2):125-40 (2003)). In addition, platelet α2β1 may play a role in the regulation of the size of the platelet aggregate (Siljander et al., Blood 103(4):1333-1341 (2004)).

α2β1 integrin has also been shown as a laminin-binding integrin expressed on endothelial cells (Languino et al., J Cell Bio. 109:2455-2462 (1989)). Endothelial cells are thought to attach to laminin through an integrin-mediated mechanism, however it has been suggested that the α2 I domain may function as a ligand-specific sequence involved in mediating endothelial cell interactions (Bahou et al., Blood. 84(11): 3734-3741 (1994)).

It is anticipated that a therapeutic antibody that binds α2β1 integrin, including the α2β1 integrin on platelets, could result in bleeding complications. For example, antibodies targeting other platelet receptors such as GPIb (Vanhoorelbeke et al., Curr. Drug Targets Cardiovasc. Haemool. Disord. 3(2):125-40 (2003) or GP IIb/IIIa (Schell et al., Ann. Hematol. 81:76-79 (2002), Nieswandt and Watson, Blood 102(2):449-461 (2003), Merlini et al., Circulation 109:2203-2206 (2004)) have been associated with thrombocytopenia, although the mechanisms behind this are not well understood. It has been hypothesized that binding of an antibody to a platelet receptor can alter its three dimensional structure, and expose normally unexposed epitopes which then leads to platelet elimination (Merlini et al., Circulation 109:2203-2206 (2004). Indeed, the bleeding complications associated with oral doses of GP IIa/IIIb antagonists have been described as the "dark side" of this class of compounds (Bhatt and Topol, Nat. Rev. Drug Discov. 2(1):15-28 (2003)). If α2β1 integrin plays an important role in the movement of leukocytes through inflammatory tissue, it would be desirable to develop therapeutic agents that could target α2β1 for diseases α2β1 integrin-associated disorders and/or cellular processes associated with the disorders, including cancer, inflammatory diseases and autoimmune diseases, if such agents would not activate platelets. Thus, there is a need in the art for the development of compounds capable of targeting α2β1 integrin, such as the α2β1 integrin on leukocytes, which would not be associated with adverse bleeding complications.

The anti-human α2β1 integrin blocking antibody BHA2.1 was first described by Hangan et al., (Cancer Res. 56:3142-3149 (1996)). Other anti-α2β1 integrin antibodies are known and have been used in vitro, such as the commercially available antibodies AK7 (Mazurov et al., Thromb. Haemost. 66(4):494-9 (1991), P1E6 (Wayner et al., J. Cell Biol. 107(5): 1881-91 (1988)), 10G11 (Giltay et al., Blood 73(5):1235-41 (1989) and A2-11E10 (Bergelson et al., Cell Adhes. Commun. 2(5):455-64 (1994). Hangan et al., (Cancer Res. 56:3142-3149 (1996)) used the BHA2.1 antibody in vivo to study the effects of blocking α2β1 integrin function on the extravasation of human tumor cells in the liver, and the ability of these tumor cells to develop metastatic foci under antibody treatment. The Ha1/29 antibody (Mendrick and Kelly, Lab Invest. 69(6):690-702 (1993)), specific for rat and murine α2β1 integrin, has been used in vivo to study the upregulation of α2β1 integrin on T cells following LCMV viral activation (Andreasen et al., J. Immunol. 171:2804-2811 (2003)), to study SRBC-induced delayed type hypersensitivity and FITC-induced contact type-hypersensitivity responses and collagen-induced arthritis (de Fougerolles et. al., J. Clin. Invest. 105:721-720 (2000)), to study the role of α2β1 integrin in VEGF regulated angiogenesis (Senger et al., Am. J. Pathol. 160(1):195-204 (2002); Senger et al., PNAS 94(25): 13612-7 (1997)), and to study the role of α2β1 integrin in PMN locomotion in response to platelet activating factor (PAF) (Werr et al., Blood 95:1804-1809 (2000)).

The use of murine monoclonal antibodies, such as those described above, as human therapeutic agents in non-immunocompromised patients has been limited by the robust immune responses directed against administered murine antibodies, particularly in repeated administration. This response cannot only curtail the effective half-life of the murine antibody in circulation but also can lead to profound injection site and/or anaphylactic responses (Shawler et al., J. Immunol. 135(2):1530 (1985)). In addition, the rodent effector functions associated with the constant regions (Fc) are much less effective than their human counterparts when administered to humans, resulting in a loss of potentially desirable complement activation and antibody-dependent, cell-mediated cytotoxicity (ADCC) activity.

Thus, there is a need for the development of antibodies directed against α2β1 integrin, including for treatment of α2β1 integrin-associated disorders, mechanisms, and cellular processes including inflammatory diseases and autoimmune diseases. Moreover, it would be desirable to develop anti-α2β1 integrin antibodies that would not be associated with the development of an anti-murine antibody response in a patient.

SUMMARY OF THE INVENTION

Figure 1:
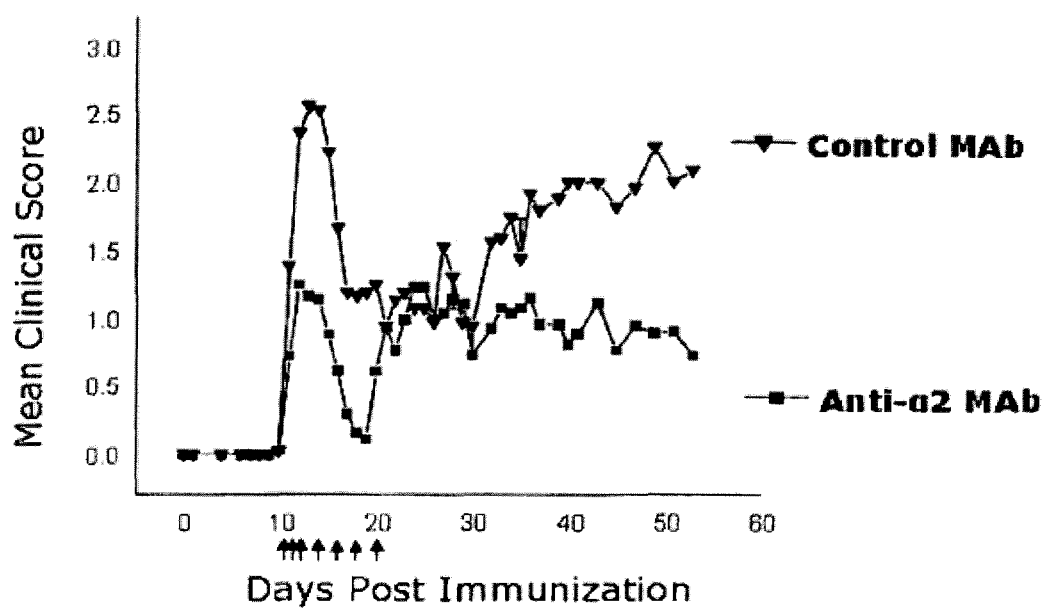
FIG. 1: Graphical results of studies of effects of anti-α2 integrin antibody on paralytic disease in mouse EAE model when administered at first sign of disease (See Example 7).

The present invention provides anti-alpha 2 (α2) integrin antibodies and methods for their use, notably humanized anti-alpha 2 (α2) integrin antibodies and methods for their use.

In certain embodiments, the anti-α2 integrin antibody includes one or more human constant regions (e.g., $C_L$ and/or $C_H$) and a light chain variable region comprising the amino acid sequence of SEQ ID NO:19 and/or a heavy chain variable region comprising the amino acid sequence of SEQ ID NO:21 or amino acid sequence variants thereof. Various forms of the antibody are contemplated herein. For example, the anti-α2 integrin antibody may be a full length antibody (e.g., comprising human immunoglobulin constant regions) or an antibody fragment (e.g. Fab or F(ab')$_2$ or Fab' or Fv or scFv fragments). Furthermore, the antibody may be labeled with a detectable label, immobilized on a solid phase and/or conjugated with a heterologous compound (such as a cytotoxic agent).

Diagnostic and therapeutic uses for anti-α2 integrin antibodies are contemplated as well as prophylactic or preventative uses. For diagnostic uses, a method for determining the presence of α2β1 integrin protein is provided comprising exposing a sample suspected of containing the α2β1 integrin protein to an anti-α2 integrin antibody and determining binding of the antibody to the sample. For this use, a kit is provided comprising an anti-α2 integrin antibody and instructions for using the antibody to detect the α2β1 integrin protein. Therapeutic uses included but are not limited to the treatment of α2β1 integrin-associated disorders, mechanisms, and cellular processes including inflammatory diseases and autoimmune diseases, particularly multiple sclerosis.

Gene therapy applications for anti-α2 integrin antibodies are contemplated. Various vectors (e.g., retroviral vectors, chromosomes) encoding the anti-α2β1 heavy and light chain gene sequences, may be transferred to cells (e.g., fibroblasts, stem cells) to generate populations of cells secreting anti-α2β1 MAb. These cells may possess specific "homing" properties to different cell types, tissues, and/or organs. These antibody-producing cells in turn may be introduced into a patient for localized delivery of the anti-α2β1 MAb. As an example, mesenchymal stem cells modified with an anti-α2β1 MAb vector could be injected into the brain of a patient suffering from multiple sclerosis. The stem cells differentiate into neural cells and secrete the anti-α2β1 MAb to treat the inflammation associated with the multiple sclerosis. In addition, anti-α2β1 may be conjugated to viruses encoding therapeutic genes (e.g., ricin). The modified viruses would bind specifically to cells expressing α2β1 on the cell surface, enabling increased transgene transfer efficiency. Further, immunoconjugates composed of anti-α2β1 antibody-liposome complexes encapsulating nucleic acids encoding therapeutic genes may be introduced intravenously into a patient. The anti-α2β1-immunoconjugate would bind to cells expressing α2β1 integrin and facilitate efficient uptake of the therapeutic genes.

Further provided is an isolated nucleic acid encoding an anti-α2 integrin antibody; a vector comprising that nucleic acid, optionally operably linked to control sequences recognized by a host cell transformed with the vector; a host cell comprising that vector; a process for producing the anti-α2 integrin antibody comprising culturing the host cell so that the nucleic acid is expressed and, optionally, recovering the antibody from the host cell culture (e.g., from the host cell culture medium).

Also provided is a composition comprising a humanized anti-α2 integrin antibody and a pharmaceutically acceptable carrier or diluent. Compositions for therapeutic uses may be sterile and may be lyophilized. Further provided is a method for treating an α2β1 integrin-associated disorder, comprising administering to a subject a pharmaceutically effective amount of an anti-α2 integrin antibody such as a humanized anti-α2 integrin antibody to the mammal. For such therapeutic uses, other agents (e.g., another α2β1 integrin antagonist) may be co-administered to the mammal either before, after, or simultaneously with, the anti-α2 integrin antibody.

Also provided is a humanized anti-α2 integrin antibody comprising a heavy chain variable region comprising the amino acid sequence of (a) HCDR2 (VIWARGFTNYN-SALMS, SEQ ID NO:2), (b) HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3), or (c) SEQ ID NO:40.

In an embodiment, the above-mentioned heavy chain variable region comprises the amino acid sequence of SEQ ID NO:185.

In a further embodiment, the above-mentioned heavy chain variable region comprises the amino acid sequence of SEQ ID NO:185 in which (a) position 71 is Lys, (b) position 73 is Asn, (c) position 78 is Val, or (d) any combination of (a)-(c).

In a further embodiment, the above-mentioned heavy chain variable region comprises an amino acid sequence selected from SEQ ID NOs:70-79 and SEQ ID NOs:109-111.

In an embodiment, the above-mentioned anti-α2 integrin antibody further comprises a FW4 region comprising the amino acid sequence WGQGTLVTVSS (SEQ ID NO:13).

In an embodiment, the above-mentioned anti-α2 integrin antibody comprises the amino acid sequence of HCDR1 (SEQ ID NO:1), HCDR2 (SEQ ID NO:2) and HCDR3 (SEQ ID NO:3).

In an embodiment, the above-mentioned anti-α2 integrin antibody further comprises a light chain.

The invention further provides a humanized anti-α2 integrin antibody comprising a light chain variable region comprising the amino acid sequence of (a) an LCDR1 selected from SANSSVNYIH (SEQ ID NO:4) or SAQSSVNYIH (SEQ ID NO:112), (b) LCDR2 (DTSKLAS; SEQ ID NO:5) and (c) LCDR3 (QQWTTNPLT, SEQ ID NO:6).

In an embodiment, the above-mentioned light chain variable region comprises the amino acid sequence of SEQ ID NO:186.

In an embodiment, the above-mentioned light chain variable region comprises the amino acid sequence of SEQ ID NO:186 in which (a) position 2 is Phe, (b) position 45 is Lys, (c) position 48 is Tyr, or (d) any combination of (a)-(c).

In an embodiment, the above-mentioned light chain variable region comprises an amino acid sequence selected from SEQ ID NO:41, SEQ ID NOs:80-92 and SEQ ID NO:108.

In an embodiment, the above-mentioned humanized anti-α2 integrin antibody further comprises a FW4 region comprising the amino acids sequence FGQGTKVEIK of SEQ ID NO:38.

In an embodiment, the above-mentioned humanized anti-α2 integrin antibody comprises the amino acid sequence of LCDR1 (SEQ ID NO:4), LCDR2 (SEQ ID NO:5) and LCDR3 (SEQ ID NO:6)

In an embodiment, the above-mentioned humanized anti-α2 integrin antibody further comprises a heavy chain.

The invention further provides a humanized anti-α2 integrin antibody comprising:
(i) a heavy chain variable region comprising the amino acid sequence of (a) HCDR2 (VIWARGFTNYNSALMS, SEQ ID NO:2), (b) HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3), or (c) SEQ ID NO:40; and (ii) a light chain variable region comprising the amino acid sequence of (a) an LCDR1 selected from SANSSVNYIH (SEQ ID NO:4) or SAQSSVNYIH (SEQ ID NO:112), (b) LCDR2 (DTSKLAS; SEQ ID NO:5) and (c) LCDR3 (QQWTTNPLT, SEQ ID NO:6).

Also provided is the above-mentioned humanized anti-α2 integrin antibody, wherein (a) the heavy chain variable region comprises the amino acid sequence of SEQ ID NO:185, (b) the light chain variable region comprises the amino acid sequence of SEQ ID NO:186, or (c) both (a) and (b).

Also provided is the above-mentioned humanized anti-α2 integrin antibody, wherein (i) the heavy chain variable region comprises the amino acid sequence of SEQ ID NO:185 in which (a) position 71 is Lys, (b) position 73 is Asn, (c) position 78 is Val, or (d) any combination of (a)-(c); (ii) the light chain variable region comprises the amino acid sequence of SEQ ID NO:186 in which (a) position 2 is Phe, (b) position 45 is Lys, (c) position 48 is Tyr, or (d) any combination of (a)-(c); or (iii) both (i) and (ii).

Also provided is the above-mentioned humanized anti-α2 integrin antibody, wherein (a) the heavy chain variable region comprises an amino acid sequence selected from SEQ ID NOs:70-79 and SEQ ID NOs:109-111; (b) the light chain variable region comprises an amino acid sequence selected from SEQ ID NO:41, SEQ ID NOs:80-92 and SEQ ID NO:108; or (c) both (a) and (b).

In an embodiment, the above-mentioned anti-α2 integrin antibody recognizes the I domain of human α2 integrin.

In an embodiment, the above-mentioned anti-α2 integrin antibody binds α2β1 integrin.

In an embodiment, the above-mentioned anti-α2 integrin antibody binds an epitope of α2 integrin, the epitope comprising:

(a) a Lys residue corresponding to position 192 of the α2 integrin amino acid sequence set forth in SEQ ID NO:8 or position 40 of the α2 integrin I domain amino acid sequence set forth in SEQ ID NO:11;
(b) an Asn residue corresponding to position 225 of the α2 integrin amino acid sequence set forth in SEQ ID NO:8 or position 73 of the α2 integrin I domain amino acid sequence set forth in SEQ ID NO:11;
(c) a Gln residue corresponding to position 241 of the α2 integrin amino acid sequence set forth in SEQ ID NO:8 or position 89 of the α2 integrin I domain amino acid sequence set forth in SEQ ID NO:11;
(d) a Tyr residue corresponding to position 245 of the α2 integrin amino acid sequence set forth in SEQ ID NO:8 or position 93 of the α2 integrin I domain amino acid sequence set forth in SEQ ID NO:11;
(e) an Arg residue corresponding to position 317 of the α2 integrin amino acid sequence set forth in SEQ ID NO:8 or position 165 of the α2 integrin I domain amino acid sequence set forth in SEQ ID NO:11;
(f) an Asn residue corresponding to position 318 of the α2 integrin amino acid sequence set forth in SEQ ID NO:8 or position 166 of the α2 integrin I domain amino acid sequence set forth in SEQ ID NO:11; or
(g) any combination of (a) to (f).

Also provided is an anti-α2 integrin antibody, wherein the antibody binds an epitope of α2 integrin, the epitope comprising:

(a) a Lys residue corresponding to position 192 of the α2 integrin amino acid sequence set forth in SEQ ID NO:8 or position 40 of the α2 integrin I domain amino acid sequence set forth in SEQ ID NO:11;
(b) an Asn residue corresponding to position 225 of the α2 integrin amino acid sequence set forth in SEQ ID NO:8 or position 73 of the α2 integrin I domain amino acid sequence set forth in SEQ ID NO:11;
(c) a Gln residue corresponding to position 241 of the α2 integrin amino acid sequence set forth in SEQ ID NO:8 or position 89 of the α2 integrin I domain amino acid sequence set forth in SEQ ID NO:11;
(d) a Tyr residue corresponding to position 245 of the α2 integrin amino acid sequence set forth in SEQ ID NO:8 or position 93 of the α2 integrin I domain amino acid sequence set forth in SEQ ID NO:11;
(e) an Arg residue corresponding to position 317 of the α2 integrin amino acid sequence set forth in SEQ ID NO:8 or position 165 of the α2 integrin I domain amino acid sequence set forth in SEQ ID NO:11;
(f) an Asn residue corresponding to position 318 of the α2 integrin amino acid sequence set forth in SEQ ID NO:8 or position 166 of the α2 integrin I domain amino acid sequence set forth in SEQ ID NO:11; or
(g) any combination of (a) to (f).

In an embodiment, the above-mentioned humanized anti-α2 integrin antibody is a full length antibody.

In an embodiment, the above-mentioned humanized anti-α2 integrin antibody is an antibody fragment.

In an embodiment, the above-mentioned humanized anti-α2 integrin antibody is bound to a detectable label.

In an embodiment, the above-mentioned humanized anti-α2 integrin antibody is immobilized on solid phase.

In an embodiment, the above-mentioned humanized anti-α2 integrin antibody inhibits binding of α2 or α2β1 integrin to an α2β1 integrin ligand.

In an embodiment, the above-mentioned α2β1 integrin ligand is selected from collagen, laminin, Echovirus-1, decorin, E-cadherin, matrix metalloproteinase I (MMP-I), endorepellin, collectin and C1q complement protein.

The invention further provides a method for determining whether a sample contains α2 integrin, α2β1 integrin, or both, comprising contacting the sample with the above-mentioned humanized anti-α2 integrin antibody and determining whether the antibody binds to the sample, said binding being an indication that the sample contains α2 integrin, α2β1 integrin, or both.

The invention further provides a kit comprising the above-mentioned humanized anti-α2 integrin, optionally further comprising instructions for its use to detect α2 or α2β1 integrin protein.

The invention further provides an isolated nucleic acid encoding a humanized anti-α2β1 integrin antibody mentioned above.

The invention further provides a vector comprising the above-mentioned nucleic acid.

The invention further provides a host cell comprising the above-mentioned nucleic acid or vector.

The invention further provides a process of producing a humanized anti-α2 integrin antibody comprising culturing the above-mentioned host cell under conditions permitting expression of the antibody. In an embodiment, the method further comprises recovering the humanized anti-α2 integrin antibody from the host cell. In a further embodiment, the method further comprises recovering the humanized anti-α2 integrin antibody from the host cell culture medium.

The invention further provides a screening method comprising: detecting binding of α2 or α2β1 integrin to an antibody comprising the VL region of SEQ ID NO:19 and the VH region of SEQ ID NO:21 in the presence versus the absence of a test antibody; and selecting the test antibody if its presence correlates with decreased binding of the α2 or α2β1 integrin to the antibody comprising the VL region of SEQ ID NO:19 and the VH region of SEQ ID NO:21. In an embodiment, the α2 or α2β1 integrin is immobilized on a solid support.

The invention further provides a screening method comprising: detecting binding of α2β1 integrin to collagen in the presence of a test antibody, wherein test antibody refers to an antibody that binds to an α2 I domain; detecting binding of the test antibody to the α2 I domain in the presence of $Mg^{++}$ ions; detecting binding of the test antibody to the α2 I domain in the presence of $Ca^{++}$ ions; detecting binding of the test antibody to the α2 I domain in the presence of cation-free media; and selecting the test antibody if inhibits the binding of α2β1 integrin to collagen and binds to the α2 I domain in the presence of $Mg^{++}$ ions and $Ca^{++}$ ions and cation-free media.

The invention further provides a composition comprising the above-mentioned humanized anti-α2 integrin antibody and a pharmaceutically acceptable carrier.

The invention further provides a method of treating an α2β1 integrin-associated disorder in a subject, the method comprising administering to the subject a therapeutically effective amount of the above-mentioned anti-α2 integrin antibody or composition.

The invention further provides a method for inhibiting leukocyte binding to collagen comprising administering to a subject an amount of the above-mentioned anti-α2β1 integrin antibody effective to inhibit the binding of the leukocytes to collagen.

The invention further provides a use of the above mentioned humanized anti-α2 integrin antibody as a medicament.

The invention further provides a use of the above mentioned humanized anti-α2 integrin antibody or composition for the treatment of an α2β1 integrin-associated disorder.

The invention further provides a use of the above mentioned humanized anti-α2 integrin antibody or composition for the preparation of a medicament for the treatment of an α2β1 integrin-associated disorder.

The invention further provides a composition for the treatment of an α2β1 integrin-associated disorder, the composition comprising the above-mentioned humanized anti-α2 integrin antibody and a pharmaceutically acceptable carrier or diluent.

The invention further provides a package comprising the above-mentioned humanized anti-α2 integrin antibody or composition together with instructions for the treatment of an α2β1 integrin-associated disorder.

In embodiments, the α2β1 integrin-associated disorder is selected from inflammatory disease, autoimmune disease and a disease characterized by abnormal or increased angiogenesis.

In embodiments, the α2β1 integrin-associated disorder is selected from inflammatory bowel disease, Crohn's disease, ulcerative colitis, reactions to transplant, optical neuritis, spinal cord trauma, rheumatoid arthritis, systemic lupus erythematosus (SLE), diabetes mellitus, multiple sclerosis, Reynaud's syndrome, experimental autoimmune encephalomyelitis, Sjorgen's syndrome, scleroderma, juvenile onset diabetes, diabetic retinopathy, age related macular degeneration, cardiovascular disease, psoriasis, cancer as well as infections that induce an inflammatory response.

In embodiments, the α2β1 integrin-associated disorder is selected from multiple sclerosis (e.g., characterized by relapse, acute treatment, delayed treatment), rheumatoid arthritis, optical neuritis and spinal cord trauma.

In embodiments, the above-mentioned method is not associated with (a) platelet activation, (b) platelet aggregation, (c) a decrease in circulating platelet count, (d) bleeding complications, or (e) any combination of (a) to (d).

In an embodiment, the above-mentioned anti-α2 integrin antibody comprises a heavy chain comprising SEQ ID NO:174 or SEQ ID NO:176 and a light chain comprising SEQ ID NO:178.

In an embodiment, the above-mentioned anti-α2 integrin antibody competively inhibits the binding of an antibody comprising the UL region of SEQ ID NO:19 and the VH region of SEQ ID NO:21 to human α2β1 integrin or the I domain thereof.

In an embodiment, the above-mentioned method is associated with an alleviation of a flare or neurological sequalae associated with multiple sclerosis.

In an embodiment, the above-mentioned anti-α2 integrin antibody inhibits the binding of α2β1 integrin to collagen and is not a ligand mimetic.

Also provided is a method of targeting a moiety, such as a molecule, protein, nucleic acid, vector, composition, complex, etc., to a site characterized by the presence of an α2β1 integrin ligand, the method comprising attaching or binding the moiety to the above-mentioned humanized anti-α2 integrin antibody.

Also provided is an α2 integrin epitope that binds an anti-α2 integrin antibody, wherein the epitope does not comprise the ligand-binding site of α2 integrin. In embodiments, binding to the epitope is not associated with (a) platelet activation, (b) platelet aggregation, (c) a decrease in circulating platelet count, (d) bleeding complications, (e) α2 integrin activation, or (f) any combination of (a) to (e).

Preferred antibodies bind to the I-domain of human α2β1 integrin. In particular, the preferred antibodies are able to block α2-dependent adhesion of cells to the extracellular matrix (ECM), particularly to at least one or both of collagen and laminin. Humanized antibodies are provided, including antibodies based on an antibody referred to herein as TMC-2206. Anti-α2 integrin antibodies are provided that are highly specific for human α2β1 integrin, and whose administration is not associated with undesired effects such as bleeding complications or complications due to cellular activation. The binding specificity (e.g., epitope specificity) of these antibodies is associated with their unexpected non-hemorrhagic profile.

The humanized anti-α2β1 integrin antibody may have a heavy chain variable region comprising the amino acid sequence of HCDR1 (GFSLTNYGIH; SEQ ID NO:1) and/or HCDR2 (VIWARGFTNYNSALMS; SEQ ID NO:2) and/or HCDR3 (ANDGVYYAMDY; SEQ ID NO:3). The humanized anti-α2β1 integrin antibody may have a light chain variable region comprising the amino acid sequence of LCDR1 (SANSSVNYIH; SEQ ID NO:4 or; SAQSSVNYIH SEQ ID NO:112) and/or LCDR2 (DTSKLAS; SEQ ID NO:5) and/or LCDR3 (QQWTTNPLT; SEQ ID NO:6). In certain embodiments, the humanized anti-α2β1 integrin antibodies have a heavy chain comprising HCDR1 (GFSLTNYGIH; SEQ ID NO:1) and/or HCDR2 (VIWARGFTNYNSALMS; SEQ ID NO:2) and/or HCDR3 (ANDGVYYAMDY; SEQ ID NO:3) and a light chain variable region comprising the amino acid sequence of LCDR1 (SANSSVNYIH; SEQ ID NO:4) and/or LCDR2 (DTSKLAS; SEQ ID NO:5) and/or LCDR3 (QQWTTNPLT; SEQ ID NO:6). In other embodiments, the antibody comprises an amino acid sequence variant of one or more of such CDRs, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants).

DETAILED DESCRIPTION OF THE INVENTION

The present invention provides antibodies specifically reactive with human alpha 2 (α2) integrin, including humanized antibodies, and methods for their use. The humanized antibodies may have human framework regions (FWs) and complementarity determining regions (CDRs) from a non-human antibody, typically a mouse, specifically reactive with human α2 integrin. Nucleotide sequences encoding, and amino acid sequences comprising heavy and light chain antibodies are provided. In preferred embodiments, one or more of the CDR regions are derived from or based on the murine antibody secreted by the hybridoma clone, BHA2.1 [referred to herein as the TMC-2206 antibody]. Further provided are antibodies having similar binding properties and antibodies (or other antagonists) having similar functionality as the antibodies disclosed herein. Preferred anti-α2 integrin antibodies include those that (a) bind to the I domain of α2 integrin, (b) inhibit the function of α2 integrin (e.g., collagen or laminin binding), (c) bind to α2 integrin on resting platelets without inducing platelet activation and (d) recognize the binding epitope of TMC-2206 (e.g., compete with TMC-2206 for the binding to α2 integrin). Such antibodies may bind preferentially to the inactive or closed conformation of the target α2 integrin molecule without competing for the ligand binding site. Unexpected advantages of anti-α2 integrin antibodies as described herein that bind preferentially to the closed conformation of the α2β1 integrin and/or bind to α2β1 integrin without competing for the ligand binding site (e.g., are not a ligand mimetic) include preventing potential platelet activation, platelet aggregation, decreases in circulating platelet count and/or bleeding complications in a treated subject.

"Bleeding complications" as used herein refers to any adverse effect on blood levels and physiology, including platelet thrombotic responses, thrombocytopenia, increased time to clot, increased bleeding time and blood loss that limit therapeutic use of the anti-α2 integrin antibody.

α2β1 integrin is a molecule comprised of an α2 integrin subunit (see, e.g., SEQ ID NO:7, for DNA sequence and SEQ ID NO:8 for protein sequence of human α2) from the family of alpha integrins, and a integrin subunit (see, e.g., SEQ ID NO:9 for DNA sequence and SEQ ID NO:10 protein sequence of human α1) from the family of beta integrins, and may be from any subject including a mammal, but preferably is from a human. The α2β1 integrin may be purified from any natural source, or may be produced synthetically (e.g., by use of recombinant DNA technology). The nucleic acid coding sequences for α2 integrin and for β1 integrin are described in Takada and Hemler J. Cell Biol. 109(1):397-407 (1989; GenBank submission X17033; subsequently updated to entry NM 002203) and Argraves, W. S, J. Cell. Biol. Sep 105(3):1183-90 (1987; Genbank submission X07979.1 and related sequences representing alternatively spliced variants), respectively.

The 'I' domain of the α2β1 integrin molecule refers to a region of this α2β1 integrin molecule within the α2 subunit, and is described, for example, in Kamata et al., J Biol. Chem. 269:9659-9663 (1994); Emsley et al., J. Biol. Chem. 272: 28512 (1997) and Cell 101:47 (2000). The amino acid sequence of a human I domain of α2 integrin is shown as SEQ ID NO:11 (see also, e.g., SEQ ID NO: 107). The I domain of α2 integrin contains a MIDAS type of ligand binding site (Metal on Dependent Adhesion Site) which has a requirement and a specificity for a given divalent cation to support ligand binding. The amino acid sequences for an I domain of α2 integrin in rat shown as SEQ ID NO:93 (see also, e.g., SEQ ID NO:113) and in mouse shown as SEQ ID NO:94 (see also, e.g., SEQ ID NO:114) are shown in Table 28. Cynomolgus monkey and rhesus monkey I domain sequences were cloned from the leukocyte fraction derived from whole blood and are provided in SEQ ID NO:103 (DNA), SEQ ID NO:171 (amino acid) for cynomolgus and SEQ ID NO:104 (DNA), SEQ ID NO:172 (amino acid) for rhesus, respectively.

A TMC-2206 (BHA2.1) epitope refers to a region of the I domain of human α2 integrin to which the TMC-2206 antibody binds. This epitope spans a region encompassing amino acid residues, K40, N73, Q89, Y93, R165, and N166 and optionally, other amino acid residues of the α2 integrin I domain.

An α2 integrin-associated disorder refers to a disorder, disease, or condition that involves α2 integrin-dependent processes/function (e.g., binding, activity) that mediate aberrant cellular reactions within target tissue. Examples of α2 integrin-dependent processes involved in disease include collagen-dependent cellular responses such as those involved in increases in cytokine expression and proliferation, aspects of T-cell-, mast cell- and neutrophil-function, inflammatory disorders, mammary gland ductal morphogenesis, epidermal wound healing, and angiogenesis. Examples of α2 integrin-associated disorders include, but are not limited to, inflammatory diseases or disorders including but not limited to inflammatory bowel disease (such as Crohn's disease and ulcerative colitis), reactions to transplant (including transplant rejection), optic neuritis, spinal cord trauma, rheumatoid arthritis, multiple sclerosis (including treatment of neurological sequalae associated therewith as well as multiple sclerosis characterized by relapse), autoimmune diseases or disorders (including systemic lupus erythematosus (SLE), diabetes mellitus, Reynaud's syndrome, experimental autoimmune encephalomyelitis, Sjorgen's syndrome, scleroderma), juvenile onset diabetes, and disorders associated with abnormal or higher than normal angiogenesis (such as diabetic retinopathy, age related macula degeneration, cardiovascular disease, psoriasis, rheumatoid arthritis and cancer) as well as infections that induce an inflammatory response.

Treatment of an α2β1 integrin-associated disorder refers to both therapeutic use and prophylactic or preventative use of the anti-α2 integrin antibodies described herein. Those in need of treatment include those already diagnosed with the disorder as well as those in which the onset of the disorder is to be prevented or delayed.

A mammal, including for purposes of treatment, refers to any animal classified as a mammal, including humans, domestic and farm animals, and zoo, sports or pet animals such as dogs, horses, cats, cows etc. Preferably, the mammal is human.

Intermittent or periodic dosing is a dosing that is continuous for a certain period of time and is at regular intervals that are preferably separated more than by one day.

The term antibody or immunoglobulin is used in the broadest sense, and covers monoclonal antibodies (including full length monoclonal antibodies), polyclonal antibodies, multi-specific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')$_2$, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions ($V_H$, $V_H$-$V_H$), anticalins, PepBodies™, antibody-T-cell epitope fusions (Troybodies) or Peptibodies.

A monoclonal antibody refers to an antibody obtained from a population of substantially homogeneous antibodies, e.g., the individual antibodies comprising the population are identical except for possible naturally occurring mutations that may be present in minor amounts. Monoclonal antibodies are highly specific, being directed against a single antigenic site. Furthermore, in contrast to conventional (e.g., polyclonal) antibody preparations which typically include different antibodies directed against different determinants (e.g., epitopes) on an antigen, each monoclonal antibody is directed against at least a single determinant on the antigen. The modifier "monoclonal" indicates the character of the antibody as being obtained from a substantially homogeneous population of antibodies, and is not to be construed as requiring production of the antibody by any particular method. For example, monoclonal antibodies may be made by the hybridoma method first described by Kohler et al., Nature 256:495 (1975), or may be made by recombinant DNA methods (see, e.g., U.S. Pat. No. 4,816,567). Monoclonal antibodies may also be isolated from phage antibody libraries, for example, using the techniques described in Clackson et al., Nature 352:624-628 (1991) and Marks et al., J. Mol. Biol. 222:581-597 (1991). Monoclonal antibodies can also be isolated using the techniques described in U.S. Pat. Nos. 6,025,155 and 6,077,677 as well as U.S. Patent Application Publication Nos. 2002/0160970 and 2003/0083293 (see also, e.g., Lindenbaum, et al., Nucleic Acids Research 32 (21):0177 (2004)).

Monoclonal antibodies can include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA 81: 6851-6855 (1984) for mouse-human chimeric antibodies).

A hypervariable region refers to the amino acid residues of an antibody which are responsible for antigen-binding. The hypervariable region comprises amino acid residues from a complementarity determining region or CDR (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a hypervariable loop (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196: 901-917 (1987)). Framework or FR residues are those variable domain residues other than the hypervariable region residues. For antibodies described herein, the CDR and framework regions are identified based on the Kabat numbering system except that the CDR1 of the heavy chain is defined by Oxford Molecular's AbM definition as spanning residues 26 to 35. The Oxford Molecular's AbM antibody modeling software (http://people.cryst.cck.ac.uk/~ubc07s/) (Martin et al., Proc. Natl. Acad. Sci. USA, 86, 9268-9272 (1989); Martin et al., Methods Enzymol., 203, 121-153 (1991); Pedersen et al., Immunomethods, 1, 126 (1992); and Rees et al., In Sternberg M. J. E. (ed.), Protein Structure Prediction. Oxford University Press, Oxford, 141-172. (1996)) combines the Kabat CDR and the Chothia hypervariable region numbering systems to define CDRs.

Humanized forms of non-human (e.g., murine) antibodies may be chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In addition, individual or groups of Fv framework region (FR) residues of the human immunoglobulin may be replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable regions or domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (e.g., Fc), typically that of a human immunoglobulin (see, e.g., Queen et al., Proc. Natl. Acad. Sci. USA 86:10029 (1989), and Foote and Winter, J. Mol. Biol. 224: 487 (1992)).

Single-chain Fv or scFv antibody fragments may comprise the $V_H$ and $V_L$ regions or domains of antibody, wherein these domains are present in a single polypeptide chain. Generally, the Fv polypeptide further comprises a polypeptide linker between the $V_H$ and $V_L$ domains which enables the scFv to form the desired structure for antigen binding (for a review, see, e.g., Pluckthun in The Pharmacology of Monoclonal Antibodies, vol. 113, Rosenburg and Moore eds. Springer-Verlag, New York, pp. 269-315 (1994)).

Diabody refers to small antibody fragments with two antigen-binding sites, which fragments comprise a heavy chain variable domain ($V_H$) connected to a light chain variable domain ($V_L$) in the same polypeptide chain ($V_H$—$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90: 6444-6448 (1993).

Linear antibody refers to antibodies such as those described in Zapata et al., Protein Eng. 8(10): 1057-1062 (1995). Briefly, these antibodies comprise a pair of tandem Fd segments ($V_H$—$C_H$1—$V_H$—$C_H$1) which form a pair of antigen binding regions. Linear antibodies can be bispecific or monospecific.

An isolated antibody refers to one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An epitope tagged antibody refers to one wherein the antibody of the invention is fused to an epitope tag. The epitope tag polypeptide has enough residues to provide an epitope against which an antibody thereagainst can be made, yet is short enough such that it does not interfere with activity of the anti-α2β1 integrin antibody. The epitope tag preferably is sufficiently unique so that the antibody thereagainst does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 (Field et al., Mol. Cell. Biol. 8: 2159-2165 (1988)); the c-myc tag and the 8F9, 3C7, 6E10, G4, B7 and 9E10 antibodies thereto (Evan et al., Mol. Cell. Biol. 5(12):3610-3616 (1985)); and the Herpes Simplex virus glycoprotein D (gD) tag and its antibody (Paborsky et al., Protein Engineering 3(6): 547-553 (1990)). In certain embodiments, the epitope tag is a salvage receptor binding epitope which is an epitope of the Fc region of an IgG molecule (e.g., $IgG_1$, $IgG_2$, $IgG_3$, or $IgG_4$) that is responsible for increasing the in vivo serum half-life of the IgG molecule.

A cytotoxic agent refers to a substance that inhibits or prevents the function of cells and/or causes destruction of cells. The can include radioactive isotopes (e.g., $^{131}I$, $^{125}I$, $^{90}Y$ and $^{186}Re$), chemotherapeutic agents, and toxins such as enzymatically active toxins of bacterial, fungal, plant or animal origin, or fragments thereof. A non-cytotoxic agent refers to a substance that does not inhibit or prevent function of cells and/or does not cause destruction of cells. A non-cytotoxic agent may include an agent that can be activated to become cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an anti-α2β1 integrin antibody as described herein.

A chemotherapeutic agent refers to a chemical compound useful in the treatment of cancer. Examples of chemotherapeutic agents include but are not limited to Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see U.S. Pat. No. 4,675,187), Melphalan and other related nitrogen mustards.

A prodrug refers to a precursor or derivative form of a pharmaceutically active substance that is less cytotoxic to tumor cells compared to the parent drug and is capable of being enzymatically activated or converted into the more active parent form (see, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are mot limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form can be those chemotherapeutic agents described above.

A label refers to a detectable compound or composition which is conjugated or coupled directly or indirectly to the antibody. The label may itself be detectable by itself (e.g., radioisotope labels or fluorescent labels) or, in the case of an enzymatic label, may catalyze chemical alteration of a substrate compound or composition which is detectable.

Solid phase refers to a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A liposome refers to a small vesicle composed of various types of lipids, phospholipids and/or surfactant which is useful for delivery of a drug (such as the antibodies of the invention and, optionally, a chemotherapeutic agent) to a mammal. The components of the liposome are commonly arranged in a bilayer formation, similar to the lipid arrangement of biological membranes.

An isolated nucleic acid molecule refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

A viral vector refers to a vehicle for the transfer of a nucleic acid (e.g. DNA or RNA) to cells through viral infection or transduction. Examples of viral vectors include retroviruses, adenoviruses, pox viruses, and baculovirus.

A non-viral vector refers to a nucleic acid vehicle such as a CAN, plasmid or chromosome that is delivered to cells by non-viral methods such as electroporation, injections, and cationic reagent mediated transfection.

Expression control sequences refer to those DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked DNA sequences are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A further aspect of the present invention is the treatment of α2β1 integrin-associated disorders by administering to a subject a nucleic acid molecule encoding an anti-α2 integrin antibody of the invention. Suitable methods of administration include gene therapy methods (see below).

A nucleic acid of the invention may be delivered to cells in vivo using methods such as direct injection of DNA, receptor-mediated DNA uptake, viral-mediated transfection or non-viral transfection and lipid based transfection, all of which may involve the use of gene therapy vectors. Direct injection has been used to introduce naked DNA into cells in vivo (see e.g., Acsadi et al. (1991) Nature 332:815-818; Wolff et al. (1990) Science 247:1465-1468). A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor (see for example Wu, G. and Wu, C. H. (1988) J. Biol. Chem. 263: 14621; Wilson et al. (1992) J. Biol. Chem. 267:963-967; and U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122-2126).

Defective retroviruses are well characterized for use as gene therapy vectors (for a review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include .psi.Crip, .psi.Cre, .psi.2 and .psi.Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

For use as a gene therapy vector, the genome of an adenovirus may be manipulated so that it encodes and expresses a nucleic acid compound of the invention, but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle cells (Quantin et al. (1992) Proc. Natl. Acad. Sci. USA 89:2581-2584).

Adeno-associated virus (AAV) may be used as a gene therapy vector for delivery of DNA for gene therapy purposes. AAV is a naturally occurring defective virus that requires another virus, such as an adenovirus or a herpes virus, as a helper virus for efficient replication and a productive life cycle (Muzyczka et al. Curr. Topics in Micro. and Immunol. (1992) 158:97-129). AAV may be used to integrate DNA into non-dividing cells (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). An AAV vector such as that described in Tratschin et al. (1985) Mol. Cell. Biol. 5:3251-3260 may be used to introduce DNA into cells (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790). Lentiviral gene therapy vectors may also be adapted for use in the invention.

General methods for gene therapy are known in the art. See for example, U.S. Pat. No. 5,399,346 by Anderson et al. A biocompatible capsule for delivering genetic material is described in PCT Publication WO 95/05452 by Baetge et al. Methods of gene transfer into hematopoietic cells have also previously been reported (see Clapp, D. W., et al., Blood 78: 1132-1139 (1991); Anderson, Science 288:627-9 (2000); and Cavazzana-Calvo et al., Science 288:669-72 (2000)).

Cell, cell line, and cell culture are often used interchangeably and all such designations include progeny. Transformants and transformed cells (e.g., obtained by transfection, transformation or transduction of nucleic acids, vectors, virus, etc.) include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Humanized antibodies as described herein include antibodies that have variable region frameworks derived from a human acceptor antibody molecule, hypervariable or CDR sequences from a donor murine antibody, and constant regions, if present, derived from human sequences.

Antibodies of the present invention have been constructed comprising CDRs from both the heavy chain variable and light chain variable regions of the murine monoclonal antibody clone BHA2.1 (Hangan et al., Cancer Res. 56:3142-3149 (1996)). Preferred starting materials for constructing antibodies are anti-α2 integrin antibodies such as those secreted by the BHA2.1 hybridoma (e.g., TMC-2206) that are function-blocking antibodies directed against human α2 integrin and are dependent for binding and activity on the presence of an intact I-domain within the targeted α2 integrin. Preferred are antibodies with the epitope specificity of TMC-2206 (or BHA2.1), including antibodies which bind to the inactive conformation of the α2 integrin molecule, and/or do not act as ligand mimetics. Preferred are antibodies with the epitope specificity of TMC-2206 (or BHA2.1) that, although they interact with α2β1 integrin present on both leukocytes and platelets, do not cause platelet activation, impair aggregation of activated platelets on collagen, have minimal or no effect on bleeding and/or are not associated with bleeding complications at administered concentrations, including therapeutic doses in vivo.

Antibodies may be constructed wherein the human acceptor molecule for the light chain variable region is selected based on homology considerations between potential acceptor molecule variable regions and with the light chain variable region of the murine antibody. Germline candidate human acceptor molecules are preferred to reduce potential antigenicity. Germline databases are made up of antibody sequences that read through the end of the heavy chain FW3 region and partially into the CDR3 sequence. For selection of a FW4 region, it is preferred to search databases of mature antibody sequences which have been derived from the selected germline molecule, and also preferred to select a reasonably homologous FW4 region for use in the recombinant antibody molecule. Human acceptor molecules are preferably selected from the same light chain class as the murine donor molecule, and of the same canonical structural class of the variable region of the murine donor molecule. Secondary considerations for selection of the human acceptor molecule for the light chain variable region include homology in CDR length between the murine donor molecule and the human acceptor molecule. Human acceptor antibody molecules are preferably selected by homology searches to the V-BASE database, and other databases such as the Kabat and the public NCBI databases may be used as well. For humanized anti-α2 integrin antibodies with the same or similar epitope specificity and/or functional properties as TMC-2206, a preferred light chain human acceptor molecule is SEQ ID NO:37 with the germline antibody sequence A14 for the FW 1-3 region and the sequence FGQGTKVEIK for FW4 (SEQ ID NO:38) which represents a common FW-4 of mature kappa 1 light chains (e.g., light chain sequence AAB24132 (NCBI entry gi/259596/gb/AAB24132).

Antibodies may be constructed wherein the human acceptor molecule for the heavy chain variable region is selected based on homology considerations between potential acceptor molecule variable regions and the heavy chain variable region of the murine antibody. Germline candidate human acceptor molecules are preferred to reduce potential antigenicity. Germline databases are made up of antibody sequences that read through the end of the heavy chain FW3 region and partially into the CDR3 sequence. For selection of a FW4 region, it is preferred to search databases of mature antibody sequences which have been derived from the selected germline molecule, and also preferred to select a reasonably homologous FW4 region for use in the recombinant antibody molecule. Human acceptor molecules are preferably selected from the same heavy chain class as the murine donor molecule, and of the same canonical structural class of the variable region of the murine donor molecule. Secondary considerations for selection of the human acceptor molecule for the heavy chain variable region include homology in CDR length between the murine donor molecule and the human acceptor molecule. Human acceptor antibody molecules are preferably selected by homology search to the V-BASE database, although other databases such as the Kabat and the public NCBI databases may be used as well. For anti-α2 integrin antibodies with the same or similar epitope specificity and/or functional properties as TMC-2206, a preferred heavy chain acceptor molecule is SEQ ID NO:39 with the germline antibody sequence 4-59 for the FW 1-3 region (SEQ ID NO:12) and antibody, CAA48104.1 (NCBI entry, gi/33583/emb/CAA48104.1) a mature antibody derived from the 4-59 germline sequence for the FW 4 region (SEQ ID NO:13).

Methods for humanizing a nonhuman α2 integrin antibody are described herein, including in the Examples below. In order to humanize an anti-α2 integrin antibody, the nonhuman antibody starting material is obtained, including by preparation from immunization or by purchase of commercially available antibodies. Exemplary techniques for generating antibodies are described herein.

The α2β1 integrin antigen to be used for production of antibodies may be, for example, a soluble form of α2β1 integrin or other fragment of α2β1 integrin (e.g., an α2β1 integrin fragment comprising a human α2 integrin I-domain (SEQ ID NO:11); see also, e.g., SEQ ID NO: 107). Other forms of α2 integrin useful for generating antibodies will be apparent to those skilled in the art based on the sequence of α2 integrin (e.g., a human α2 integrin as in SEQ ID NO:8).

Polyclonal antibodies are preferably raised in animals by multiple subcutaneous (sc), intravenous (iv) or intraperitoneal (ip) injections of the relevant antigen with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals may be immunized against the antigen, immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with ⅕ to ¹⁄₁₀ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025, 155 and 6,077,677 as well as U.S. Patent Application Publication Nos. 2002/0160970 and 2003/0083293 (see also, e.g., Lindenbaum, et al., Nucleic Acids Research 32 (21):0177 (2004)).

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell (see, e.g., Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (e.g., Kozbor, J. Immunol., 133: 3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can be determined, for example, by the Scatchard analysis of Munson et al., Anal. Biochem., 107: 220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures including, for example, protein A chromatography, hydrophobic interaction chromatography, hydroxylapatite chromatography, gel electrophoresis, dialysis, and/or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells, including those that do not otherwise produce immunoglobulin protein, to obtain the synthesis of monoclonal antibodies in the recombinant host cells. Recombinant production of antibodies is described in further detail below.

The Examples herein describe methods for humanization of an exemplary anti-α2 integrin antibody. In certain embodiments, it may be desirable to generate amino acid sequence variants of the humanized antibody, particularly where these improve the binding affinity or other biological properties of the humanized antibody.

Amino acid sequence variants of humanized anti-α2β1 integrin antibody are prepared by introducing appropriate nucleotide changes into a humanized anti-α2β1 integrin antibody DNA, or by peptide synthesis. Such variants include, for example, deletions from, and/or insertions into and/or substitutions of, residues within the amino acid sequences shown for the anti-α2 integrin antibody TMC-2206 (e.g., derived from or based on variable region sequences as shown in SEQ ID NOS: 19 and 21). Any combination of amino acid deletion, insertion, and substitution is made to arrive at the final construct, provided that the final construct possesses the desired characteristics. The amino acid changes also may alter post-translational processes of the humanized anti-α2 integrin antibody, such as changing the number or position of glycosylation sites.

There are a number of methods used to make antibodies human or human-like (e.g., "humanization"). Approaches to humanize antibodies have varied over the years. One approach was to generate murine variable regions fused to human constant regions, so-called murine-human Fc chimeras (see, e.g., Morrison et al, Proc. Natl. Acad. Sci. USA 81:6851-6855 (1984); U.S. Pat. No. 5,807,715). Another approach exploited the fact that CDRs could be readily identified based on their hypervariable nature (Kabat et al, J. Biol. Chem. 252:6609-6616 (1977)), Kabat, Adv. Protein Chem. 32:1-75 (1978)) and canonical structure (Chothia and Lesk, J. Mol. Biol. 196(4):901-17 (1987); Lazakani et al., J. Mol. Biol. 272:929 (1997) and humanized by grafting just the non-human CDR regions (referred to as donor CDRs) onto a human framework (referred to as acceptor frameworks) as shown, for example by Jones et al., Nature 321(6069):522-5 (1986); (see, e.g., U.S. Pat. No. 5,225,539; U.S. Pat. No. 6,548,640). The six CDR loops are presented in a cluster, and based on crystallographic analysis, critical framework residues within the so-called "Vernier" zone flanking the CDRs or in the heavy-light chain interface can be readily identified (see, e.g., Chothia and Lesk, J. Mol. Biol. 196(4):901-17 (1987); Chothia et al., J. Mol. Biol. 186(3):651-63 (1985); Chothia et al., Nature 342(6252):877-83 (1989)). These residues can be back-mutated to the murine residue to restore the correct relative orientation of the six CDRs (see, e.g., Verhoyen et al., Science 239(4847):1534-6 (1988); Reichman et al., Nature 332(6162):323-7 (1988); Tempest et al., Biotechnology (NY) 9(3):266-71 (1991)). Since variable regions can be classified in families that bear relatively high homology between mouse and human (reviewed in e.g., Pascual and Capra Adv. Immunol. 49:1-74 (1991)), these early studies also indicated that the potential for loss in affinity could be minimized in the grafted antibody by selecting the human germline sequence with the highest homology to the murine antibody of interest for use as the human acceptor molecule (see, e.g., U.S. Pat. No. 5,225,539; Verhoyen et al., Science 239(4847):1534-6 (1988)).

Family homologies and structural relationships between frameworks that impact correct presentation of a given type of CDR canonical structure have been reported (see, e.g., Al-Lazakani et al., J. Mol. Biol. 273(4):927-48 (1997) and references therein). Preferably, a best fit human or germline sequence is chosen. Available databases of antibody germline sequences may be used to determine the family subtype of a given murine heavy and light chain and to identify best fit sequences useful as human acceptor frameworks within that human subfamily. Both the linear amino acid homology of the donor and acceptor frameworks as well as the CDR canonical structure are preferably taken into account.

Exemplary heavy chain residues which may be substituted in a humanized anti-α2 integrin antibody include any one or more of the following framework residue numbers: H37, H48, H67, H71, H73, H78 and H91 (Kabat numbering system). Preferably at least four of these framework residues are substituted. A particularly preferable set of substitutions for the heavy chain in humanized anti-α2 integrin antibodies as exemplified herein is H37, H71, H73 and H78. Similarly, residues in the light chain can also be substituted. Exemplary light chain residues for substitution include any one or more of the following residue numbers: L1, L2, L4, L6, L46, L47, L49 and L71. Preferably at least three of these framework residues are substituted. A particularly preferable set of substitutions for the light chain in humanized anti-α2 integrin antibodies as exemplified herein is L2, L46 and L49.

A useful method for identification of certain residues or regions of a humanized anti-α2 integrin antibody that are preferred locations for mutagenesis is called "alanine scanning mutagenesis" (see, e.g., Cunningham and Wells Science, 244: 1081-1085 (1989)). Here, a residue or group of target residues are identified (e.g., charged residues such as arg, asp, his, lys, and glu) and replaced by a neutral or negatively charged amino acid (preferably alanine or polyalanine) to affect the interaction of the amino acids with α2β1 integrin antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed humanized anti-α2 integrin antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a humanized anti-α2 integrin antibody with an N-terminal methionyl residue or the antibody fused to an epitope tag. Other insertional variants of a humanized anti-α2 integrin antibody molecule include the fusion to the N- or C-terminus of a humanized anti-α2 integrin antibody of an enzyme or a polypeptide which increases the serum half-life of the antibody (see below).

Another type of variant is an amino acid substitution variant. These variants have at least one amino acid residue in a humanized anti-α2 integrin antibody molecule removed and a different residue inserted in its place. The sites of greatest interest for substitutional mutagenesis include the hypervariable loops, but framework alterations are also contemplated. Hypervariable region residues or framework residues involved in antigen binding are generally substituted in a relatively conservative manner. Such conservative substitutions are shown below under the heading of "preferred substitutions". If such substitutions result in a change in biological activity, then more substantial changes, denominated "exemplary substitutions" or as further described below in reference to amino acid classes, are introduced and the products screened.

| Original Residue | Exemplary Substitutions | Preferred Substitutions |
|---|---|---|
| Ala (A) | val; leu; ile | Val |
| Arg (R) | lys; gln; asn | Lys |
| Asn (N) | gln; his; lys; arg | Gln |
| Asp (D) | glu | Glu |
| Cys (C) | ser | Ser |
| Gln (Q) | asn | Asn |
| Glu (E) | asp | Asp |
| Gly (G) | pro; ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | leu |
| Phe (F) | leu; val; ile; ala; tyr | Leu |
| Pro (P) | ala | Ala |
| Ser (S) | thr | Thr |
| Thr (T) | ser | Ser |
| Trp (W) | tyr; phe | Tyr |
| Tyr (Y) | trp; phe; thr; ser | Phe |
| Val (V) | ile; leu; met; phe; ala; norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper confirmation of a humanized anti-α2 integrin antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetyl-galactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that it contains or lacks one or more of the above-described tripeptide sequences (for N-linked glycosylation sites). The alteration may also be made by the addition of, substitution by, or deletion of, one or more serine or threonine residues to the sequence of the original antibody (for O-linked glycosylation sites). Nucleic acid molecules encoding amino acid sequence variants of humanized anti-α2 integrin antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, or cassette mutagenesis of an earlier prepared variant or a non-variant version of humanized anti-α2 integrin antibody.

Ordinarily, amino acid sequence variants of a humanized anti-α2 integrin antibody will have an amino acid sequence having at least 75% amino acid sequence identity with the original humanized antibody amino acid sequences of either the heavy or the light chain (e.g., variable region sequences as in SEQ ID NO:21 or SEQ ID NO:19, respectively), more preferably at least 80%, more preferably at least 85%, more preferably at least 90%, and most preferably at least 95%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with the humanized anti-α2 integrin residues, after aligning the sequences and introducing gaps, if necessary, to achieve the maximum percent sequence identity, and not considering any conservative substitutions (as described above) as part of the sequence identity. None of N-terminal, C-terminal, or internal extensions, deletions, or insertions into the antibody sequence shall be construed as affecting sequence identity or homology. Thus sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a pre-determined portion of one or both sequences). The programs provide a default opening penalty and a default gap penalty, and a scoring matrix such as PAM250 (a standard scoring matrix; see Dayhoff et al., in Atlas of Protein Sequence and Structure, vol 5, supp. 3 (1978)) can be used in conjunction with the computer program. For example, the percent identity can the be calculated as: the total number of identical matches multiplied by 100 and then divided by the sum of the length of the longer sequence within the matched span and the number of gaps introduced into the longer sequences in order to align the two sequences.

Antibodies having the characteristics identified herein as being desirable in a humanized anti-α2 integrin antibody are screened for by methods as described herein. For example, methods for screening candidate anti-α2 integrin antibodies for preferred characteristics and functionalities are provided that include screening for antibodies which bind to the epitope on α2β1 integrin bound by an antibody of interest (e.g., those which compete with, inhibit or block binding of the TMC-2206 antibody to α2β1 integrin). Exemplary methods and materials are described in Example 13. Cross-blocking assays can be performed and are described, for example, in Antibodies, A Laboratory Manual, Cold Spring Harbor Laboratory, Ed Harlow and David Lane (1988). In addition, or alternatively, epitope mapping, for example, as described in Champe et al., J. Biol. Chem. 270:1388-1394 (1995), can be performed to determine whether the antibody binds an epitope of interest (see, e.g., Example 12 for epitope mapping studies of TMC-2206).

Immobilized α2β1 integrin can similarly be used to determine relative binding potencies by measuring $K_i$ values in competition assays (see, e.g., Example 2). For example, fluorescently labeled Eu-TMC-2206 is used in the presence of varying concentrations of unlabeled candidate antibody, for example, using an assay system similar to that described above. Following a specified incubation time, the amount of bound Eu-TMC-2206 is determined. The inhibition curves are fitted with the "one site competition" model using Prism software (GraphPad, Inc. CA) to obtain $IC_{50}$ values and to calculate the $K_i$ using the equation of Cheng and Prusoff (Biochem, Pharmacol. 22(23):3099-108 (1973)).

It is desirable to prepare, identify and/or select humanized anti-α2 integrin antibodies which have beneficial binding properties, for example, under conditions as described in Example 2, wherein candidate antibodies are tested for their ability to block α2β1-integrin mediated cell adhesion in comparison to TMC-2206 and the mouse-human chimeric antibody derived from TMC-2206 as described in Example 2. For example, CHO cells expressing human α2 integrin and endogenous hamster β1 (Symington et al., J. Cell Biol. 120 (2):523-35 (1993)) are prepared and labeled with CFSE (Molecule Probes, OR). Labeled cells are prepared and the cell concentration is adjusted; cells are kept in the dark until used. A collagen-coated plate (rat-tail collagen Type I; BD Biosciences) is prepared and each serially diluted antibody solution is added to the collagen plate. Labeled cells are then added to the well and the plate is incubated. After washing, cells are lysed and the fluorescence intensity (excitation, 485 nm; emission, 535 nm) is read. The inhibitory activity of each antibody is calculated.

Additionally, binding constants of the candidate antibodies for the immobilized α2β1 integrin ligand can be calculated as described in Example 2. Wells in a 96 well microtiter plate are coated with platelet α2β1-integrin (custom-coated with human platelet α2β1 by GTI Inc., WI) and then blocked. For example, to determine the affinity of TMC-2206 for its α2 integrin antigen, fluorescently labeled TMC-2206 or isotype control IgG antibody are used (see Examples below). The fluorescently labeled antibody, including Eu-TMC-2206 or Eu-isotype control IgG, is applied to the blocked α2β1-integrin microtiter plates. After incubating the sealed plates to allow the antibody-antigen interaction to reach equilibrium, samples are transferred from each well into a fresh well containing an enhancement solution for the measurement of free (unbound) label. The enhancement solution is also added to the emptied wells for the measurement of bound label. The $K_d$ values of the anti-α2 integrin antibody is calculated by Scatchard analysis. The relative affinity of TMC-2206 derivatives (including humanized antibodies derived from or based on TMC-2206) can be determined by determining the Ki value in a competition assay. For example, for the competition assay, Eu-labelled TMC-2206 is added to α2β1-coated wells in the presence of unlabelled anti-α2 integrin antibodies, including TMC-2206 or chimeric (including humanized)

antibodies derived from or based on TMC-2206, or isotype control IgG antibody at various concentrations. After a period of incubation to reach equilibrium, the wells are washed and the bound labeled antibody levels are measured as retained Eu label in each well. The Ki value can be derived from the EC50 values using the $K_d$ value obtained for the Eu-TMC-2206 antibody by the direct binding studies as described above.

In certain embodiments, the humanized anti-α2 integrin antibody is an antibody fragment. Various techniques have been developed for the production of antibody fragments. Traditionally, these fragments were derived via proteolytic digestion of intact antibodies (see, e.g., Morimoto et al., Journal of Biochemical and Biophysical Methods 24: 107-117 (1992) and Brennan et al., Science 229: 81 (1985)). However, these fragments can be produced directly by recombinant host cells, such as bacteria (see, e.g., Better et al., Science 240(4855):1041-1043 (1988); U.S. Pat. No. 6,204,023. For example, Fab'-SH fragments can be directly recovered from *E. coli* and chemically coupled to form $F(ab')_2$ fragments (Carter et al., Bio/Technology 10: 163-167 (1992)). According to another approach, $F(ab')_2$ fragments can be isolated directly from recombinant host cell culture. Other techniques for the production of antibody fragments will be apparent to the skilled practitioner.

In some embodiments, it may be desirable to generate multispecific (e.g., bispecific) humanized anti-α2 integrin antibodies having binding specificities for at least two different epitopes. Exemplary bispecific antibodies (e.g., with two different binding arms) may bind to two different epitopes of the α2β1 integrin protein. Alternately, an anti-α2 integrin arm may be combined with an arm which binds to a triggering molecule on a leukocyte such as a T-cell receptor molecule (e.g., CD2 or CD3), or Fc receptors for IgG (FcγR), such as FcγR1 (CD64), FcγRII (CD32) and FcγRIII (CD16) so as to focus cellular defense mechanisms on a cell which has α2β1 integrin bound to its surface. Bispecific antibodies can be used to localized cytotoxic agents to cells with α2β1 integrin bound to their surface. These antibodies possess a α2β1 integrin binding arm and an arm which binds the cytotoxic agent (e.g., gelonin, saporin, anti-interferon alpha, vinca alkaloid, ricin A chain, or radioisotope hapten). Bispecific antibodies can be prepared as full length antibodies or antibody fragments (e.g., $F(ab')_2$ bispecific antibodies).

According to another approach for making bispecific antibodies, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains are replaced with larger side chains (e.g., tyrosine or tryptophan). Compensatory cavities of identical or smaller size to the large side chain(s) are created on the interface of the second antibody by replacing large amino acid side chains with smaller ones (e.g., alanine or threonine). This provides a mechanism for increasing the yield of the heterodimers over other unwanted end-products such as homodimers (see, e.g., WO96/27011).

Bispecific antibodies include cross-linked or heteroconjugate antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed, for example, in U.S. Pat. No. 4,676,980 along with a number of cross-linking techniques.

Techniques for generating bispecific antibodies from antibody fragments have also been described in the literature. Bispecific antibodies can be prepared using chemical linkage. For example, Brennan et al., (Science 229:81 (1985)) describe a procedure wherein intact antibodies are proteolytically cleaved to generate $F(ab')_2$ fragments. These fragments are reduced in the presence of the dithiol complexing agent sodium arsenite to stabilize vincal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab'-SH fragments, recovered from *E. coli*, can be chemically coupled to form bispecific antibodies. For example, Shalaby et al., (J. Exp. Med. 175:217-225 (1992)) describe the production of a fully humanized bispecific antibody $F(ab')_2$ molecule. Where each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers (see, e.g., Kostgelny et al., J. Immunol. 148(5):1547-1553 (1992)). The leucine zipper peptides from the Fos and Jun proteins were linked to Fab' portions of two different antibodies by gene fusion. The antibody homodimers were reduced at the hinge region to form monomers and then re-oxidized to form antibody heterodimers. This method can also be utilized for the production of antibody heterodimers. The diabody technology (see, e.g., Hollinger et al., Proc. Natl. Acad. Sci. USA 90:6444-6448 (1993) has provided an alternative mechanism for making bispecific antibody fragments. The fragments comprise a heavy chain variable region (VH) connected to a light-chain variable region (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv or scFv) dimers also has been reported (see, e.g., Gruber et al., J. Immunol. 152:5368 (1994)). Alternatively, the bispecific antibody, may be a linear antibody, for example, produced as described in Zapata et al., Protein Eng. 8(10):1057-1062 (1995).

Antibodies with more than two valencies are contemplated. For example, trispecific antibodies can be prepared (see, e.g., Tutt et al., J. Immunol. 147:60 (1991)).

Other modifications of the humanized anti-α2 integrin antibodies are contemplated. For example, it may be desirable to modify the antibody with respect to effector function, so as to enhance or decrease the effectiveness of the antibody, for example, in treating cancer. Cysteine residue(s) may be introduced in the Fc region, thereby allowing interchain disulfide bond formation in the region. The homodimeric antibody thus generated may have improved internalization capability and/or increased complement mediated cell killing (CMC) and/or antibody-dependent cellular cytotoxicity (ADCC) (see e.g., Caron et al., J. Exp. Med. 176:1191-1195 (1992) and Shopes, B. J. Immunol. 148:2918-2922 (1992)). Homodimeric antibodies with enhanced anti-tumor activity may also be prepared using heterobifunctional cross-linkers (see, e.g., those described in Wolff et al., Cancer Research 53:2560-2565 (1993)). Alternatively, an antibody can be engineered which has dual Fc regions and may thereby have enhanced CMC and/or ADCC capabilities (see, e.g., Stevenson et al., Anti-Cancer Drug Design 3:219-230 (1989)).

Immunoconjugates comprising a humanized anti-α2 integrin antibody conjugated to a moiety, e.g., a molecule, composition, complex, or agent, for example a cytotoxic agent such as a chemotherapeutic agent, toxin (e.g., an enzymatically active toxin of bacterial, fungal, plant or animal origin, or fragments thereof), or a radioactive isotope (e.g., a radioconjugate), for the targeting of the agent to an anti-α2 integrin-expressing cell, tissue or organ. Such an immunoconjugate may be used in a method of targeting the moiety or agent to a particular site of action characterized by the presence of α2 or α2β1 integrin.

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin or the tricothecenes. A variety of radionuclides are available for the production of radioconjugated anti-alpha 2 integrin antibodies. Examples include $^{212}$Bi, $^{131}$In, $^{90}$Y or $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as gluteraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), or bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody (see, e.g., WO94/11026).

In another embodiment, the antibody may be conjugated to a receptor (such as streptavidin) for utilization in pretargeting α2 integrin-expressing cell, tissue or organ wherein the antibody-receptor conjugate is administered to the patient, followed by removal of unbound conjugate from the circulation using a clearing agent and then administration of a ligand (e.g., avidin) which is conjugated to an agent, for example a cytotoxic agent (e.g., a radio-nuclide).

The anti-α2 integrin antibodies disclosed herein may also be formulated as immunoliposomes. Liposomes containing the antibody are prepared by methods known in the art, such as described in Epstein et al., Proc. Natl. Acad. Sci. USA 82: 3688 (1985); Hwang et al., Proc. Natl. Acad. Sci. USA 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an anti-α2 integrin antibody can be conjugated to the liposomes as described in Martin et al., J. Biol. Chem. 257: 286-288 (1982) via a disulfide interchange reaction. A chemotherapeutic agent (e.g., doxorubicin) is optionally contained within the liposome (see, e.g., Gabizon et al., J. National Cancer Inst. 81(19): 1484 (1989)).

Humanized anti-α2 integrin antibodies may also be used in Antibody Directed Enzyme Prodrug Therapy (ADEPT) by conjugating the antibody to a prodrug-activating enzyme which converts a prodrug (e.g., a peptidyl chemotherapeutic agent, see, e.g., WO81/01145) to an active drug. (see, e.g., WO88/07378 and U.S. Pat. No. 4,975,278). The enzyme component of the immunoconjugate useful for ADEPT includes any enzyme capable of acting on a prodrug in such a way so as to covert it into its more active form. Enzymes that are useful include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known as abzymes, can be used to convert the prodrugs of the invention into free active drugs (see, e.g., Massey, Nature 328: 457-458 (1987)). Antibody-abzyme conjugates can be prepared as described herein, including for delivery of the abzyme to a α2 integrin-expressing cell, tissue or organ.

Enzymes may be covalently bound to the anti-α2 integrin antibodies by techniques well known in the art, including the use of the heterobifunctional crosslinking reagents discussed above. Alternatively, fusion proteins comprising at least the antigen binding region of an anti-α2 integrin antibody linked to at least a functionally active portion of an enzyme can be constructed using recombinant DNA techniques well known in the art (see, e.g., Neuberger et al., Nature 312: 604-608 (1984)).

In certain embodiments of the invention, it may be desirable to use an antibody fragment, rather than an intact antibody, for example, to increase tissue or tumor penetration. It may also be desirable to modify the antibody fragment in order to increase its serum half-life. This may be achieved by incorporation of a salvage receptor binding epitope into the antibody fragment, for example, by mutation of the appropriate region in the antibody fragment or by incorporating the epitope into a peptide tag that is then fused to the antibody fragment at either end or in the middle, for example, by DNA or peptide synthesis (see, e.g., WO96/32478).

Covalent modifications of the humanized anti-α2 integrin antibodies may be made, for example, by chemical synthesis or by enzymatic or chemical cleavage of the antibody. Other types of covalent modifications of the antibody are introduced into the molecule by reacting targeted amino acid residues of the antibody with an organic derivatizing agent that is capable of reacting with selected side chains or the N- or C-terminal residues. Cysteinyl residues, for example, most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues, for example, are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino-terminal residues, for example, are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate. Arginyl residues, for example, are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group. Tyrosyl residues, for example, are specifically modified with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay. Carboxyl side groups, for example, aspartyl or glutamyl, are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions. Glutaminyl and asparaginyl residues are frequently deamidated to the corresponding glutamyl and aspartyl residues, respectively. These residues are deamidated under neutral or basic conditions. The deamidated form of these residues falls within the scope of this invention. Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine (see, e.g., WO87/05330; Aplin and Wriston, CRC Crit. Rev. Biochem., pp. 259-306 (1981)).

Removal of any carbohydrate moieties present on the antibody may be accomplished, for example, chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact (see, e.g., Hakimuddin, et al., Arch. Biochem. Biophys. 259: 52 (1987); Edge et al., Anal. Biochem., 118: 131 (1981)). Enzymatic cleavage of carbohydrate moieties on antibodies can be achieved by the use of a variety of endo- and exo-glycosidases, (see, e.g., Thotakura et al., Meth. Enzymol. 138: 350 (1987)).

Another type of covalent modification of the antibody comprises linking the antibody to one of a variety of nonproteinaceous polymers, such as polyethylene glycol, polypropylene glycol, or polyoxyalkylenes (see, e.g., U.S. Pat. No. 4,640,835; 4,496,689; 4,301,144; 4,670,417; 4,791,192 or 4,179,337).

Isolated nucleic acid(s) encoding a humanized anti-α2 integrin antibody, as well as vectors and host cells comprising the nucleic acid, and recombinant techniques for the production of the antibody are described herein. For recombinant production of the antibody, the nucleic acid(s) encoding the antibody are isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

An anti-α2 integrin antibody may be produced recombinantly, including as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a eukaryotic signal sequence (e.g., an immunoglobulin signal sequence), the signal sequence is substituted by a prokaryotic signal sequence including, for example, pectate lysase (such as pelB), alkaline phosphatase, penicillinase, lpp, or heat-stable enterotoxin II leaders. For yeast secretion, a yeast signal sequence may be utilized, including, for example, the yeast invertase leader, a factor leader (including Saccharomyces and Kluyveromyces α-factor leaders), or acid phosphatase leader, the C. albicans glucoamylase leader, or the signal described in WO90/13646. In mammalian cell expression, mammalian signal sequences as well as viral secretory leaders, for example, the herpes simplex gD signal, are available and may be utilized. The DNA for such a precursor region (e.g., the signal sequence) is ligated in reading frame to DNA encoding an anti-α2 integrin antibody.

Both expression and cloning vectors contain a nucleic acid sequence that enables the vector to replicate in one or more selected host cells. Generally, in cloning vectors, this sequence is one that enables the vector to replicate independently of the host chromosomal DNA, and includes origins of replication or autonomously replicating sequences. Such sequences are well known for a variety of bacteria, yeast, and viruses. For example, the origin of replication from the plasmid pBR322 is suitable for most gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (e.g., the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, (e.g., the gene encoding D-alanine racemase for Bacilli).

One example of a selection scheme utilizes a drug to arrest growth of a host cell. Those cells that are successfully transformed with a heterologous gene produce a protein conferring drug resistance and thus survive the selection regimen. Examples of such dominant selection use the drugs methotrexate, neomycin, histidinol, puromycin, mycophenolic acid and hygromycin.

Another example of suitable selectable markers for mammalian cells are those that enable the identification of cells competent to take up the anti-α2 integrin antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding anti-α2 integrin antibody, wild-type DHFR protein, and another selectable marker such as aminoglycoside 3'-phosphotransferase (APH) can be selected by cell growth in medium containing a selection agent for the selectable marker, including an aminoglycosidic antibiotic, such as kanamycin, neomycin, or G418 (see e.g., U.S. Pat. No. 4,965,199).

One suitable selection gene for use in yeast is the trp1 gene present in the yeast plasmid YRp7 (Stinchcomb et al., Nature, 282: 39 (1979)). The trp1 gene provides a selection marker for a mutant strain of yeast lacking the ability to grow in tryptophan, for example, ATCC No. 44076 or PEP4-1 (see, e.g., Jones, Genetics, 85: 12 (1977)). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6μ circular plasmid pKD1 can be used for transformation of *Kluyveromyces* yeasts. Alternatively, an expression system for large-scale production of recombinant calf chymosin was reported for *K. lactis* by Van den Berg, Bio/Technology, 8:135 (1990). Stable multi-copy expression vectors for secretion of mature recombinant human serum albumin by industrial strains of *Kluyveromyces* have also been disclosed (see, e.g., Fleer et al., Bio/Technology, 9: 968-975 (1991)).

Expression and cloning vectors usually contain a promoter that is recognized by the host organism and is operably linked to the anti-α2 integrin antibody nucleic acid. Promoters suitable for use with prokaryotic hosts include the arabinose promoter (e.g., araB), phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-α2 integrin antibody.

Promoter sequences are known for eukaryotes. Most eukaryotic genes have an AT-rich region located approximately 25 to 30 bases upstream from the site where transcription is initiated. Another sequence found 70 to 80 bases upstream from the start of transcription of many genes is a CNCAAT (SEQ ID NO:115) region where N may be any nucleotide. At the 3' end of most eukaryotic genes is an AATAAA (SEQ ID NO:116) sequence that may be the signal for addition of the poly A tail to the 3' end of the coding sequence. Such sequences are suitably inserted into eukaryotic expression vectors.

Examples of suitable promoter sequences for use with yeast hosts include but are not limited to the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-α2 integrin antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus or Simian Virus 40 (SV40), from heterologous mammalian promoters, for example, the actin promoter or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446, and a modification of this system is described in U.S. Pat. No. 4,601,978 (see, also Reyes et al., Nature 297: 598-601 (1982) on expression of human β-interferon cDNA in mouse cells under the control of a thymidine kinase promoter from herpes simplex virus). Alternatively, the rous sarcoma virus long terminal repeat can be used as the promoter.

Transcription of DNA encoding an anti-α2 integrin antibody by higher eukaryotes is often increased by inserting an enhancer sequence into the vector. Many enhancer sequences are now known from mammalian genes (globin, elastase, albumin, α-fetoprotein, and insulin). Often, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers (see, also, e.g., Yaniv, Nature 297: 17-18 (1982) on enhancing elements for activation of eukaryotic promoters). The enhancer may be spliced into the vector at a position 5' or 3' to the anti-α2 integrin antibody-encoding sequence, but is preferably located at a site 5' from the promoter. Other gene regulation systems well known in the art (e.g. inducible systems, such as tetracycline inducible systems and GeneSwitch™) can be used to control the transcription of DNA encoding an anti-α2 integrin.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an anti-α2 integrin antibody. One useful transcription termination component is the bovine growth hormone polyadenylation region (see, e.g., WO94/11026 and the expression vector disclosed therein).

Suitable host cells for cloning or expressing the DNA in the vectors herein are the prokaryote, yeast, or higher eukaryote cells as described above. Suitable prokaryotes for this purpose include eubacteria, including gram-negative or gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. Suitable *E. coli* cloning hosts include *E. coli* 294 (ATCC 31,446), *E. coli* B, *E. coli* X1776 (ATCC 31,537), and *E. coli* W3110 (ATCC 27,325).

In addition to prokaryotes, eukaryotic microbes such as filamentous fungi or yeast are suitable cloning or expression hosts for anti-alpha 2 integrin antibody-encoding vectors. *Saccharomyces cerevisiae*, or common baker's yeast, is the most commonly used among lower eukaryotic host microorganisms. However, a number of other genera, species, and strains are commonly available and useful, such as *Schizosaccharomyces pombe; Kluyveromyces* hosts including *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, or *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi including *Neurospora, Penicillium, Tolypocladium*, or *Aspergillus* hosts such as *A. nidulans* or *A. niger.*

Suitable host cells for the expression of glycosylated anti-α2 integrin antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, for example, the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells, including a variety of mammalian cells, has become routine procedure. Examples of useful mammalian host cells include: a monkey kidney CV1 line transformed by SV40 (e.g., COS-7, ATCC CRL 1651); a human embryonic kidney line 293 or 293 cells subcloned for growth in suspension culture (see e.g., Graham et al., J. Gen Virol. 36: 59 (1977)); baby hamster kidney cells (e.g., BHK, ATCC CCL 10); Chinese hamster ovary (CHO) cells, including CHO cells lacking DHFR (see, e.g., DHFR Urlaub et al., Proc. Natl. Acad. Sci. USA 77: 4216 (1980)); mouse sertoli cells ((e.g., TM4, Mather, Biol. Reprod. 23: 243-251 (1980)); monkey kidney cells (e.g., CV1 ATCC CCL 70); African green monkey kidney cells (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); mouse mammary tumor (e.g., MMT 060562, ATCC CCL51); TRI cells (see, e.g., Mather et al., Annals N.Y. Acad. Sci. 383: 44-68 (1982)); MRC 5 cells; FS4 cells; or a human hepatoma line (e.g., Hep G2).

Host cells are transformed with an above-described expression or cloning vectors for anti-α2 integrin antibody production and cultured in conventional nutrient media modified as appropriate for inducing promoters, selecting transformants and/or amplifying the genes encoding the desired sequences.

The host cells used to produce an anti-α2 integrin antibody may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. No. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. Culture conditions, such as temperature, pH, and the like, are selected by those skilled in the art, including those culture conditions previously used with the host cell selected for expression.

Anti-α2 integrin antibodies can be purified from cells, including microbial or mammalian cells using, for example, protein A chromatography, ion exchange chromatography, hydrophobic interaction chromatography, gel electrophoresis, dialysis, and/or affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (see, e.g., Lindmark et al., J. Immunol. Meth. 62:1-13 (1983)). Protein G is useful for mouse isotypes and for human γ3 (see, e.g., Guss et al, EMBO J. 5:1516-1517 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ (J. T. Baker, Phillipsburg, N.J.) is useful for purification. Protein purification can include one or more of the following techniques such as fractionation on an ion-exchange column, ethanol precipitation, Reverse Phase HPLC, chromatography on silica, chromatography on heparin SEPHAROSE™, chromatography on an anion or cation exchange resin (e.g., a polyaspartic acid column), chromatofocusing, SDS-PAGE, ammonium sulfate precipitation and/or hydrophobic interaction chromatography. For example, it may be useful following any purification step(s), to subject a mixture comprising the antibody of interest and contaminants to low pH hydrophobic interaction chromatography using an elution buffer at a pH between about 2.5-4.5, preferably performed at low salt concentrations (e.g., from about 0-0.25M salt).

Formulations of an anti-α2 integrin antibody, including those for therapeutic administration, are prepared for storage by mixing the antibody having the desired degree of purity with optional physiologically acceptable carriers, diluents, excipients or stabilizers (Remington's Pharmaceutical Sciences 16th edition, Osol, A. Ed. (1980)), in the form of lyophilized formulations or aqueous solutions. Acceptable carriers, diluents, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, or other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The antibody formulation may also contain more than one active compound for the particular indication being treated, preferably those with complementary activities that do not adversely affect each other. It may be desirable to use anti-α2 integrin antibody in addition to one or more agents currently used to prevent or treat the disorder in question. In addition, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles or nanocapsules) or in macroemulsions. Such techniques are disclosed, for example, in Remington's Pharmaceutical Sciences 16th edition, Osol, A. Ed. (1980).

Formulations to be used for in vivo administration are preferably sterile. This is readily accomplished, for example, by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The anti-α2 antibodies may be used as affinity purification agents. In this process, the antibodies are immobilized on a solid phase such a Sephadex resin or filter paper, using methods well known in the art. The immobilized antibody is contacted with a sample containing the α2β1 integrin protein (or fragment thereof) to be purified, and thereafter the support is washed with a suitable solvent that will remove substantially all the material in the sample except the α2β1 integrin protein, which is bound to the immobilized antibody. Finally, the support is washed with another suitable solvent, such as glycine buffer at pH 5.0, that will release the α2β1 integrin protein from the antibody.

Anti-α2 integrin antibodies may also be useful in diagnostic assays for α2β1 integrin protein, e.g., detecting its expression in specific cells, tissues, or serum. For diagnostic applications, the antibody typically will be labeled with a detectable moiety. Numerous labels are available which can be generally grouped into the following categories of radioisotopes, fluorescent labels and enzyme-substrate labels. Radioisotopes, such as $^{35}$S, $^{14}$C, $^{125}$I, $^{3}$H, and $^{131}$I, are useful labels. The antibody can be labeled with the radioisotope, for example, using the techniques described in Current Protocols in Immunology, Volumes 1 and 2, Coligen et al., Ed. Wiley-Interscience, New York, N.Y., Pubs. (1991) and radioactivity can be measured, for example, using scintillation counting. Fluorescent labels such as rare earth chelates (europium chelates) or fluorescein and its derivatives, rhodamine and its derivatives, dansyl, Lissamine, phycoerythrin and Texas Red are also useful. The fluorescent labels can be conjugated to the antibody, for example, using the techniques disclosed in Current Protocols in Immunology, supra. Fluorescence can be quantified, for example, using a fluorimeter. Various enzyme-substrate labels are also useful (see, e.g., U.S. Pat. No. 4,275, 149 for a review). The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (e.g., using a chemiluminometer) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described, for example, in O'Sullivan et al., Methods for the Preparation of Enzyme-Antibody Conjugates for use in Enzyme Immunoassay, in Methods in Enzym. (ed J. Langone & H. Van Vunakis), Academic press, N.Y., 73: 147-166 (1981). Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase. Numerous other enzyme-substrate combinations are available to those skilled in the art (see, e.g., U.S. Pat. Nos. 4,275,149 and 4,318,980 for a general review).

Sometimes, a label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (e.g., digoxin) and one of the different types of labels mentioned above can be conjugated with an anti-hapten antibody (e.g., anti-digoxin antibody). Thus, indirect conjugation of the label with the antibody can be achieved.

An anti-α2 integrin antibody need not be labeled, and the presence thereof can be detected using a labeled antibody which binds to the anti-α2 integrin antibody. Anti-α2 integrin antibodies may be employed in any known assay method, such as competitive binding assays, direct and indirect sandwich assays, and immunoprecipitation assays (see, e.g., Zola, Monoclonal Antibodies: A Manual of Techniques, pp. 147-158 (CRC Press, Inc. 1987)). Competitive binding assays rely on the ability of a labeled standard to compete with the test sample analyte for binding with a limited amount of antibody. For example, the amount of α2β1 integrin protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound. Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex (see, e.g., U.S. Pat. No. 4,376,110). The second antibody may itself be labeled with a detectable moiety (e.g., direct sandwich assays) or may be measured using an anti-immunoglobulin antibody that is labeled with a detectable moiety (e.g., indirect sandwich assay). For example, one type of sandwich assay is an ELISA assay, in which case the detectable moiety is an enzyme.

For immunohistochemistry, a tissue sample, including a tumor sample, may be fresh or frozen or may be embedded in paraffin and fixed with a preservative such as formalin.

Anti-α2 integrin antibodies may also be used for in vivo diagnostic assays. Generally, the antibody is labeled with a radionuclide ($^{111}$In, $^{99}$TC, $^{14}$C, $^{131}$I, $^{125}$I, $^3$H, $^{32}$P or $^{35}$S) so that the tissue, for example, a tumor, can be localized using immunoscintiography.

As a matter of convenience, an anti-α2 integrin antibody can be provided in a kit, such as a packaged combination of reagents in predetermined amounts with instructions, including for performing a diagnostic assay. Where the antibody is labeled with an enzyme, the kit will include substrates and cofactors required by the enzyme (e.g., a substrate precursor which provides the detectable chromophore or fluorophore). Other additives may be included in the kit such as stabilizers, buffers (e.g., a block buffer or lysis buffer) and the like. The relative amounts of the various reagents provided in the kit may be varied widely, for example, to provide for concentrations in solution of the reagents which substantially optimize the sensitivity of the assay. The reagents may be provided as dry powders, usually lyophilized, including excipients, for example, which on dissolution will provide a reagent solution having the appropriate concentration.

An anti-α2 integrin antibody may be used to treat various α2β1 integrin associated disorders as described herein. The anti-α2 integrin antibody is administered by any suitable means, including parenteral, subcutaneous, intraperitoneal, intrapulmonary, or intranasal. If desired for local immunosuppressive treatment, intralesional administration of the antibody (including perfusing or otherwise contacting the graft with the antibody before transplantation) is done. Parenteral administration includes intramuscular, intravenous, intraarterial, intraperitoneal, or subcutaneous administration. In addition, the anti-α2 integrin antibody is suitably administered by pulse infusion, for example, with declining doses of the antibody. Preferably the dosing is given by injections, most preferably intravenous or subcutaneous injections. This may depend in part on whether the administration is brief or chronic.

For the prevention or treatment of disease, the appropriate dosage of antibody will depend on the type of disease to be treated, as defined above, the severity and course of the disease, whether the anti-α2 integrin antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease [from about 1 µg/kg to about 15 mg/kg or from about 0.05 µg/kg to about 20 mg/kg] of antibody is an initial candidate dosage for administration to the subject, whether, for example, by one or more separate administrations, or by continuous infusion. A typical daily dosage might range [from about 1 μg/kg to about 100 mg/kg] or more, depending on the factors mentioned above. For repeated administrations over several days or longer, depending on the condition, the treatment is sustained until a desired suppression of disease symptoms occurs. However, other dosage regimens may be useful. The progress of this therapy is readily monitored by those skilled in the art.

An anti-α2 integrin antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, results from pharmacological and toxicity studies and other factors known to medical practitioners. A therapeutically effective amount of the antibody to be administered is determined by consideration of such, and is the minimum amount necessary to prevent, ameliorate, or treat an α2β1 integrin-associated disorder. Such amount is preferably below the amount that is toxic to the host or renders the host significantly more susceptible to infections.

The anti-α2 integrin antibody need not be, but may be optionally formulated, co-administered or used as an adjunct therapy with one or more agents currently used to prevent or treat the disorder in question. For example, in rheumatoid arthritis, the antibody may be given in conjunction with a glucocorticosteroid, Remicaid® or any approved treatment for rheumatoid arthritis. For multiple sclerosis, the antibody may be given in conjunction with an interferonβ, Avonex, Copaxon, or other approved therapies for treatment of the signs and symptoms of multiple sclerosis. For transplants, the antibody may be administered concurrently with or separate from an immunosuppressive agent as defined above, such as cyclosporin A, to modulate the immunosuppressant effect. Alternatively, or in addition, α2β1 integrin antagonists may be administered to the mammal suffering from an α2β1 integrin-associated disorder. The effective amount of such other agents depends on the amount of anti-α2 integrin antibody present in the formulation, the type of disorder or treatment, and other factors discussed above. These are generally used in the same dosages and with administration routes as used hereinbefore or about from 1 to 99% of the heretofore employed dosages.

An article of manufacture containing materials, including an anti-α2 integrin antibody, useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is an anti-alpha 2 integrin antibody. The label on, or associated with, the container indicates that the composition is used for treating the condition of choice. The article of manufacture may further comprise a second container comprising a pharmaceutically-acceptable buffer, such as phosphate-buffered saline, Ringer's solution or dextrose solution. It may further include other materials desirable from a commercial and user standpoint, including other buffers, diluents, filters, needles, syringes, and package inserts with instructions for use.

The principles described above have been applied, for example, to the anti-α2 integrin antibody secreted by the BHA2.1 hybridoma (Hangan et al., Cancer Res., 56(13): 3142-9 (1996)). This antibody binds to human and rat α2β1 integrin, but does not bind the murine counterpart. The antibody so produced by the BHA2.1 hybridoma is referred to herein as TMC-2206 and is commercially available from Chemicon (now part of Millipore, catalog number MAB1998). Chimeric, including humanized, variants of TMC-2206 were produced and subjected to in vitro analysis. Studies were also carried out in vivo, using either the TMC-2206 antibody or a similar antibody, including one capable of recognizing murine α2β1 integrin. The following examples are offered by way of illustration and not by way of limitation. The disclosures of all citations in the specification are expressly incorporated herein by reference.

EXAMPLE 1

Antibodies with specificity for α2β1 integrin were designed and prepared. The previously unknown sequences of variable regions of a murine antibody designated TMC-2206 secreted by the hybridoma BHA2.1 were determined as described herein. The VH and VL cDNAs were cloned from mRNA from BHA2.1 hybridoma cells by RT-PCR using one set of primers corresponding to amino acids at the N-terminus of the murine variable region of the heavy (VH) or light (VL) chain, and a second set of primers corresponding to the respective heavy γ1 and κ light chain constant regions. The sequence was determined from cDNA that had been synthesized from mRNA isolated according to standard methods is described herein.

Cytoplasmic mRNA was isolated from approximately 1 million ($1\times10^6$) BHA2.1 hybridoma cells expressing TMC-2206 using standard molecular techniques for those skilled in the art. To isolate poly A mRNA, cells were lysed in 5M guanidinium thiocyanate, mixed with oligo (dT) cellulose (Ambion, TX) and incubated at room temperature with gentle agitation for 60 minutes. The oligo(dT) cellulose-bound poly (A) RNA was pelleted, washed, then applied to a wash spin column (Ambion, TX). The column was centrifuged at 3000×g for 1 minute, then the RNA eluted with 200 μL of 10 mM Tris, 1 mM EDTA (TE) buffer, pH 8.0 and precipitated with 0.1 volume of 5 M ammonium acetate ($NH_4Ac$) and 2.5 volumes of 100% ethanol at −20° C. The RNA was pelleted by centrifugation, dried and dissolved in DEPC-treated water.

cDNAs were synthesized from the isolated BHA2.1 mRNA via reverse transcription initiated with primers based on the either the N-terminus of the murine variable region of the heavy (VH) or light (VL) chain, and a second set of primers corresponding to the murine γ1 heavy or κ light chain constant regions. The sequence of the BHA2.1 antibody was unknown, thus, commercial degenerate antibody primers for the N-terminus of murine light and heavy chain variable regions were used (Light primer mix, #27-1583-01 and Heavy Primer mix, #27-1586-01, from Amersham Biosciences) as shown in Table 1. These primers are reported to encompass the heterogeneous amino acid composition at the N-terminus of the murine light and heavy chains, respectively. RT-PCR reactions (Qiagen RT kit) were set up as follows: 0.5 μg of mRNA, 10 μL of 5×RT buffer, 2 μL of 10 mM of dNTP mix, 5 μL of each 10 mM primer solution and 2 μL of enzyme mix in 50 μL of total volume. The reaction was initiated with reverse transcription at 50° C. for 30 minutes followed by a PCR activation step at 95° C. for 15 minutes and ended with a PCR program suitable for the degenerate primer mixes used to amplify the variable regions of both heavy and light chains: 94° C. for 30 seconds, 56° C. for 30 seconds and 72° C. for 1 minute for 28 cycles with a final extension run for 10 minutes at 72° C. Subsequent PCR reactions used the primer pairs listed in Table 2, which were synthesized by Retrogen (San Diego, Calif.). All primers are listed as 5' to 3'

TABLE 1

| Primer name | Nucleotide sequences (5'-3') |
| --- | --- |
| VHL-for (SEQ ID NO: 14) | CCATGGCTGTCTTGGGGCTGCTCTTCT |
| HC-rev (SEQ ID NO: 15) | GGGGCCAGTGGATAGAC |
| VLL-for (SEQ ID NO: 16) | CCATGGATTTTCAAGTGCAGATTTTCAG |
| LCκ-rev (SEQ ID NO: 17) | GTTGGTGCAGCATCAGC |

TABLE 2

| Primer name | Nucleotide sequences (5'-3') |
| --- | --- |
| Igκ-S (SEQ ID NO: 27) | TCGAGCCACCATGGAGACAGACACACTCCTGCTATGGGTACTGCTGCTCTGGG TTCCAGGTTCCACTGGAGACGCG |
| Igκ-AS (SEQ ID NO: 28) | AATTCGCGTCTCCAGTGGAACCTGGAACCCAGAGCAGCAGTACCCATAGCAGG AGTGTGTCTGTCTCCATGGTGGC |
| TMC-2206-r5' (SEQ ID NO: 22) | CCCGAATTCACAGGTGCAGTTGAAGGAGTCA |
| TMC-2206-r3' (SEQ ID NO: 23) | CGGGATCCTTAGGATCATTTACCAGGAGAGTGGGA |
| TMC-2206-k5' (SEQ ID NO: 24) | CCCGAATTCACAATTTGTTCTCACCCAGTCT |
| TMC-2206-k3' (SEQ ID NO: 25) | CGGGATCCTTATCTCTAACACTCATTCCTGTTGAA |
| TMC-2206VH-hIgG1/4Fc-SalI (SEQ ID NO: 29) | CTTGGTCGACGCTGAGGAGACGGTGACTGAGGT |
| TMC2206VL-hKc-SalI (SEQ ID NO: 32) | TCGTTTGATGTCGACCTTGGTCCCAGCACCGAACGTGAG |
| hIgG1/4Fc-SalI-F (SEQ ID NO: 30) | TCAGCGTCGACCAAGGGCCCATCSGTCTTC |
| hIgG1/4Fc-NotI-R SEQ ID NO: 31) | AAGGGAAGCGGCCGCTTATCATTTACCCYGAGACAGGGAGAGGCTCTT |
| hKc-SalI-F (SEQ ID NO: 33) | ACCAAGGTCGACATCAAACGAACTGTGGCTGCACC |
| Kappa-F (SEQ ID NO: 95) | CGAACTGTGGCTGCACCATCTGTCTT |
| Kappa-BamHI-R (SEQ ID NO: 96) | AATTCGGATCCTTACTAACACTCTCCCCTGTTGAAGCTCTT |
| hKc-NotI-R SEQ ID NO: 34) | AAGGGAAGCGGCCGCTTATCARCACTCTCCCCTGTTGAAGCTCTT |
| TMC-2206VLwt-hKc-F (SEQ ID NO: 35) | AGGGTGGAGCTGAAACGAACTGTGGCTGC |
| TMC-2206VLwt-hKc-R (SEQ ID NO: 36) | TCGTTTCAGCTCCACCCTGGTCCC |

PCR products of approximately 350 bp in length were obtained for both VH and VL. These PCR products were recovered from a 1% agarose gel, cloned into the pCR2.1-TOPO cloning vector (Invitrogen, CA) and sequenced.

The sequencing was performed on a CEQ DNA sequencer using M13 forward and reverse primers (Invitrogen, CA). Plasmid DNA was made from 1.5 mL bacterial cultures using Qiagen kits according to manufacturer's directions. Approximately 300 ng of DNA were used for each PCR sequencing reaction, typically in a volume of 10 μL. The DNA was denatured at 96° C. for 2 minutes and then mixed with sequencing primer at a final concentration of 0.3 μM. Four μL of DTCS Quick Start Master Mix (Beckman Coulter, Fullerton, Calif.) were added to the mix and sequencing proceeded for 30 cycles: 96° C. for 20 seconds, 50° C. for 20 seconds and 60° C. for 2 minutes. The sequencing reactions were precipitated with ethanol in the presence of sodium acetate (NaAc), EDTA and glycogen. The pellet was washed twice with 70% ethanol, air-dried, and resuspended in 20 μL of the Sample Loading Solution (provided in the kit). Eight individual VH and VL clones were sequenced by standard techniques, and the deduced amino acid sequences of VH (SEQ ID NO:21) and VL (SEQ ID NO:19) are shown in Tables 3 and 4, respectively. The sequences obtained from all eight clones were identical except for the first one or two amino acids. In the VL clones, Glu-Asn or Gln-Phe occurred in equal frequency. In the VH clones, Gln or Glu occurred in equal frequency. The sequences were checked against the NCBI protein BLAST database, Ye et al., Nucleic acids Res., Jul 1: 34 (Web Server Issue): W6-9). All sequences along with the query (e.g. VH or VL of TMC-2206) were aligned by CLUSTALW (Multiple Sequence Alignment) (Aiyar, Methods Mol Biol., 132:221-41 (2000)). The cloned inserts showed the best match with murine heavy (IgG1) and light (κ) chains, which was the expected isotype. The sequences of the cloned VH and VL regions suggested likely leader and flanking constant region sequences, which were used to design more exact primers to clone the entire heavy and light variable region of TMC-2206 from the hybridoma mRNA. All primers were synthesized by Retrogen (San Diego, Calif.). The primer pair, VHL-for CCATGGCTGTCTTGGGGCTGCTCTTCT (SEQ ID NO:14) and HC-rev GGGGCCAGTGGATAGAC (SEQ ID NO:15; from mouse Feγ CH1), was used to re-clone the heavy chain variable region and the primer pair, VLL-for CCATGGATTTTCAAGTGCAGATTTTCAG (SEQ ID NO:16) and LCκ-rev GTTGGTGCAGCATCAGC (SEQ ID NO:17), was used to re-clone the light chain variable region from the hybridoma mRNA using the same PCR conditions outlined above. Sequencing of the products confirmed the identity of the first two residues in the TMC-2206 VL to be L1-Q and L2-F and the identity of the first two residues in the heavy chain to be H1-Q and H2-V. The remaining nucleotide sequences were identical to those cloned using the degenerate primer mixes.

Frameworks and CDRs were identified based on the Kabat numbering system (Kabat et al., 1983) except that the CDR1 of the heavy chain was defined by the Oxford Molecular's AbM definition as spanning residues 26 to 35. The Oxford Molecular's AbM antibody modeling software (http://people.cryst.bbk.ac.uk/~ubcg07s/, Martin et al., *Proc. Natl. Acad. Sci. USA*, 86, 9268-9272 (1989); Martin et al., *Methods Enzymol.*, 203, 121-153 (1991); Pedersen et al., *Immunomethods*, 1, 126 (1992); and Rees et al., In Sternberg M. J. E. (ed.), *Protein Structure Prediction*. Oxford University Press, Oxford, 141-172. (1996)) combines the Kabat CDR and the Chothia hypervariable region numbering systems to define CDRs. For numbering consistency, insertions in both framework regions and CDRs relative to the standards are named as the residue position followed by an alphabetic sequence (for example, residues 82A, 82B, 82C are inserted between residues 82 and 83 in the heavy chain as shown in Table 3). Both the VH and VL sequences have relatively short CDR3s. There is a potential glycosylation site (Asp-Ser-Ser, NSS) within the CDR1 of the cloned light chain. This is consistent with the observation that the TMC-2206 light chain has a molecular weight of 29 kD by SDS-PAGE that can be shifted by endoglycosidase treatment to 25 kD (typical molecular weight of antibody light chains).

To confirm that the cloned sequences represented the bioactive VH and VL of the TMC-2206 antibody, the antibody purified from the hybridoma medium was subjected to

TABLE 3

| Name | FW1 | HCDR1 | FW2 | HCDR2 |
|---|---|---|---|---|
| Kabat No: | ---------1---------2----- 123456789012345678901 2345 | ----3----- 6789012345 | ----4--------- 67890123456789 | 5---------6----- 0123456789012345 |
| TMC-2206 VH (SEQ ID NO: 21) | QVQLKESGPGLVAPSQSLSITCTVS | GFSLTNYGIH | WVRQPPGKGLEWLG | VIWARGFTNYNSALMS |

| Name | FW3 | HCDR3 | FW4 |
|---|---|---|---|
| Kabat No: | ----7---------8-------------9---- 67890123456789012ABC345678901234 | ----10----- 567890ABC12 | -------11-- 34567890123 |
| TMC-2206 VH (SEQ ID NO: 21) | RLIITKDNSQSQVFLKMNSLQPDDSATYFCAR | ANDGVYYAMDY | WGQGTSVTVSS |

TABLE 4

| Name | FW1 | LCDR1 | FW2 | LCDR2 |
|---|---|---|---|---|
| Kabat No: | ---------1---------2--- 12345678901234567890123 | ------3---- 45678901234 | -----4--------- 567890123456789 | 5------ 0123456 |
| TMC-2206 VL (SEQ ID NO: 19) | QFVLTQSPAFLSASPGEKVTMTC | SANS-SVNYIH | WYQQKSGTSPKKWIY | DTSKLAS |

| Name | FW3 | LCDR3 | FW4 |
|---|---|---|---|
| Kabat No: | ---6---------7---------8-------- 78901234567890123456789012345678 | -9------- 901234567 | -10------ 8901234567 |
| TMC-2206 VL (SEQ ID NO: 19) | GVPVRFSGSGSGTSYSLTISSMETEDAATYYC | QQWTTNPLT | FGAGTRVELK |

The cloned VL region was 106 amino acids and the VH was 119 amino acids in length. As shown in Tables 3 and 4, there are three CDRs (CDR1-3) and four frameworks (FW1-4) in both the cloned heavy (VH) and light (VL) variable regions.

Edman degradation N-terminal peptide sequencing. The deduced amino acid sequence of both the VH and VL clones indicated the likely presence of an N-terminal glutamine on each, which raised the possibility of N-terminal blockage arising from cyclization of the N-terminal glutamine residue to yield pyroglutamate (pGlu). Therefore, to remove any potentially cyclized terminal glutamine, the protein was subjected to pyroglutamate aminopeptidase digestion using a heat tolerant enzyme from the thermophilic *Pyrococcus furiosus* before subjecting the heavy and light chains to N-terminal peptide sequencing. Purified pyroglutamate aminopeptidase (0.01 U) from *Pyrococcus furiosus* (Sigma, St. Louis, Mo.) was reconstituted in 50 µL Digestion Buffer (50 mM sodium phosphate, pH 7.0, 1 mM EDTA and 10 mM dithiothreitol (DTT)). A preparation of TMC-2206 was digested using a 1:100 molar ratio of pyroglutamate aminopeptidase: protein at 95° C. for 1 hour. The digested proteins were resolved using a standard 10% SDS-PAGE gel (Tris-glycine, BioRad Laboratories, Hercules, Calif.) with sodium mercaptoacetate (0.1 g in 150 mL of Running Buffer) in the upper reservoir. The gel was then blotted onto Immobilon P PVDF membrane (Millipore, Billerica, Mass.) in Transfer Buffer (10 mM CAPS, pH 10.5, 0.5 g/L DTT and 15% methanol) at 250 mAmp for 1 hour. The blot was stained using a fresh solution of 0.1% Ponceau S in 1% acetic acid for 1 minute followed by destaining in 1% acetic acid. The blot was subjected to peptide sequencing where it was found that 20 of the first 21 N-terminal amino acids of the light chain were successfully sequenced and showed exact identity with the deduced peptide sequence obtained by cloning. This confirmed the identity of the first amino acid in the cloned VL to be a Glu. The pyroglutamate aminopeptidase digested VH failed to yield any peptide sequence data.

EXAMPLE 2

Chimeric antibodies with specificity for α2β1 integrin were designed and prepared, including mouse-human chimeric antibodies. VH and VL regions of the cloned TMC-2206 as described in Example 1 were used to design and prepare chimeric heavy and light chains, respectively, using standard molecular cloning techniques (see, e.g. Molecular Biology Manual by Sambrook and Russell, 2001).

Heavy and light chains were cloned with the introduction of restriction sites as follows. The primers, TMC-2206-r5' CCCGAATTCACAGGTGCAGTTGAAGGAGTCA SEQ ID NO:22) and TMC-2206-r3' CGGGATCCTTAGGAT-CATTTACCAGGAGAG TGGGA (SEQ ID NO:23), were used to clone out the TMC-2206 heavy chain by RT-PCR from BHA2.1 hybridoma mRNA and the primers TMC-2206-k5' CCCGAATTCACAATTTGTTCTCACCCAGTCT (SEQ ID NO:24) and TMC-2206-k3' CGGGATCCT-TATCTCTAACACTCATTCCTGTTGAA (SEQ ID NO:25) were used to clone out the TMC-2206 light chain. These primers introduced EcoRI and BamHI sites at the 5' and 3' ends, respectively, to allow cloning of the cloned heavy and light chains into the pIRES2-GFP and pIRES2-Ds Red mammalian expression vectors (Clontech, catalog nos. 632306 and 632420), respectively. Both vectors were engineered to carry an Igκ leader sequence METDTLLLWVLLL-WVPGGSTGD (SEQ ID NO:26).

To isolate the mRNA, approximately 1 million hybridoma cells expressing TMC-2206 were pelleted at low speed (10 minutes at 800 rpm), washed with PBS, and lysed with 1 mL of Trizol (Invitrogen, CA). After vigorously vortexing, the cell suspension was extracted with 0.2 mL of chloroform and after centrifugation (14,000 rpm for 5 minutes at 4° C.), the supernatant was transferred to a new tube where the RNA was precipitated by mixing with 0.5 mL isopropanol followed by centrifugation (14,000 rpm for 10 minutes at 4° C.). The RNA pellet was washed with 1 mL 75% ethanol and dissolved in 50 µL DEPC-treated H$_2$O.

The RT-PCR reaction (Qiagen RT kit) was performed as described above using 0.5 µg of RNA, 10 µL of 5×RT buffer, 2 µL of 10 mM of dNTP mix, 5 µL of each 10 mM primer solution and 2 µL of enzyme mix in a total volume of 50 µL. PCR products were digested with EcoRI and BamHI restriction enzymes and the purified fragments from 1% agarose gel were then ligated into the EcoRI/BamHI sites of the pIRES2-GFP (heavy chain) and pIRES2-Ds Red (light chain) vectors. Subsequent sequencing of the variable regions confirmed that no mutations had been introduced by the RT-PCR.

pCI-neo (Promega, catalog no. E1841) was chosen as the expression vector for cloning chimeric, including humanized, antibody molecules based on or derived from TMC-2206 as described below. To reduce the possibility of introducing mutations into the constant regions through PCR, cloning cassettes were prepared for both the VH and VL. First, the DNA encoding an Igκ leader (SEQ ID NO:26) was cloned into the XhoI and EcoRI cloning sites of pCI-neo using the oligonucleotides Igκ-S (SEQ ID NO:27) and Igκ-AS (SEQ ID NO:28) listed in Table 2, which were annealed to each other and then ligated directly into XhoI-EcoRI digested pCI-neo using T4 ligase. This provided the parental vector for all subsequent cloning steps. From this, two expression cassettes were made: one for cloning in the VH regions adjacent to a human IgG1 Fc (hFc) and the second for cloning in the VL regions upstream from the constant region of the human kappa chain (hKc).

There are no EcoRI, XbaI, HindIII or SalI sites found on sequences of human IgG1 Fc (hFc) or the constant region of the kappa chain (hκc), therefore any one of these restriction sites could be introduced at the 5' end of the constant regions to facilitate cloning. SalI was chosen as the cloning site since this would minimize the number of changes in amino acids at the variable-constant junction. For the heavy chain chimera, introduction of a SalI site at the mouse VH-human Fc junction was accomplished without causing any change in amino acid sequence. First, an EcoRI-SalI VH fragment was made by PCR using the primer pairs TMC-2206-r5' (SEQ ID NO:22) and TMC2206VH-hIgG1/4Fc-SalI (SEQ ID NO:29) shown in Table 2 to introduce a SalI restriction site at the 3' end of the murine VH sequence using the cloned heavy chain in the pIRES-GFP vector as a template. The human IgG1 Fc was obtained from amplification of IMAGE clone 20688 (Invitrogen, Catalog No. 4764519) DNA using the primers shown in Table 2, hIgG1/4Fc-SalI-F (SEQ ID NO:30) and hIgG1/4Fc-NotI-R (SEQ ID NO:31). The two PCR products were digested with EcoRI/SalI and SalI/NotI, respectively, purified, and ligated with EcoRI/NotI digested pCI-neo-Igκ vector. The resulting vector was named pCI-neo-Igκ-TMCVH-hFc.

For the light chain chimera, it was not possible to design a SalI site without changing two amino acids at the VL-κC junction, E105D and L106I. This was accomplished by generating a PCR product using the primers shown in Table 2, TMC-2206-k5' (SEQ ID NO:24) and TMC2206VL-hKc-SalI (SEQ ID NO:32) to amplify the 2206VL region from the plasmid, pIRES-DsRed2-TMC-2206LC from above. The PCR product was digested with EcoRI/SalI separated on a 1% agarose gel, purified with a Gel Extraction Kit (Qiagen) and ligated with the human Igκ light chain constant region amplified from the IMAGE clone #4704496 (ATCC) using the primers hKc-SalI-F (SEQ ID NO:33) and hKc-NotI-R (SEQ ID NO:34) and the vector described above, pCL-neo-Igκ. The resulting plasmid was named pCI-neo-Igκ-TMC2206VL-hKc.

To evaluate whether the two amino acid change at the VL-κC junction would impact antibody activity, a second light chain chimera was constructed that encoded the parental amino acid sequence light chain chimera plasmid. First, the VL and the human kappa constant regions were amplified with the primer pair TMC-2206VLwt-hKc-R and TMC-2206-k5' (SEQ ID NOS: 36 and 24) and primer pair TMC-2206VLwt-hKc-F and hKc-NotI-R (SEQ ID NOS: 35 and 34) respectively, using the pIRES2-DsRed2-Igk-TMC2206LC vector from above as a template. Second, splicing by overlapping extension PCR (Horton et al., Gene 77(1): 61-8 (1989)) with the TMC-2206-k5' (SEQ ID NO:24) and hKc-NotI-R (SEQ ID NO:34) primers was performed to link the two products, and the final PCR product was digested and cloned into pCI-neo-Igκ.

To confirm that the cloned mouse-human chimeric antibody bore the same specificity as the original monoclonal TMC-2206 antibody secreted by the BHA2.1 hybridoma, the mouse-human chimeric antibody was expressed in 293F cells using transient transfection methodology using a transfection mixture was composed of equal parts DNA/OptiMEM and 293 fectin/OptiMEM (Invitrogen). Each solution was made with OptiMEM prewarmed to room temperature. The DNA/OptiMEM mixture contained 20 μg of the heavy chain (HC) expression plasmid, 20 μg of the light chain (LC) expression plasmid, and OptiMEM to a total volume of 1.3 mL. The 293 fectin OptiMEM mixture contained 53 μL of 293 fectin and OptiMEM to a total volume of 1.3 mL. The 293 fectin mixture was added to the DNA mixture, mixed and incubated for 20 minutes at room temperature. The 2.6 mL transfection mixture was added to a flask containing 40 mL 293F cell culture at $10^6$ cells/mL. The flask was incubated at 37° C., 8% $CO_2$ with shaking at 120 rpm. After 3 days, the cell suspension was centrifuged and immediately subjected to Protein A affinity chromatography to purify the antibody. The final product was concentrated, analyzed by SDS-PAGE and protein concentration determined by Lowry assays.

To confirm that the purified mouse-human chimeric antibody had the same binding activity as the parent TMC-2206 antibody, purified mouse-human chimeric antibody was tested for its ability to block α2β1-integrin mediated cell adhesion. CHO cells expressing a human α2 integrin (SEQ ID NO:8) and an endogenous hamster β1 (Symington et al., J Cell Biol. 120(2):523-35. (1993)) were detached from the culture flask by incubating in $Ca^{++}/Mg^{++}$-free PBS containing 5 mM EDTA. Cells were then centrifuged (1200 rpm for 8 minutes in a Beckman GH 38 rotor) and the pellet was resuspended in 10 mL of RPMI-1640. 30 μL of 17 mM CFSE (Molecular Probes, OR) was added to the cell suspension and the mixture was incubated at 37° C. for 15 minutes. Labeled cells were pelleted at low speed, resuspended in 10 mL of RPMI-1640 with 0.1% BSA and counted. The cell concentration was adjusted to $8\times10^5$ cells/mL and kept in the dark until used. A collagen-coated plate (rat-tail collagen Type I; BD Biosciences) was blocked with 100 μL/well of 0.1% BSA in PBS and incubated at room temperature for 30 minutes. Protein samples were serially diluted in serum-free media and 50 μL of each serially diluted antibody solution was added to the collagen plate. 50 μL/well of labeled cells were then added to the well and the plate was incubated for 1.5 hours at 37° C. After washing, cells were lysed with 0.1% Triton X-100 and the fluorescence intensity (excitation, 485 nm; emission, 535 nm) was read using a Victor2 1420 multi-label counter (Perkin-Elmer). The cloned TMC-2206 chimera was a potent inhibitor of α2β1-mediated cell adhesion to collagen Type I and showed potency equivalent to TMC-2206 with an EC50 value of 1.8 nM compared to 1.2 nM, respectively. In these experiments, use of control Ig gave no inhibition of binding while use of the murine TMC-2206 or the chimera antibody showed binding inhibition when tested over a range of $10^{-11}$ to $10^{-6}$ molar concentration.

The affinity of the mouse-human chimeric antibody for immobilized α2β1 integrin was also compared with the parent antibody TMC-2206 for its ability to compete binding of Eu-labelled TMC-2206 to α2β1-coated plates, e.g., by determining Ki values. First, the affinity of the parent antibody TMC-2206 for the immobilized α2β1-integrin was determined by equilibrium binding. Wells in a 96 well microtiter plate were coated with platelet α2β1-integrin (custom-coated with human platelet α2β1 by GTI Inc., WI) and then blocked with nonfat milk. For the binding and competition assays, fluorescently labeled TMC-2206 or isotype control IgG antibody were used. To label antibodies with Eu-N1-ITC reagent, approximately 2 mg of either TMC-2206 or the isotype control, MOPC-21 (Invitrogen) were suspended into and dialyzed against phosphate buffered saline (PBS; 1.47 mM $KH_2PO_4$, 8.1 mM $Na_2HPO_4$; pH 7.4, 138 mM NaCl and 2.67 mM KCl). After concentration in prewashed MicroSep concentrators (30-kDa cutoff; Pall Life Sciences at 9500 rpm (7000×g) in a JA-20 rotor (Beckman Instruments, Inc.) for 20 minutes at 4° C.), antibodies were adjusted to 4.0 mg/mL with PBS containing a final concentration of 100 mM $NaHCO_3$, pH 9.3. The mAb/bicarbonate mixture (0.250 mL) was gently mixed into a vial containing 0.2 mg $N^1$-(p-isothiocyanatobenzyl)-diethylenetriamine-$N^1,N^2,N^3,N^3$-tetraacetic acid chelated with $Eu^{3+}$ (Eu-N1-ITC; Perkin Elmer Life Sciences) and reacted overnight at 4° C. without stirring. Each labeled antibody mixture was applied to a separate PD-10 column (GE Biosciences, Piscataway, N.J.) pre-equilibrated with Running Buffer (50 mM Tris, pH 7.4 and 138 mM NaCl). Fractions (0.5 mL) were collected and assayed for total protein (Bradford reagent; Bio-Rad Laboratories, Hercules, Calif.) using a SpectraMax 384 absorbance plate reader and for europium after 1:10.000 dilution in DELFIA Enhancement Solution (Perkin-Elmer) by time-resolved fluorescence (TRF) using a Victor2 multi-label plate reader (Perkin Elmer). The fractions that were positive for both protein and Eu label were pooled and applied to new PD-10 columns and samples collected and assayed for total protein and for europium content by TRF calibrated against a europium standard solution (Perkin-Elmer) to calculate the fluor: protein ratio. The fluorescently labeled antibody, either Eu-TMC-2206 or Eu-isotype control IgG, was then applied to the blocked α2β1-integrin microtiter plates in a volume of 10 μL/well. After incubating the sealed plates for 1 hr at 37° C. to allow binding to reach equilibrium, 2 μL samples were transferred from each well into a fresh well containing DELFIA Enhancement Solution (100 μL/well; Perkin-Elmer) for the measurement of free (unbound) label. Enhancement Solution (100 μL/well) was added to the emptied wells for the measurement of bound label. The plate was shaken (Titer Plate Shaker speed setting of 5 for 5 minutes at room temperature) and time-resolved fluorescent (TRF) intensities were read using a Victor2 multi-label plate reader (Perkin-Elmer Wallac, Boston, Mass.). The $K_d$ value was calculated by Scatchard analysis to be 0.374 nM for TMC-2206.

Relative binding potencies to immobilized α2β1 integrin were analyzed by measuring $K_i$ values in a competition assay using 100 pM fluorescently labeled Eu-TMC-2206 in the presence of varying concentrations of unlabeled TMC-2206 antibody or the chimeric antibody as competitors, using an assay system similar to that described above. Test antibody combinations were then applied to the α2β1 integrin coated wells, tested over a concentration range of from $10^{-11}$ to $10^{-7}$ M, and following the specified time, the amount of bound Eu-TMC-2206 was determined. The inhibition curves were fitted with the "one site competition" model using Prism software (GraphPad, Inc.) to obtain $IC_{50}$ values and to calculate the $K_i$ using the equation of Cheng and Prusoff (1973) and the value for $K_d$ of 0.374 nM from above. The parental TMC-2206 antibody exhibited a $K_i$ of 0.22±0.04 nM (n=10) compared to a value of 0.27±0.07 nM (n=5) for the wild type (wt) chimera. The activity of the wt chimera was comparable to that of the chimeric form carrying the two LC mutations introduced by engineering a SalI site ($K_i$ also 0.27 nM), confirming that these mutations did not affect activity. In these experiments, BSA coated control wells tested with either control IgG or with TMC-2206 did not demonstrate any antibody binding.

EXAMPLE 3

Humanized antibodies with specificity for α2β1 integrin were designed and prepared. Residues of the cloned TMC-2206 antibody that comprise the CDR regions of the heavy and light chains were determined and humanized variants were prepared as follows. Three regions of hypervariability within the less variable framework regions are found in both the heavy and light chain variable regions. In most cases, these hypervariable regions correspond to, but may extend beyond, the CDRs. The amino acid sequences of the TMC-2206 heavy and light chain variable regions are specified above in Tables 3 and 4, respectively. The CDR and framework regions were elucidated generally in accordance with Kabat by alignment with other VH and VL regions using general homology searches using the NCBI protein BLAST database (Ye et al., Nucleic acids Res., Jul 1: 34 (Web Server Issue): W6-9)), except for HCDR1. HCDR1 was defined by the AbM definition as spanning residues 26 to 35. The Oxford Molecular's AbM antibody modeling software (Martin et al., *Proc. Natl. Acad. Sci. USA*, 86, 9268-9272 (1989); Martin et al., *Methods Enzymol.*, 203, 121-153 (1991); Pedersen et al., *Immunomethods*, 1, 126 (1992); and Rees et al., In Sternberg M. J. E. (ed.), *Protein Structure Prediction*. Oxford University Press, Oxford, 141-172. (1996)) combines Kabat and Chothia numbering systems in defining CDRs. Thus the heavy chain CDR regions were defined as follows:

| HCDR1 | aa26-aa35 |
| HCDR2 | aa50-aa65 |
| HCDR3 | aa95-aa102 |

Similarly, the light chain CDR regions were defined as follows:

| LCDR1 | aa24-aa34 |
| LCDR2 | aa50-aa56 |
| LCDR3 | aa89-aa97 |

It is desirable to retain the binding affinity of the murine antibody in the humanized counterpart antibody. It may be desirable to choose a human acceptor molecule that shares homology with the murine antibody. Preferred human acceptors are human germline frameworks because the lack of somatic mutations may lower the degree of immunogenicity, however, individual mature antibody frameworks may also be used as acceptor molecules. The V-BASE database provides a comprehensive listing of human heavy and light chain germline sequences and was used as a source of human germline sequences to compare with the VH and VL from TMC-2206; the Kabat database was also used (Johnson, G. and Wu, T. T. (2001), *Nucleic Acids Res.*, 29, 205-206).

The TMC-2206 VH aligned well with three of 51 human germline sequences in the V-BASE database, 4-59, 4-61 and 4-30.4, with no sequences showing a good fit in framework 3. The CDR H1 and H2 lengths in 4-59 were identical to those of the TMC-2206 VH, and 4-59 (SEQ ID NO:39) was selected as an acceptor framework. It carried the same canonical structure class 1 for CDR H1 and CDR H2 as the TMC-2206 CDR H1 and CDR H2. The CDR3 and FW4 regions of VH are not included in the VBASE germline sequences, because part of the CDR3 and framework 4 regions are derived from a different and noncontiguous gene that varies during the maturation of each antibody. The sequence of the antibody, CAA48104 (NCBI entry: gi/33583/emb/CAA48104) was used to provide CDR3 and FW 4 sequences for alignment, and a FW4 acceptor molecule sequence. A comparison of the TMC-2206 VH with 4-59 and the CDR3 and FW4 region of the CAA48104 antibody sequence is provided in Table 5.

TABLE 5

| Name | FW1 | HCDR1 | FW2 | HCDR2 |
|---|---|---|---|---|
| Kabat No: | ---------1---------2----- 123456789012345678901234 | ----3----- 6789012345 | ----4---------- 67890123456789 | 5---------6----- 0123456789012345 |
| TMC-2206 (SEQ ID NO: 21) | QVQLKESGPGLVAPSQSLSITCTVS | GFSLTNYGIH | WVRQPPGKGLEWLG | VIWARGFTNYNSALMS |
| 4-59 (SEQ ID NO: 39) | QVQLQESGPGLVKPSETLSLTCTVS | GGSISSYYWS | WIRQPPGKGLEWIG | YIYYSGSTNYNPSLKS |

| Name | FW3 | HCDR3 | FW4 |
|---|---|---|---|
| Kabat No: | ----7---------8------------9---- 67890123456789012ABC345678901234 | ----10------- 567890ABCDE12 | -------11-- 34567890123 |
| TMC-2206 (SEQ ID NO: 21) | RLIITKDNSQSQVFLKMNSLQPDDSATYFCAR | ANDGVYYAM--DY | WGQGTSVTVSS |
| 4-59 (SEQ ID NO: 39) | RVTISVDTSKNQFSLKLSSVTAADTAVYYCAR | HNSSSWYGRYFDY | WGQGTLVTVSS |
| CAA48104 (SEQ ID. 183) | | HNSSSWYGRYFDY | WGQGTLVTVSS |

The germline sequence, A14 (SEQ ID NO:37), was one of 38 human VL antibody sequences in the V-BASE database and was selected as an acceptor VL framework. A14 is in the VK VI family and its LCDR1 and LCDR2 fall into canonical classes 2 and 1, respectively. The TMC-2206 LCDR2 is also class 1, although the TMC-2206 LCDR1 is similar, but not identical, to a canonical class 1 structure. Germline VL sequences extend through CDR-L3, so an additional sequence for FW4 of a human VL was selected. The selected sequence represents a commonly used framework 4 gene for kappa light chains in mature human antibodies (e.g., AAB24132, NCBI entry gi/259596/gb/AAB24132). Although with the introduction of the SalI site, two amino acid changes were made in the sequence during the construction of the light chain chimera (E105D and L106I, which did not impact antibody binding, see above), the human light chain acceptor FW-4 already has an isoleucine at position 106 so this change introduced only a single conservative amino acid mutation (E105D) in the humanized variants. A comparison of the TMC-2206 VL with A14 and the FW4 region of the AAB24132 antibody sequence is provided in Table 6.

differences are positions H37, H48, H67, H71, H73, H78, and H91 for the heavy chain and L2, L4, L46, L47, L49, and L71 in the light chain variable framework regions. These residues were identified and selected as candidates for back-mutation.

TABLE 7

| VL | | | VH | | |
|---|---|---|---|---|---|
| Kabat residue# | TMC-2206 | A14 acceptor | Kabat residue# | TMC-2206 | 4-59 acceptor |
| 2 | F | *V* | 2 | V | V |
| 4 | L | *M* | 47-49 | W, L, G | W, *I*, G |
| 35-36 | W, Y | W, Y | 67 | L | *V* |
| 46-49 | K, W, I, Y | *L*, L, I*K* | 69 | I | I |
| 64 | G | G | 71 | K | *V* |
| 66 | G | G | 73 | N | *T* |
| 68-69 | G, T | G, T | 78 | V | *F* |
| 71 | Y | *F* | 93-94 | A, R | A, R |
| 98 | F | F | 103 | W | W |

TABLE 6

| Name | FW1 | LCDR1 | FW2 | LCDR2 |
|---|---|---|---|---|
| Kabat No: | ---------1---------2--- | ------3---- -----4--------- | | 5------ |
| | 123456789012345678901234 | 45678901234 567890123456789 | | 0123456 |
| TMC-2206 (SEQ ID NO: 19) | QFVLTQSPAFLSASPGEKVTMTC | SANS-SVNYIH | WYQQKSGTSPKKWIY | DTSKLAS |
| A14 (SEQ ID NO: 37) | DVVMTQSPAFLSVTPGEKVTITC | QASEGIGNYLY | WYQQKPDQAPKLLIK | YASQSIS |

| Name | FW3 | LCDR3 | FW4 |
|---|---|---|---|
| Kabat No: | ---6---------7---------8-------- | -9------- | -10------ |
| | 78901234567890123456789012345678 | 901234567 | 8901234567 |
| TMC-2206 (SEQ ID NO: 19) | GVPVRFSGSGSGTSYSLTISSMETEDAATYYC | QQWTTNPLT | FGAGTRVELK |
| A14 (SEQ ID NO: 37) | GVPSRFSGSGSGTDFTFTISSLEAEDAATYYC | QQWTTNPLT | FGQGTKVEIK |
| AAB24132 (SEQ ID NO: 184) | | QQGNTLPWT | FGQGTKVEIK |

Humanized variants of TMC-2206 were prepared using CDR sequences from TMC-2206 VH and VL sequences and the human frameworks selected as described above. To maintain proper CDR presentation, some canonical residues of acceptor frameworks (see e.g., Chothia et al, 1985, 1992; Queen et al., 1989; Foote and Winter, 1992; http://people-.cryst.bbk.ac.uk/~ubcg07s) may be exchanged for the counterpart donor murine canonical residues, a process called back-mutation. Tables 7 and 8 list residues that may affect CDR conformation and interchain packing, respectively, and show differences between the TMC-2206 donor VH and VL residues and the corresponding human acceptor framework residues (highlighted in bold italics). The L46 residue marked with an asterisk in Table 8 may play a role in both CDR canonical structure presentation and interchain packing.

As shown in Tables 7 and 8, eleven framework residues affecting CDR canonical presentation and two residues affecting interchain packing differ between TMC-2206 donor and the A14 and 4-59 human acceptor germline sequences, with residue L46 falling in both categories. Specifically, these

TABLE 8

| VL | | | VH | | |
|---|---|---|---|---|---|
| Kabat residue# | TMC-2206 | A14 acceptor | Kabat Residue# | TMC-2206 | 4-59 acceptor |
| 34 | H | Y | 35 | H | *S* |
| 36 | Y | Y | 37 | V | *I* |
| 38 | Q | Q | 39 | Q | Q |
| 44 | P | P | 45 | L | L |
| 46* | K | *L** | 47 | W | W |
| 87 | Y | Y | 91 | F | *Y* |
| 89 | Q | Q | 93 | A | A |
| 91 | W | *G* | 95 | A | *H* |
| 96 | L | L | 100c | M | *R* |
| 98 | F | F | 103 | W | W |

*Mutation also affecting CDR conformation

The 13 candidate back-mutations as identified, with 11 involving proper canonical structure presentation and 2 involving interchain packing, were included in the first humanized variant of TMC-2206. In addition an amino terminal Q was retained in the humanized VL. This position was retained with the murine identity because it is adjacent to the Phe at L2, which is an unusual amino acid for this position. These humanized light chain and heavy chain variants were termed TMC-2206VH1.0 and TMC-2206VL1.0. Additional humanized variants were prepared with fewer back mutations by changing the murine residues back to human framework residues. In this way, framework residues were identified that were sensitive to a reversion to the human residue (in terms of maintaining antibody potency). In parallel, computer modeling was performed to assist in the selection of candidate residues for changing back to the human counterpart.

The light and heavy chain chimera pCI-neo expression vectors described in Example 1 were used for expression of all the humanized variants. The version 1.0 of the humanized TMC-2206 VH (hVH1.0, SEQ ID NO:40) and version 1.0 of the humanized VL (hVL1.0, SEQ ID NO:41) incorporating the 14 back-mutations defined above were translated to a nucleotide sequence optimized for mammalian cell expression using Vector NTI software. These sequences were custom synthesized in tandem within a single plasmid construct by Retrogen (San Diego, Calif.) and cloned into the EcoRI and SalI sites of the parental TMC-2206 LC and HC expression vectors replacing the mouse VH and VL regions. Specifically, EcoRI-SalI digestion of the plasmid DNA resulted in two fragments of different sizes, the larger being hVH1.0 and the small fragment hVL1.0. These two fragments were then cloned into the EcoRI and SalI sites of the parental pCI-TMC-2206 chimeric LC and HC expression vectors, replacing the mouse VH and VL regions, respectively, following EcoRI and SalI digestion and gel purification of the large fragment from pCI-neolgk-TMC2206VG-hFc and pCI-neolgK-TMC-2206VLhκc, respectively. This strategy was used for preparation of subsequent variants. The resultant plasmids contained Igκ leader, optimal Kozak translation initiation sequence, variable region and human constant region.

The variant with version 1.0 of the humanized TMC-2206 VH (SEQ ID NO:40) and version 1.0 of the humanized VL (SEQ ID NO:41) as described above was tested for activity in the α2β1-integrin mediated cell adhesion assay and in the competition assay for binding to immobilized α2β1 integrin along with the chimera and the original TMC-2206 antibody as described in Example 2. The $K_i$ value for humanized prototype was 0.32 nM which was comparable to the measured $K_i$ of the parent antibody TMC-2206 (0.21 nM) as well as the chimera (0.27 nM), indicating that this first humanized version retained binding affinity. Similarly, the first humanized prototype showed comparable inhibitory activity to the TMC-2206 parent antibody in blocking α2β1-mediated cell adhesion to collagen (e.g., $EC_{50}$ of 1.5 nM for both).

Using the data generated by the version 1.0 variant, a series of mutations back to the human VH or VL framework residues were made using PCR methodology and minimum numbers of back-mutations (murine residues) were determined to avoid compromising the specificity and affinity of the original TMC-2206 mAb. Desirable humanized variants include those that retain the biological activity of the parent murine antibody and also contain fewer murine residues to decrease potential immunogenicity.

The individual primer sequences were synthesized by Sigma-Genosys and their sequences are listed in Table 9. The primer pairs and templates used for variants generated are shown in Tables 10 and 11. PCR reactions were carried out using the following conditions: Primer 1 and 2 (0.6 µM final concentration), dNTP (1 mM final concentration), DNA template (1 to 10 ng), and 1 unit of Pfx DNA polymerase (Invitrogen, CA) typically in a final volume of 50 µL. A PCR program consisted of initial denaturation at 95° C. for 2 minutes, followed by 30 cycles with each cycle being 95° C. for 30 seconds, 56° C. for 45 seconds and 68° C. for one and a half minutes. The final step was 68° C. for 10 minutes.

TABLE 9

| Primer name | Nucleotide sequences (5'-3') |
|---|---|
| hVH3.0-F (SEQ ID NO: 42) | AGCGTGGACACCAGCAAGAACCAGTTCAGCCTGAAGCTGAGCAGCGTG |
| hVH3.0-R (SEQ ID NO: 43) | GTTCTTGCTGGTGTCCACGCTGATGGTCACGCGGGACATGAGAGCGCTGTT |
| hVH4.0-F (SEQ ID NO: 44) | CCTCCAGGCAAGGGCCTGGAGTGGATCGGCGTGATATGGGCTCGCGGC |
| hVH4.0-R (SEQ ID NO: 45) | CTCCAGGCCCTTGCCTGGAGGCTGGCGTATCCAGTGGATGCCATAGTTGGT |
| hVL3.0-F (SEQ ID NO: 46) | CCCAAGCTCCTGATCTATGACACTTCCAAGCTG |
| hVL3.0-R (SEQ ID NO: 47) | AGTGTCATAGATCAGGAGCTTGGGGGCCTGGTCGGGCTTCTG |
| hVL4.0-F (SEQ ID NO: 48) | GACGCGAATTCAGACGTGGTGATGACCCAGTCTCCAGCATTCCTG |
| hVH2.0-F (SEQ ID NO: 49) | GTGACCATCAGCAAGGACAACAGC |
| hVH2.0-R (SEQ ID NO: 50) | GCTGTTGTCCTTGCTGATGGTCACGCGGGACATGAGAGCGCTGTT |
| hVH5.0-F (SEQ ID NO: 51) | ATCGGCGTGATATGGGCTCGCGGCTTC |
| hVH5.0-R (SEQ ID NO: 52) | GCCGCGAGCCCATATCACGCCGATCCACTCCAGGCCCTTGCCTGG |

TABLE 9-continued

| Primer name | Nucleotide sequences (5'-3') |
|---|---|
| hVH6.0-F (SEQ ID NO: 53) | ATATGGGCTCGCGGCTTCACAAAC |
| hVH6.0-R (SEQ ID NO: 54) | GTTTGTGAAGCCGCGAGCCCATAT |
| hVH7.0-F (SEQ ID NO: 55) | GCCGCGGACACCGCCGTGTACTACTGCGCCAGAGCCAACGACGGG |
| hVH7.0-R (SEQ ID NO: 56) | GTAGTACACGGCGGTGTCCGCGGCGGT |
| hVH8.0-F (SEQ ID NO: 57) | ATATCCAACTATGGCATCCACTGGGTT |
| hVH8.0-R (SEQ ID NO: 58) | CCAGTGGATGCCATAGTTGGATATGCTAAATCCAGAGACGGTACAGGT |
| VH12.0-(K71V)-F (SEQ ID NO: 97) | GCCTGACCATCAGCGTGGACAACAGCAAGAACCAGGTGAG |
| VH12.0-(K71V)-R (SEQ ID NO: 98) | CTCACCTGGTTCTTGCTGTTGTCCACGCTGATGGTCAGGC |
| VH13.0-(N73T)-F (SEQ ID NO: 99) | CTGACCATCAGCAAGGACACCAGCAAGAACCAGGTGAGCC |
| VH13.0-(N73T)-R (SEQ ID NO: 100) | GGCTCACCTGGTTCTTGCTGGTGTCCTTGCTGATGGTCAG |
| VH14.0-(V78F)-F (SEQ ID NO: 101) | GCAAGGACAACAGCAAGAACCAGTTTAGCCTGAAGCTGAGC |
| VH14.0-(V78F)-R (SEQ ID NO: 102) | GCTCAGCTTCAGGCTAAACTGGTTCTTGCTGTTGTCCTTGC |
| hVL2.0-R (SEQ ID NO: 59) | CAGCTTGGAAGTGTCATAGATCAATTTCTTGGGGGCCTGGTCGGG |
| hVL5.0-F (SEQ ID NO: 60) | GACGCGAATTCAGAC TTCGTGCTGACCCAGTCTCCAGCATTCCTG |
| hVL6.0-F (SEQ ID NO: 61) | GACGCGAATTCACAG TTCGTGATGACCCAGTCTCCAGCATTCCTG |
| hVL7.0-F (SEQ ID NO: 62) | GACGCGAATTCAGACTTCGTGATGACCCAGTCTCCAGCATTCCTG |
| hVL8.0-F (SEQ ID NO: 63) | TTCACCTTCACCATCAGCAGCCTGGAG |
| hVL8.0-R (SEQ ID NO: 64) | CTCCAGGCTGCTGATGGTGAAGGTGAAGTCGGTGCCGCTGCCGCTGCC |
| VH12.0-(K71V)-F (SEQ ID NO: 97) | GCCTGACCATCAGCGTGGACAACAGCAAGAACCAGGTGAG |
| VH12.0-(K71V)-R (SEQ ID NO: 98) | CTCACCTGGTTCTTGCTGTTGTCCACGCTGATGGTCAGGC |
| hLCQ3-F (SEQ ID NO: 65) | CCAATCAAGCGTGAACTACATTCACTGG |
| hLCQ3-R (SEQ ID NO: 66) | CCAGTGAATGTAGTTCACGCTTGATTGGGCGCTGCAGGTGATGGTCAC |
| Igκ-For (SEQ ID NO: 67) | ACTCCTGCTATGGGTACTGCTGC |
| hIgG1Fc-CH1-R (SEQ ID NO: 68) | GAAGTAGTCCTTGACCAGGCAG |
| CI-neo-msc3' (SEQ ID NO: 69) | TTTCACTGCATTCTAGTTGTGG |

TABLE 10

| VH variants | PCR primers for Fragment 1 | PCR primers for Fragment-2 | PCR primers for complete VH |
|---|---|---|---|
| 2.0 | Igk-For & hVH2.0-R | hVH2.0-F & hIgG1 Fc-CH1-R | Igk-For & hIgG1 Fc-CH1-R |
| 3.0 | Igk-For & hVH3.0-R | hVH3.0-F & hIgG1 Fc-CH1-R | Igk-For & hIgG1 Fc-CH1-R |
| 4.0 | Igk-For & hVH4.0-R | hVH4.0-F & hIgG1 Fc-CH1-R | Igk-For & hIgG1 Fc-CH1-R |
| 5.0 | Igk-For & hVH5.0-R | HVH5.0-F & hIgG1 Fc-CH1-R | Igk-For & hIgG1 Fc-CH1-R |
| 6.0 | Igk-For & hVH6.0-R | hVH6.0-F & hIgG1 Fc-CH1-R | Igk-For & hIgG1 Fc-CH1-R |
| 7.0 | Igk-For & hVH7.0-R | hVH7.0-F & hIgG1 Fc-CH1-R | Igk-For & hIgG1 Fc-CH1-R |
| 8.0 | Igk-For & hVH8.0-R | hVH8.0-F & hIgG1 Fc-CH1-R | Igk-For & hIgG1 Fc-CH1-R |
| 9.0 | Igk-For & hVH7.0-R | hVH7.0-F & hIgG1 Fc-CH1-R | Igk-For & hIgG1 Fc-CH1-R |
| 10.0 | Igk-For & hVH7.0-R | hVH7.0-F & hIgG1 Fc-CH1-R | Igk-For & hIgG1 Fc-CH1-R |
| 11.0 | Igk-For & hVH2.0-R | hVH2.0-F & hIgG1 Fc-CH1-R | Igk-For & hIgG1 Fc-CH1-R |
| 12.0 | Igk-For & VH12.0-R | VH12.0-F & hIgG1 Fc-CH1-R | Igκ-For & hIgG1 Fc-CH1-R |
| 13.0 | Igk-For & VH13.0-R | VH13.0-F & hIgG1 Fc-CH1-R | Igκ-For & hIgG1 Fc-CH1-R |
| 14.0 | Igk-For & VH14.0-R | VH14.0-F & hIgG1 Fc-CH1-R | Igκ-For & hIgG1 Fc-CH1-R |

TABLE 11

| VL variants | PCR primers for Fragment 1 | PCR primers for Fragment-2 | PCR primers for complete VL |
|---|---|---|---|
| 2.0 | Igk-For & hVL2.0-R | hVL2.0-F & Cl-neo-msc3' | Igk-For & Cl-neo-msc3' |
| 3.0 | Igk-For & hVL3.0-R | hVL3.0-F & Cl-neo-msc3' | Igk-For &' Cl-neo-msc3' |
| 4.0 | N/A | N/A | hVL4.0-F & Cl-neo-msc3' |
| 5.0 | N/A | N/A | hVL5.0-F & Cl-neo-msc3' |
| 6.0 | N/A | N/A | hVL6.0-F & Cl-neo-msc3' |
| 7.0 | N/A | N/A | hVL7.0-F & Cl-neo-msc3' |
| 8.0 | Igk-For & hVL8.0-R | hVL8.0-F & Cl-neo-msc3' | Igk-For & Cl-neo-msc3' |
| 9.0 | Igk-For & hVL2.0-R | hVL2.0-F & Cl-neo-msc3' | Igk-For & Cl-neo-msc3' |
| 10.0 | Igk-For & hVL8.0-R | hVL8.0-F & Cl-neo-msc3' | Igk-For & Cl-neo-msc3' |
| 11.0 | Igk-For & hVL8.0-R | hVL8.0-F & Cl-neo-msc3' | Igk-For & Cl-neo-msc3' |
| 12.0 | Igk-For & VL12.0-R | VL12.0-F & Cl-neo-msc3' | Igκ-For & Cl-neo-msc3' |

Table 12 lists VH variants and Table 13 lists VL variants and compares the chosen human acceptor frameworks with the initial (1.0) VH and VL variants. VH variants as listed in Table 12 include: hVH1.0 (SEQ ID NO:21); hVH2.0 (SEQ ID NO:70); hVH3.0 (SEQ ID NO:71); hVH4.0 (SEQ ID NO:72); hVH5.0 (SEQ ID NO:73); hVH6.0 (SEQ ID NO:74); hVH7.0 (SEQ ID NO:75); hVH8.0 (SEQ ID NO:76); hVH9.0 (SEQ ID NO:77); hVH10.0 (SEQ ID NO:78); hVH11.0 (SEQ ID NO:79); hVH12.0 (SEQ ID NO:109); hVH13.0 (SEQ ID NO:110); hVH14.0 (SEQ ID NO:111). VL variants as listed in Table 13 include: hVL1.0 (SEQ ID NO:41); hVL2.0 (SEQ ID NO:80); hVL3.0 (SEQ ID NO:81); hVL4.0 (SEQ ID NO:82); hVL5.0 (SEQ ID NO:83); hVL6.0 (SEQ ID NO:84); hVL7.0 (SEQ ID NO:85); hVL8.0 (SEQ ID NO:86); hVL9.0 (SEQ ID NO:87); hVL10.0 (SEQ ID NO:88); hVL11.0 (SEQ ID NO:89); hVL12.0 (SEQ ID NO:108). The retained murine residues are indicated in bold type. Each additional variant constructed (see below) is also shown. Each variant shown in Table 12 below VH1.0 has the same sequence as VH1.0 (indicated by a dash [-]) unless a specific amino acid substitution, changing the retained murine residue to the human framework counterpart, is shown. Similarly, each VL variant shown in Table 13 has the same sequence as the VL1.0 variant except for the specific amino acid substitutions indicated.

TABLE 12

| Name | FW1 | CDR1 | FW2 | CDR2 |
|---|---|---|---|---|
| Kabat | ---------1---------2----- | ----3----- | ----4--------- | 5---------6----- |
| TMC-2206 VH | QVQLKESGPGLVAPSQSLSITCTVS | GFSLTNYGIH | WVRQPPGKGLEWLG | VIWARGFTNYNSALMS |
| 4-59 VH | QVQLQESGPGLVKPSETLSLTCTVS | GGSISSYYWS | WIRQPPGKGLEWIG | YIYYSGSTNYNPSLKS |
| hVH1.0 | QVQLQESGPGLVKPSETLSLTCTVS | GFSLTNYGIH | WVRQPPGKGLEWLG | VIWARGFTNYNSALMS |
| hVH2.0 | ------------------------- | ---------- | -------------- | ---------------- |
| hVH3.0 | ------------------------- | ---------- | -------------- | ---------------- |
| hVH4.0 | ------------------------- | ---------- | -I----------I- | ---------------- |
| hVH5.0 | ------------------------- | ---------- | ------------I- | ---------------- |
| hVH6.0 | ------------------------- | ---------- | ------------I- | ---------------- |
| hVH7.0 | ------------------------- | ---------- | -------------- | ---------------- |
| hVH8.0 | ------------------------- | ----IS---- | -------------- | ---------------- |
| hVH9.0 | ------------------------- | ---------- | -------------- | ---------------- |
| hVH10.0 | ------------------------- | ---------- | -------------- | ---------------- |
| hVH11.0 | ------------------------- | ---------- | -------------- | ---------------- |

TABLE 12-continued

| Name | | | |
|------|---|---|---|
| hVH12.0 | ------------------------- | ---------- | -I------------ | ---------------- |
| hVH13.0 | ------------------------- | ---------- | -------------I- | ---------------- |
| hVH14.0 | ------------------------- | ---------- | -I------------ | ---------------- |

| Name | FW3 | CDR3 | FW4 |
|------|-----|------|-----|
| Kabat | ----7---------8--ABC-------9---- | -----10----- | -------11-- |
| TMC-2206 VH | RLIITKDNSQSQVFLKMNSLQPDDSATYFCAR | ANDGVYYAM DY | WGQGTSVTVSS |
| 4-59 VH | RVTISVDTSKNQFSLKLSSVTAADTAVYYCAR | HNSSSWYGRYFDY | WGQGTLVTVSS |
| hVH1.0 | RLTISKDNSKNQVSLKLSSVTAADTAVYFCAR | ANDGVYYAM DY | WGQGTLVTVSS |
| hVH2.0 | -V------------------------ | ------------ | ----------- |
| hVH3.0 | -V---V-T----F------------------ | ------------ | ----------- |
| hVH4.0 | ------------------------------- | ------------ | ----------- |
| hVH5.0 | ------------------------------- | ------------ | ----------- |
| hVH6.0 | -V----------------------------- | ------------ | ----------- |
| hVH7.0 | --------------------------Y--- | ------------ | ----------- |
| hVH8.0 | ------------------------------- | ------------ | ----------- |
| hVH9.0 | -----V------------------------- | ------------ | ----------- |
| hVH10.0 | -------T---------------------- | ------------ | ----------- |
| hVH11.0 | ------------F------------------ | ------------ | ----------- |
| hVH12.0 | --------------------------Y--- | ------------ | ----------- |
| hVH13.0 | -V------------------------Y--- | ------------ | ----------- |
| hVH14.0 | -V------------------------Y--- | ------------ | ----------- |

TABLE 13

| Name | FW1 | CDR1 | FW2 | CDR2 |
|------|-----|------|-----|------|
| Kabat | ---------1----------2--- | ------3---- | -----4--------- | 5------ |
| TMC-2206 VL | QFVLTQSPAFLSASPGEKVTMTC | SANSS VNYIH | WYQQKSGTSPKKWIY | DTSKLAS |
| A14 VL | DVVMTQSPAFLSVTPGEKVTITC | QASEGIGNYLY | WYQQKPDQAPKLLIK | YASQSIS |
| hVL1.0 | QFVLTQSPAFLSVTPGEKVTITC | SANSS VNYIH | WYQQKPDQAPKKWIY | DTSKLAS |
| hVL2.0 | ----------------------- | ----------- | -------------L-- | ------- |
| hVL3.0 | ----------------------- | ----------- | ------------LL-- | ------- |
| hVL4.0 | DV-M------------------- | ----------- | ---------------- | ------- |
| hVL5.0 | D---------------------- | ----------- | ---------------- | ------- |
| hVL6.0 | ---M------------------- | ----------- | ---------------- | ------- |
| hVL7.0 | D--M------------------- | ----------- | ---------------- | ------- |
| hVL8.0 | ----------------------- | ----------- | ---------------- | ------- |
| hVL9.0 | ----------------------- | ----------- | --------------K | ------- |
| hVL10.0 | D--M------------------- | ----------- | -------------L-- | ------- |
| hVL11.0 | D--M------------------- | ----------- | ---------------- | ------- |
| hVL12.0 | D--M------------------- | ----------- | -------------L-- | ------- |

TABLE 13-continued

| Name | FW3 | CDR3 | FW4 |
|---|---|---|---|
| Kabat | ---6---------7---------8-------- | -9------- | --10------ |
| TMC-2206 VL | GVPVRFSGSGSGTSYSLTISSMETEDAATYYC | QQWTTNPLT | FGAGTRVELK |
| A14 VL | GVPSRFSGSGSGTDFTFTISSLEAEDAATYYC | QQGNKHPLT | FGQGTKVEIK |
| Hvl1.0 | GVPSRFSGSGSGTDYTFTISSLEAEDAATYYC | QQWTTNPLT | FGQGTKVEIK |
| hVL2.0 | ------------------------------- | --------- | ---------- |
| hVL3.0 | ------------------------------- | --------- | ---------- |
| hVL4.0 | ------------------------------- | --------- | ---------- |
| hVL5.0 | ------------------------------- | --------- | ---------- |
| hVL6.0 | ------------------------------- | --------- | ---------- |
| hVL7.0 | ------------------------------- | --------- | ---------- |
| hVL8.0 | --------------F---------------- | --------- | ---------- |
| hVL9.0 | ------------------------------- | --------- | ---------- |
| hVL10.0 | ------------------------------- | --------- | ---------- |
| hVL11.0 | --------------F---------------- | --------- | ---------- |
| hVL12.0 | --------------F---------------- | --------- | ---------- |

Amino acid sequence alignment of TMC-2206 with germline sequences showed a clustering of framework residues that had been back-mutated to the murine equivalent in the initial humanized TMC-2206 variant (TMC-2356)]. As shown by the alignment, there were two clusters that fell within FW2 and FW3 in the heavy chain, and similarly there were two clusters, one located in FW1 and one in FW2, in the light chain. Two hVH and hVL variants containing back mutations to human residues in the sites of interest were the 3.0 and 4.0 variants, designed to carry clusters of mutations to help define the regions where the residues of interest might lie (Tables 12 and 13). In addition to the differences in residues highlighted in Tables 7 and 8 for the VL regions, the L1 position was changed to the human Asp in VL4.0, since this is a common residue for human κ light chains. The hVH3.0 and hVH4.0 heavy chains were co-transfected with hVL3.0 and hVL4.0 light chains in various VH/VL combinations and the resultant antibodies were compared with the hVH1.0/hVL1.0 antibody described above for ligand affinity by head-to-head comparisons with the unlabelled TMC-2206 monoclonal antibody. In Table 14, the residues in version 1.0 of humanized VH or VL that were reverted back to the human residues are indicated in bold italics. The numbers in parenthesis in Table 14 represent the fold shift in potency compared to the hVH1.0, hVL1.0 variant.

TABLE 14

| | VH | | |
|---|---|---|---|
| VL | hVH1.0 $K_i$ values [nM] | hVH3.0 (H67, H71, H73, H78) $K_i$ values [nM] | hVH4.0 (H37, H48) $K_i$ values [nM] |
| hVL1.0 | 0.33 | 12.0 (36x) | 0.44 (1.3x) |
| HVL3.0 (L46, L47) | 0.64 (1.9x) | 202 (631x) | 1.34 (4.2x) |

TABLE 14-continued

| | VH | | |
|---|---|---|---|
| VL | hVH1.0 $K_i$ values [nM] | hVH3.0 (H67, H71, H73, H78) $K_i$ values [nM] | hVH4.0 (H37, H48) $K_i$ values [nM] |
| hVL4.0 (L1, L2, L4) | 1.40 (4.2x) | 118 (358x) | 2.60 (7.9x) |

From the $K_i$ values it was evident that the changes in the VH 3.0 variant (human residues inserted at H67, H71, H73 and H78, designated the FW-3 cluster) induced a large decrease in potency in the hVH3.0 containing antibodies; similarly, a decrease was also observed for the hVL4.0 variants (human residues inserted at L1, L2 and L4, designated the FW-1 cluster). Except for the hVH1.0/hVL3.0 and hVH4.0/hVL1.0 combination antibodies, which showed a 1.9 and 1.3-fold shift in potency when compared to the hVH1.0/hVL1.0 antibody, respectively, all remaining combinations showed a greater than 4-fold decrease in potency (Table 14). These data indicated that the H37 (V to I) and H48 (L to I) back mutations, both of which are conservative amino acid changes, were well tolerated. The L46 (K to L) and L47 (W to L) changes of the murine residues back to human residues were reasonably well tolerated in combination with hVH1.0 but had a marked synergistic adverse effect on antibody affinity when in combination with the hVH3.0 variant.

Examination of the differences in residues that existed between the human and murine VH and VL frameworks indicated that some were conservative changes. Additionally, three-dimensional computer modeling of the murine TMC-2206 VH and VL, the human acceptor molecules, and the hVH 1.0 and hVL 1.0 structures was performed. To guide in the computer modeling, a BLAST search was done to identify database structures with close fits to the TMC-2206 VL and VH. The structure ISY6.pdb (2.0 Å resolution) was chosen for the TMC-2206 VL and the structure IGIG.pdb (2.3 Å resolution) was chosen for the TMC-2206 VH. For the human light chain acceptor molecule A14, the structure ICE1.pdb was chosen (1.9 Å resolution) while for the human VH heavy chain acceptor molecule, 4-59, IDN0 (2.3 Å resolution) was chosen.

Modeling predicted that the murine residues retained in the humanized VL 1.0 were likely to contact antigen, except for two (L1 and L4). The models also indicated that the retained human germline framework residues did not contact the CDRs whereas the retained murine framework residues were generally clustered around the CDRs.

In the heavy chain variable regions, three areas of difference were identified between the modeled murine and human VH regions. The first area was residues H27-H33 which were predicted as likely to contact antigen and CDR H1. These residues can also affect the VL/VH interface angle and have additional indirect effects on antigen binding. The second area was the first loop of CDR H2 which may require FW residue H71. The third area was the CDR H3.

For the light chain regions, three areas of difference were also noted between the modeled murine and human VL structures. The first structure was CDR1 which was one residue longer in the murine TMC-2206 VL. The murine Y at L71 (F in A14) was useful to accommodate this difference. The second area was the L40 to L43 murine loop which was pushed out further into solvent compared to the human which indicated that human L40-43 might be problematic, although activity of the first humanized prototype demonstrated that these back mutations were tolerated in hVL1.0. The third area was human framework residues L55 to L59 which were displaced relative to murine structure. Framework residue L73 (L in murine, F in human) was predicted to be responsible for this difference, although back mutation was tolerated in hVL1.0.

Using the in silico analysis, results were predicted for the specific heavy chain residues of interest and are summarized in Table 15 below. Similar results for the light chain residues of interest are listed in Table 16.

TABLE 15

| Residue | Murine | Human | Position | Type of change |
|---|---|---|---|---|
| H37 | V | I | Possibly in the VH/VL interface | Conservative |
| H48 | L | I | Interior, away from the binding site, near H67 | Conservative |
| H67 | L | V | Interior, away from the binding site, near H48 | Conservative |
| H71 | K | V | Behind CDR H2 residues H53-55 | Large |
| H73 | N | T | Behind CDR H2, solvated, near H71 | Moderate |
| H78 | V | F | Contacts CDR H1 residue H34, buried | Large |
| H91 | F | Y | In the VH/VL interface | Conservative |

TABLE 16

| Residue | Murine | Human | Position | Type of change |
|---|---|---|---|---|
| L1 | Q | D | Behind CDR L3, solvated | Conservative |
| L2 | F | V | Extensive contacts with CDR L3, partially solvated | Large |
| L4 | L | M | Behind CDR L3, partially solvated | Conservative |
| L46 | K | L | In the VH/VL interface | Large |
| L47 | W | L | VL interior behind CDR L2 | Large |

TABLE 16-continued

| Residue | Murine | Human | Position | Type of change |
|---|---|---|---|---|
| L49 | Y | K | Possible direct antigen contacts | Large |
| L71 | Y | F | Behind CDR L1 | Conservative |

Using the in silico analysis, positions were accessed and ranked in order to reflect the likelihood that a human substitution would cause an effect on antibody performance: H48, H67<H37, H91<H73<H78, H71. In this ranking, a human back mutation at position H48 was predicted most likely to be the most well tolerated, while a back mutation at positions H78 or H71 was predicted to be the least tolerated. Similarly, the following order was predicted for positions of interest within the light chain region: L1<L4<L71<L2<L47<L46<L49. Generally, these rankings were in agreement with $K_i$ values obtained with hVH3.0, hVH4.0, and hVL4.0 variants. However, a difference between the substitution affects predicted by the computer modeling and the observed effects seen with the constructed variants was observed in the activity for the hVL3.0 variant. For example, the antibody variant comprising a combination between the VH1.0/VL3.0 gave fair activity, although the computer data above predicted that the hVL3.0 variant would have greatly decreased activity. The impact of the retained murine framework residues were further assessed by constructing additional humanized variants, including eight VH and six VL variants, each carrying a single mutation from the retained murine to its human counterpart. The relative contributions of the changes to activity were measured. Table 12 lists the VH variants and Table 13 lists the VL variants.

$K_i$ values that were obtained for these variants indicated that the mouse residues at H71, H78, L2 and L46 were preferably retained to maximize activity, while H37, H48, H67, H91, L1, L4 and L71 could be changed to their human counterparts without resulting in a significant loss in activity. Using computer modeling, changing the mouse residue, L47 (Tryptophan, a rare residue for this position in human antibodies) and H73 was predicted to impact antigen binding. However, the change to the human Val-L47 did not significantly affect antigen binding, and the change to Thr-H73 caused only a minor shift (1.6-fold decrease) as measured by $K_i$. L49 (Tyrosine) was predicted to bind antigen by in silico modeling and the change to a human lysine was predicted to cause a large change in potency. However, the change to the human lysine for this position caused only a 3.3-fold decrease in potency as measured by $K_i$.

A significant change was observed in the VH for the change at H78 from the murine valine to human phenylalanine, which caused a 70-fold decrease in potency for the hVH11.0, hVL1.0 variant compared to the hVH1.0, hVL1.0 variant as measured by $K_i$. Modeling indicated this residue plays a role in the canonical structure of HCDR1. These results suggest that HCDR1 plays an important role in antigen binding. To maximize activity, H71 also is retained. Changing this residue from Lys to a Val resulted in a 6.4-fold decrease observed with the hVH9.0, hVL1.0 antibody variant. Additionally, among canonical residues in the light chain, the phenylalanine at L2 was sensitive to change as evidenced by the marked loss in binding affinity observed with the hVL4.0 variant compared to the hVL5.0, hVL6.0 and hVL7.0 variants. Computer modeling indicated that this Phe-L2 may make extensive contact with LCDR3. Database searches of human and murine antibodies additionally indicated that this Phe at the L2 position is rare, suggesting that it may represent a somatic mutation that has an impact on antigen binding.

Those residues selected after analysis as described above to be tolerant of back mutation were combined in the hVH variants 12.0 through 14.0 and the VL variants VL10.0 through 12 and the activity of these variants were compared against the original TMC-2206 monoclonal antibody and the mouse-human chimeric TMC-2206 antibody. The results indicated that the number of murine residues in the hVL could be reduced to three (e.g., L2 [Phe], L46 [Lys] and L49 [Tyr]) without causing any loss in activity of the variants. Similarly the number of murine residues in the hVH could be reduced from seven to three (e.g., H71 [Lys], H73 [Asn] and H78 [Val]) without causing statistically significant changes in affinity and potency. These results are summarized in Table 17.

TABLE 17

| VH | VL | Changes back to human | #murine residues | $K_i$(nM) Mean ± SD | $EC_{50}$ (nM) Mean ± SD |
|---|---|---|---|---|---|
| TMC-2206 mAb | N/A | | | 0.22 ± 0.04 | 1.18 ± 0.35 |
| Chimera | N/A | | | 0.26 ± 0.07 | 1.66 ± 0.64 |
| 1.0 | 1.0 | N/A | 14 | 0.27 ± 0.06 | 2.70 ± 1.66 |
| 1.0 | 1.0Q | N/A | 14 | 0.35 ± 0.03 | 3.00 ± 1.20 |
| 12.0 | 10.0 | H37, H91, L1, L4, L47 | 9 | 0.29 ± 0.05 | 2.20 ± 0.58 |
| 12.0 | 10.0Q | H37, H91, L1, L4, L47 | 9 | 0.31 ± 0.05 | 2.36 ± 1.06 |
| 14.0 | 10.0 | H37, H67, H91, L1, L4, L47 | 8 | 0.32 ± 0.07 | 2.90 ± 2.71 |
| 14.0 | 10.0Q | H37, H67, H91, L1, L4, L47 | 8 | 0.29 ± 0.05 | 2.98 ± 1.98 |
| 14.0 | 12.0 | H37, H67, H91, L1, L4, L47, L71 | 7 | 0.38 ± 0.10 | 2.93 ± 1.37 |
| 14.0 | 12.0Q | H37, H67, H91, L1, L4, L47, L71 | 7 | 0.33 ± 0.11 | 2.95 ± 0.32 |

[ANOVA analysis with Dunnett multiple comparison test showed no statistically significant differences with TMC-2206 or the chimera].

In parallel, homologues to these variants were constructed where the consensus glycosylation sequence within LCDR1 was changed. Elimination of the glycosylation site (NSS to QSS) may be useful for downstream manufacturing and process development. The N26Q change in the hVL1.0, hVL10.0 and hVL12.0 variants (denoted hVL1.0Q [SEQ ID NO:90], hVL10.0Q [SEQ ID NO:91] and hVL12.0Q [SEQ ID NO:92]) was introduced into the relevant variant VL using the primer pairs indicated in Table 18 whose sequences are provided in Table 9. The N26Q change had no statistically significant effect on activity of any of the resultant antibodies as shown in Table 17. Although this glycosylation site occurs on the light chain CDR 1 of the wild-type TMC-2206 antibody, these data indicate that it does not appear to play a role in the affinity of function-blocking activity of the TMC-2206 antibody.

TABLE 18

| VL variants | PCR primers for Fragment 1 | PCR primers for Fragment-2 | PCR primers for complete VL |
|---|---|---|---|
| 1.0Q | Igκ-For & hLCQ3-R | hLCQ3-F & Cl-neo-msc3' | Igκ-For & Cl-neo-msc3' |
| 10.0Q | Igκ-For & Hlcq3-R | Hlcq3-F & Cl-neo-msc3' | Igκ-For & Cl-neo-msc3' |
| 12.0Q | Igκ-For & Hlcq3-R | Hlcq3-F & Cl-neo-msc3' | Igκ-For & Cl-neo-msc3' |

EXAMPLE 4

Human antibodies of the γ1 class carry effector functions associated with complement and Fc receptor mediated functions. It is appreciated by those skilled in the art that to avoid antibody-dependent cellular cytotoxicity (ADCC) and complement responses a γ chain lacking this functionality, such as a human γ4 constant region, is preferred. To generate a γ4 version of the VH12.0, VL10.0Q and the VH14.0, VL10.0Q antibodies, a γ1 constant region sequence was replaced by a γ4 constant region sequence in the VH12.0 and VH14.0 heavy chains as follows. The γ4 constant region sequence was obtained from Genbank sequence KO1316. Both a γ1 Fc sequence derived from IMAGE clone 20688 used to generate the intact heavy chains of IgG1 antibodies with hVH and hVL regions as described herein and the γ4 Fc derived from the KO1316 sequence contain a naturally occurring Apa1 restriction site near the junction of the variable and constant regions. This site was used to clone a γ4 constant region to replace a γ1 constant region. BamH1 and Not1 restriction sites were placed at the 3' end of the sequence to facilitate subcloning into the pCI-neo expression vector. The γ4 sequence (SEQ ID NOS: 105 and 106) was then synthesized as a de novo synthetic gene by Blue Heron Biotechnology (Bothell, Wash.). The plasmid from Blue Heron Biotechnology, containing the de novo synthesized IgG4 constant region, was digested with ApaI and NotI, the 1 kb-γ4 constant region fragment was gel purified and ligated into the ApaI/NotI digested pCI-VH12.0 and the pCI-VH14.0 plasmids to produce plasmids encoding VH12.0-γ4 and VH14.0-γ4. These were combined individually with the pCI-VL10.0Q plasmid and transfected into CHO cells. Four days after transfection, culture supernatants were harvested and the IgG4 isotypes of the VH12.0, VL10.0Q and the VH14.0, VL10.0Q antibodies purified by Protein A affinity chromatography. New transient transfections of the γ1 constructs of these variants were performed in parallel.

After acid elution and neutralization, analytical size exclusion chromatography by HPLC indicated the presence of higher order oligomeric forms in the Protein-A purified IgG4 preparations. Therefore, a second purification step was performed by Sephacryl S-300 26/60 size exclusion chromatography to obtain the monomeric fraction. For this, the Sephacryl S-300 26/60 column was pre-equilibrated in 660 ml SEC Running Buffer (40 mM HEPES, pH 6.5, 20 mM L-histidine, 100 mM NaCl and 0.02% Tween-80). The pooled fractions containing protein eluted from the Protein A column were loaded (12.5 ml sample injection) via a Superloop (Amersham Biosciences). SEC fractions (5 ml each) were collected at a flow rate of 2.0 ml/min. The fractions corresponding to the monomeric form (peak elution at 168.4 ml) were pooled, and protein content determined by Lowry assay.

Exemplary IgG1 antibodies have a hVH 14.0 γ heavy chain (SEQ ID NO:181) or a hVH12.0 γ1 heavy chain (SEQ ID NO:182) and a hVL10.0Q light chain (SEQ ID NO:178). Exemplary IgG4 antibodies have a hVH14.0 γ4 heavy chain (SEQ ID NO:174) or a hVH12.0 γ4 heavy chain (SEQ ID NO:176) and a hVL 10.0 Q light chain (SEQ ID NO:178). Purified antibodies were tested in the competition assay to compare potency by $K_i$ values as well as in the cell adhesion to collagen assay, where potency is measured as $EC_{50}$ values. No significant difference was observed between the isotypes of the different variants nor did they differ significantly from the original TMC-2206 mAb in either assay as shown in Table 19.

TABLE 19

|  | Isotype | VH | VL | $K_i$ (nM) | $EC_{50}$ (nM) |
| --- | --- | --- | --- | --- | --- |
| TMC-2206 | IgG1/κ | Murine | Murine | 0.22 | 1.03 ± 0.29 |
|  | hIgG1/κ | 14.0 | 10.0Q | 0.24 | 1.30 ± 0.10 |
|  | hIgG1/κ | 12.0 | 10.0Q | 0.27 | 2.20 ± 012 |
|  | hIgG4/κ | 14.0 | 10.0Q | 0.36 | 2.82 ± 1.04 |
|  | hIgG4/κ | 12.0 | 10.0Q | 0.27 | 1.83 ± 0.27 |

EXAMPLE 5

The effect of anti-α2 on neutrophil extravasation was studied in a murine and rat peritonitis model of inflammation. Intraperitoneal administration of certain antigens such as casein, carrageenan or thioglycollate induces a rapid mast-cell response that initiates an acute peritonitis response (Edelson et al., Blood 103(6):2214-2220 (2004)). This peritonitis is characterized by a rapid infiltration of neutrophils (within hours) followed by a slower infiltration and proliferation of macrophages (3-5 days). Thus, this model was employed to evaluate for the first time the use of anti-α2 integrin antibodies in functionally preventing or lessening neutrophil response.

The acute peritonitis model was performed in rats and in mice. The TMC-2206 antibody recognizes rat α2β1-integrin, but not its murine counterpart. However, many in vivo models of inflammatory models are performed in mice and a surrogate anti-α2 antibody, Ha 1/29 (Pharmingen, Becton Dickenson, CA, catalog no. 559987), was used in the murine acute peritonitis model.

Animals were injected either IV or IP with an anti-α2 integrin or isotype control antibody at doses ranging from 0.1 to 10 mg/kg 15 minutes prior to challenge. A 1 mL injection of either 9% casein (mice) or carrageenan (rats) was given IP and the animals returned to their cage for specific time periods: 3 hours (mice) or 5 hours (rats) (n=4 per group). The animals were then euthanized with halothane and the peritoneal cavity was lavaged with 5 mL (mice) or 10 mL (rats) of PBS containing 5 mM EDTA. Cells were collected by low speed centrifugation, resuspended in 5 mL of PBS/EDTA and a 100 μL aliquot was viewed by microscopy, where the majority of cells were observed to have a polymorphonuclear morphology consistent with neutrophils. The cells in the remaining suspension were subjected to low speed centrifugation to obtain a washed cell pellet.

Neutrophil content was quantitated by assaying the level of myeloperoxidase (MPO) activity (e.g., Speyer et al., Am J Pathol. 163(6):2319-28 (2003)). The cell pellet recovered from the lavage fluid was re-suspended in 500 μL of 50 mM $KH_2PO_4$ buffer (pH 6.0) containing 0.5% hexadecyl-trimethyl-ammonium bromide (HTAB; Sigma-Aldrich, MI). The samples were sonicated for 60-90 seconds and centrifuged at 14,000 rpm for 5 minutes at 4° C. A 2:1 serial dilution of the cleared supernatant was made by transferring 50 μL of sample to 50 μL of HTAB buffer in the well of a microtiter plate. Next, 50 μL of this solution in the well was transferred into anther 50 μL buffer, and so forth down the dilution series. 200 μL of substrate buffer (50 mM $KH_2PO_4$ buffer (pH 6.0) containing 0.168 mg/mL o-dianisidine and 0.0005% $H_2O_2$) was added to each sample to initiate the colorimetric reaction, which was monitored with a Molecular Devices plate-reader set at a wavelength of 460 nm. The number of Units of enzymatic activity in the original cell suspension (500 μl of washed cell suspension for each individual animal) were then calculated. A calibration curve, set up to titrate neutrophils/mL (assessed by direct neutrophil count) against MPO activity indicated a strong linear correlation between U/mL and number of neutrophils/mL within the range measured.

As shown in Table 20, both the anti-murine α2β1-integrin antibody Ha1/29 and TMC-2206 had a marked effect on neutrophil infiltration into the peritoneal cavity following challenge with 9% casein in mice or 1% carrageenan in rats as measured by the total MPO activity recovered in the peritoneal lavage fluid. The $ED_{50}$ value obtained in mouse with Ha1/29 was ~0.07 mg/kg while the $ED_{50}$ for TMC-2206 in rat was ~5 mg/kg. This difference correlates in part with the relative affinity of the anti-human α2β1-integrin for rat α2β1-integrin as compared to the affinity of the Ha1/29 antibody for mouse α2β1-integrin, and in part with differences in antigen used in the rat and mouse models (carrageenan and casein respectively).

TABLE 20

|  | Dose | MPO content (U) | |
| --- | --- | --- | --- |
|  | (mg/kg) | Mean ± SEM | (n) |
| Ha 1/29 | 0.0 | 44.6 ± 10.1 | (4) |
| Mouse | 0.05 | 28.1 ± 3.4 | (3) |
| (9% casein) | 0.1 | 13.6 ± 0.8 | (4) | P < 0.01 |
|  | 0.5 | 7.3 ± 2.7 | (3) | P < 0.01 |
|  | 1.0 | 7.5 ± 1.6 | (4) | P < 0.01 |
| TMC-2206 | 0.0 | 362 ± 49 | (5) |
| Rat | 5.0 | 172 ± 41 | (6) | P < 0.01 |
| (1% carrageenan) | 10.0 | 136 ± 24 | (5) | P < 0.01 |
|  | 15.0 | 82 ± 18 | (6) | P < 0.01 |

EXAMPLE 6

The effect of anti-α2 integrin antibodies in mouse model (dextran sulphate-induced colitis) of inflammatory bowel disease was studied. In this model, colitis is induced in mice by administering a 5% dextran sodium sulphate solution (DSS) in the drinking water (Elson et al., Gastroenterology 109(4): 1344-67 (1995); Egger B., et al., Digestion 62(4):240-8 (2000)) The effect of treatment with an anti-murine α2β1-integrin antibody on the development of the clinical signs and symptoms of colitis as well as the effect on infiltration of pro-inflammatory leukocytes into the colon was assessed.

Balb/C mice (Harlan, Ind.) weighing 16-21 grams were housed in pairs. Animals were given either distilled water or water containing 5% dextran sodium sulfate (DSS); (ICN, Irvine, Calif.) ad libitum for 7 days. At this stage the mice exhibit diarrhea and noticeable weight loss. The study design was four groups of six mice each; one to serve as naïve control, one to serve as the DSS control and two assigned to receive intraperitoneal injections of either 2 or 5 mg/kg doses of anti-α2 integrin antibody PS/2 on Days 0, 2, 4, and 6. Mice were euthanized on Day 7 (168 hours after start of DSS feeding). They were weighed to observe any changes from study initiation, colon length measured and then scored on a scale of 0 to 2, with 2 being most severe, for diarrhea, colon bleeding and rectal bleeding as follows:

| rectal bleeding: | score of 0 = no visible blood; | | 2 = visible blood |
|---|---|---|---|
| stool consistency: | score of 0 = normal; | 1 = loose; | 2 = watery |
| colon bleeding: | score of 0 = no visible blood; | | 2 = visible blood. |

Colons were then processed for immunohistochemistry. The colons, from ceacum to rectum, were carefully removed and fixed for 2 hours at 4° C. in 4% paraformadehyde (PFA), left overnight in 20% sucrose and then rapidly frozen in OCT freezing compound (Tissue Tek). Thin (10 μM thickness) serial sections were cut using a Leica cryostat, air-dried, blocked for 2 hours in 3% goat serum in PBS and incubated overnight at room temperature in primary antibody. The primary antibodies used included rat anti-murine CD11b/mac-1 (a marker for macrophage and activated neutrophils, Clone M1/70, BD-Pharmingen), hamster anti-murine CD3 (a T cell marker, BD-Pharmingen), and clone F4/80 (a marker of macrophages, Research Diagnostics, Inc). The slides were then washed, incubated 2 hours in the corresponding Alexa 488- or TRITC-labeled secondary antibody (Molecular Probes, OR) and washed three times for 5 minutes in PBS and mounted in Vectashield medium containing DAPI (Vector Labs, CA). Sections were viewed with a Leica epifluorescence microscope connected to a Spot RT camera (Research Diagnostics). The fluorescence intensity and number of fluorescent cells within a selected region of interest (ROI) that delineated the region between the lamina propria and tips of the villi but eliminated the serosal surface (high autofluorescence) and enteric lumen, from a total of 5 fields of view on five separate sections, were quantified for each animal using ImagePro software (Media Cybernectics, MD).

As shown in Table 21, treatment with the anti-murine α2 integrin had a statistically significant dose effect on reversing weight loss and stool consistency associated with DSS feeding. Both treatment groups (2 mg/kg and 5 mg/kg) had significant effects on rectal bleeding and colon bleeding, but no significant effect on the colon shortening associated with the development of colitis. Treatment also correlated with a marked decrease in the number of infiltrating leukocytes (data not shown).

TABLE 21

| | | DSS | | |
|---|---|---|---|---|
| | Water | Saline | 2 mg/kg anti-α2 | 5 mg/kg anti-α2 |
| Weight gain (gm) | 3.02 ± 1.19 | −9.16 ± 0.63 | −0.44 ± 0.81*** | −2.30 ± 0.64** |
| Colon Length (cm) | 7.43 ± 0.26 | 5.22 ± 0.17 | 5.35 ± 0.17 | 5.32 ± 0.43 |
| Rectal Bleed | 0 | 1.67 ± 0.21 | 0.83 ± 0.31 | 0.83 ± 0.31 |
| Colon Bleed | 0 | 1.0 ± 0.45 | 0* | 0* |
| Stool Consistency | 0 | 1.0 ± 0.0 | 0.50 ± 0.22* | 0.17 ± 0.17** |

*p < 0.05
**p < 0.01

In another study, the effect of anti-α4 integrin (clone PS/2; Southern Biotech, AL), anti-α2 integrin (clone Ha1/29, BD Pharmingen, CA) and anti-α1 integrin (clone Ha8/31; Invitrogen, CA) were examined in comparison with DSS-only treated mice (n=8 per group). Antibody treatment doses were 5 mg/kg. These anti-integrin function-blocking antibodies have been reported to modulate experimental colitis (Kriegelstein et al., J Clin Invest. 110(12):1773-82 (2002); Watanabe et al, Am J Physiol Gastrointest Liver Physiol. 283(6):G1379-87 (2002)). As shown in Table 22, the three anti-integrin antibodies were associated with a reversal in colon shortening, but only the anti-α2 treatment was associated with a significant improvement in stool consistency (diarrhea). Both the anti-α2 and anti-α4 treatment resulted in a significant improvement in colon bleeding. In this study, none of the antibody treatments induced a significant effect on weight loss. When numbers of resident T-cells, macrophages and neutrophils were assessed by indirect immunofluorescence using anti-CD3, F4/80 and anti-Mac1 (as described previously), the three anti-integrin treated groups showed significant decrease compared to the Saline control as shown in Table 23. These data support the conclusion that antagonizing α2-function has a profound effect on the steady state levels of these immune effector cells accumulating in the inflamed colon in response to DSS and that these changes correlate concurrently with an improvement in clinical measures associated with colitis.

TABLE 22

| Clinical | | DSS | | | |
|---|---|---|---|---|---|
| signs | Water | Saline | Anti-α2 | Anti-α1 | Anti-α4 |
| Weight gain (gm) | 7.10 ± 0.70 | −1.67 ± 0.76 | −1.10 ± 1.69 | −0.43 ± 1.17 | 1.62 ± 0.69 |
| Colon length (cm) | 7.43 ± 0.26 | 4.73 ± 0.16 | 6.08 ± 0.25** | 5.85 ± 0.22** | 5.92 ± 0.09** |

TABLE 22-continued

| Clinical signs | Water | DSS Saline | Anti-α2 | Anti-α1 | Anti-α4 |
|---|---|---|---|---|---|
| Rectal bleed | 0.0 | 2.00 ± 0.21 | 0.50 ± 0.33* | 0.50 ± 0.33* | 0.83 ± 0.31 |
| Colon bleed | 0.0 | 1.5 ± 0.33 | 0.25 ± 0.25** | 0.75 ± 0.37 | 0.00** |
| Stool Consistency | 0.0 | 1.0 ± 0.0 | 0.38 ± 0.182* | 0.63 ± 0.18 | 0.67 ± 0.21 |

*p < 0.05
**p < 0.01

TABLE 23

| Cell counts | Water | DSS Saline | Anti-α2 | Anti-α1 | Anti-α4 |
|---|---|---|---|---|---|
| T cells (CD3 positive cells) | 6.1 ± 1.5 | 618 ± 160 | 211 ± 78* | 174 ± 48** | 112 ± 36** |
| Macrophages (F4/80 positive cells) | 21 ± 3 | 778 ± 94 | 298 ± 45** | 510 ± 132 | 328 ± 53** |
| Neutrophils + Macrophages (CD11b/Mac-1 positive cells) | 19 ± 5 | 1937 ± 239 | 499 ± 144** | 524 ± 141** | 574 ± 192** |

*p < 0.05
**p < 0.01

EXAMPLE 7

The effects of anti-α2 integrin antibody were studied on clinical signs and symptoms in an experimental allergic encephalomyelitis (EAE) model of multiple sclerosis. The EAE model of multiple sclerosis, induced by injection of the synthetic encephalogenic peptide $PLP_{139-151}$ together with Freund's adjuvant in SJL mice, is considered to be a predictive model of relapsing-remitting multiple sclerosis (Encinas et al., J Neurosci Res. 45(6):655-69 (1996)).

Figure 2:
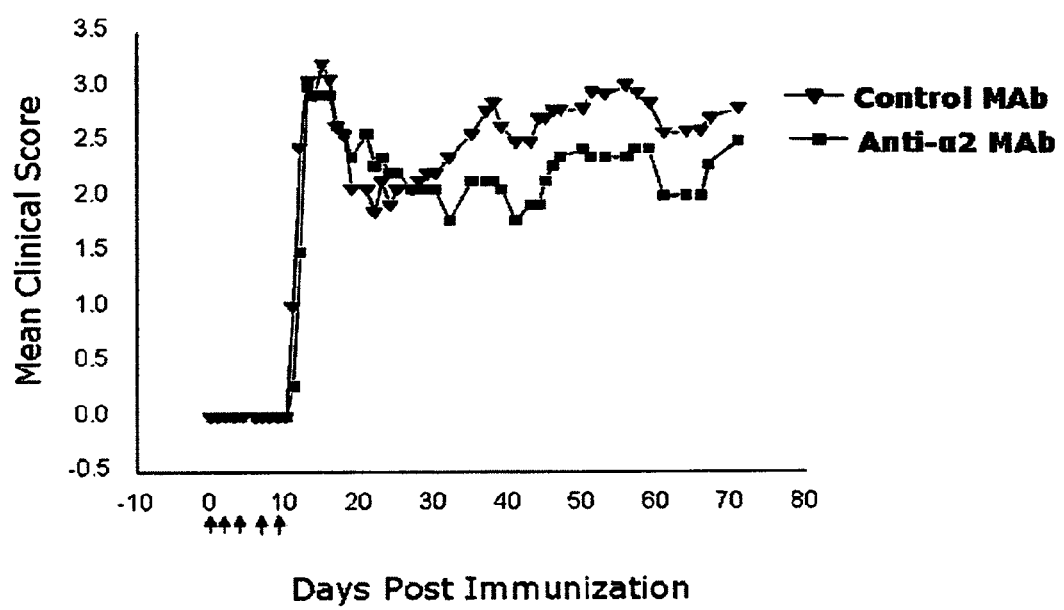
FIG. 2: Graphical results of studies of effects of anti-α2 integrin on paralytic disease when administered during induction phase (See Example 7).

In a study of 4 groups of mice (8/group; see FIG. 1), two groups were dosed with 5 mg/kg on Days 10, 11, 12, 14, 15, 18 and 20 with either isotype control or the anti-murine α2 integrin antibody, Ha1/29, from the onset of disease symptoms through Day 20, which is through the first acute flare. This was an acute dose regimen. Day 0 was defined as the onset of priming with the synthetic peptide PLP139-151 plus Freund's adjuvant. Onset of disease was defined as the second day of consecutive weight loss. The two other groups were assigned to a delayed dose regimen where they received either 5 mg/kg anti-murine α2 integrin antibody or saline three times a week from Day 18 through Day 36, which was to coincide with the second flare/first relapse. The mice were scored for clinical signs and symptoms as follows:
  score of 0.5=2 consecutive days of weight loss
  score of 1=limp tail
  score of 2=ataxia
  score of 3=hind limb paralysis
  score of 4=moribund
  score of 5=death As shown in Table 24, treatment with 5 mg/kg of the anti-α2 antibody from the onset of the first flare (e.g., acute treatment) dampened the extent of the first flare and also limited the extent of the second flare. When dosing was initiated after the end of the first flare on Day 18 (e.g., delayed treatment; see FIG. 1), mice treated with 5 mg/kg anti-murine α2 integrin antibody also showed lower clinical scores during the first relapse through Day 32, at which point the two groups showed similar disease scores as shown in Table 24. When mice were dosed only during the induction phase as shown in FIG. 2, the anti-α2 integrin mAb had little or no effect on the first attack or subsequent phases of the EAE model and the mice essentially developed the disease equivalent to that of animals treated with the isotype control. These results contrast with those previously obtained using the anti-α4 antibody, PS/2, in the EAE model (Yednock et al., Nature 356 (6364):63-6 (1992); Theien et al., J. Clin. Invest. 107(8):995-1006 (2001)), used to support treatment of relapsing multiple sclerosis with the anti-α4 antibody natalizumab (Miller et al., N. Engl. J. Med. 348(1):15-23 (2003)). These results indicate that in contrast to the role α4 integrin plays in neuro-inflammatory disorders, where antagonism of this receptor may delay onset of the flaring relapses associated with multiple sclerosis, antagonizing α2 integrin is a useful treatment modality for the dampening and treatment of flares when they occur.

TABLE 24

| | Clinical Scores | |
|---|---|---|
| | Study 1 Mean ± SEM (n = 6-8) | Study 2 Mean ± SEM (n = 17-20) |
| Day 15 | | |
| Control IgG | 1.56 ± 0.42 | 2.22 ± 0.29 |
| anti-α2 | 1.00 ± 0.37 | 0.88 ± 0.21 (p < 0.01) |
| anti-α4 | — | 1.64 ± 0.25 |
| Day 20 | | |
| Control IgG | 1.13 ± 0.48 | 1.25 ± 0.28 |
| anti-α2 | 0.58 ± 0.41 | 0.61 ± 0.20 |
| anti-α4 | — | 1.11 ± 0.22 |
| Day 35 | | |
| Control IgG | 1.13 ± 0.48 | 1.49 ± 0.29 |
| anti-α2 | 0.33 ± 0.33 | 1.08 ± 0.29 |
| anti-α4 | — | 1.47 ± 0.27 |

TABLE 24-continued

| | Clinical Scores | |
|---|---|---|
| | Study 1 Mean ± SEM (n = 6-8) | Study 2 Mean ± SEM (n = 17-20) |
| Day 55 | | |
| Control IgG | 1.63 ± 0.63 | 2.00 ± 0.28 |
| anti-α2 | 1.00 ± 0.59 | 0.75 ± 0.31 (p < 0.001) |
| anti-α4 | — | 1.33 ± 0.35 |

Histological analysis was performed on brains and spinal cords obtained from the mice either when moribund (stage 4) or at the end of the study. Mice were euthanized with halothane when moribund (clinical score 4), or after the 55-60 day observation period. Animals were perfused with PBS, followed with a 4% paraformaldehyde solution. The brains were divided into five coronal slabs, the spinal cords into ten to twelve transverse slabs and the tissues were paraffin embedded and 4μ thick sections stained with Luxol Blue to visualize myelination. Tissues were scored in a blinded fashion for degree of myelination, infiltration (meningitis) and perivascular cuffing. For scoring spinal cord sections, each spinal cord section was divided into quadrants: the anterior funiculus, the posterior funiculus and each lateral funiculus. Any quadrant containing meningitis, perivascular cuffing or demyelination was given a score of 1 in that pathologic class. The total number of positive quadrants for each pathologic class was determined, then divided by the total number of quadrants present on the slide and multiplied by 100 to give the percent involvement for each pathologic class. An overall pathologic score was also determined by giving a positive score if any lesions were present in the quadrant.

Noticeable demyelinating inflammatory lesions were observed in the spinal cord, most frequently in the graciles fasciculus of the posterior funiculus and ventral root exit zone in the anterolateral funiculus. Only mild perivascular cuffing was observed. Meningitis and demyelination showed a strong correlation with clinical signs (r=0.84 and 0.79, respectively) and showed significantly lower scores in the anti-α2-treated group (P<0.01 between anti-α2 and control IgG-treated groups for both parameters). These data indicate that treatment with anti-α2 integrin antibody inhibits the meningitis and demyelination associated with a flare and/or facilitates remyelination and repair. The overall result is an improved clinical outcome.

Another study was performed (n=17 to 20 per group) to compare anti-α2 integrin with anti-α4 integrin antibody, PS/2 (obtained from Southern Biotech), treatment during the first acute flare through to the onset of remission (Days 10 through 20). Two additional groups were treated with either control IgG or anti-α2 integrin from the start of remission (Day 18) through the first relapse (Day 36) and at the start of the chronic phase of disease. Again the anti-α2 integrin treatment had a marked effect on the incidence of neurological sequelae (paralysis) and a statistically significant reduction in the maximum mean clinical score during the first EAE flare as well as in the subsequent relapse phase (chronic phase of EAE; Table 24). There was a slight ameliorating effect of delayed anti-α2 treatment on clinical scores during the chronic phase of disease. Disease incidence during the first attack (anti-α2, 61%; control IgG 85%) and during the chronic phase (anti-α2, 77%; control IgG 100%) was lower for the group of anti-α2 treated mice compared to control. In the case of the group treated with anti-α4, disease incidence during the first attack (anti-α4 treatment, 94%; control 82%) and relapse (anti-α4 treatment, 89%; control, 92%) were similar between the anti-α4 antibody treated versus control group. However, the extent of subsequent relapses was markedly reduced. These data with respect to an anti-α4 antibody are comparable with previous reports on the effect of anti-α4 antibody treatment on clinical outcome in EAE (Theien et al., J. Clin. Invest. 107(8):995-1006 (2001)).

EXAMPLE 8

The effects of binding to platelet α2β1 integrin (α2β1 is expressed on the surface of platelets) were studied, including effects on platelet function. Different sets of assays were performed to study these effects.

The first studies assessed whether binding of TMC-2206 leads to platelet activation as measured by up-regulation of P-selectin or activation of platelet αIIbβ3 integrin which was measured using an αIIbβ3 activation-specific antibody such as PAC-1. Human venous blood was collected using a 21-gauge needle from the cubital vein of healthy donors who had abstained from medications for at least 10 days into 1/10 volume of acidified citrate-dextrose buffer (ACD: 85 mM sodium citrate, 111 mM dextrose, and 71 mM citric acid, with no adjustment in pH) which contained 500 ng/mL prostaglandin $I_2$ (PGI$_2$, Sigma-Aldrich) if being used for making washed platelets. Whole blood was centrifuged at 160×g for 20 minutes at ambient temperature and platelet rich plasma (PRP) was removed without disrupting the buffy coat. Washed platelets were prepared by diluting the PRP 2.5-fold with citrate glucose saline buffer (CGS; 13 mM trisodium citrate, 120 mM sodium chloride and 30 mM dextrose, pH 7.0) buffer and PGI$_2$ (500 ng/ml) and centrifuging at 160×g for 20 minutes at ambient temperature to remove any contaminating leukocytes. The supernatant was collected and centrifuged at 1100×g for 10 minutes and the resulting platelet pellet was gently resuspended in CGS buffer, washed and resuspended in normal Tyrodes-Hepes buffer (12 mM NaHCO$_3$, 138 mM NaCl, 5.5 mM glucose, 2.9 mM KCl, 10 mM HEPES, 1 mM CaCl$_2$, 1 mM MgCl$_2$, pH 7.4). The platelets were allowed to recover for up to 30 minutes at 37° C. Washed platelets were then counted before adding CaCl$_2$ and MgCl$_2$ to 1 mM. Washed platelets from rat were prepared in a similar manner, although blood was drawn from the vena cava to minimize platelet activation during the blood draw.

50 μL of freshly prepared PRP were incubated with 5 μg/mL of TMC-2206 or mouse IgG control antibody for 30 minutes, washed and then incubated with Alexa-594 labeled goat anti-mouse in the presence or absence of Alexa 488-labelled P-selectin antibody (BD Pharmingen, catalog no. 555523), Alexa-488 labelled-PAC-1 antibody (BD Pharmingen, catalog no. 340507) or 150 ng Alexa-488 labeled fibrinogen (Molecular Probes) for 40 minutes at room temperature. P-selectin and PAC-1 are markers of platelet activation, and activated platelets are able to bind to fibrinogen. At the end of the incubation period, platelets were fixed with 1/10 volume of 4% parafomaldehyde and analyzed using a FACScalibur™ flow cytometer. The results from these experiments unexpectedly demonstrated that although platelets clearly bound TMC-2206, as indicated by a log shift in increased fluorescence intensity observed in the TMC-2206 treated but not the control IgG treated platelets; there was no concomitant increase in P-selectin or PAC1 staining, indicating that TMC-2206 binding did not activate platelets.

The next studies assessed whether binding of TMC-2206 leads to platelet activation, as measured by effects on collagen-induced platelet aggregation. Soluble collagen is a potent agonist of platelet aggregation and is used as a routine measure of platelet responsiveness (see e.g., *Hemostasis and Thrombosis*; (2001), ed. Colman et al). Studies with α2-knock out mice have suggested that platelets from these mice exhibit a mild impaired response to collagen (Holtkotter et al, J. Biol. Chem. 277(13):10789-94 (2002) E. pub Jan. 11, 2002; Chen et al., Am. J. Pathol. 161(1):337-344 (2002)). To test whether TMC-2206 would have any adverse effects on platelet responses to collagen, human and rat platelet aggregation assays were performed by classical light transmission aggregometry using a Bio-data PAR4 aggregometer. PRP was prepared as described above and platelet count was adjusted to $3 \times 10^8$/mL. 450 μL of PRP or washed platelets were stirred with a magnetic bead for 1 minute at 37° C. in the presence of 5 μg/mL TMC-2206 before adding calf-skin Type I collagen (Biodata Corp) to initiate aggregation. Final volume to 500 μL was made up with Tyrodes buffer for washed platelet aggregation and with platelet-poor plasma (PPP) for platelet-rich plasma (PRP) assays. 500 μL of Tyrodes buffer or PPP were used as blanks for the assays. PPP was prepared by pelleting platelets in PRP by centrifuging at 3000 rpm for 5 minutes in a microfuge. The rate and extent of platelet aggregation following addition of soluble collagen was comparable in the presence or absence of TMC-2206. The results of these experiments demonstrated that binding of TMC-2206 to platelets unexpectedly had no effect on collagen-induced platelet aggregation when tested in vitro at the concentrations tested.

The next studies assessed whether binding of TMC-2206 leads to thrombocytopenia, a potential consequence of antibodies binding to platelets in vivo. (Hansen and Balthasar, J Pharmacol Exp Ther. 298(1):165-71 (2001)). To test if thrombocytopenia would occur upon TMC-2206 administration, rats were given a dose of 10 mg/kg TMC-2206 or control murine IgG by IP injection. Prior to injection, a tail bleed was used to measure baseline blood cell counts. Blood samples were taken at specific time points after IP drug administration (e.g., 10, 30, 60 minutes and 4, 24 and 72 hours) from non-anesthetized rats by retro-orbital draw using a capillary Unopipet. Approximately 40 μL of blood was then transferred to a tube containing 5 μL of ACD and immediately sampled in a Hemavet blood cell counter (Drew Scientific). The results of this study unexpectedly showed no significant change from baseline platelet counts at doses of 5 mg/kg or 10 mg/kg of TMC-2206. In contrast, injection of 0.1 mg/kg of an antibody to another platelet receptor (αIIb, anti-CD41 antibody (BD Pharmingen, CA)) induced thrombocytopenia, with platelet count declining by almost 80% within 15 minutes of administering the antibody.

EXAMPLE 9

The effects of anti-α2 integrin antibodies were studied on platelet adhesion to collagen including adhesion to various subtypes of collagen. α2β1-integrin is the only collagen-binding integrin, albeit not the only collagen receptor, to be expressed by platelets. However, as discussed above, other mechanisms exist, especially upon platelet activation, to facilitate firm adhesion to a collagen matrix. In this example, the ability of the TMC-2206 antibody to block platelet adhesion to Type I, II, III, IV and VI collagens was evaluated, both for resting platelets and platelets activated with the moderate platelet agonist, ADP.

Immulon II platelets were coated with collagen types I, II, III, VI (Rockland Immunochemical) and IV (Sigma, St. Louis, Mo.) which had been solubilized without frothing in 5 mM acetic acid, to final concentration of 1 mg/mL. Wells were washed twice using modified Tyrode's-HEPES buffer without $Ca^{++}$ or BSA, but with 2 mM/$Mg^{++}$ and blocked with 100 μL/well Tyrode's—HEPES buffer containing 2 mM/$Mg^{++}$ and 0.35% BSA, but without $Ca^{++}$.

Human venous blood was used for the preparation of platelets, including PRP, as described above in Example 8. Platelet poor plasma (PPP) was made by centrifuging the PRP at 1100×g for 10 minutes at room temperature. The resulting platelet pellet was resuspended gently for labeling in 1.0 mL CGS (13 mM trisodium citrate, 120 mM sodium chloride and 30 mM dextrose pH 7.0), transferred to a 5 mL round-bottomed tube and 3 μL CFSE stock (53.7 μM final concentration) was added with gentle rocking for exactly 20 minutes. The labeled platelets were diluted in CGS buffer and washed. The platelet pellet was re-suspended in 1 mL CMFTH buffer (5 mM HEPES, pH 7.3, 12 mM sodium bicarbonate, 137 mM NaCl, 3 mM KCl, 0.3 mM $NaH_2PO_4$, 5 mM dextrose and 0.35% BSA) and kept in the dark as much as possible. Washed platelets from rat were prepared in a similar manner, although blood was drawn from the vena cava into a syringe containing 500 ng/mL $PGE_1$ in ACD to minimize platelet activation during the blood draw.

CFSE-labeled platelets were diluted to $2.0 \times 10^5$/μL using Tyrode's-HEPES Buffer containing 0.35% BSA. Labeled platelets ($1.0 \times 10^7$ well) were applied to wells containing 20 μM ADP in Tyrode's-HEPES buffer with 0.35% BSA and variable concentrations of test inhibitor. Microtiter plates containing platelet mixtures were centrifuged at 550×g for 10 minutes at room temperature followed by incubation in the dark for an additional 10 minutes. Wells were washed with Tyrode's-HEPES buffer. Fluorescence was read using a Victor2 fluorescence plate reader. To determine the relationship of fluorescence intensity versus platelet number, labeled platelets were diluted to various levels in Tyrode's-HEPES buffer containing 0.35% BSA (without $Ca^{++}$ or ADP), applied to wells coated with collagen Type I or Type IV, centrifuged, and CFSE fluorescence measurements taken. As shown in Table 25, TMC-2206 blocked binding to collagen under these static conditions, with an EC50 of 1.7 nM. Similar studies were performed with rat platelets using TMC-2206. The EC50 values for inhibiting binding of rat platelets to rat collagen Type I was 6.3 nM indicating an approximately 5-fold shift in affinity for the rat compared to human α2β1 on platelets.

TABLE 25

| Collagen type | Human Collagen source | ADP stim. (μM) | $EC_{50}$ (nM) |
|---|---|---|---|
| Type I | placenta | 0 | 1.7 |
|  |  | 20 | 9.5 |
| Type II | knee cartilage | 0 | 1.9 |
|  |  | 20 | 27 |
| Type III | placenta | 0 | 1.6 |
|  |  | 20 | 11 |
| Type IV | placenta | 0 | 10 |
|  |  | 20 | >1000 |
| Type VI | placenta | 0 | 2.3 |
|  |  | 20 | 23 |

As shown in Table 25, TMC-2206 was a potent inhibitor of platelet adhesion to the fibrillar collagens, but was less potent for the non-fibrillar Type IV collagen (10 nM compared to 1-2 nM). Unexpectedly in the presence of ADP, there was an approximately 10- to 20-fold decrease in potency for inhibiting the binding to the fibrillar collagens and the antibody no longer was effective at preventing adhesion to Type IV collagen. These unexpected observations suggest that the TMC- 2206 and antibodies with the epitope binding specificity of TMC-2206 are less active at inhibiting the interactions of activated platelets to fibrillar collagen, and would have little or no effect [in the therapeutic dosing range] on binding to Type IV collagen, the predominant collagen subtype of the endothelial vessel wall.

EXAMPLE 10

The effects of anti-α2 integrin antibodies were studied on bleeding time. There is an expectation of those skilled in the art that administration of an antibody against a platelet integrin would cause bleeding disorders and lead to an increased time to clot in a subject receiving such an antibody following acute injury. To assess whether antibodies directed against α2 integrin would increase the propensity for bleeding in vivo, the effect of TMC-2206 on bleeding time in the rat was determined.

Rats were given either an IP or IV injection of TMC-2206 15 minutes prior to testing for bleeding time. Non-anesthetized rats were immobilized in a restraining device and 0.8 cm of the tip of the tail cut rapidly to initiate bleeding. The tail was promptly inserted into a beaker containing 30 mL of PBS maintained at 37° C. The time required for the tail to stop bleeding was recorded as bleeding time. As shown in Table 26, the data demonstrated that administration of doses of TMC-2206 up to 10 mg/kg had no significant effect on bleeding time.

TABLE 26

| TMC-2206 Dose mg/kg | Bleeding Time (n) minutes |
|---|---|
| 0.0 | 3.86 ± 0.32 (5) |
| 5.0 | 4.51 ± 0.32 (4) |
| 10.0 | 4.62 ± 0.67 (7) |

EXAMPLE 11

The effects of anti-α2 integrin antibodies were studied in a model of arterial thrombosis. Another potential manifestation of a bleeding disorder from administration of antibodies reactive with α2β1 on platelets could be an increased time for thrombotic occlusion to occur following acute arterial injury due to undesired affects of platelet function. Thus, anti-α2 integrin antibodies such as TMC-2206, were tested in a rat ferric chloride-induced model of arterial thrombosis. This is a standard model that has been used for development of anti-thrombotic agents and activity is manifest as a delay in time to occlusion following exposure of the endothelial lining of the blood vessel to a FeCl$_3$ solution (Kurz et al., Thromb Res. 60(4):269-80. (1990); Hoekstra et al., J Med Chem. 42(25): 5254-65 (1999)).

TMC-2206 antibody was administered to rats via tail vein injection approximately 30 minutes before induction of arterial injury at the doses ranging from 1 mg/kg to 15 mg/kg. For IV injections, most antibodies were concentrated to 4-5 mg/mL to reduce the injection volumes required for the higher doses. The treatment groups were 1.0, 2.5, 5.0, 10.0 and 15 mg/kg TMC-2206, 5.0 mg/kg control murine IgGI (κ) (clone MOPC21) 5.0 mg/kg rabbit polyclonal anti-vWF (DAKO) or saline; there were 3-4 animals in each treatment group.

Sprague-Dawley rats (Harlan) weighing 220-270 grams were anesthetized with 60 mg/kg sodium pentobarbital. Once they reached a sufficient plane of anesthesia the carotid artery was exposed and placed on a piece of filter paper (4 mm×5 mm) which was folded along the 4 mm side to cradle the carotid artery and provide a surface for the ferric chloride (35%) to bathe the carotid. Twelve μL of 35% FeCl$_3$ was applied for 5 minutes, then the filter paper removed and the flow probe of a Transonic Systems Inc. flow system (Ithaca, N.Y.) placed around the carotid artery. Flow was measured for up to 45 minutes.

The mean values and SEM for flow rates of several animals per group at specific time points after ferric chloride was administered were recorded. There were no significant differences in time-to-occlusion observed with any of the doses of TMC-2206 tested, even as high as 15 mg/kg, compared to the saline control indicating that there appears to be no adverse effects on thrombosis due to TMC-2206 administration. Although the starting flow values can vary substantially between animals, the time-to-occlusion occurred consistently between 10 and 16 minutes after ferric chloride administration in the TMC-2206 treated groups, which was very similar to the saline and control IgG treated groups, which had mean times to occlusion of 12 and 14 minutes, respectively. The only treatment tested that was associated with the prevention of occlusion was the positive control, a polyclonal anti-vWf antibody, which resulted in no reduction in flow parameters for periods as long as 45 minutes after the addition of FeCl$_3$.

EXAMPLE 12

The binding properties of anti-α2 integrin antibodies were studied, including epitope mapping studies, to characterize the nature of the TMC-2206 binding site on the α2 integrin subunit. An anti-α2 integrin antibody that binds directly to the target's binding site and serves as a direct competitor for ligand binding may be expected to cause platelet activation upon binding the α2β1 integrin. Alternately, an anti-α2 integrin antibody that binds to the α2β1 integrin in an inactive state and does not cause the integrin to become activated might have a similar platelet non-activating profile to that which was unexpectedly found for TMC-2206. Antibodies with the same or similar binding epitope as TMC-2206 would inhibit cell adhesion of leukocytes to collagen, and thus have significant therapeutic utility, but would not be associated with the bleeding complications that an antibody that bound to, and activated, α2β1 integrin might have.

Studies were conducted to investigate whether the epitope recognized by TMC-2206 lay within the ligand-binding I domain of the α2 integrin subunit, or whether it was simply dependent on the presence of an intact I domain (Hangan et al., Cancer Res. 56:3142-3149 (1996)). For these studies, a GST-α2 I domain fusion protein was made using a modified version of the protocol described by Tuckwell et al., J. Cell Sci. 108 (Pt 4):1629-37 (1995). The human α2 I domain was cloned from mRNA isolated from approximately $10^6$ CHO cells expressing human α2 integrin (Symington et al., J Cell Biol. 120(2):523-35. (1993). Cells were lysed in Trizol reagent (Gibco) and chloroform was added to extract the aqueous phase before adding 0.2 volumes of isopropanol to precipitate the RNA which was collected by centrifugation and resuspended in RNAse free water.

Primers flanking the I-domain of human α2 were synthesized by Sigma-Genosys. The primers were engineered with BamHI and EcoRI sites at the 5' and 3' ends respectively for cloning into the pGEX-2TK vector (GE Biosciences). The primers halphaI F (5'GGGGATCCAGTCCT-GATTTTCAGCTCTCAG; SEQ ID NO:117) and halphaI R (5'GGGAATTCAACAGTACCTTCAATGCTG; SEQ ID NO:118) (see Table 27) were used for a single-step RT-PCR reaction using a standard Qiagen kit to amplify amino acids 123 through 346 of the mature α2 integrin subunit and to incorporate a BamHI site at the amino terminus (which adds a GS upstream of residue 124 of the I domain) and an additional EFIVTD hexapeptide as part of the EcoRI cloning site through to the stop codon. A single band was detected by agarose gel electrophoresis. The PCR reaction was cleaned using a Qiagen PCR Quick Kit, the product digested with restriction enzymes and cloned into the pGEX-2TK vector (Amersham, GE) using standard molecular biology techniques. Transformed bacteria were screened for inserts and several clones sequenced using a CEQ system from Beckman-Coulter. The deduced amino acid sequence as cloned was identical to the available sequence of a human α2 I domain (SEQ ID NO:11, shown in Table 28). A single clone containing the correct DNA insert was amplified in DH5α cells (Invitrogen) and re-transformed into BL21 electro-competent bacteria (Invitrogen).

TABLE 27

| Primer name | Nucleotide sequences (5'-3') |
|---|---|
| halphaI F (SEQ ID NO: 117) | GGGGATCCAGTCCTGATTTTCAGCTCTCAG |
| halphaI R (SEQ ID NO: 118) | GGGAATTCAACAGTACCTTCAATGCTG |
| malphaI F (SEQ ID NO: 121) | GGGGATCCAGTCCAGACTTTCAGTTCTTG |
| malphaI R (SEQ ID NO: 122) | TGGGAATTCAACAGTGCCTTCAATGCTG |
| ralphaI F (SEQ ID NO: 123) | GGGGATCCAGTCCAGACTTTCAGTCGTTGAC |
| ralphaI R (SEQ ID NO: 124) | TGGGAATTCTGCCATTTCCATCTGGAAGTTG |
| halphaI I21V F (SEQ ID NO: 125) | CAGCCCTGCCCTTCCCTCGTAGATGTTGTGGTTG |
| halphaI I21V R (SEQ ID NO: 126) | CAACCACAACATCTACGAGGGAAGGGCAGGGCTG |
| halphaI E44V (SEQ ID NO: 127) | CAGTAAAGAATTTTTTGGTAAAATTTGTCAAGG |
| halphaI E44V R (SEQ ID NO: 128) | CCTTGACAAATTTTACCAAAAAATTCTTTACTG |
| halphaI Q48T F (SEQ ID NO: 129) | TTTTGGAAAAATTTGTAACAGGCCTGGATATAGGC |
| halphaI Q48T R (SEQ ID NO: 130) | GCCTATATCCAGGCCTGTTACAAATTTTTCCGGGG |
| halphaI N67E F (SEQ ID NO: 131) | CAGTATGCCAATGAGCCAAGAGTTGTGTTTAAC |
| halphaI N67E R (SEQ ID NO: 132) | GTTAAACACAACTCTTGGCTCATTGGCATACTG |
| halphaI V70I F (SEQ ID NO: 133) | TGCCAATAATCCAAGAATTGTGTTTAACTTGAAC |
| halphaI V70I R (SEQ ID NO: 134) | GTTCAAGTTAACACAATTCTTGGATTATTGGCA |
| halphaI V71I F (SEQ ID NO: 135) | CCAATAATCCAAGAGTTATCTTTAACTTGAACAC |
| halphaI V71I R (SEQ IF NO: 136) | GTGTTCAAGTTAAAGATAACTCTTGGATTATTGG |
| halphaI T76D F (SEQ ID NO: 137) | GTGTTTAACTTGAACGACTATAAAACCAAAGAA |
| halphaI T76D R (SEQ ID NO: 138) | TTCTTTGGTTTTATAGTCGTTCAAGTTAAACAC |
| halphaI Y77F F (SEQ ID NO: 139) | TTTAACTTGAACACATTTAAAACCAAAGAAGAA |
| halphaI Y77F R (SEQ ID NO: 140) | TTCTTCTTTGGTTTTAAATGTGTTCAAGTTAAA |

TABLE 27-continued

| Primer name | Nucleotide sequences (5'-3') |
|---|---|
| halphaI K78E F (SEQ ID NO: 141) | AACTTGAACACATATGAAACCAAAGAAGAAATG |
| halphaI K78E R (SEQ ID NO: 142) | CATTTCTTCTTTGGTTTCATATGTGTTCAAGTT |
| halphaI Y93H F (SEQ ID NO: 143) | TCCCAGACATCCCAACATGGTGGGGACCTCACA |
| halphaI Y93H R (SEQ ID NO: 144) | TGTGAGGTCCCCACCATGTTGGGATGTCTGGGA |
| halphaI Y93F F (SEQ ID NO: 145) | ACATGGGAGACATCCCAATTTGGTGGGGACCTCACAAAC |
| halphaI Y93F R (SEQ ID NO: 146) | GTTTGTGAGGTCCCCACCAAATTGGGATGTCTCCCATGT |
| halphaI Q105E F (SEQ ID NO: 147) | TTCGGAGCAATTGAATATGCAAGAAAATATGCC |
| halphaI Q105E R (SEQ ID NO: 148) | GGCATATTTTCTTGCATATTCAATTGCTCCGAA |
| halphaI A114Q F (SEQ ID NO: 149) | AAATATGCCTATTCACAAGCTTCTGGTGGGCGACGAAGT |
| halphaI A114Q R (SEQ ID NO: 150) | ACTTCGTCGCCCACCAGAAGCTTGTGAATAGGCATATTT |
| halphaI A115T F (SEQ ID NO: 151) | AAATATGCCTATTCAGCAACTTCTGGTGGGCGACGAAGT |
| halphaI A115T R (SEQ ID NO: 152) | ACTTCGTCGCCCACCAGA AGTTGCTGAATAGGCATATTT |
| halphaI A115Q F (SEQ ID NO: 153) | AAATATGCCTATTCAGCACAGTCTGGTGGGCGACGAAGT |
| halphaI A115Q R (SEQ ID NO: 154) | ACTTCGTCGCCCACCAGACTGTGCTGAATAGGCATATTT |
| halphaI R165D F (SEQ ID NO: 155) | GTTCTTGGGTACTTAAACGACAACGCCCTTGATACTAAA |
| halphaI R165D R (SEQ ID NO: 156) | TTTAGTATCAAGGGCGTTGTCGTTTAAGTACCCAAGAAC |
| halphaI N166D F (SEQ ID NO: 157) | CTTGGGTACTTAAACAGGGACGCCCTTGATACTAAAAAT |
| halphaI N166D R (SEQ ID NO: 158) | ATTTTTAGTATCAAGGGCGTCCCTGTTTAAGTACCCAAG |
| halphaI E195W F (SEQ ID NO: 159) | TTCAATGTGTCTGATTGGGCAGCTCTACTAGAAAAGGCTG |
| halphaI E195W R (SEQ ID NO: 160) | CAGCCTTTTCTAGTAGAGCTGCCCAATCAGACACATTGAA |
| halphaI K40D F (SEQ ID NO: 161) | ATCCTTGGGATGCAGTAGACAATTTTTTGGAAAAATTT |
| halphaI K40D R (SEQ ID NO: 162) | AAATTTTTCCAAAAAATTGTCTACTGCATCCCAAGGAT |
| halphaI R69D F (SEQ ID NO: 163) | CAGTATGCCAATAATCCAGACGTTGTGTTTAACTTGAAC |
| halphaI R69D R (SEQ ID NO: 164) | GTTCAAGTTAAACACAACGTCTGGATTATTGGCATACTG |
| halphaI N73D F (SEQ ID NO: 165) | AATCCAAGAGTTGTGTTTGACTTGAACACATATAAA |
| halphaI N73D R (SEQ ID NO: 166) | TTTATATGTGTTCAAGTCAAACACAACTCTTGGATT |

TABLE 27-continued

| Primer name | Nucleotide sequences (5'-3') |
|---|---|
| halphaI Q89H F (SEQ ID NO: 167) | ATGATTGTAGCAACATCCCACACATCCCAATATGGTGGG |
| halphaI Q89H R (SEQ ID NO: 168) | ATGATTGTAGCAACATCCCACACATCCCAATATGGTGGG |
| malphaIH93Y F (SEQ ID NO: 169) | CACATCTGAGACGCGCCAATATGGTGGGGACCTCACAAAC |
| malphaIH93Y R (SEQ ID NO: 170) | GTTTGTGAGGTCCCCACCATATTGGCGCGTCTCAGATGTG |

The GST-fusion protein with the human α2I domain was expressed in logarithmically growing BL21 bacteria using IPTG as an inducing agent. Approximately 4 hours after induction, the bacteria were harvested and pelleted at 3000 RPM in 50 mL conical tubes. The pellet was resuspended in PBS containing 1% Triton X-100 and protease inhibitors. The homogenate was sonicated for 1 minute and centrifuged at 3000 RPM to clear the lysate of cellular debris. The GST-fusion protein was purified from bacterial lysates using glutathione-Sepharose beads (GE-Amersham) according to the manufacturer's instructions and eluted in TBS (pH 8.0) containing 20 mM free glutathione. The purified GST-α2 I domain bound collagen with same specificity as has been previously reported (Tuckwell et al., J Cell Sci. 108 (Pt 4):1629-37 (1995)), namely a greater affinity for Type I compared to Type IV collagen. It bound to immobilized TMC-2206 with an apparent $K_d$ by ELISA of 0.31 nM, which was comparable to the observed affinity of TMC-2206 binding to intact α2β1 integrin of 0.37 nM derived from the direct binding studies described in Example 2. The soluble GST-α2 I domain fusion protein was then evaluated for its ability to compete Eu-labeled TMC-2206 for binding to α2β1-coated plates as described in Example 2. The $K_i$ value for soluble GST-α2 I domain was found to be similar (0.18 nM compared to 0.28 nM to that obtained for unlabelled TMC-2206, indicating that the binding site for TMC-2206 lay within the α2 I domain and did not require the presence of the β1 subunit.

Studies were conducted to investigate the cation dependency of binding by TMC-2206. Cation dependency indicates that a binding moiety is targeting the divalent cation-binding site (MIDAS) of an integrin, and thus acting as a ligand mimetic. Collagen-binding to α2 is $Mg^{++}$-dependent under normal physiological conditions, whereas no binding occurs when $Mg^{++}$ is replaced by $Ca^{++}$ (Staatz et al., Cell Biol. 108(5):1917-24 (1989); Emsley et al., Cell 101(1):47-56 (2000)). For these studies, the GST-α2 I domain fusion protein was immobilized on Reacti-Bind glutathione-coated microtiter plates (Pierce Biotechnology, Inc. Rockford, Ill.) and the ability of Eu-labeled TMC-2206 to bind under different cation conditions (Ca- and Mg-free, $Ca^{++}$ or $Mg^{++}$ in concentrations ranging from 0.1 μM to 3 mM) was determined. Plates were coated by incubating 100 μL/well GST-α2I fusion protein (2.0 μg/mL in Divalent Cation-Free Binding Buffer: 50 mM HEPES, pH 7.4, 150 mM NaCl and 0.5% Tween-20) for 1 hour at room temperature, and wells were washed four times in divalent cation-free Wash Buffer. Wells were blocked using 100 μL/well Blocking Buffer (Wash Buffer containing 3.0 mg/mL IgG-free BSA [Jackson ImmunoResearch Laboratories, Inc., West Grove, Pa.]) for 1 hour at room temperature, washed four times in divalent cation-free Wash Buffer, and soaked in divalent cation-free Wash Buffer (300 μL/well) for 45 minutes at room temperature. Wells were further equilibrated in Wash Buffer (300 μL/well) containing the desired level of divalent cations for 30 minutes and then incubated for 1 hour at 37° C. in the presence of 41 pM, 199 pM 345 pM or 1 nM Eu-labeled TMC-2206 or control antibody. The murine TMC-2206 antibody bound in a concentration-dependent manner, with similar potency under all conditions, indicating that its binding to the α2 I domain was cation-independent, and therefore did not involve the MIDAS site. Eu-labeled control IgG did not bind to the α2β1 integrin-coated wells confirming that the binding was specific.

Additional studies were conducted to investigate the binding site of TMC-2206. Integrin ligands typically have a key acid which forms the final chelating bond for the divalent metal ion (Haas and Plow, Curr. Opin. Cell. Bio. 1994; Lee et al., Structure 1955) a feature shared by many integrin antagonists, including the anti-α1 integrin mAb, AQC2 (Karpusas et al., J. Mol. Biol. 2003) where the acid is provided by residue D101 within CDR-H3. By analogy, the D100 of the TMC-2206 CDR-H3 might provide such an interaction with the α2 MIDAS. Therefore, two variant murine VH-containing antibodies were generated, one carrying a D100A and one a D100R mutation. Their ability to compete for Eu-TMC-2206 binding was then evaluated in the $K_i$ assay in comparison with the TMC-2206 mouse-human chimeric antibody. The D100A mutant was completely inactive at concentrations up to 0.9 μM which represented a greater than 1600-fold shift in potency relative to that of the mouse-human chimeric TMC-2206 antibody. In contrast, the reverse charge mutant D100R was almost as potent as the mouse-human TMC-2206 chimeric antibody as evidenced by the similar $K_i$ values (0.41 nM compared to 0.52 nM). This provides evidence against any role for D100 residue of TMC-2206 in docking into the metal chelation complex that forms the MIDAS ligand site.

Additional studies were conducted to investigate the binding specificity of TMC-2206, including epitope mapping studies, with this murine monoclonal antibody that is directed against the human α2β1 integrin I domain. TMC-2206 cross-reacts with rat α2β1 integrin but does not cross react with mouse α2β1 integrin. Since α2β1 integrin proteins share high homology across species, residues within the α2β1 that are important for antibody binding were identified by methods that would identify the differences that exist between those species that cross react with the antibody compared with those that do not (e.g., Champe et al., J. Biol. Chem. 270(3): 1388-94 (1995); Karpusas et al., J. Mol. Biol. 327(5):1031-41 (2003); Bonnefoy et al., Blood 101(4):1375-83). The I crystal structure of the domain of α2 integrin alone and when complexed with its target ligand, collagen, has been analyzed (Emsley et al., J. Biol. Chem. 272(45):28512-7 (1997); Emsley et al., Cell 101(1):47-56 (2000)). A sequence comparison of human α2 I (SEQ ID NO:11), rat α2 I (SEQ ID NO:93), and mouse α2 I (SEQ ID NO:94), domains obtained from Genbank submissions is shown in Table 28. This analysis reveals that mouse I domain contains 14 residues that differ from both the rat and human α2 I domains (shown in bold and underlined in Table 28). These residues were used to study further the TMC-2206 binding epitope.

to the deposited sequence, which allowed the region between residue 16 and 21 (residues 139 through 144 of the intact α2 integrin) of the rat domain to be accurately translated. This amino acid sequence, ACPSLV, was identical to the mouse residues at these positions.

TABLE 28

```
Human α2I    1 SPDFQLSASF SPATQPCPSL IDVVVVCDES NSIYPWDAVK NFLEKFVQGL DIGPTKTQVG
Rat   α2I    1 SPDFQSLTSF SPAV------ QDVVVVCDES NSIYPWEAVK NFLEKFVQGL DIGPKKTQVA
Mouse α2I    1 SPDFQFLTSF SPAVQACPSL VDVVVVCDES NSIYPWEAVK NFLVKFVTGL DIGPKKTQVA Human α2I   61 LIQYANNPRV VFNLNTYKTK EEMIVATSQT SQYGGDLTNT FGAIQYARKY AYSAASGGRR
Rat   α2I   61 LIQYANDPRV VFNLTTYKNK EDMVQATSET RQYGGDLTNT FKAIQFARDI AYLPESGGRP
Mouse α2I   61 LIQYANEPRI IFNLNDFETK EDMVQATSET RQHGGDLTNT FRAIEFARDY AYSQTSGGRP Human α2I  121 SATKVMVVVT DGESHDGSML KAVIDQCNHD NILRFGIAVL GYLNRNALDT KNLIKEIKAI
Rat   α2I  121 GATKVMVVVT DGESHDGSKL QTVIQQCNDD EILRFGIAVL GYLNRNALDT KNLIKEIKAI
Mouse α2I  121 GATKVMVVVT DGESHDGSKL KTVIQQCNDD EILRFGIAVL GYLNRNALDT KNLIKEIKAI Human α2I  181 ASIPTERYFF NVSDEAALLE KAGTLGEQIF SIEGTVQGGD NFQMEM
Rat   α2I  181 ASTPTERYFF NVADEAALLE KAGTLGEHIF SIEGTVQGGD NFQMEMAQ
Mouse α2I  181 ASTPTERYFF NVSDEAALLE KAGTLGEQIF SIEGTVQGGD NFQMEMSQ
```

Both mouse and rat GST-α2 I domain were cloned as GST-fusion proteins to confirm the appropriate cross-reactivity was retained by the respective I domains by PCR methodology such as that described in Example 3. The murine α2 I domain was cloned from mRNA isolated from a Balb/C mouse kidney by RT-PCR using the primers malphal F (SEQ ID NO:121) and malphal R (SEQ ID NO:122) and the rat α2 I domain from a Sprague Dawley rat kidney by RT-PCR using the primers ralphal F (SEQ ID NO:123) and ralphal R (SEQ ID NO:124). In addition two non-human primate α2 I domains were cloned from white blood cell pellets obtained by low speed centrifugation of fresh blood drawn from individual rhesus and cynomolgus monkeys. The white cells were then snap-frozen in liquid nitrogen. A total of $5\times10^6$ (rhesus) and $2\times10^6$ (cynomolgus) cells were lysed in 1 mL of Trizol (Invitrogen, Cat#15596-026) and total RNA was prepared as described above. The final RNA pellet was resuspended in 50 μl of DEPC-treated $H_2O$. This served as the template for the first reverse transcriptase (RT) step. The RT reaction consisted of 8 μl (2.24 μg for Rhesus mRNA, 1.44 μg for cynomolgus mRNA) cellular RNA, 1 μl (10 mM) of DNTPs and 1 μl (2 μM) of the human I domain forward primer (GGG-GATCCAGTCCTGATTT; SEQ ID NO:119). This mixture was incubated at 65° C. for 5 min, chilled on ice. Five μl of this cDNA was then used as the template for the PCR amplification reaction, using the human forward and reverse primers (Forward: GGGGATCCAGTCCTGATTT, SEQ ID NO:119; Reverse: GGAATTCAACAGTACCTT, SEQ ID NO:120). The cycle times were 1 cycle at 94° C. for 30 sec, 94° C. for 30 sec., 55° C. for 30 sec., 40 cycles at 68° C. for 1 min. and 1 cycle at 68° C. for 5 min. The PCR products were separated by 1% agarose gel electrophoresis and the band (of expected size) was purified directly from the agarose gel, digested with BamHI and EcoRI and cloned into the same sites in the pGEX-2TK vector and transformed into BL21 bacteria.

Single colonies were isolated and the inserts sequenced using a Beckman CEQ 8000 DNA analyzer to verify the identity of the murine and rat α2 I domain and determine the sequence homology of the two monkey species with human. The cloned murine sequence showed exact identity with I domain region of the deposited sequence, NM_008396.1. Similarly, the cloned rat sequence was identical to the Genbank entry for the rat integrin, XM_34156.1, with the exception that the cloned sequence contained 6 additional residues At the nucleotide level the two primate sequences showed a very high homology with human α2 I domain sequences. The rhesus α2 I domain in nucleotide sequence (SEQ ID NO:104) showed only one nucleotide difference to the human nucleotide sequence, within codon 50, a change from CTT to CTG, but since both encode a leucine, the deduced protein sequences were identical to human. The cynomolgus α2 I domain nucleotide sequence (SEQ ID NO:103) was identical to human except for codon 40, where there was a change from the human AAG to GAC. This results in a change from a lysine to an aspartic acid residue at this position. However, further studies revealed that this nucleotide change is due to a polymorphism that is not conserved across animals, as other cynomolgus exhibited a 100% homology to the human α2 I domain (see Example 18).

The fusion proteins were then expressed and purified as described above for the human GST-α2 I domain fusion protein. Analysis of the material eluted off the glutathione-Sepharose column indicated that the rodent fusion proteins contained aggregated forms. Therefore, these and the primate fusion proteins were further purified by size exclusion chromatography on a Sephadex 75 10/30 (GE-Amersham) column (primate) by FPLC on an Akta-Basic FPLC system (GE-Amersham) to yield a monomeric fraction. The GST-fusion proteins were then tested for their ability to bind immobilized TMC-2206 as well as their ability to compete Eu-labeled TMC-2206 from binding to immobilized human α2β1 integrin. The $K_i$ assays were performed as described above in Example 2. To assess direct binding to TMC-2206, Immulon 4 plates were coated using 50 μL of a bicarbonate solution (pH 9.0) containing 5 μg/ml of TMC-2206. Plates were sealed and coating occurred overnight at 4° C. The next morning, the plates were washed twice with TBS solution and then blocked using 200 μL of the blocking solution described above for 1 hour at room temperature with shaking. After blocking, the blocking solution was removed but the wells were not washed. Instead, a serial dilution of GST fusion protein was made, added to the wells and then incubated for 2 hours at room temperature with shaking. The wells were then aspirated and a TBS washing buffer applied for 5 minutes at room temperature. The washing step was repeated twice more before the secondary antibody was applied. The secondary antibody step consisted of Amersham's HRP-conjugated rabbit anti-GST antibody diluted 1:2000 in blocking buffer. One hundred μL of secondary antibody was added to each well and incubated at room temperature for 1.5 hours with shaking. The wells were again aspirated and washed three times with wash buffer before adding the substrate reaction mixture. One hundred μL of substrate reaction mixture (1:1 dilution of TMB kit) was then added to each well for 6 minutes. The reaction was stopped by adding 100 μL of 0.1M $H_2SO_4$. The reaction within the wells was then read and quantified by spectrophotometric absorption using the Molecular Dynamics plate reader and associated Softmax software, respectively. $K_d$ values were then estimated from the $EC_{50}$ values using Prism software (Graphpad, CA).

There was a 3-fold shift in $K_d$ for rat α2 I binding to TMC-2206 compared to human α2, while the murine α2 I-GST fusion protein showed only slight specific binding at the highest concentration, representing a greater than 1500-fold shift in affinity (see Table 29). The rhesus GST-α2 I showed comparable affinity to human whereas unexpectedly the cynomolgus monkey GST-α2 I showed no detectable affinity for TMC-2206 up to concentrations of 1 μMa. These relative rankings were also observed in the $K_i$ assay. The lack of cross-reactivity of the cynomolgus I domain-GST fusion protein for TMC-2206 indicates that the K40 residue may be a determinant of the epitope. The difference in affinity of the cloned rat GST-α2 I ($K_d$ of 0.54 nM and $K_i$ value of 3.8 nM) as compared with the GST-human α2 I fusion protein ($K_d$ of 0.18 and $K_i$ value of 0.33 nM) is consistent with the shift in $EC_{50}$ values found in assays of TMC-2206 for its ability to antagonize the adhesion of fresh rat platelets compared to human platelets to Type I collagen, as described above in Example 9. Similarly the lack of cross reactivity of the GST-mouse α2 I fusion protein for TMC-2206 is consistent with the lack of cross reactivity of the antibody with intact mouse α2β1 integrin.

TABLE 29

| Fusion Protein | $K_d$ (nM) | $K_i$ (nM) |
| --- | --- | --- |
| hα2I | 0.18 | 0.33 |
| Rat-α2 | 0.54 | 3.8 |
| Mouse-α2 | ND* | ND* |
| Cynomolgus α2 | ND@40 nM | ND* |
| Rhesus α2 | 0.04 | 4.4 |
| GST | ND* | ND* |

*ND indicates not detectable up to concentrations of ~1 μM

In additional studies, the 14 residues corresponding to the unique differences in the murine α2 I domain as compared to the human and rat α2 I domains were individually mutated in the cloned human α2 I domain-fusion protein by PCR using standard molecular biology methods (primer sequences are shown in Table 30). Individual bacterial clones were sequenced to verify the correct mutation had been incorporated into the I domain. One intended variant, the G101R mutant, did not yield a correct clone and was not studied further. The primers designed to create the Y93H mutation resulted in one set of clones that carried instead a Y93D mutation. Both Y93 variants were evaluated. The remainders were all correct in sequence. The resulting protein variants were expressed and purified as described above for the wt human α2 I domain-GST fusion proteins. These were then tested for activity in three ways: first for their relative ability to bind the different collagens to ensure that the mutations did not introduce gross conformational perturbations that would interfere with ligand binding; second, for their apparent affinity for TMC-2206 (direct binding to immobilized TMC-2206 measured by ELISA) and third, for their ability to act as competitive ligands in the $K_i$ assay. The $K_i$ and apparent $K_d$ data are also summarized in Table 30.

TABLE 30

| Fusion Protein Mutations | $K_{d\ apparent}$ (nM) | $K_i$ (nM) |
| --- | --- | --- |
| hα2 I domain | 0.31 | 0.18 |
| hα2 I domain I21V | 0.28 | 0.24 |
| hα2 I domain E44V | 0.23 | 0.35 |
| hα2 I domain Q48T | 0.19 | 0.73 |
| hα2 I domain N67E | 0.28 | 0.40 |
| hα2 I domain V70I | 0.44 | 0.86 |
| hα2 I domain V71I | 0.19 | 0.83 |
| hα2 I domain T76D | 0.17 | 0.15 |
| hα2 I domain Y77F | 0.22 | 0.39 |
| hα2 I domain K78E | 0.16 | 0.51 |
| hα2 I domain Y93D | ND@440 nM | ND* |
| hα2 I domain Y93H | 6.1 | ND* |
| hα2 I domain Q105E | 0.15 | 0.38 |
| hα2 I domain A114Q | 0.19 | 0.64 |
| hα2 I domain A115T | 0.19 | 0.76 |

*ND = not detectable up to concentrations of ~1 μM.

Of the 13 residues evaluated, 12 were changed to the murine counterpart with minor effects on affinity, but the changes in Y93 caused a marked loss in affinity as shown in Table 31. The Y93D mutation abolished the ability to bind to antigen even at concentrations 3-logs above the $\kappa_d$ value for the wt I domain GST fusion protein. The change to the murine histidine (Y93H) caused a 23-fold decrease in apparent affinity for the TMC-2206 antigen. Both mutations abolished the ability of the GST-I domain to antagonize binding of Eu-labeled antibody to its antigen. Changing the murine H93 to a Y conferred the ability of the murine α2 I domain to bind TMC-2206, albeit with a 200-fold decrease in potency relative to the wt human α2 I domain, as shown in Table 31.

TABLE 31

| | Primers used | | $K_i$ (NM) |
| --- | --- | --- | --- |
| Fusion Protein Mutations | | | |
| hα2 I domain | | | 0.28 |
| hα2 I domain E195W | halphaIE195W F | (SEQ ID NO: 159) | 12.8 |
| | halphaIE195W R | (SEQ ID NO: 160) | |
| hα2 I domain R165D | halphaIR165D F | (SEQ ID NO: 155) | 1987 |
| | halphaIR165D R | (SEQ ID NO: 156) | |
| hα2 I domain N166D | halphaIN166G F | (SEQ ID NO: 157) | ND |
| | halphaIN166G R | (SEQ ID NO: 158) | |

TABLE 31-continued

| | Primers used | $K_i$ (NM) |
|---|---|---|
| hα2 I domain Y93F | HalphaIY93F F (SEQ ID NO: 145)<br>halphaIY93F R (SEQ ID NO: 146) | ND |
| hα2 I domain K40D | halphaIK40D F (SEQ ID NO: 161)<br>halphaIK40D R (SEQ ID NO: 162) | ND |
| hα2 I domain N73D | halphaIN73D F (SEQ ID NO: 165)<br>halphaIN73D R (SEQ ID NO: 166) | 2.17 |
| hα2 I domain Q89H | halphaIQ89H F (SEQ ID NO: 167)<br>halphaIQ89H R (SEQ ID NO: 168) | 4.46 |
| Murine α2I mutations | | |
| mα2 I domain H93Y | malphaIH93Y F (SEQ ID NO: 169)<br>malphaIH93Y R (SEQ ID NO: 170) | 20.2 |

Comparison of the crystal structures for the human α2 I domain in the closed (NCBI PDB entry 1AOX) and open, ligand-bound (PDB entry 1DZI) conformation reveals that Y93 is located on a face of the I domain that is behind the α7 helix, which was shown to undergo a large downward movement upon ligand binding (Emsley et al., J. Biol. Chem. 272:28512 (1997) and Cell 100:47 (2000). Although not previously identified as a conformational change associated with ligand binding, examination of the crystal structures indicates that in the closed conformation, the aromatic ring of Y93 extends out from the protein surface, but flips sideways and downwards to align along the face of the I domain in the open, ligand-bound conformation. To investigate whether the binding of to TMC-2206 to α2β1 integrin depends on a given conformational state, mutations were introduced in the I domain to favor an open conformation of the I domain. The E195W mutation (E318 in the intact α2 integrin) has been reported to lock the human α2 I domain in the open conformation (Aquilina et al., Eur. J. Biochem. 269(4):1136-44 (2002)) so its use enables a distinction to be made as to whether an antibody recognizes an activation-dependent conformation or not. In addition, the crystallographic studies have shown that E195 forms a buried salt bridge with residue R165 located in the αC loop, serving to hold the αC loop in a conformation that shields the ligand binding site (Emsley et al., Cell 100:47 (2000)). The αC loop assumes an extended conformation in the open position and both the R165 and the adjacent R166 residue have been postulated to contribute to collagen binding (Emsley et al., J Biol Chem 272:28512 (1997) and Cell 100:47 (2000); Käpylä et al., J Biol Chem 275:3348 (2000)). Therefore, four mutations were constructed, the E195W; an R165D mutation to reverse the charge and hence disrupt the salt bridge that forms with E195W in the closed conformation, and an N166D mutation, again to reverse the charge within the αC helix. The E195W change caused a 45-fold decrease in $K_i$ values as shown in Table 31 indicating that the TMC-2206 antibody exhibits a higher affinity for the closed conformation. Both the R165D and N166D change abolished the ability of the I domain to bind the TMC-2206 epitope even at concentrations as high as 1 μM, again suggesting that the TMC-2206 antibody recognizes a closed conformation.

From the mutagenesis and conformation studies, it appears that the Y93 in the closed conformation may play a role in TMC-2206 binding, and may provide one determinant for the species specificity of the binding. The unexpected results obtained with the polymorphic cynomolgus I domain indicated that the K40 residue may also play a role in the antigen—TMC-2206 interaction. Computer modeling of the TMC-2206 antibody indicated that the CDRs form a relatively flat binding site, which suggests that the antibody makes multiple antigen contacts. Since several residues within the CDRs are charged, the charged residues surrounding the Y93 in the closed position that also show marked positional changes in the open conformation were identified from the PDB structures of the two open and closed conformers as K40, R69, N73 and Q89. The charges of three of these residues were reversed by generating the following mutants, K40D, R69D, and N73D and modified in the fourth by generating a Q89H variant, as shown in Table 31. In addition, a third variant of residue 93 was made, a change from tyrosine to phenylalanine, to determine whether the aromatic character of the tyrosine was the important structural characteristic, or whether activity was dependent on the aromatic-hydroxyl character that is characteristic of tyrosine. In the case of this set of mutations, all were subjected to HPLC purification to enrich for the monomeric fraction of the protein preparations obtained off the glutathione-Sepharose affinity column. Each variant was first tested for functionality by assessing collagen binding. All except the R69D variant bound collagen with a similar $EC_{50}$ value to the wt human α2 I domain. Consequently, the R69D was not studied further. Of the remaining mutants, introducing the K40D variant abolished the ability to compete for binding to the TMC-2206 epitope. This was consistent with the results obtained with the cloned cynomolgus I domain which shows polymorphism at this residue (lysine to aspartic acid change). Likewise, the Y93F mutation also abolished the ability to compete for EU-TMC-2206 binding. The N73D and the Q89H showed a 7.8 and 15.9-fold decrease in Ki values respectively (Table 30). Taken together the mutation data indicate that the K40, Y93, R165 and N166 residues may be determinants for TMC-2206 binding to its epitope, and that the N73 and Q89 also contribute towards energy of binding.

These data indicate that the TMC-2206 antibody, its derivatives and antibodies like TMC-2206 (e.g., AK7) that recognize the same or similar epitope as TMC-2206, (see e.g., Example 13) are atypical, non-ligand mimetic antagonists of α2β1-collagen interactions. This conclusion is supported by i) their ability to block α2β1 integrin-mediated adhesion to collagen in a divalent cation-independent manner, ii) this inhibition does not involve the interaction of a critical acidic group, such as D100 within H-CDR3, with the MIDAS, iii) the antibody binds to a surface of the I domain that is distal from the direct ligand binding site, iv) the TMC-2206 binding site favors the closed conformation of the receptor and encompasses amino acid residues K40, N73, Q89, Y93, R165 and N166. Consequently, TMC-2206 and antibodies like TMC-2206 (e.g., that recognize the same or similar epitope as TMC-2206) binding will not support the integrin-mediated outside-in signaling that would normally occur upon engagement of the cognate collagen ligand, and it is this mode of binding that may contribute to the non-bleeding profile of this antibody and antibodies like TMC-2206.

EXAMPLE 13

Studies were carried out to compare the binding of other function blocking anti-α2 integrin antibodies with TMC-2206. Results from mapping studies as described in Example 12 indicated that the TMC-2206 antibody appeared to bind to a closed conformation of the α2 integrin I domain and/or did not act as a ligand mimetic. These unexpected results, along with the unexpected results from the platelet-related studies described in Examples 8, 9, 10 and 11, demonstrated that the TMC-2206 epitope is particularly advantageous and that antibodies similar in their functional properties to TMC-2206 are particularly useful. Screening methods for identifying such similar antibodies were developed as described herein, and antibodies were identified by such methods.

To determine which function blocking anti-α2 integrin antibodies bound in a similar manner to TMC-2206, a series of cross competition studies were performed. For studies of commercially available anti-human α2 integrin antibodies, human GST-α2 I fusion protein was immobilized on microtiter plates as above. The antibodies tested were AK7 (Mazurov et al., Thromb. Haemost. 66(4):494-9 (1991)), P1E6 (Wayner et al., J. Cell Biol. 107(5):1881-91 (1988)), 10G11 (Giltay et al., Blood 73(5):1235-41 (1989)) and A2-11E10 (Bergelson et al., Cell Adhes. Commun. 2(5):455-64 (1994)) commercially available from Chemicon, (Temecula, Calif.; catalogue numbers, CBL477 (AK7); MAB1950 (P1E6); MAB1988 (10G11) and Upstate, (Waltham, Mass.; A2-11E10, catalogue number 05-227), respectively. The antibodies were tested together with the same lot of platelet α2β1-coated microtiter plates used in the epitope mapping studies for their ability to antagonize the binding of Eu-labelled TMC-2206. In another set of studies, the ability of the antibodies to antagonize binding of freshly isolated, resting platelets to Type I collagen was determined. Thus, the ability of different antibodies directed against human α2 integrin to antagonize binding of Eu-labelled TMC-2206 antibody to platelet α2β1-coated microtiter plates were measured as $K_i$ values, and to antagonize adhesion of resting platelets to Type I collagen under static conditions were measured as $EC_{50}$ values. The results, presented in Table 32, demonstrate that the AK7 antibody is an effective competitor of TMC-2206. Clone 10G11 showed a clear biphasic competition of TMC-2206, suggesting that it did not act as a simple competitive antagonist. A2-IIE10 showed a 10-fold shift compared to TMC-2206 at blocking platelet adhesion, but an approximately 350-fold shift in its ability to compete Eu-labeled TMC-2206, again indicating that there was not a direct concordance between the two antibodies. P1E6 failed to show any effect in either assay, which indicated that it recognizes an activated conformation.

TABLE 32

| Competing antibody | $K_i$ (nM) | $EC_{50}$ |
|---|---|---|
| TMC-2206 | 0.11 | 6 |
| AK7 | 0.07 | |
| 10G11 | High affinity: 0.05 | >200 |
| | Low affinity: 7.7 | |
| A2-IIE10 | 29.6 | 68 |
| P1E6 | *[No competition] | *[No effect] |
| Control IgG | *[No competition] | *[No effect] |

*Not detected under assay conditions described.

These data demonstrate for the first time that not all function blocking antibodies bind to α2 integrin in the same manner, and further demonstrate methods for the identification of a novel subgroup of antibodies similar in epitope specificity to TMC-2206 with similar function blocking activities. These data also demonstrate that this novel subgroup of anti-α2 antibodies, that includes TMC-2206 and antibodies similar in epitope specificity to TMC-2206, are characterized by an unexpected lack of in vivo bleeding complications and/or by a lack of platelet α2β1 integrin activation. The epitope specificity, function blocking activities, and advantages (e.g., not activating platelets) are not characteristics of all anti human α2β1 function blocking antibodies, but rather the novel characteristic of a novel subgroup of antibodies that include TMC-2206 and similar antibodies, including derivatives and/or variants of TMC-2206 that can be identified and/or selected as described herein.

Having shown that not all function-blocking antibodies that bind to the α2 I domain bind to the same or similar (e.g., overlapping) TMC-2206 epitope, studies were performed to determine whether the surrogate antibody used for murine efficacy studies had similar properties to TMC-2206. Since the Ha1/29 antibody cross-reacts with rat and mouse α2 integrin, and the TMC-2206 antibody binds to both human and rat α2 integrin, the rat GST-fusion protein was used to determine whether the two antibodies bound to overlapping sites (e.g., shared epitope specificity). For this, rat GST-α2 I domain fusion protein was immobilized on Reacti-Bind glutathione-coated microtiter plates (Pierce Biotechnology, Inc. Rockford, Ill.). First the $K_d$ of Eu-TMC-2206 binding to immobilized GST-α2 I domain from human and rat at 37° C. was determined as described in Example 2. Scatchard analysis of bound versus free Eu-TMC-2206 indicated the $K_d$ values to be 0.2 nM for human α2 I domain and 1.3 nM (a 6-fold decrease) for rat α2 I domain. Next, the ability of Eu-labeled TMC-2206 to bind to the rat α2 I domain in the presence of different concentrations of competing antibody was assessed as described in Example 2 using the $K_d$ value of 1.3 nM to derive the Ki value from the observed $EC_{50}$ values. The Ha1/29 (Mendrick and Kelly, Lab Invest. 69(6):690-702 (1993)) but not the HMα2 antibody (Miyake et al., Eur. J. Immunol. 24:2000-2005 (1994)) was an effective antagonist of Eu-TMC-2206 binding, indicating that the Ha1/29 antibody bound to similar (e.g., overlapping) sites to the TMC-2206 binding site.

EXAMPLE 14

Another study was conducted on exemplary IgG4 antibodies having a hVH14.0 γ4 heavy chain (SEQ ID NO:174) or a hVH12.0 γ4 heavy chain (SEQ ID NO:176) and a hVL 10.0 Q light chain (SEQ ID NO:178). This study assessed whether binding of these IgG4 antibodies leads to platelet activation, as measured by effects on collagen-induced platelet aggregation. Blood samples were collected via venipuncture from the antecubital vein into vacuum filled tubes contain 3.8% sodium citrate after discarding the first 3.0 ml of free running blood. All antibodies were diluted in saline to final concentrations of 140 µg/ml. Each disposable cuvette (containing a disposable electrode assembly) was aliquoted with 0.5 ml citrated whole blood and with 0.5 ml of saline or an antibody solution. Each cuvette was pre-warmed to 37° C. for 5 minutes in the warming well of the aggregometer (Model 591A, Chrono-Log, Havertown, Pa.), then placed into the reaction well, the baseline set, and then either 20 µl of saline or collagen (1 mg/ml; equine type I, Chrono-Log)) was added to initiate the aggregation reaction. During aggregation an accumulation of platelets formed on the exposed surfaces of the electrodes, resulting in an increase in impedance. Data acquisition proceeded for 6 minutes with the change in impedance (ΔΩ, ohms) recorded by a chart recorder (Model 707, Chrono-Log).

The data (Table 33) were analyzed by the Kruskal-Wallis test, which tested the hypothesis that the population medians of each (saline or collagen) of the four groups were equivalent, and would reject this hypothesis (95% confidence) if the P-values were less than or equal to 0.05. For the saline group (P-value=0.148) neither the isotype-control nor the two humanized antibodies induced human platelet aggregation compared to the saline negative control. For the collagen group (P-value=0.201), neither the isotype-control nor the two humanized antibodies inhibited collagen-induced aggregation compared to the saline negative control. The results of this study and those from Example 8 show that the binding of TMC-2206 and both humanized IgG4 variant antibodies has no effect on collagen-induced platelet aggregation when tested in vitro at all the concentrations tested.

TABLE 33

| | | Test Article | | | |
|---|---|---|---|---|---|
| Agonist | Saline | hIgG4/κ | hIgG4/κ VH14.0/ VL10.0Q | hIgG4/κ VH12.0/ VL10.0Q | P-value |
| Saline | 1.0, 2.4, 2.8, 2.8, 2.8, 3.8 | 2.4, 5.2, 5.6, 5.6 | 2.2, 3.0, 3.4, 4.2 | 2.8, 3.6, 3.8, 5.2 | 0.148 |
| Collagen | 17.8, 18.2, 19.4, 20.4, 21.1, 21.6 | 15.3, 17.2, 18.4 | 15.0, 15.2, 16.0, 21.8 | 13.2, 14.8, 18.1, 20.0 | 0.201 |

EXAMPLE 15

Humanized TMC-2206 (hIgG4/κVH12.0/VL10.0Q) was tested in its ability to block the binding α2β1-integrin mediated cell adhesion to type-I collagen using CHO-α2 cells, HT1080 (human fibrosarcoma) cells, and human platelets following the procedures outlined in Example 2. Humanized TMC-2206 was a potent inhibitor of cell binding to collagen with $EC_{50}$ values comparable to TMC-2206 (Table 34).

TABLE 34

| Type I Collagen Source | Cells | TMC-2206 $EC_{50}$(nm) (mean ± SEM) | Humanized TMC-2206 $EC_{50}$(nm) (mean ± SEM) |
|---|---|---|---|
| Rat Tail | Human Platelets | 3.1 ± 0.3 | 4.7 ± 0.3 |
| | HT1080 | 0.90 ± 0.02 | 0.90 ± 0.27 |
| | CHO-α2 | 0.58 ± 0.51 | 1.9 ± 1.5 |

TABLE 34-continued

| Type I Collagen Source | Cells | TMC-2206 $EC_{50}$(nm) (mean ± SEM) | Humanized TMC-2206 $EC_{50}$(nm) (mean ± SEM) |
|---|---|---|---|
| Human Placenta | Human Platelets (n = 1) | 8.44 | 13.1 |

EXAMPLE 16

Humanized TMC-2206 was evaluated for its ability to bind to immobilized human α1β1 in an ELISA format. Human α1β1 integrin (Chemicon International) was diluted in Coating Buffer (25 mM Tris, pH 7.5, 150 mM NaCl, 1 mM $MgCl_2$) to a final concentration of 0.5 µg/ml. 96-well immunoplates were coated with α1β1 at 50 ng/well and incubated overnight at 4° C. The plates were washed three times with Wash Buffer (50 mM Tris, pH 7.5, 150 mM NaCl, 2 mM $MgCl_2$, 0.5% Tween-20) and blocked with 5% w/v/skim milk in Wash Buffer for one hour at room temperature. Humanized TMC-2206, human IgG4/κ (isotype control), mouse anti-human α1 (FB-12, Chemicon International) antibodies were serially diluted in Binding Buffer (0.1 mg/ml BSA, IgG free, in Wash Buffer). Fifty microliters/well of the diluted antibody solutions were added to the α1β1-coated plates, incubated for one hour at room temperature, and then washed three times. Goat anti-human IgG alkaline phosphatase conjugate (secondary antibody; Jackson ImmunoResearch Laboratories, West Grove, Pa.) was added to the wells containing the isotype control and humanized TMC-2206; goat anti-mouse IgG alkaline phosphatase conjugate (Sigma) was added to wells containing FB-12. After a one-hour incubation at room temperature, the plates were washed three times, incubated in substrate solution (1 mg/ml 4-nitrophenyl phosphate, 0.1 M diethanolamine, 5 mM $MgCl_2$, pH 9.8) for 20 minutes, and terminated with NaOH. The absorbance (405 nm) was read using a Spectramax Plus plate reader using Softmax Pro software. Similar to TMC-2206, humanized TMC-2206 and the IgG4/κ antibodies did not bind to α1β1. The control anti-α1β1 antibody (FB-12) bound to α1β1 with an $EC_{50}$ of 0.79±0.15 nM.

EXAMPLE 17

The $K_D$ and $K_i$ values for both the TMC-2206 and humanized TMC-2206 MAbs binding to immobilized α2β1 were determined using the competitive binding assay. Wells in a 96-well microtiter plate were coated with platelet α2β1-integrin (custom-coated with human platelet α2β1 by GTI Inc., WI) and then blocked with nonfat milk. Humanized TMC-2206 antibody was labeled with Eu-N1-ITC reagent, approximately 2 mg was suspended into and dialyzed against phosphate buffered saline (PBS; 1.47 mM $KH_2PO_4$, 8.1 mM $Na_2HPO_4$; pH 7.4, 138 mM NaCl and 2.67 mM KCl). After concentration in prewashed MicroSep concentrators [30-kDa cutoff; Pall Life Sciences at 9500 rpm (7000×g) in a JA-20 rotor (Beckman Instruments, Inc.] for 20 minutes at 4° C.), the antibody was adjusted to 4.0 mg/mL with PBS, 100 mM $NaHCO_3$, pH 9.3. The MAb/bicarbonate mixture (0.250 mL) was gently mixed into a vial containing 0.2 mg $N^1$-(p-isothiocyanatobenzyl)-diethylenetriamine-$N^1,N^2,N^3,N^3$-tetraacetic acid chelated with $Eu^{3+}$ (Eu-N1-ITC; Perkin Elmer Life Sciences) and incubated overnight at 4° C. without stirring. The labeled antibody mixture was applied to a PD-10 column (GE Biosciences, Piscataway, N.J.) pre-equilibrated with Running Buffer (50 mM Tris, pH 7.4 and 138 mM NaCl). Fractions (0.5 mL) were collected and assayed for total protein (Bradford reagent; Bio-Rad Laboratories, Hercules, Calif.) using a SpectraMax 384 absorbance plate reader and for europium after 1:10.000 dilution in DELFIA Enhancement Solution (Perkin-Elmer) by time-resolved fluorescence (TRF) using a Victor2 multi-label plate reader (Perkin Elmer). The fractions that were positive for both protein and europium label were pooled, applied to a new PD-10 column, and samples collected and assayed for total protein and for europium content by TRF calibrated against a europium standard solution (Perkin-Elmer) to calculate the fluor:protein ratio. The Eu-humanized-TMC-2206 was then applied to the blocked $\alpha2\beta1$-integrin microtiter plates in a volume of 10 μL/well. After incubating the sealed plates for 1 hr at 37° C. to allow binding to reach equilibrium, 2 μL samples were transferred from each well into a fresh well containing DELFIA Enhancement Solution (100 μL/well) for the measurement of free (unbound) label. Enhancement Solution (100 μL/well) was added to the emptied wells for the measurement of bound label. The plate was shaken (Titer Plate Shaker, speed setting of 5, 5 minutes at room temperature) and TRF intensities were read using the Victor2 multi-label plate reader. The $K_D$ values were calculated by Scatchard analyses.

Relative binding potencies to immobilized $\alpha2\beta1$ integrin were analyzed by measuring $K_i$ values in a competition assay using 100 pM Eu-humanized-TMC-2206 in the presence of varying concentrations of unlabeled TMC-2206 antibody or humanized TMC-2206 as competitors, using an assay system similar to that described above in this example. Test antibody combinations were then applied to the $\alpha2\beta1$ integrin coated wells, tested over a concentration range of from $10^{-11}$ to $10^{-7}$ M, and following the specified time, the amount of bound Eu-humanized-TMC-2206 was determined. The inhibition curves were fitted with the "one site competition" model using Prism software (GraphPad, Inc.) to obtain $IC_{50}$ values and to calculate the $K_i$ using the equation of Cheng and Prusoff (1973) and the respective values for $K_D$ from above.

The $K_D$ and $K_i$ values for TMC-2206 and humanized TMC-2206 were within 2-fold of each other (Table 35). Therefore the binding affinities of TMC-2206 and humanized TMC-2206 to immobilized $\alpha2\beta1$ were similar.

TABLE 35

| Affinity Parameter | TMC-2206 | Humanized TMC-2206 |
|---|---|---|
| $K_D$ | 0.72 ± 0.18 nm | 1.29 ± 0.17 nm |
| $K_i$ | 0.21 ± 0.08 nm | 0.41 ± 0.06 nm |

TMC-2206 and humanized TMC-2206 were subjected to surface plasmon resonance (SPR) analysis to determine the kinetic dissociation and associate constants, $k_d$ and $k_a$ (also known as $k_{off}$ and $k_{on}$), respectively to the $\alpha2$ I domain. SPR, a method for characterizing macromolecular interactions, is an optical technique that uses the transient wave phenomenon to exquisitely measure minute changes in refractive index very close to a sensor surface. The binding between an antigen in solution (e.g., fusion protein) and its MAb receptor (immobilized on the surface of a sensor chip) results in a change in refractive index. The interaction is monitored in real time and the amount of bound antigen and the association and dissociation rate constants can be measured with high precision. The equilibrium dissociation constant can be easily calculated from: $K_D = k_d/k_a = k_{off}/k_{on}$. The cloning of the human $\alpha2$ I domain and the purification of the expressed GST-human $\alpha2$ I domain fusion protein was described in Example 12. Analyses were performed at 20° C. using a Biacore 2000 optical sensor with a research-grade CM5 sensor chip (Biacore Life Sciences, Uppsala, Sweden) and equilibrated with running buffer (50 mM HEPES, 150 mM NaCl, 0.25 mM $MgCl_2$, 0.25 mM $CaCl_2$, 0.5% Tween-20, 0.1 mg/ml BSA, pH 7.4). For the capture of TMC-2206 on the sensor chip, two of the chip's flow cell surfaces were coated with anti-mouse IgGs; the other two flow cells were coated with Protein A for the capture of humanized TMC-2206. Each cycle of antigen (GST-human-$\alpha2$ I domain fusion protein) binding to surface-tethered anti-mouse IgGs involved three steps. In the first step, TMC-2206 was captured on one anti-mouse surface and then humanized TMC-2206 was captured on one Protein A surface. [The other two surfaces (one anti-mouse and one Protein A) served as analytic references.] In the second step, GST-human-$\alpha2$ I domain fusion protein was injected across the four surfaces. Responses obtained from the reference surfaces (due to refractive index mismatches between the antigen and running buffer) were subtracted from the responses obtained from the reaction surfaces. In the third step, the antigen/antibody complexes were stripped from the surfaces such that the surfaces could be used for another binding cycle. The highest GST-human-$\alpha2$ I domain fusion protein concentration was 41 nM. The antigen solution was flowed over the surfaces for 2 minutes at 50 μl/min and the antigen dissociation from the surface was monitored for six minutes. The rate constants for the binding of GST-human-$\alpha2$ I domain fusion protein to TMC-2206 and humanized TMC-2206 were determined and found to be similar (Table 37)

The competitive binding assays and the SPR analyses both confirm that the humanization process did not effect the binding affinity of humanized TMC-2206 to the human $\alpha2$ I domain.

EXAMPLE 18

Species cross-reactivity to humanized TMC-2206 was evaluated by biochemical analytical techniques. In the first study, the binding affinities ($K_i$ values) of TMC-2206, humanized TMC-2206, and the GST-$\alpha2$-I-domain fusion proteins derived from different species were determined (Ki values) by competitive binding with europium-labelled humanized TMC-2206 to $\alpha2\beta1$-coated plates (Example 17). The cloning of the human, rhesus macaque, rat, and mouse $\alpha2$ I domains were described in Example 12. Cynomolgus and additional rhesus monkey $\alpha2$ I domains were cloned from cDNA derived from total RNA extracted from skin tissue (MediCorp, Inc., Montreal, QC). There was a 9-fold decrease in $K_i$ for rat $\alpha2$ I binding to humanized TMC-2206 compared to the human $\alpha2$ I domain, while the murine $\alpha2$ I-GST fusion protein showed only slight specific binding at the highest concentration (4 μM; Table 36). [Both the GST-fusion protein negative control and the IgG4/k isotype negative control did not show any competitive binding effects at 0.4 μM concentrations.] The rhesus, cynomolgus, and human $\alpha2$ I-GST fusion proteins showed comparable binding. Therefore, all four species demonstrated cross-reactivity to humanized TMC-2206.

TABLE 36

| Competitor | $K_i$ (nM) |
|---|---|
| TMC-2206 | 0.14 ± 0.01 |
| Humanized TMC-2206 | 0.34 ± 0.00 |
| GST-human-$\alpha2$ I domain fusion protein | 0.57 ± 0.06 |
| GST-cynomolgous-$\alpha2$ I domain fusion protein | 0.47 ± 0.00 |
| GST-rhesus-$\alpha2$ I domain fusion protein | 0.40 ± 0.02 |
| GST-rat-$\alpha2$ I domain fusion protein | 5.23 ± 0.14 |
| GST-mouse-$\alpha2$ I domain fusion protein | Not Detected at 4.0 μM |

TABLE 36-continued

| Competitor | $K_i$ (nM) |
| --- | --- |
| GST fusion protein (negative control) | Not Detected at 0.4 μM |
| Human IgG4/κ (negative isotype control) | Not Detected at 0.4 μM |

In a second study, the rate and equilibrium binding constants of both TMC-2206 and humanized TMC-2206, and selected α2 I-GST fusion proteins were evaluated by SPR analyses (Table 37). All of the kinetic and equilibrium constants derived for parental and humanized TMC-2206 for the human and rat α2 I domains were similar. In addition, the rate constants of humanized TMC-2206 for the human and cynomolgus α2 I domains were similar. Humanized TMC-2206 did not bind to the mouse α2 I domain at concentrations of 4.0 μM of the mouse α2 I-GST fusion protein. The comparable binding of the GST-cynomolgus-α2-I domain fusion protein to humanized TMC-2206 was not consistent with the result in Example 12—where no competitive binding was seen at concentrations up 1 μM (Table 29). However, DNA sequence analyses performed on the cDNAs populations derived from mRNA extracted from monkeys (Medicorp Inc.) revealed a polymorphism at a single amino acid (position 40) compared to the human α2 I domain. This polymorphism was not conserved across animals, in that one cynomolgus and one rhesus monkey exhibited heteromorphism while the other animals exhibited a 100% homology to the human α2 I domain. The GST-cynomolgus-α2-I-domain studied in this example by the competitive binding and SPR analyses encoded the identical sequence to the human α2 I domain. These biochemical studies demonstrated that humanized TMC-2206 cross-reacted with the human, rhesus, cynomolgus, and rat derived α2 I domains but not with the mouse α2 I domain. In vitro cellular cross-reactivity studies (Example 20) were performed to verify that humanized TMC-2206 cross-reacted to different species blood cells.

TABLE 37

| MAb | GST-α2 I domain | $k_d$ (s$^{-1}$) | $k_a$ (M$^{-1}$s$^{-1}$) | $K_D$ (=$k_d/k_a$; nM) |
| --- | --- | --- | --- | --- |
| TMC-2206 | Human | (11.0 ± 0.5) × 10$^{-4}$ | (3.8 ± 0.1) × 10$^5$ | 2.9 ± 0.1 |
|  | Rat | (8.2 ± 0.1) × 10$^{-4}$ | (4.2 ± 0.1) × 10$^5$ | 2.0 ± 0.1 |
| Humanized TMC-2206 | Human | (8.2 ± 0.3) × 10$^{-4}$ | (3.5 ± 0.0) × 10$^5$ | 2.3 ± 0.1 |
|  | Rat | (5.7 ± 0.4) × 10$^{-4}$ | (3.3 ± 0.3) × 10$^5$ | 1.7 ± 0.1 |
|  | Human | (2.4 ± 0.9) × 10$^{-4}$ | (5.8 ± 0.6) × 10$^5$ | 4.0 ± 0.1 |
|  | Cynomolgus | (3.0 ± 0.1) × 10$^{-4}$ | (5.0 ± 0.1) × 10$^5$ | 5.0 ± 0.1 |
|  | Mouse | Not Detected at 4.0 μM | Not Detected at 4.0 μM | Not Detected at 4.0 μM |

EXAMPLE 19

Species cross-reactivity was further evaluated by binding humanized TMC-2206 to blood cells from different species by flow cytometry. In the first study, humanized TMC-2206 cross-reactivity to different species platelets was evaluated. Blood was obtained via veni-puncture from human donors, rats, and rhesus/cynomolgus monkeys. Human blood was collected in 3.8% sodium citrate; rhesus and cynomolgus blood were collected in 10 mM EDTA; and rat blood was collected in heparin. Primate whole blood (human, rhesus, cynomolgus) was incubated with humanized TMC-2206 at a final concentration of 140 μg/ml for 10 minutes at room temperature, followed by a 10-minute incubation with mouse anti-human IgG4-FITC conjugated MAb (Clone HP6023; Southern Biotech), followed by a incubation with species-specific platelet marker antibodies conjugated with fluorescent molecules. Human platelets were identified with PE-conjugated-mouse-anti-human CD42b (BD Biosciences) and rhesus/cynomolgus platelets were identified with PE-conjugated-mouse-anti-human-CD41a (BD Biosciences). Rat whole blood was incubated with 500 μg/ml of humanized TMC-2206 conjugated to Alexa-488 (Alexa Fluor 488 Protein Labeling kit, A10235, Molecular Probes) for 10 minutes at room temperature, followed by incubation with the PE-conjugated-hamster-anti-mouse-CD61 (rat platelet marker; BD Biosciences). All samples were washed once, suspended in phosphate buffered saline, and then subjected to flow cytometry analyses. [Both of the forward scatter and side scatter gates were set to logarithmic scales to further discriminate platelets from the larger red blood cells and leukocytes.] Humanized TMC-2206 bound to the platelets from all four species (Table 38).

In the second study, humanized TMC-2206 cross-reactivity to different species leukocytes was evaluated. Blood was obtained from the same four species, except that the human blood was collected in 10 mM EDTA. Humanized TMC-2206 conjugated to Alexa 488 was added to whole blood (final concentrations 225-400 μg/mL) for 10 minutes, followed by a 30-minute incubation at room temperature with marker antibodies. Anti-CD45 antibodies were used to stain all leukocytes [for human leukocytes PE-Cy5-conjugated-mouse-anti-human (clone H130, BD Biosciences); for rhesus and cynomolgus leukocytes PE-Cy5-conjugated mouse anti-human (clone Tü116, BD Biosciences); and for rat leukocytes PE-Cy5-conjugated-mouse-anti-rat (BD Biosciences). Marker antibodies were used to stain platelets: for human platelets PE-Cy5-conjugated-mouse-anti-human-CD42b (BD Biosciences); for rhesus and cynomolgus platelets R-PE-conjugated-mouse-anti-human-CD41a (BD Biosciences); and for rat platelets R-PE-conjugated-hamster-anti-mouse-CD61 (BD Biosciences]. One milliliter of water was added to the reaction mixture (approximately 250 μl), incubated for 5 minutes at room temperature to lyse red blood cells, followed by the addition of 2 ml of PBS (to bring tonicity to levels that would prevent leukocyte lysis), and centrifuged. The cell pellet was resuspended in 0.5 mls of PBS and subjected to flow cytometry analyses. [The side scatter channel was set to linear scale and the CD45 channel was set to log scale to discriminate granulocytes, monocytes, and lymphocytes.] As varying levels of endogenous platelet activation will lead to platelet-leukocyte micro-aggregate formation, it was critical to identify leukocytes that were not bound to platelets (which constitutively express α2β1 integrin). Therefore only those cells that were CD45+/CD41a−, CD45+/CD42b−, or CD45+/CD61− were evaluated for humanized TMC-2206 binding. Humanized TMC-2206 bound to the lymphocytes, monocytes, and granulocytes from all four species (Table 38).

These results are consistent with the results from Example 19 that humanized TMC-2206 cross-reacts with the human, rhesus, cynomolgus, and rat GST-α2-I domain fusion proteins (by $K_i$ and SPR analyses). There were relatively lower percentages of rat blood cells binding to humanized TMC-2206 compared to primate blood cells. In three earlier studies (Examples 9, 19, and 12), the binding affinities of the parental and humanized TMC-2206 antibodies to the rat α2 integrin subunit were shown to be an order of magnitude less than the binding affinities to the human α2 subunit. In the first study, Example 9, the $EC_{50}$ values for TMC-2206 inhibiting binding of rat platelets and human platelets to rat collagen type I was 6.3 nM and 1.7 nM, respectively. In the second study, Example 19 (Table 38), the $K_i$ values for the inhibition of humanized TMC-2206 binding to immobilized α2β1 by competitors GST-human-α2-I domain and GST-rat-α2-I domain fusion proteins were 0.57 nM and 5.23 nM, respectively. Similarly, in the third study, Example 12 (Table 29), the $K_i$ values for the inhibition of TMC-2206 binding to α2β1 by GST-human-α2-I domain and GST-rat-α2-I domain fusion proteins were 0.33 nM and 3.8 nM, respectively. In addition, in both platelet and leukocyte studies, all cell samples were washed before being subjected to flow cytometry analyses, with more humanized TMC-2206 being washed away from the lower affinity rat α2 subunit compared to the primate α2 subunits. Combined with the previous results, this led to a relatively lower percentage of rat blood cells being scored as "positive" compared to primate blood cells (assuming similar α2β1 receptor densities). In summary, the platelets, lymphocytes, monocytes, and granulocytes for all four species tested (human, rhesus monkey, cynomolgus monkey, and rat) all bound humanized TMC-2206.

TABLE 38

| | | Percentage Cell Binding (Mean ± SEM) | | | |
|---|---|---|---|---|---|
| Species | N | Platelets | Lymphocytes | Monocytes | Granulocytes |
| Human | 3 | 94.5 ± 0.9 | 63.7 ± 8.9 | 78.6 ± 9.1 | 75.5 ± 9.3 |
| Rhesus | 4 | 97.2 ± 0.0 | 72.3 ± 9.7 | 90.4 ± 4.9 | 95.3 ± 2.2 |
| Cynomolgus | 4 | 96.5 ± 0.3 | 73.5 ± 12.1 | 87.4 ± 7.0 | 95.2 ± 3.0 |
| Rat | 3 | 21.5 ± 2.3 | 38.2 ± 1.7 | 37.4 ± 1.6 | 43.2 ± 2.1 |

EXAMPLE 20

Another study assessed whether binding of humanized TMC-2206 to α2β1 led to platelet activation, as measured by flow cytometry. Platelet activation was measured as either the up-regulation of P-selectin or activation of GPIIbIIIa (αIIbβ3) integrin. Blood samples were collected via venipuncture from the antecubital vein into vacuum filled tubes contain 3.8% sodium citrate after discarding the first 3.0 ml of free running blood. The whole blood was diluted 1:10 in TBS (pH 7.4) and was followed by a 10-minute incubation at room temperature with either saline, IgG4/κ isotype control (132 µg/ml final concentration), or humanized TMC-2206 (144 µg/ml final concentration). For platelet activation, either thrombin-receptor-activating-peptide-6 (TRAP-6, 10 µM final concentration; AnaSpec Inc., San Jose, Calif.) or adenosine diphosphate (ADP, 20 µM final concentration; Sigma) was added to the samples, followed by a 5-minute incubation at room temperature. Cells were processed for flow cytometry by the incubation with marker antibodies: PE-Cy5-conjugated-mouse-anti-human-CD42b (BD Biosciences) to stain platelets; PE-conjugated-mouse-anti-human-CD62P (BD Biosciences) to stain P-selectin; and FITC-conjugated-PAC-1 (BD Biosciences) to stain activated GPIIbIIIa (PAC-1 binds to active conformation of the GPIIbIIIa integrin). The sampling error for each sample was less than 5% (95% confidence level).

The first experiments assessed whether binding of humanized TMC-2206 leads to platelet activation as measured by P-selectin upregulation. Activation was scored as the percentage of platelets (CD42b+) that were stained by the P-selectin-marker (CD62P) (Table 39). By ANOVA analyses (one-way, 95% confidence interval), the P-selectin expression of platelets incubated with either saline, IgG4/κ, and humanized TMC-2206 was not statistically different (P=0.96). Therefore, the binding of humanized TMC-2206 to platelets did not induce platelet activation. In side-by-side experiments, TRAP-6 induced significant increases in P-selectin expression. The addition of humanized TMC-2206 did not statistically affect TRAP-6 induced P-selectin expression compared to saline or the isotype control (P—0.96; one-way ANOVA, 95% confidence interval). Therefore the binding of humanized TMC-2206 did not inhibit TRAP-6 induced platelet activation.

TABLE 39

| | Test Articles Incubated with Whole Blood | | | | | |
|---|---|---|---|---|---|---|
| Expt. | Saline | IgG4/κ | huTMC-2206 | TRAP-6 | TRAP-6 + IgG4/κ | TRAP-6 + huTMC-2206 |
| 1 | 2.44 | 1.21 | 0.85 | 76.60 | 80.35 | 79.50 |
| 2 | 8.40 | 9.10 | 5.29 | 97.01 | 86.73 | 83.32 |
| 3 | 29.54 | 30.08 | 25.70 | 92.71 | 95.63 | 96.88 |
| Mean ± SEM | 13.5 ± 8.2 | 13.5 ± 8.6 | 10.6 ± 7.7 | 88.8 ± 6.2 | 87.6 ± 4.4 | 86.6 ± 5.3 |

The next study assessed P-selectin up-regulation after incubation with/without the agonist ADP (percentage of platelets expressing P-selectin, Table 40). As before, P-selectin expression on platelets incubated with humanized TMC-2206, IgG4/κ, and saline were comparable—therefore humanized TMC-2206 did not induce platelet activation. ADP induced P-selectin expression comparable to TRAP-6 induction. There appeared to be an additionally increase in P-selectin expression with platelets incubated with ADP and then either IgG4/κ or humanized TMC-2206. However, the increase in P-selectin upregulation was similar for both the isotype control and humanized TMC-2206; indicating again that the binding of humanized TMC-2206 to platelets does not induce platelet activation. Concomitantly, P-selectin expression from ADP-induced platelets incubated with IgG4/κ or humanized TMC-2206 did not decrease. Therefore the binding of humanized TMC-2206 did not inhibit ADP-induced platelet activation.

TABLE 40

| | Test Articles Incubated with Whole Blood | | |
|---|---|---|---|
| Agonist | Saline | IgG4/κ | huTMC-2206 |
| Saline | 29.54 | 30.08 | 25.70 |
| ADP | 79.90 | 96.24 | 96.87 |

The next study assessed GPIIbIIIa activation after incubation with/without agonists TRAP-6 or ADP by scoring the percentage of platelets binding to the PAC-1 marker antibody (which binds to the active conformation of GPIIbIIIa; Table 41). The level of activated GPIIbIIIa expression on platelets incubated with humanized TMC-2206, IgG4/k, and saline were comparable—humanized TMC-2206 did not induce platelet activation. Both IgG4/k and humanized TMC-2206 did not inhibit TRAP-6 nor ADP induced activation.

TABLE 41

| | Test Articles Incubated with Whole Blood | | |
|---|---|---|---|
| Agonist | Saline | IgG4/κ | huTMC-2206 |
| Saline | 26.5 | 24.3 | 18.6 |
| TRAP-6 | 79.9 | 93.8 | 88.9 |
| ADP | 69.1 | 93.1 | 86.0 |

In summary, humanized TMC-2206 did not induce platelet activation (no increase in P-selectin up-regulation or GPIIbIIIa activation), nor inhibit agonist (TRAP-6, ADP) induced platelet activation. This data complements the platelet aggregation study (Example 15, Table 34) that showed that humanized TMC-2206 did not induced platelet aggregation nor inhibited collagen-induced aggregation.

EXAMPLE 21

Humanized TMC-2206 was evaluated for its effect on both the extrinsic and intrinsic coagulation pathways by measuring prothrombin time (PT) and activated partial thromboplastin time (aPTT). A qualified lyophilized preparation of human plasma (Citrex I, Bio/Data Corporation, Horsham, Pa.) was used for the measurement of both PT and aPTT. Humanized TMC-2206 was added to the plasma to attain final concentrations of 179, 214, and 286 μg/mL (corresponding to the $C_{max}$ of a single dose of antibody at 12.5, 15.0, and 20.0 mg/kg, respectively) before subjecting the samples to the coagulation tests. Standard procedures were followed for both PT and aPTT with the coagulation times measured by a BBL fibrometer (BD, Franklin Lakes, N.J.). Table 42 summarizes the data for a series of six experiments (3 PT and 3 aPTT). A saline control was run for each experiment. Student-t statistical analyses of each matched pair (humanized TMC-2206 and saline) demonstrated that for each experiment that there were no statistically significant differences between the mean coagulation times for humanized TMC-2206 compared to saline. (The hypotheses that coagulation times were different would be rejected at 95% confidence levels if the individual calculated P values were less than 0.05) Therefore humanized TMC-2206 did not effect coagulation as measured by PT and aPTT.

TABLE 42

| | | Humanized TMC-2206 | Saline | |
|---|---|---|---|---|
| Coagulation Parameter | Concentration | Coagulation Time (seconds, mean ± SEM) | Coagulation Time (seconds, mean ± SEM) | P-value |
| Prothrombin Time | 179 μg/mL | 10.8 ± 0.1 | 10.8 ± 0.1 | 1.00 |
| | 214 μg/mL | 11.3 ± 0.1 | 11.1 ± 0.1 | 0.67 |
| | 286 μg/mL | 11.5 ± 0.2 | 11.6 ± 0.1 | 0.62 |
| Activated Partial Thromboplastin Time | 179 μg/mL | 25.6 ± 0.7 | 24.8 ± 0.6 | 0.43 |
| | 214 μg/mL | 24.1 ± 0.3 | 23.5 ± 0.5 | 0.30 |
| | 286 μg/mL | 27.9 ± 0.2 | 27.9 ± 0.4 | 1.00 |

EXAMPLE 22

The effects of humanized TMC-2206 on rat bleeding times were evaluated. Sprague-Dawley rats (190-200 g) were injected intravenously (tail vein) with either saline, heparin (0.6 mg/kg, positive control), or humanized TMC-2206 at doses of 5 and 15 mg/kg one hour before standardized transection of the tip (0.5 mm) of each tail. The rats were non-anesthetized and were conscious during the bleeding time observation. The tip of the cut tail of each rat was immediately immersed 2-cm deep into a test tube containing saline at 37° C. The time required for the beginning of a 15-second period of bleeding cessation was scored as the bleeding time. A maximum cut-off time of 20 minutes was used. Blood loss was scored by the amount of hemoglobin released after hemolysis (spectrophotometrically) from the blood collected in the test tube. Humanized TMC-2206 displayed no statistically significant effect on bleeding time at both doses tested compared to naïve and saline controls (Table 43; P=0.08, one-way ANOVA analyses). Humanized TMC-2206 displayed no statistically significant effect on blood loss at both doses tested compared to naïve and saline controls (P=0.22, one-way ANOVA analyses). Therefore humanized TMC-2206 does not effect in vivo bleeding time or blood loss.

TABLE 43

Test Articles injected intravenously into rats

|  | Naïve | Saline | Humanized TMC-2206 5 mg/kg | Humanized TMC-2206 15 mg/kg | Heparin |
|---|---|---|---|---|---|
| n | 10 | 10 | 10 | 10 | 10 |
| Bleeding Time (minutes, mean ± SEM) | 3.5 ± 0.4 | 4.5 ± 0.4 | 5.2 ± 0.6 | 4.3 ± 0.3 | 17.8 ± 1.1 |
| Blood Loss (mg hemoglobin, mean ± SEM) | 10.3 ± 3.0 | 17.6 ± 2.0 | 20.5 ± 4.1 | 21.2 ± 5.9 | 115 ± 31 |

EXAMPLE 23

A study was conducted to determine the effect of a single dose of humanized TMC-2206 on circulating cytokine levels in rats as a means to determine whether humanized TMC-2206 causes detectable in vivo activation of leukocytes. Saline (negative control), human IgG4/κ isotype control (15 mg/kg), humanized TMC-2206 (15 mg/kg) or lipopolysaccharide (LPS, positive inflammation control; 0.75 mg/kg) was administered to rats intravenously. Non-injected rats were used as naïve controls. At 2, 4, 6, and 8 hours post-injection, blood samples were collected via saphenous vein and processed for plasma. Plasma samples were subjected to bead-based multiplex immunoassay (MIA; Linco Diagnostics, St. Charles, Mo.) to determine the levels of IL-1α, IL-1β, IL-2, IL-4, IL-5, IL-6, IL-12, GM-CSF, IFN-γ, and TNF-α (Table 44; pg/mL, mean±SEM). MIA involves the simultaneous detection of analytes (up to 100) in the same sample volume (25 μl) by combining several individual antigen/antibody binding reactions on spectrally distinct sets of microspheres. Depending on the antigen, the sensitivity of MIA is between 1.5-50 pg/ml. Each cytokine data set was subjected to two-way ANOVA analyses, 95% confidence interval, testing the hypotheses that the individual cytokine levels for all four time points and for all four conditions (naïve, vehicle, IgG4/κ, and humanized TMC-2206) were equivalent. The hypotheses would be rejected if the P-values were less than 0.05. There were no statistically significant differences in each of the ten sets (all P-values ranged from 0.18 to 1.0, Table 44) of cytokine levels observed in rats injected with vehicle, IgG4/κ, humanized TMC-2206, or non-injected (naïve). Therefore, the intravenous injection of a single dose (15 mg/kg) of humanized TMC-2206 did not induce an increase in the expression of cytokines involved in inflammation.

TABLE 44

| Cyt. | Time | Naïve (n = 3) | Vehicle n = 3 | IgG4 (15 mg/kg) (n = 6) | huTMC-2206 (15 mg/kg) (n = 6) | LPS (.75 mg/kg) (n = 4) | P-values, 2way ANOVA |
|---|---|---|---|---|---|---|---|
| IL-1α | 2-hr | 61 ± 30 | 84 ± 37 | 75 ± 29 | 133 ± 66 | 788 ± 550 | 1.00 |
|  | 4-hr | 69 ± 38 | 75 ± 22 | 101 ± 46 | 150 ± 63 | 806 ± 641 |  |
|  | 6-hr | 58 ± 16 | 90 ± 54 | 57 ± 26 | 80 ± 53 | 640 ± 524 |  |
|  | 8-hr | 36 ± 5 | 85 ± 11 | 57 ± 17 | 101 ± 48 | 591 ± 372 |  |
| IL-1β | 2-hr | 24 ± 0 | 24 ± 0 | 24 ± 0 | 24 ± 0 | 733 ± 277 | 0.17 |
|  | 4-hr | 45 ± 15 | 107 ± 70 | 44 ± 17 | 30 ± 4 | 527 ± 109 |  |
|  | 6-hr | 153 ± 78 | 76 ± 27 | 61 ± 27 | 44 ± 14 | 282 ± 70 |  |
|  | 8-hr | 24 ± 0 | 24 ± 0 | 53 ± 29 | 24 ± 0 | 525 ± 324 |  |
| IL-6 | 2-hr | 118 ± 35 | 291 ± 136 | 300 ± 174 | 309 ± 155 | 31386 ± 7981 | 1.00 |
|  | 4-hr | 137 ± 58 | 271 ± 123 | 329 ± 207 | 362 ± 163 | 15971 ± 4334 |  |
|  | 6-hr | 265 ± 125 | 359 ± 130 | 416 ± 209 | 364 ± 174 | 8966 ± 4379 |  |
|  | 8-hr | 117 ± 40 | 341 ± 67 | 219 ± 133 | 335 ± 163 | 3682 ± 2431 |  |
| IL-12 | 2-hr | 54 ± 30 | 237 ± 62 | 159 ± 67 | 199 ± 106 | 950 ± 823 | 1.00 |
|  | 4-hr | 43 ± 19 | 201 ± 44 | 173 ± 79 | 219 ± 119 | 991 ± 876 |  |
|  | 6-hr | 43 ± 17 | 205 ± 93 | 184 ± 108 | 169 ± 124 | 941 ± 812 |  |
|  | 8-hr | 43 ± 19 | 212 ± 31 | 132 ± 55 | 214 ± 102 | 794 ± 685 |  |
| IFN-γ | 2-hr | 31 ± 7 | 82 ± 58 | 121 ± 72 | 156 ± 94 | 959 ± 453 | 1.00 |
|  | 4-hr | 24 ± 0 | 67 ± 43 | 127 ± 77 | 153 ± 94 | 7740 ± 629 |  |
|  | 6-hr | 24 ± 0 | 57 ± 33 | 127 ± 103 | 115 ± 91 | 3288 ± 756 |  |
|  | 8-hr | 24 ± 0 | 76 ± 52 | 99 ± 59 | 156 ± 102 | 1773 ± 757 |  |
| TNF-α | 2-hr | 24 ± 0 | 24 ± 0 | 24 ± 0 | 24 ± 0 | 1571 ± 633 | 1.00 |
|  | 4-hr | 24 ± 0 | 24 ± 0 | 24 ± 0 | 24 ± 0 | 85 ± 38 |  |
|  | 6-hr | 24 ± 0 | 24 ± 0 | 24 ± 0 | 24 ± 0 | 48 ± 15 |  |
|  | 8-hr | 24 ± 0 | 24 ± 0 | 24 ± 0 | 24 ± 0 | 27 ± 3 |  |
| IL-2 | 2-hr | 49 ± 25 | 31 ± 7 | 47 ± 17 | 73 ± 49 | 93 ± 24 | 0.96 |
|  | 4-hr | 24 ± 0 | 33 ± 9 | 52 ± 23 | 90 ± 62 | 79 ± 14 |  |
|  | 6-hr | 24 ± 0 | 47 ± 23 | 69 ± 36 | 33 ± 9 | 52 ± 16 |  |
|  | 8-hr | 24 ± 0 | 92 ± 31 | 47 ± 23 | 86 ± 39 | 39 ± 15 |  |
| IL-4 | 2-hr | 24 ± 0 | 24 ± 0 | 24 ± 0 | 24 ± 0 | 46 ± 22 | 0.85 |
|  | 4-hr | 24 ± 0 | 24 ± 0 | 24 ± 0 | 25 ± 1 | 49 ± 25 |  |
|  | 6-hr | 24 ± 0 | 24 ± 0 | 24 ± 0 | 24 ± 0 | 46 ± 22 |  |
|  | 8-hr | 24 ± 0 | 24 ± 0 | 24 ± 0 | 24 ± 0 | 41 ± 17 |  |

TABLE 44-continued

| Cyt. | Time | Naïve (n = 3) | Vehicle n = 3) | IgG4 (15 mg/kg) (n = 6) | huTMC-2206 (15 mg/kg) (n = 6) | LPS (.75 mg/kg) (n = 4) | P-values, 2way ANOVA |
|---|---|---|---|---|---|---|---|
| IL-5 | 2-hr | 24 ± 0 | 24 ± 0 | 24 ± 0 | 24 ± 0 | 24 ± 0 | 1.00 |
|  | 4-hr | 24 ± 0 | 24 ± 0 | 24 ± 0 | 24 ± 0 | 24 ± 0 |  |
|  | 6-hr | 24 ± 0 | 24 ± 0 | 24 ± 0 | 24 ± 0 | 24 ± 0 |  |
|  | 8-hr | 24 ± 0 | 24 ± 0 | 24 ± 0 | 24 ± 0 | 24 ± 0 |  |
| GM-CSF | 2-hr | 66 ± 0 | 66 ± 0 | 66 ± 0 | 66 ± 0 | 66 ± 0 | 1.00 |
|  | 4-hr | 66 ± 0 | 66 ± 0 | 66 ± 0 | 66 ± 0 | 66 ± 0 |  |
|  | 6-hr | 66 ± 0 | 66 ± 0 | 66 ± 0 | 66 ± 0 | 66 ± 0 |  |
|  | 8-hr | 66 ± 0 | 66 ± 0 | 66 ± 0 | 66 ± 0 | 66 ± 0 |  |

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

```
SEQUENCE LISTING

<160> NUMBER OF SEQ ID NOS: 186

<210> SEQ ID NO 1
<211> LENGTH: 10
<212> TYPE: PRT
<213> ORGANISM: Homo Sapiens
<220> FEATURE:
<221> NAME/KEY: MISC_FEATURE
<223> OTHER INFORMATION: hCDR1 [CDR1 of heavy chain variable region]

<400> SEQUENCE: 1

Gly Phe Ser Leu Thr Asn Tyr Gly Ile His
1               5                   10

<210> SEQ ID NO 2
<211> LENGTH: 16
<212> TYPE: PRT
<213> ORGANISM: Homo Sapiens
<220> FEATURE:
<221> NAME/KEY: MISC_FEATURE
<223> OTHER INFORMATION: hCDR2  [CDR2 of heavy chain variable region]

<400> SEQUENCE: 2

Val Ile Trp Ala Arg Gly Phe Thr Asn Tyr Asn Ser Ala Leu Met Ser
1               5                   10                  15

<210> SEQ ID NO 3
<211> LENGTH: 11
<212> TYPE: PRT
<213> ORGANISM: Homo Sapiens
<220> FEATURE:
<221> NAME/KEY: MISC_FEATURE
<223> OTHER INFORMATION: hCDR3  [CDR3 of heavy chain variable region]

<400> SEQUENCE: 3

Ala Asn Asp Gly Val Tyr Tyr Ala Met Asp Tyr
1               5                   10

<210> SEQ ID NO 4
<211> LENGTH: 10
<212> TYPE: PRT
<213> ORGANISM: Homo Sapiens
<220> FEATURE:
<221> NAME/KEY: MISC_FEATURE
<223> OTHER INFORMATION: lCDR1  [CDR1 of light chain variable region]

<400> SEQUENCE: 4
```

```
Ser Ala Asn Ser Ser Val Asn Tyr Ile His
1               5                   10

<210> SEQ ID NO 5
<211> LENGTH: 7
<212> TYPE: PRT
<213> ORGANISM: Homo Sapiens
<220> FEATURE:
<221> NAME/KEY: MISC_FEATURE
<223> OTHER INFORMATION: lCDR2  [CDR2 of light chain variable region]

<400> SEQUENCE: 5

Asp Thr Ser Lys Leu Ala Ser
1               5

<210> SEQ ID NO 6
<211> LENGTH: 9
<212> TYPE: PRT
<213> ORGANISM: Homo Sapiens
<220> FEATURE:
<221> NAME/KEY: MISC_FEATURE
<223> OTHER INFORMATION: lCDR3  [CDR3 of light chain variable region]

<400> SEQUENCE: 6

Gln Gln Trp Thr Thr Asn Pro Leu Thr
1               5

<210> SEQ ID NO 7
<211> LENGTH: 5361
<212> TYPE: DNA
<213> ORGANISM: Homo Sapiens
<220> FEATURE:
<221> NAME/KEY: misc_feature
<223> OTHER INFORMATION: Human alpha2 integrin DNA

<400> SEQUENCE: 7
ctgcaaaccc agcgcaacta cggtcccccg gtcagaccca ggatggggcc agaacggaca      60
ggggccgcgc cgctgccgct gctgctggtg ttagcgctca gtcaaggcat tttaaattgt     120
tgtttggcct acaatgttgg tctcccagaa gcaaaaatat tttccggtcc ttcaagtgaa     180
cagtttgggt atgcagtgca gcagtttata aatccaaaag gcaactggtt actggttggt     240
tcaccctgga gtggctttcc tgagaaccga atgggagatg tgtataaatg tcctgttgac     300
ctatccactg ccacatgtga aaaactaaat ttgcaaactt caacaagcat tccaaatgtt     360
actgagatga aaccaacat  gagcctcggc ttgatcctca ccaggaacat gggaactgga     420
ggttttctca catgtggtcc tctgtgggca cagcaatgtg ggaatcagta ttacacaacg     480
ggtgtgtgtt ctgacatcag tcctgatttt cagctctcag ccagcttctc acctgcaact     540
cagccctgcc cttccctcat agatgttgtg gttgtgtgtg atgaatcaaa tagtatttat     600
ccttgggatg cagtaaagaa ttttttggaa aaatttgtac aaggccttga tataggcccc     660
acaaagacac aggtggggtt aattcagtat gccaataatc aagagttgtg tttaacttg     720 aacacatata aaaccaaaga agaaatgatt gtagcaacat cccagacatc ccaatatggt     780
ggggacctca caaacacatt cggagcaatt caatatgcaa gaaaatatgc ctattcagca     840
gcttctggtg gcgcgaag tgctacgaaa gtaatggtag ttgtaactga cggtgaatca     900
catgatggtt caatgttgaa agctgtgatt gatcaatgca accatgacaa tatactgagg     960
tttggcatag cagttcttgg gtacttaaac agaaacgccc ttgatactaa aaatttaata    1020
aaagaaataa aagcgatcgc tagtattcca acagaaagat acttttttca tgtgtctgat    1080
gaagcagctc tactagaaaa ggctgggaca ttaggagaac aaatttttca cattgaaggt    1140
```

```
actgttcaag gaggagacaa ctttcagatg gaaatgtcac aagtgggatt cagtgcagat    1200
tactcttctc aaaatgatat tctgatgctg ggtgcagtgg gagcttttgg ctggagtggg    1260
accattgtcc agaagacatc tcatggccat ttgatctttc ctaaacaagc ctttgaccaa    1320
attctgcagg acagaaatca cagttcatat ttaggttact ctgtggctgc aatttctact    1380
ggagaaagca ctcactttgt tgctggtgct cctcgggcaa attataccgg ccagatagtg    1440
ctatatagtg tgaatgagaa tggcaatatc acggttattc aggctcaccg aggtgaccag    1500
attggctcct attttggtag tgtgctgtgt tcagttgatg tggataaaga caccattaca    1560
gacgtgctct tggtaggtgc accaatgtac atgagtgacc taaagaaaga ggaaggaaga    1620
gtctacctgt ttactatcaa aaagggcatt ttgggtcagc accaatttct gaaggcccc     1680 gagggcattg aaaacactcg atttggttca gcaattgcag ctcttttcaga catcaacatg    1740 gatggcttta atgatgtgat tgttggttca ccactagaaa atcagaattc tggagctgta    1800
tacatttaca atggtcatca gggcactatc cgcacaaagt attcccagaa atcttggga     1860 tccgatggag cctttaggag ccatctccag tactttggga ggtccttgga tggctatgga    1920
gatttaaatg gggattccat caccgatgtg tctattggtg cctttggaca gtggttcaa     1980 ctctggtcac aaagtattgc tgatgtagct atagaagctt cattcacacc agaaaaaatc    2040
actttggtca acaagaatgc tcagataatt ctcaaactct gcttcagtgc aaagttcaga    2100
cctactaagc aaaacaatca agtggccatt gtatataaca tcacacttga tgcagatgga    2160
ttttcatcca gagtaacctc caggggggtta tttaaagaaa acaatgaaag gtgcctgcag    2220
aagaatatgg tagtaaatca agcacagagt tgccccgagc acatcattta tatacaggag    2280
ccctctgatg ttgtcaactc tttggatttg cgtgtggaca tcagtctgga aaaccctggc    2340
actagccctg cccttgaagc ctattctgag actgccaagg tcttcagtat ccttttccac    2400 aaaagactgtg gtgaggatgg actttgcatt tctgatctag tcctagatgt ccgacaaata    2460
ccagctgctc aagaacaacc ctttattgtc agcaaccaaa acaaaaggtt aacatttttca    2520 gtaacactga aaaataaaag ggaaagtgca tacaacactg gaattgttgt tgatttttca    2580
gaaaacttgt ttttttgcatc attctcccta ccggttgatg ggacagaagt aacatgccag    2640
gtggctgcat ctcagaagtc tgttgcctgc gatgtaggct accctgctttt aaagagagaa    2700 caacaggtga cttttactat taactttgac ttcaatcttc aaaaccttca gaatcaggcg    2760
tctctcagtt tccaagcctt aagtgaaagc caagaagaaa acaaggctga taatttggtc    2820 aaccctcaaaa ttcctctcct gtatgatgct gaaattcact taacaagatc taccaacata    2880 aattttatg aaatctcttc ggatgggaat gttccttcaa tcgtgcacag ttttgaagat    2940
gttggtccaa aattcatctt ctccctgaag gtaacaacag gaagtgttcc agtaagcatg    3000
gcaactgtaa tcatccacat ccctcagtat accaaagaaa agaacccact gatgtaccta    3060
actggggtgc aaacagacaa ggctggtgac atcagttgta atgcagatat caatccactg    3120
aaaataggac aaacatcttc ttctgtatct ttcaaaagtg aaaatttcag gcacaccaaa    3180
gaattgaact gcagaactgc ttcctgtagt aatgttacct gctggttgaa agacgttcac    3240
atgaaaggag aatactttgt taatgtgact accagaattt ggaacgggac tttcgcatca    3300
tcaacgttcc agacagtaca gctaacggca gctgcagaaa tcaacaccta aaccctgag    3360 atatatgtga ttgaagataa cactgttacg attcccctga tgataatgaa acctgatgag    3420
aaagccgaag taccaacagg agttataata ggaagtataa ttgctggaat ccttttgctg    3480
ttagctctgg ttgcaatttt atggaagctc ggcttcttca aaagaaaata tgaaaagatg    3540
```

```
accaaaaatc cagatgagat tgatgagacc acagagctca gtagctgaac cagcagacct    3600
acctgcagtg ggaaccggca gcatcccagc cagggtttgc tgtttgcgtg catggatttc    3660 ttttaaatc ccatattttt tttatcatgt cgtaggtaaa ctaacctggt attttaagag    3720
aaaactgcag gtcagtttgg atgaagaaat tgtgggggt ggggggaggtg cgggggcag    3780 gtagggaaat aatagggaaa atacctattt tatatgatgg gggaaaaaaa gtaatcttta    3840
aactggctgg cccagagttt acattctaat ttgcattgtg tcagaaacat gaaatgcttc    3900
caagcatgac aacttttaaa gaaaatatg atactctcag attttaaggg ggaaaactgt    3960
tctctttaaa atatttgtct ttaaacagca actacagaag tggaagtgct tgatatgtaa    4020
gtacttccac ttgtgtatat tttaatgaat attgatgtta acaagagggg aaaacaaaac    4080
acaggttttt tcaatttatg ctgctcatcc aaagttgcca cagatgatac ttccaagtga    4140 taatttatt tataaactag gtaaaatttg ttgttggttc cttttatacc acggctgccc    4200
cttccacacc ccatcttgct ctaatgatca aaacatgctt gaataactga gcttagagta    4260
tacctcctat atgtccattt aagttaggag agggggcgat atagagacta aggcacaaaa    4320
ttttgtttaa aactcagaat ataacatta tgtaaaatcc catctgctag aagcccatcc    4380
tgtgccagag gaaggaaaag gaggaaattt cctttctctt ttaggaggca caacagttct    4440
cttctaggat ttgtttggct gactggcagt aacctagtga attttgaaa gatgagtaat    4500 ttctttggca accttcctcc tcccttactg aaccactctc ccacctcctg gtggtaccat    4560
tattatagaa gccctctaca gcctgacttt ctctccagcg gtccaaagtt atcccctcct    4620 ttaccccctca tccaaagttc ccactccttc aggacagctg ctgtgcatta gatattaggg    4680
gggaaagtca tctgtttaat ttacacactt gcatgaatta ctgtatataa actccttaac    4740
ttcagggagc tattttcatt tagtgctaaa caagtaagaa aaataagcta gagtgaattt    4800
ctaaatgttg gaatgttatg ggatgtaaac aatgtaaagt aaaacactct caggatttca    4860
ccagaagtta cagatgaggc actggaaacc accaccaaat tagcaggtgc accttctgtg    4920
gctgtcttgt ttctgaagta cttttcttc cacaagagtg aatttgacct aggcaagttt    4980
gttcaaaagg tagatcctga gatgatttgg tcagattggg ataaggccca gcaatctgca    5040
ttttaacaag cacccagtc actaggatgc agatggacca cactttgaga aacaccaccc    5100
atttctactt tttgcacctt attttctctg ttcctgagcc cccacattct ctaggagaaa    5160
cttagattaa aattcacaga cactacatat ctaaagcttt gacaagtcct tgacctctat    5220
aaacttcaga gtcctcatta taaatgggaa agactgagct ggagttcagc agtgatgctt    5280
tttagtttta aaagtctatg atctgatctg gacttcctat aatacaaata cacaatcctc    5340
caagaatttg acttggaaaa g                                              5361
```

<210> SEQ ID NO 8
<211> LENGTH: 1181
<212> TYPE: PRT
<213> ORGANISM: Homo Sapiens
<220> FEATURE:
<221> NAME/KEY: MISC_FEATURE
<223> OTHER INFORMATION: Human alpha2 integrin

<400> SEQUENCE: 8

```
Met Gly Pro Glu Arg Thr Gly Ala Ala Pro Leu Pro Leu Leu Leu Val
1               5                   10                  15

Leu Ala Leu Ser Gln Gly Ile Leu Asn Cys Cys Leu Ala Tyr Asn Val
            20                  25                  30
```

-continued

```
Gly Leu Pro Glu Ala Lys Ile Phe Ser Gly Pro Ser Ser Glu Gln Phe
         35                  40                  45
Gly Tyr Ala Val Gln Gln Phe Ile Asn Pro Lys Gly Asn Trp Leu Leu
     50                  55                  60
Val Gly Ser Pro Trp Ser Gly Phe Pro Glu Asn Arg Met Gly Asp Val
 65                  70                  75                  80
Tyr Lys Cys Pro Val Asp Leu Ser Thr Ala Thr Cys Glu Lys Leu Asn
                 85                  90                  95
Leu Gln Thr Ser Thr Ser Ile Pro Asn Val Thr Glu Met Lys Thr Asn
            100                 105                 110
Met Ser Leu Gly Leu Ile Leu Thr Arg Asn Met Gly Thr Gly Gly Phe
        115                 120                 125
Leu Thr Cys Gly Pro Leu Trp Ala Gln Gln Cys Gly Asn Gln Tyr Tyr
    130                 135                 140
Thr Thr Gly Val Cys Ser Asp Ile Ser Pro Asp Phe Gln Leu Ser Ala
145                 150                 155                 160
Ser Phe Ser Pro Ala Thr Gln Pro Cys Pro Ser Leu Ile Asp Val Val
                165                 170                 175
Val Val Cys Asp Glu Ser Asn Ser Ile Tyr Pro Trp Asp Ala Val Lys
            180                 185                 190
Asn Phe Leu Glu Lys Phe Val Gln Gly Leu Asp Ile Gly Pro Thr Lys
        195                 200                 205
Thr Gln Val Gly Leu Ile Gln Tyr Ala Asn Asn Pro Arg Val Val Phe
    210                 215                 220
Asn Leu Asn Thr Tyr Lys Thr Lys Glu Glu Met Ile Val Ala Thr Ser
225                 230                 235                 240
Gln Thr Ser Gln Tyr Gly Gly Asp Leu Thr Asn Thr Phe Gly Ala Ile
                245                 250                 255
Gln Tyr Ala Arg Lys Tyr Ala Tyr Ser Ala Ala Ser Gly Gly Arg Arg
            260                 265                 270
Ser Ala Thr Lys Val Met Val Val Thr Asp Gly Glu Ser His Asp
        275                 280                 285
Gly Ser Met Leu Lys Ala Val Ile Asp Gln Cys Asn His Asp Asn Ile
    290                 295                 300
Leu Arg Phe Gly Ile Ala Val Leu Gly Tyr Leu Asn Arg Asn Ala Leu
305                 310                 315                 320
Asp Thr Lys Asn Leu Ile Lys Glu Ile Lys Ala Ile Ala Ser Ile Pro
                325                 330                 335
Thr Glu Arg Tyr Phe Phe Asn Val Ser Asp Glu Ala Ala Leu Leu Glu
            340                 345                 350
Lys Ala Gly Thr Leu Gly Glu Gln Ile Phe Ser Ile Glu Gly Thr Val
        355                 360                 365
Gln Gly Gly Asp Asn Phe Gln Met Glu Met Ser Gln Val Gly Phe Ser
    370                 375                 380
Ala Asp Tyr Ser Ser Gln Asn Asp Ile Leu Met Leu Gly Ala Val Gly
385                 390                 395                 400
Ala Phe Gly Trp Ser Gly Thr Ile Val Gln Lys Thr Ser His Gly His
                405                 410                 415
Leu Ile Phe Pro Lys Gln Ala Phe Asp Gln Ile Leu Gln Asp Arg Asn
            420                 425                 430
His Ser Ser Tyr Leu Gly Tyr Ser Val Ala Ala Ile Ser Thr Gly Glu
        435                 440                 445
Ser Thr His Phe Val Ala Gly Ala Pro Arg Ala Asn Tyr Thr Gly Gln
    450                 455                 460
```

```
Ile Val Leu Tyr Ser Val Asn Glu Asn Gly Asn Ile Thr Val Ile Gln
465                 470                 475                 480

Ala His Arg Gly Asp Gln Ile Gly Ser Tyr Phe Gly Ser Val Leu Cys
                485                 490                 495

Ser Val Asp Val Asp Lys Asp Thr Ile Thr Asp Val Leu Leu Val Gly
            500                 505                 510

Ala Pro Met Tyr Met Ser Asp Leu Lys Lys Glu Glu Gly Arg Val Tyr
        515                 520                 525

Leu Phe Thr Ile Lys Lys Gly Ile Leu Gly Gln His Gln Phe Leu Glu
    530                 535                 540

Gly Pro Glu Gly Ile Glu Asn Thr Arg Phe Gly Ser Ala Ile Ala Ala
545                 550                 555                 560

Leu Ser Asp Ile Asn Met Asp Gly Phe Asn Asp Val Ile Val Gly Ser
                565                 570                 575

Pro Leu Glu Asn Gln Asn Ser Gly Ala Val Tyr Ile Tyr Asn Gly His
            580                 585                 590

Gln Gly Thr Ile Arg Thr Lys Tyr Ser Gln Lys Ile Leu Gly Ser Asp
        595                 600                 605

Gly Ala Phe Arg Ser His Leu Gln Tyr Phe Gly Arg Ser Leu Asp Gly
    610                 615                 620

Tyr Gly Asp Leu Asn Gly Asp Ser Ile Thr Asp Val Ser Ile Gly Ala
625                 630                 635                 640

Phe Gly Gln Val Val Gln Leu Trp Ser Gln Ser Ile Ala Asp Val Ala
                645                 650                 655

Ile Glu Ala Ser Phe Thr Pro Glu Lys Ile Thr Leu Val Asn Lys Asn
            660                 665                 670

Ala Gln Ile Ile Leu Lys Leu Cys Phe Ser Ala Lys Phe Arg Pro Thr
        675                 680                 685

Lys Gln Asn Asn Gln Val Ala Ile Val Tyr Asn Ile Thr Leu Asp Ala
690                 695                 700

Asp Gly Phe Ser Ser Arg Val Thr Ser Arg Gly Leu Phe Lys Glu Asn
705                 710                 715                 720

Asn Glu Arg Cys Leu Gln Lys Asn Met Val Val Asn Gln Ala Gln Ser
                725                 730                 735

Cys Pro Glu His Ile Ile Tyr Ile Gln Glu Pro Ser Asp Val Val Asn
            740                 745                 750

Ser Leu Asp Leu Arg Val Asp Ile Ser Leu Glu Asn Pro Gly Thr Ser
        755                 760                 765

Pro Ala Leu Glu Ala Tyr Ser Glu Thr Ala Lys Val Phe Ser Ile Pro
770                 775                 780

Phe His Lys Asp Cys Gly Glu Asp Gly Leu Cys Ile Ser Asp Leu Val
785                 790                 795                 800

Leu Asp Val Arg Gln Ile Pro Ala Ala Gln Glu Gln Pro Phe Ile Val
                805                 810                 815

Ser Asn Gln Asn Lys Arg Leu Thr Phe Ser Val Thr Leu Lys Asn Lys
            820                 825                 830

Arg Glu Ser Ala Tyr Asn Thr Gly Ile Val Val Asp Phe Ser Glu Asn
        835                 840                 845

Leu Phe Phe Ala Ser Phe Ser Leu Pro Val Asp Gly Thr Glu Val Thr
850                 855                 860

Cys Gln Val Ala Ala Ser Gln Lys Ser Val Ala Cys Asp Val Gly Tyr
865                 870                 875                 880

Pro Ala Leu Lys Arg Glu Gln Gln Val Thr Phe Thr Ile Asn Phe Asp
```

|   |   |   |   |   |   |   |   |   |   |
|---|---|---|---|---|---|---|---|---|---|
| | | | 885 | | | 890 | | | 895 |
| Phe | Asn | Leu | Gln | Asn | Leu | Gln | Asn | Gln | Ala | Ser | Leu | Ser | Phe | Gln | Ala |
| | | | 900 | | | | 905 | | | | 910 | | | | |
| Leu | Ser | Glu | Ser | Gln | Glu | Glu | Asn | Lys | Ala | Asp | Asn | Leu | Val | Asn | Leu |
| | | | 915 | | | | 920 | | | | 925 | | | | |
| Lys | Ile | Pro | Leu | Leu | Tyr | Asp | Ala | Glu | Ile | His | Leu | Thr | Arg | Ser | Thr |
| | | | 930 | | | | 935 | | | | 940 | | | | |
| Asn | Ile | Asn | Phe | Tyr | Glu | Ile | Ser | Ser | Asp | Gly | Asn | Val | Pro | Ser | Ile |
| 945 | | | | | 950 | | | | | 955 | | | | | 960 |
| Val | His | Ser | Phe | Glu | Asp | Val | Gly | Pro | Lys | Phe | Ile | Phe | Ser | Leu | Lys |
| | | | 965 | | | | 970 | | | | 975 | | | | |
| Val | Thr | Thr | Gly | Ser | Val | Pro | Val | Ser | Met | Ala | Thr | Val | Ile | Ile | His |
| | | | 980 | | | | 985 | | | | 990 | | | | |
| Ile | Pro | Gln | Tyr | Thr | Lys | Glu | Lys | Asn | Pro | Leu | Met | Tyr | Leu | Thr | Gly |
| | | | 995 | | | | 1000 | | | | 1005 | | | | |
| Val | Gln | Thr | Asp | Lys | Ala | Gly | Asp | Ile | Ser | Cys | Asn | Ala | Asp | Ile |
| | | 1010 | | | | 1015 | | | | 1020 | | | | |
| Asn | Pro | Leu | Lys | Ile | Gly | Gln | Thr | Ser | Ser | Val | Ser | Phe | Lys |
| | | 1025 | | | | 1030 | | | | 1035 | | | | |
| Ser | Glu | Asn | Phe | Arg | His | Thr | Lys | Glu | Leu | Asn | Cys | Arg | Thr | Ala |
| | | 1040 | | | | 1045 | | | | 1050 | | | | |
| Ser | Cys | Ser | Asn | Val | Thr | Cys | Trp | Leu | Lys | Asp | Val | His | Met | Lys |
| | | 1055 | | | | 1060 | | | | 1065 | | | | |
| Gly | Glu | Tyr | Phe | Val | Asn | Val | Thr | Thr | Arg | Ile | Trp | Asn | Gly | Thr |
| | | 1070 | | | | 1075 | | | | 1080 | | | | |
| Phe | Ala | Ser | Ser | Thr | Phe | Gln | Thr | Val | Gln | Leu | Thr | Ala | Ala | Ala |
| | | 1085 | | | | 1090 | | | | 1095 | | | | |
| Glu | Ile | Asn | Thr | Tyr | Asn | Pro | Glu | Ile | Tyr | Val | Ile | Glu | Asp | Asn |
| | | 1100 | | | | 1105 | | | | 1110 | | | | |
| Thr | Val | Thr | Ile | Pro | Leu | Met | Ile | Met | Lys | Pro | Asp | Glu | Lys | Ala |
| | | 1115 | | | | 1120 | | | | 1125 | | | | |
| Glu | Val | Pro | Thr | Gly | Val | Ile | Ile | Gly | Ser | Ile | Ile | Ala | Gly | Ile |
| | | 1130 | | | | 1135 | | | | 1140 | | | | |
| Leu | Leu | Leu | Leu | Ala | Leu | Val | Ala | Ile | Leu | Trp | Lys | Leu | Gly | Phe |
| | | 1145 | | | | 1150 | | | | 1155 | | | | |
| Phe | Lys | Arg | Lys | Tyr | Glu | Lys | Met | Thr | Lys | Asn | Pro | Asp | Glu | Ile |
| | | 1160 | | | | 1165 | | | | 1170 | | | | |
| Asp | Glu | Thr | Thr | Glu | Leu | Ser | Ser |
| | | 1175 | | | | 1180 | |

<210> SEQ ID NO 9
<211> LENGTH: 3700
<212> TYPE: DNA
<213> ORGANISM: Homo Sapiens
<220> FEATURE:
<221> NAME/KEY: misc_feature
<223> OTHER INFORMATION: Human beta1 integrin DNA

<400> SEQUENCE: 9

| agccgccgcc | acccgccgcg | cccgacaccc | gggaggcccc | gccagcccgc | gggagaggcc | 60 |
| cagcgggagt | cgcggaacag | caggcccgag | cccaccgcgc | cgggccccgg | acgccgcgcg | 120 |
| gaaaagatga | atttacaacc | aatttttctgg | attggactga | tcagttcagt | ttgctgtgtg | 180 |
| tttgctcaaa | cagatgaaaa | tagatgttta | aaagcaaatg | ccaaatcatg | tggagaatgt | 240 |
| atacaagcag | ggccaaattg | tgggtggtgc | acaaattcaa | cattttttaca | ggaaggaatg | 300 |

```
cctacttctg cacgatgtga tgatttagaa gccttaaaaa agaagggttg ccctccagat      360
gacatagaaa atcccagagg ctccaaagat ataagaaaa ataaaaatgt aaccaaccgt       420
agcaaaggaa cagcagagaa gctcaagcca gaggatatta ctcagatcca accacagcag     480
ttggttttgc gattaagatc aggggagcca cagacattta cattaaaatt caagagagct     540
gaagactatc ccattgacct ctactacctt atggacctgt cttactcaat gaaagacgat     600
ttggagaatg taaaaagtct tggaacagat ctgatgaatg aaatgaggag gattacttcg    660
gacttcagaa ttggatttgg ctcatttgtg gaaaagactg tgatgcctta cattagcaca    720
acaccagcta agctcaggaa cccttgcaca agtgaacaga actgcaccag cccatttagc    780
tacaaaaatg tgctcagtct tactaataaa ggagaagtat ttaatgaact tgttggaaaa    840
cagcgcatat ctggaaattt ggattctcca aaggtggtt tcgatgccat catgcaagtt     900
gcagtttgtg gatcactgat tggctggagg aatgttacac ggctgctggt gttttccaca    960
gatgccgggt tcactttgc tggagatggg aaacttggtg gcattgtttt accaaatgat    1020
ggacaatgtc acctggaaaa taatatgtac acaatgagcc attattatga ttatccttct   1080
attgctcacc ttgtccagaa actgagtgaa aataatattc agacaatttt tgcagttact   1140
gaagaatttc agcctgttta caaggagctg aaaaacttga tccctaagtc agcagtagga   1200
acattatctg caaattctag caatgtaatt cagttgatca ttgatgcata caattccctt   1260
tcctcagaag tcattttgga aaacggcaaa ttgtcagaag gagtaacaat aagttacaaa   1320
tcttactgca agaacggggt gaatggaaca ggggaaaatg gaagaaaatg ttccaatatt   1380
tccattggag atgaggttca atttgaaatt agcataactt caaataagtg tccaaaaaag   1440
gattctgaca gctttaaaat taggcctctg ggctttacgg aggaagtaga ggttattctt   1500
cagtacatct gtgaatgtga atgccaaagc gaaggcatcc ctgaaagtcc caagtgtcat   1560
gaaggaaatg ggacatttga gtgtggcgcg tgcaggtgca atgaagggcg tgttggtaga   1620
cattgtgaat gcagcacaga tgaagttaac agtgaagaca tggatgctta ctgcaggaaa   1680
gaaaacagtt cagaaatctg cagtaacaat ggagagtgcg tctgcggaca gtgtgtttgt   1740
aggaagaggg ataatacaaa tgaaatttat tctggcaaat tctgcgagtg tgataatttc   1800
aactgtgata gatccaatgg cttaattgt ggaggaaatg gtgtttgcaa gtgtcgtgtg    1860
tgtgagtgca accccaacta cactggcagt gcatgtgact gttctttgga tactagtact    1920
tgtgaagcca gcaacggaca gatctgcaat ggccggggca tctgcgagtg tggtgtctgt    1980
aagtgtacag atccgaagtt tcaagggcaa acgtgtgaga tgtgtcagac ctgccttggt    2040
gtctgtgctg agcataaaga atgtgttcag tgcagagcct tcaataaagg agaaaagaaa    2100
gacacatgca cacaggaatg ttcctatttt aacattacca aggtagaaag tcgggacaaa    2160
ttaccccagc cggtccaacc tgatcctgtg tcccattgta aggagaagga tgttgacgac   2220
tgttggttct attttacgta ttcagtgaat gggaacaacg aggtcatggt tcatgttgtg    2280
gagaatccag agtgtcccac tggtccagac atcattccaa ttgtagctgg tgtggttgct    2340
ggaattgttc ttattggcct tgcattactg ctgatatgga agcttttaat gataattcat    2400
gacagaaggg agtttgctaa atttgaaaag gagaaaatga atgccaaatg ggacacgggt   2460
gaaaatccta tttataagag tgccgtaaca actgtggtca atccgaagta tgagggaaaa   2520
tgagtactgc ccgtgcaaat cccacaacac tgaatgcaaa gtagcaattt ccatagtcac   2580
agttaggtag ctttagggca atattgccat ggttttactc atgtgcaggt tttgaaaatg   2640
tacaatatgt ataatttta aaatgtttta ttattttgaa aataatgttg taattcatgc     2700
```

-continued

```
cagggactga caaaagactt gagacaggat ggttattctt gtcagctaag gtcacattgt    2760
gcctttttga cctttctctc ctggactatt gaaatcaagc ttattggatt aagtgatatt    2820
tctatagcga ttgaaagggc aatagttaaa gtaatgagca tgatgagagt ttctgttaat    2880
catgtattaa aactgatttt tagctttaca aatatgtcag tttgcagtta tgcagaatcc    2940
aaagtaaatg tcctgctagc tagttaagga ttgttttaaa tctgttattt tgctatttgc    3000
ctgttagaca tgactgatga catatctgaa agacaagtat gttgagagtt gctggtgtaa    3060
aatacgtttg aaatagttga tctacaaagg ccatgggaaa aattcagaga gttaggaagg    3120
aaaaaccaat agctttaaaa cctgtgtgcc attttaagag ttacttaatg tttggtaact    3180
tttatgcctt cactttacaa attcaagcct tagataaaag aaccgagcaa ttttctgcta    3240
aaaagtcctt gatttagcac tatttacata caggccatac tttacaaagt atttgctgaa    3300
tggggacctt ttgagttgaa tttattttat tattttattt tgtttaatg tctggtgctt    3360 tctatcacct cttctaatct tttaatgtat tgtttgcaa ttttggggta agacttttt    3420 atgagtactt tttctttgaa gttttagcgg tcaatttgcc ttttaatga acatgtgaag    3480 ttatactgtg gctatgcaac agctctcacc tacgcgagtc ttactttgag ttagtgccat    3540
aacagaccac tgtatgttta cttctcacca tttgagttgc ccatcttgtt tcacactagt    3600
cacattcttg ttttaagtgc ctttagtttt aacagttcac tttttacagt gctatttact    3660
gaagttattt attaaatatg cctaaaatac ttaaatcgga                          3700
```

<210> SEQ ID NO 10
<211> LENGTH: 798
<212> TYPE: PRT
<213> ORGANISM: Homo Sapiens
<220> FEATURE:
<221> NAME/KEY: MISC_FEATURE
<223> OTHER INFORMATION: Human beta1 integrin

<400> SEQUENCE: 10

```
Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190
```

```
Met Pro Tyr Ile Ser Thr Thr Pro Ala Lys Leu Arg Asn Pro Cys Thr
            195                 200                 205
Ser Glu Gln Asn Cys Thr Ser Pro Phe Ser Tyr Lys Asn Val Leu Ser
            210                 215                 220
Leu Thr Asn Lys Gly Glu Val Phe Asn Glu Leu Val Gly Lys Gln Arg
225                 230                 235                 240
Ile Ser Gly Asn Leu Asp Ser Pro Glu Gly Phe Asp Ala Ile Met
                245                 250                 255
Gln Val Ala Val Cys Gly Ser Leu Ile Gly Trp Arg Asn Val Thr Arg
            260                 265                 270
Leu Leu Val Phe Ser Thr Asp Ala Gly Phe His Phe Ala Gly Asp Gly
            275                 280                 285
Lys Leu Gly Gly Ile Val Leu Pro Asn Asp Gly Gln Cys His Leu Glu
            290                 295                 300
Asn Asn Met Tyr Thr Met Ser His Tyr Tyr Asp Tyr Pro Ser Ile Ala
305                 310                 315                 320
His Leu Val Gln Lys Leu Ser Glu Asn Asn Ile Gln Thr Ile Phe Ala
            325                 330                 335
Val Thr Glu Glu Phe Gln Pro Val Tyr Lys Glu Leu Lys Asn Leu Ile
            340                 345                 350
Pro Lys Ser Ala Val Gly Thr Leu Ser Ala Asn Ser Ser Asn Val Ile
            355                 360                 365
Gln Leu Ile Ile Asp Ala Tyr Asn Ser Leu Ser Ser Glu Val Ile Leu
            370                 375                 380
Glu Asn Gly Lys Leu Ser Glu Gly Val Thr Ile Ser Tyr Lys Ser Tyr
385                 390                 395                 400
Cys Lys Asn Gly Val Asn Gly Thr Gly Glu Asn Gly Arg Lys Cys Ser
                405                 410                 415
Asn Ile Ser Ile Gly Asp Glu Val Gln Phe Glu Ile Ser Ile Thr Ser
            420                 425                 430
Asn Lys Cys Pro Lys Lys Asp Ser Asp Ser Phe Lys Ile Arg Pro Leu
            435                 440                 445
Gly Phe Thr Glu Glu Val Glu Val Ile Leu Gln Tyr Ile Cys Glu Cys
            450                 455                 460
Glu Cys Gln Ser Glu Gly Ile Pro Glu Ser Pro Lys Cys His Glu Gly
465                 470                 475                 480
Asn Gly Thr Phe Glu Cys Gly Ala Cys Arg Cys Asn Glu Gly Arg Val
                485                 490                 495
Gly Arg His Cys Glu Cys Ser Thr Asp Glu Val Asn Ser Glu Asp Met
            500                 505                 510
Asp Ala Tyr Cys Arg Lys Glu Asn Ser Ser Glu Ile Cys Ser Asn Asn
            515                 520                 525
Gly Glu Cys Val Cys Gly Gln Cys Val Cys Arg Lys Arg Asp Asn Thr
            530                 535                 540
Asn Glu Ile Tyr Ser Gly Lys Phe Cys Glu Cys Asp Asn Phe Asn Cys
545                 550                 555                 560
Asp Arg Ser Asn Gly Leu Ile Cys Gly Gly Asn Gly Val Cys Lys Cys
                565                 570                 575
Arg Val Cys Glu Cys Asn Pro Asn Tyr Thr Gly Ser Ala Cys Asp Cys
            580                 585                 590
Ser Leu Asp Thr Ser Thr Cys Glu Ala Ser Asn Gly Gln Ile Cys Asn
            595                 600                 605
Gly Arg Gly Ile Cys Glu Cys Gly Val Cys Lys Cys Thr Asp Pro Lys
```

-continued

```
                610                 615                 620
Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
                660                 665                 670

Val Glu Ser Arg Asp Lys Leu Pro Gln Pro Val Gln Pro Asp Pro Val
                675                 680                 685

Ser His Cys Lys Glu Lys Asp Val Asp Cys Trp Phe Tyr Phe Thr
690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
                740                 745                 750

Leu Leu Met Ile Ile His Asp Arg Arg Glu Phe Ala Lys Phe Glu Lys
                755                 760                 765

Glu Lys Met Asn Ala Lys Trp Asp Thr Gly Glu Asn Pro Ile Tyr Lys
                770                 775                 780

Ser Ala Val Thr Thr Val Val Asn Pro Lys Tyr Glu Gly Lys
785                 790                 795
```

<210> SEQ ID NO 11
<211> LENGTH: 226
<212> TYPE: PRT
<213> ORGANISM: Homo Sapiens
<220> FEATURE:
<221> NAME/KEY: MISC_FEATURE
<223> OTHER INFORMATION: Human alpha2 I domain

<400> SEQUENCE: 11

```
Ser Pro Asp Phe Gln Leu Ser Ala Ser Phe Ser Pro Ala Thr Gln Pro
1               5                   10                  15

Cys Pro Ser Leu Ile Asp Val Val Val Cys Asp Glu Ser Asn Ser
                20                  25                  30

Ile Tyr Pro Trp Asp Ala Val Lys Asn Phe Leu Glu Lys Phe Val Gln
                35                  40                  45

Gly Leu Asp Ile Gly Pro Thr Lys Thr Gln Val Gly Leu Ile Gln Tyr
        50                  55                  60

Ala Asn Asn Pro Arg Val Val Phe Asn Leu Asn Thr Tyr Lys Thr Lys
65              70                  75                  80

Glu Glu Met Ile Val Ala Thr Ser Gln Thr Ser Gln Tyr Gly Gly Asp
                85                  90                  95

Leu Thr Asn Thr Phe Gly Ala Ile Gln Tyr Ala Arg Lys Tyr Ala Tyr
                100                 105                 110

Ser Ala Ala Ser Gly Gly Arg Arg Ser Ala Thr Lys Val Met Val Val
                115                 120                 125

Val Thr Asp Gly Glu Ser His Asp Gly Ser Met Leu Lys Ala Val Ile
                130                 135                 140

Asp Gln Cys Asn His Asp Asn Ile Leu Arg Phe Gly Ile Ala Val Leu
145                 150                 155                 160

Gly Tyr Leu Asn Arg Asn Ala Leu Asp Thr Lys Asn Leu Ile Lys Glu
                165                 170                 175

Ile Lys Ala Ile Ala Ser Ile Pro Thr Glu Arg Tyr Phe Phe Asn Val
```

```
                        180                 185                 190
Ser Asp Glu Ala Ala Leu Leu Glu Lys Ala Gly Thr Leu Gly Glu Gln
        195                 200                 205

Ile Phe Ser Ile Glu Gly Thr Val Gln Gly Gly Asp Asn Phe Gln Met
    210                 215                 220

Glu Met
225

<210> SEQ ID NO 12
<211> LENGTH: 71
<212> TYPE: PRT
<213> ORGANISM: Homo Sapiens
<220> FEATURE:
<221> NAME/KEY: MISC_FEATURE
<223> OTHER INFORMATION: FW1-3 4-59 [FW=1-25; FW2=26-39; FW3=40-71]

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Ser Trp Ile Arg Gln Pro Pro Gly
            20                  25                  30

Lys Gly Leu Glu Trp Ile Gly Arg Val Thr Ile Ser Val Asp Thr Ser
        35                  40                  45

Lys Asn Gln Phe Ser Leu Lys Leu Ser Ser Val Thr Ala Ala Asp Thr
    50                  55                  60

Ala Val Tyr Tyr Cys Ala Arg
65                  70

<210> SEQ ID NO 13
<211> LENGTH: 11
<212> TYPE: PRT
<213> ORGANISM: Homo Sapiens
<220> FEATURE:
<221> NAME/KEY: MISC_FEATURE
<223> OTHER INFORMATION: FW4 4-59 [NCBI entry gi/33583]

<400> SEQUENCE: 13

Trp Gly Gln Gly Thr Leu Val Thr Val Ser Ser
1               5                   10

<210> SEQ ID NO 14
<211> LENGTH: 27
<212> TYPE: DNA
<213> ORGANISM: Homo Sapiens
<220> FEATURE:
<221> NAME/KEY: misc_feature
<223> OTHER INFORMATION: VHL-for [forward primer]

<400> SEQUENCE: 14
ccatggctgt cttggggctg ctcttct                                         27

<210> SEQ ID NO 15
<211> LENGTH: 17
<212> TYPE: DNA
<213> ORGANISM: Homo Sapiens
<220> FEATURE:
<221> NAME/KEY: misc_feature
<223> OTHER INFORMATION: HC-rev [reverse primer]

<400> SEQUENCE: 15
ggggccagtg gatagac                                                    17

<210> SEQ ID NO 16
<211> LENGTH: 28
```

```
<212> TYPE: DNA
<213> ORGANISM: Homo Sapiens
<220> FEATURE:
<221> NAME/KEY: misc_feature
<223> OTHER INFORMATION: VLL-for [forward primer]

<400> SEQUENCE: 16
ccatggattt tcaagtgcag attttcag                                      28

<210> SEQ ID NO 17
<211> LENGTH: 17
<212> TYPE: DNA
<213> ORGANISM: Homo Sapiens
<220> FEATURE:
<221> NAME/KEY: misc_feature
<223> OTHER INFORMATION: LCkappa-rev [reverse primer]

<400> SEQUENCE: 17
gttggtgcag catcagc                                                  17

<210> SEQ ID NO 18
<211> LENGTH: 318
<212> TYPE: DNA
<213> ORGANISM: Homo Sapiens
<220> FEATURE:
<221> NAME/KEY: misc_feature
<223> OTHER INFORMATION: TMC-2206 VL
<220> FEATURE:
<221> NAME/KEY: CDS
<222> LOCATION: (1)..(318)

<400> SEQUENCE: 18 caa ttt gtt ctc acc cag tct cca gca ttc ttg tct gct tct cca ggg    48
Gln Phe Val Leu Thr Gln Ser Pro Ala Phe Leu Ser Ala Ser Pro Gly
1               5                   10                  15 gag aag gtc acc atg acc tgc agt gcc aac tca agt gtg aat tac att    96
Glu Lys Val Thr Met Thr Cys Ser Ala Asn Ser Ser Val Asn Tyr Ile
                20                  25                  30 cac tgg tac cag cag aag tca ggc acc tcc ccc aaa aaa tgg att tat   144
His Trp Tyr Gln Gln Lys Ser Gly Thr Ser Pro Lys Lys Trp Ile Tyr
            35                  40                  45 gac act tcc aaa ctg gct tct gga gtc cct gtt cgc ttc agt ggc agt   192
Asp Thr Ser Lys Leu Ala Ser Gly Val Pro Val Arg Phe Ser Gly Ser
        50                  55                  60 gga tct ggg acc tct tac tct ctc aca atc agc agc atg gag act gag   240
Gly Ser Gly Thr Ser Tyr Ser Leu Thr Ile Ser Ser Met Glu Thr Glu
65                  70                  75                  80 gat gct gcc act tat tac tgc cag cag tgg act act aac cca ctc acg   288
Asp Ala Ala Thr Tyr Tyr Cys Gln Gln Trp Thr Thr Asn Pro Leu Thr
                85                  90                  95 ttc ggt gct ggg acc agg gtg gag ctg aaa                           318
Phe Gly Ala Gly Thr Arg Val Glu Leu Lys
            100                 105

<210> SEQ ID NO 19
<211> LENGTH: 106
<212> TYPE: PRT
<213> ORGANISM: Homo Sapiens

<400> SEQUENCE: 19

Gln Phe Val Leu Thr Gln Ser Pro Ala Phe Leu Ser Ala Ser Pro Gly
1               5                   10                  15

Glu Lys Val Thr Met Thr Cys Ser Ala Asn Ser Ser Val Asn Tyr Ile
                20                  25                  30

His Trp Tyr Gln Gln Lys Ser Gly Thr Ser Pro Lys Lys Trp Ile Tyr
```

```
                35                  40                  45

Asp Thr Ser Lys Leu Ala Ser Gly Val Pro Val Arg Phe Ser Gly Ser
        50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Thr Thr Asn Pro Leu Thr
                85                  90                  95

Phe Gly Ala Gly Thr Arg Val Glu Leu Lys
            100                 105

<210> SEQ ID NO 20
<211> LENGTH: 357
<212> TYPE: DNA
<213> ORGANISM: Homo sapiens
<220> FEATURE:
<221> NAME/KEY: CDS
<222> LOCATION: (1)..(357)
<220> FEATURE:
<221> NAME/KEY: misc_feature
<222> LOCATION: (1)..(357)
<223> OTHER INFORMATION: TMC-2206 VH

<400> SEQUENCE: 20 cag gtg cag ttg aag gag tca gga cct ggc ctg gtg gcg ccc tca cag     48
Gln Val Gln Leu Lys Glu Ser Gly Pro Gly Leu Val Ala Pro Ser Gln
1               5                   10                  15 agc ctg tcc atc act tgt act gtc tct gga ttt tca tta acc aac tat     96
Ser Leu Ser Ile Thr Cys Thr Val Ser Gly Phe Ser Leu Thr Asn Tyr
            20                  25                  30 ggt att cac tgg gtt cgc cag cct cca gga aag ggt ctg gag tgg ctg    144
Gly Ile His Trp Val Arg Gln Pro Pro Gly Lys Gly Leu Glu Trp Leu
        35                  40                  45 gga gtg ata tgg gct cgt gga ttc aca aat tat aat tcg gct ctc atg    192
Gly Val Ile Trp Ala Arg Gly Phe Thr Asn Tyr Asn Ser Ala Leu Met
    50                  55                  60 tcc aga ctg atc atc aca aaa gac aat tcc cag agt caa gtc ttc tta    240
Ser Arg Leu Ile Ile Thr Lys Asp Asn Ser Gln Ser Gln Val Phe Leu
65                  70                  75                  80 aaa atg aac agt cta caa cct gat gac tca gcc act tac ttc tgt gcc    288
Lys Met Asn Ser Leu Gln Pro Asp Asp Ser Ala Thr Tyr Phe Cys Ala
                85                  90                  95 aga gcg aac gac ggg gtc tat tat gct atg gac tac tgg ggt cag gga    336
Arg Ala Asn Asp Gly Val Tyr Tyr Ala Met Asp Tyr Trp Gly Gln Gly
            100                 105                 110 acc tca gtc acc gtc tcc tca                                        357
Thr Ser Val Thr Val Ser Ser
        115

<210> SEQ ID NO 21
<211> LENGTH: 119
<212> TYPE: PRT
<213> ORGANISM: Homo sapiens

<400> SEQUENCE: 21

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Ile His Trp Val Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60
```

```
Ser Arg Leu Ile Ile Thr Lys Asp Asn Ser Gln Ser Gln Val Phe Leu
 65                  70                  75                  80

Lys Met Asn Ser Leu Gln Pro Asp Asp Ser Ala Thr Tyr Phe Cys Ala
                 85                  90                  95

Arg Ala Asn Asp Gly Val Tyr Tyr Ala Met Asp Tyr Trp Gly Gln Gly
            100                 105                 110

Thr Ser Val Thr Val Ser Ser
        115
```

<210> SEQ ID NO 22
<211> LENGTH: 31
<212> TYPE: DNA
<213> ORGANISM: Homo Sapiens
<220> FEATURE:
<221> NAME/KEY: misc_feature
<223> OTHER INFORMATION: TMC-2206-r5' [forward primer]

<400> SEQUENCE: 22
cccgaattca caggtgcagt tgaaggagtc a                           31

<210> SEQ ID NO 23
<211> LENGTH: 35
<212> TYPE: DNA
<213> ORGANISM: Homo Sapiens
<220> FEATURE:
<221> NAME/KEY: misc_feature
<223> OTHER INFORMATION: TMC-2206-r3' [reverse primer]

<400> SEQUENCE: 23
cgggatcctt aggatcattt accaggagag tggga                       35

<210> SEQ ID NO 24
<211> LENGTH: 31
<212> TYPE: DNA
<213> ORGANISM: Homo Sapiens
<220> FEATURE:
<221> NAME/KEY: misc_feature
<223> OTHER INFORMATION: TMC-2206-k5' [forward primer]

<400> SEQUENCE: 24
cccgaattca caatttgttc tcacccagtc t                           31

<210> SEQ ID NO 25
<211> LENGTH: 35
<212> TYPE: DNA
<213> ORGANISM: Homo Sapiens
<220> FEATURE:
<221> NAME/KEY: misc_feature
<223> OTHER INFORMATION: TMC-2206-k3' [reverse primer]

<400> SEQUENCE: 25
cgggatcctt atctctaaca ctcattcctg ttgaa                       35

<210> SEQ ID NO 26
<211> LENGTH: 22
<212> TYPE: PRT
<213> ORGANISM: Homo Sapiens
<220> FEATURE:
<221> NAME/KEY: MISC_FEATURE
<223> OTHER INFORMATION: Igkappa (Igk) leader sequence

<400> SEQUENCE: 26

```
Met Glu Thr Asp Thr Leu Leu Leu Trp Val Leu Leu Leu Trp Val Pro
 1               5                  10                  15

Gly Gly Ser Thr Gly Asp
```

<210> SEQ ID NO 27
<211> LENGTH: 76
<212> TYPE: DNA
<213> ORGANISM: Homo Sapiens
<220> FEATURE:
<221> NAME/KEY: misc_feature
<223> OTHER INFORMATION: Igkappa-S Oligonucleotides [Primer]

<400> SEQUENCE: 27
tcgagccacc atggagacag acacactcct gctatgggta ctgctgctct gggttccagg    60
ttccactgga gacgcg                                                    76

<210> SEQ ID NO 28
<211> LENGTH: 76
<212> TYPE: DNA
<213> ORGANISM: Homo Sapiens
<220> FEATURE:
<221> NAME/KEY: misc_feature
<223> OTHER INFORMATION: Igkappa-AS oligonucleotides [Primer]

<400> SEQUENCE: 28
aattcgcgtc tccagtggaa cctggaaccc agagcagcag tacccatagc aggagtgtgt    60
ctgtctccat ggtggc                                                    76

<210> SEQ ID NO 29
<211> LENGTH: 33
<212> TYPE: DNA
<213> ORGANISM: Homo Sapiens
<220> FEATURE:
<221> NAME/KEY: misc_feature
<223> OTHER INFORMATION: TMC2206VH-hIgG1/4Fc-SalI

<400> SEQUENCE: 29
cttggtcgac gctgaggaga cggtgactga ggt                                 33

<210> SEQ ID NO 30
<211> LENGTH: 30
<212> TYPE: DNA
<213> ORGANISM: Homo Sapiens
<220> FEATURE:
<221> NAME/KEY: misc_feature
<223> OTHER INFORMATION: hIgG1/4Fc-SalI-F [forward primer]

<400> SEQUENCE: 30
tcagcgtcga ccaagggccc atcsgtcttc                                     30

<210> SEQ ID NO 31
<211> LENGTH: 48
<212> TYPE: DNA
<213> ORGANISM: Homo Sapiens
<220> FEATURE:
<221> NAME/KEY: misc_feature
<223> OTHER INFORMATION: hIgG1/4Fc-NotI-R [reverse primer]

<400> SEQUENCE: 31
aagggaagcg gccgcttatc atttacccyg agacagggag aggctctt                 48

<210> SEQ ID NO 32
<211> LENGTH: 39
<212> TYPE: DNA
<213> ORGANISM: Homo Sapiens
<220> FEATURE:
<221> NAME/KEY: misc_feature
<223> OTHER INFORMATION: TMC2206VL-hKc-SalI [reverse primer]

<210> SEQ ID NO 32

<400> SEQUENCE: 32
tcgtttgatg tcgaccttgg tcccagcacc gaacgtgag          39

<210> SEQ ID NO 33
<211> LENGTH: 35
<212> TYPE: DNA
<213> ORGANISM: Homo Sapiens
<220> FEATURE:
<221> NAME/KEY: misc_feature
<223> OTHER INFORMATION: hKc-SalI-F [forward primer]

<400> SEQUENCE: 33
accaaggtcg acatcaaacg aactgtggct gcacc             35

<210> SEQ ID NO 34
<211> LENGTH: 45
<212> TYPE: DNA
<213> ORGANISM: Homo Sapiens
<220> FEATURE:
<221> NAME/KEY: misc_feature
<223> OTHER INFORMATION: hKc-NotI-R [reverse primer]

<400> SEQUENCE: 34
aagggaagcg gccgcttatc arcactctcc cctgttgaag ctctt    45

<210> SEQ ID NO 35
<211> LENGTH: 29
<212> TYPE: DNA
<213> ORGANISM: Homo Sapiens
<220> FEATURE:
<221> NAME/KEY: misc_feature
<223> OTHER INFORMATION: TMC-2206VLwt-hKc-F [forward primer]

<400> SEQUENCE: 35
agggtggagc tgaaacgaac tgtggctgc                    29

<210> SEQ ID NO 36
<211> LENGTH: 24
<212> TYPE: DNA
<213> ORGANISM: Homo Sapiens
<220> FEATURE:
<221> NAME/KEY: misc_feature
<223> OTHER INFORMATION: TMC-2206VLwt-hKc-R [reverse primer]

<400> SEQUENCE: 36
tcgtttcagc tccaccctgg tccc                         24

<210> SEQ ID NO 37
<211> LENGTH: 107
<212> TYPE: PRT
<213> ORGANISM: Homo Sapiens
<220> FEATURE:
<221> NAME/KEY: MISC_FEATURE
<223> OTHER INFORMATION: A14 VL germline protein

<400> SEQUENCE: 37

Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala

```
                65                  70                  75                  80
Glu Asp Ala Ala Thr Tyr Tyr Cys Gln Gln Trp Thr Thr Asn Pro Leu
                    85                  90                  95

Thr Phe Gly Gln Gly Thr Lys Val Glu Ile Lys
            100                 105

<210> SEQ ID NO 38
<211> LENGTH: 10
<212> TYPE: PRT
<213> ORGANISM: Homo Sapiens
<220> FEATURE:
<221> NAME/KEY: MISC_FEATURE
<223> OTHER INFORMATION: FW 4 of mature kappa light chain

<400> SEQUENCE: 38

Phe Gly Gln Gly Thr Lys Val Glu Ile Lys
1               5                   10

<210> SEQ ID NO 39
<211> LENGTH: 121
<212> TYPE: PRT
<213> ORGANISM: Homo Sapiens
<220> FEATURE:
<221> NAME/KEY: MISC_FEATURE
<223> OTHER INFORMATION: 4-59 VH germline protein

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Asn Ser Ser Ser Trp Tyr Gly Arg Tyr Phe Asp Tyr Trp Gly
            100                 105                 110

Gln Gly Thr Leu Val Thr Val Ser Ser
        115                 120

<210> SEQ ID NO 40
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH1.0

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60
```

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 41
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL1.0

<400> SEQUENCE: 41

Gln Phe Val Leu Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 42
<211> LENGTH: 48
<212> TYPE: DNA
<213> ORGANISM: Homo Sapiens
<220> FEATURE:
<221> NAME/KEY: misc_feature
<223> OTHER INFORMATION: hVH3.0-F [forward primer]

<400> SEQUENCE: 42
agcgtggaca ccagcaagaa ccagttcagc ctgaagctga gcagcgtg         48

<210> SEQ ID NO 43
<211> LENGTH: 51
<212> TYPE: DNA
<213> ORGANISM: Homo Sapiens
<220> FEATURE:
<221> NAME/KEY: misc_feature
<223> OTHER INFORMATION: hVH3.0-R [reverse primer]

<400> SEQUENCE: 43
gttcttgctg gtgtccacgc tgatggtcac gcgggacatg agagcgctgt t      51

<210> SEQ ID NO 44
<211> LENGTH: 48
<212> TYPE: DNA
<213> ORGANISM: Homo Sapiens
<220> FEATURE:
<221> NAME/KEY: misc_feature
<223> OTHER INFORMATION: hVH4.0-F [forward primer]

<400> SEQUENCE: 44
cctccaggca agggcctgga gtggatcggc gtgatatggg ctcgcggc        48

<210> SEQ ID NO 45
<211> LENGTH: 51
<212> TYPE: DNA
<213> ORGANISM: Homo Sapiens
<220> FEATURE:
<221> NAME/KEY: misc_feature
<223> OTHER INFORMATION: hVH4.0-R [reverse primer]

<400> SEQUENCE: 45
ctccaggccc ttgcctggag gctggcgtat ccagtggatg ccatagttgg t        51

<210> SEQ ID NO 46
<211> LENGTH: 33
<212> TYPE: DNA
<213> ORGANISM: Homo Sapiens
<220> FEATURE:
<221> NAME/KEY: misc_feature
<223> OTHER INFORMATION: hVL3.0-F [forward primer]

<400> SEQUENCE: 46
cccaagctcc tgatctatga cacttccaag ctg        33

<210> SEQ ID NO 47
<211> LENGTH: 42
<212> TYPE: DNA
<213> ORGANISM: Homo Sapiens
<220> FEATURE:
<221> NAME/KEY: misc_feature
<223> OTHER INFORMATION: hVL3.0-R [reverse primer]

<400> SEQUENCE: 47
agtgtcatag atcaggagct tgggggcctg gtcgggcttc tg        42

<210> SEQ ID NO 48
<211> LENGTH: 45
<212> TYPE: DNA
<213> ORGANISM: Homo Sapiens
<220> FEATURE:
<221> NAME/KEY: misc_feature
<223> OTHER INFORMATION: hVL4.0-F [forward primer]

<400> SEQUENCE: 48
gacgcgaatt cagacgtggt gatgacccag tctccagcat tcctg        45

<210> SEQ ID NO 49
<211> LENGTH: 24
<212> TYPE: DNA
<213> ORGANISM: Homo Sapiens
<220> FEATURE:
<221> NAME/KEY: misc_feature
<223> OTHER INFORMATION: hVH2.0-F [forward primer]

<400> SEQUENCE: 49
gtgaccatca gcaaggacaa cagc        24

<210> SEQ ID NO 50
<211> LENGTH: 45
<212> TYPE: DNA
<213> ORGANISM: Homo Sapiens
<220> FEATURE:
<221> NAME/KEY: misc_feature
<223> OTHER INFORMATION: hVH2.0-R [reverse primer]

<400> SEQUENCE: 50
gctgttgtcc ttgctgatgg tcacgcggga catgagagcg ctgtt        45

<210> SEQ ID NO 51
<211> LENGTH: 27
<212> TYPE: DNA
<213> ORGANISM: Homo Sapiens
<220> FEATURE:
<221> NAME/KEY: misc_feature
<223> OTHER INFORMATION: hVH5.0-F [forward primer]

<400> SEQUENCE: 51
atcggcgtga tatgggctcg cggcttc                                27

<210> SEQ ID NO 52
<211> LENGTH: 45
<212> TYPE: DNA
<213> ORGANISM: Homo Sapiens
<220> FEATURE:
<221> NAME/KEY: misc_feature
<223> OTHER INFORMATION: hVH5.0-R [reverse primer]

<400> SEQUENCE: 52
gccgcgagcc catatcacgc cgatccactc caggcccttg cctgg            45

<210> SEQ ID NO 53
<211> LENGTH: 24
<212> TYPE: DNA
<213> ORGANISM: Homo Sapiens
<220> FEATURE:
<221> NAME/KEY: misc_feature
<223> OTHER INFORMATION: hVH6.0-F [forward primer]

<400> SEQUENCE: 53
atatgggctc gcggcttcac aaac                                   24

<210> SEQ ID NO 54
<211> LENGTH: 24
<212> TYPE: DNA
<213> ORGANISM: Homo Sapiens
<220> FEATURE:
<221> NAME/KEY: misc_feature
<223> OTHER INFORMATION: hVH6.0-R [reverse primer]

<400> SEQUENCE: 54
gtttgtgaag ccgcgagccc atat                                   24

<210> SEQ ID NO 55
<211> LENGTH: 45
<212> TYPE: DNA
<213> ORGANISM: Homo Sapiens
<220> FEATURE:
<221> NAME/KEY: misc_feature
<223> OTHER INFORMATION: hVH7.0-F [forward primer]

<400> SEQUENCE: 55
gccgcggaca ccgccgtgta ctactgcgcc agagccaacg acggg            45

<210> SEQ ID NO 56
<211> LENGTH: 27
<212> TYPE: DNA
<213> ORGANISM: Homo Sapiens
<220> FEATURE:
<221> NAME/KEY: misc_feature
<223> OTHER INFORMATION: hVH7.0-R [reverse primer]

<400> SEQUENCE: 56
gtagtacacg gcggtgtccg cggcggt                                27

```
<210> SEQ ID NO 57
<211> LENGTH: 27
<212> TYPE: DNA
<213> ORGANISM: Homo Sapiens
<220> FEATURE:
<221> NAME/KEY: misc_feature
<223> OTHER INFORMATION: hVH8.0-F [forward primer]

<400> SEQUENCE: 57
atatccaact atggcatcca ctgggtt                                    27

<210> SEQ ID NO 58
<211> LENGTH: 48
<212> TYPE: DNA
<213> ORGANISM: Homo Sapiens
<220> FEATURE:
<221> NAME/KEY: misc_feature
<223> OTHER INFORMATION: hVH8.0-R [reverse primer]

<400> SEQUENCE: 58
ccagtggatg ccatagttgg atatgctaaa tccagagacg gtacaggt             48

<210> SEQ ID NO 59
<211> LENGTH: 45
<212> TYPE: DNA
<213> ORGANISM: Homo Sapiens
<220> FEATURE:
<221> NAME/KEY: misc_feature
<223> OTHER INFORMATION: hVL2.0-R [reverse primer]

<400> SEQUENCE: 59
cagcttggaa gtgtcataga tcaatttctt gggggcctgg tcggg                45

<210> SEQ ID NO 60
<211> LENGTH: 45
<212> TYPE: DNA
<213> ORGANISM: Homo Sapiens
<220> FEATURE:
<221> NAME/KEY: misc_feature
<223> OTHER INFORMATION: hVL5.0-F [forward primer]

<400> SEQUENCE: 60
gacgcgaatt cagacttcgt gctgacccag tctccagcat tcctg                45

<210> SEQ ID NO 61
<211> LENGTH: 45
<212> TYPE: DNA
<213> ORGANISM: Homo Sapiens
<220> FEATURE:
<221> NAME/KEY: misc_feature
<223> OTHER INFORMATION: hVL6.0-F [forward primer]

<400> SEQUENCE: 61
gacgcgaatt cacagttcgt gatgacccag tctccagcat tcctg                45

<210> SEQ ID NO 62
<211> LENGTH: 45
<212> TYPE: DNA
<213> ORGANISM: Homo Sapiens
<220> FEATURE:
<221> NAME/KEY: misc_feature
<223> OTHER INFORMATION: hVL7.0-F [forward primer]

<400> SEQUENCE: 62
gacgcgaatt cagacttcgt gatgacccag tctccagcat tcctg                45

<210> SEQ ID NO 63
<211> LENGTH: 27
```

```
<212> TYPE: DNA
<213> ORGANISM: Homo Sapiens
<220> FEATURE:
<221> NAME/KEY: misc_feature
<223> OTHER INFORMATION: hVL8.0-F [forward primer]

<400> SEQUENCE: 63
ttcaccttca ccatcagcag cctggag                                        27

<210> SEQ ID NO 64
<211> LENGTH: 48
<212> TYPE: DNA
<213> ORGANISM: Homo Sapiens
<220> FEATURE:
<221> NAME/KEY: misc_feature
<223> OTHER INFORMATION: hVL8.0-R [reverse primer]

<400> SEQUENCE: 64
ctccaggctg ctgatggtga aggtgaagtc ggtgccgctg ccgctgcc                 48

<210> SEQ ID NO 65
<211> LENGTH: 28
<212> TYPE: DNA
<213> ORGANISM: Homo Sapiens
<220> FEATURE:
<221> NAME/KEY: misc_feature
<223> OTHER INFORMATION: hLCQ3-F [forward primer]

<400> SEQUENCE: 65
ccaatcaagc gtgaactaca ttcactgg                                       28

<210> SEQ ID NO 66
<211> LENGTH: 48
<212> TYPE: DNA
<213> ORGANISM: Homo Sapiens
<220> FEATURE:
<221> NAME/KEY: misc_feature
<223> OTHER INFORMATION: hLCQ3-R [reverse primer]

<400> SEQUENCE: 66
ccagtgaatg tagttcacgc ttgattgggc gctgcaggtg atggtcac                 48

<210> SEQ ID NO 67
<211> LENGTH: 23
<212> TYPE: DNA
<213> ORGANISM: Homo Sapiens
<220> FEATURE:
<221> NAME/KEY: misc_feature
<223> OTHER INFORMATION: Igk-For [forward primer]

<400> SEQUENCE: 67
actcctgcta tgggtactgc tgc                                            23

<210> SEQ ID NO 68
<211> LENGTH: 22
<212> TYPE: DNA
<213> ORGANISM: Homo Sapiens
<220> FEATURE:
<221> NAME/KEY: misc_feature
<223> OTHER INFORMATION: hIgG1Fc-CH1-R [reverse primer]

<400> SEQUENCE: 68
gaagtagtcc ttgaccaggc ag                                             22

<210> SEQ ID NO 69
<211> LENGTH: 22
<212> TYPE: DNA
<213> ORGANISM: Homo Sapiens
```

```
<220> FEATURE:
<221> NAME/KEY: misc_feature
<223> OTHER INFORMATION: CI-neo-msc3' [Primer]

<400> SEQUENCE: 69
tttcactgca ttctagttgt gg                                           22

<210> SEQ ID NO 70
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH2.0

<400> SEQUENCE: 70

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 71
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH3.0

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 72
```

```
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH4.0

<400> SEQUENCE: 72

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Ile
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 73
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH5.0

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Ile
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 74
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH6.0

<400> SEQUENCE: 74

Gln Val Gln Leu Gln Glu Ser Gly Pro Gly Leu Val Lys Pro Ser Glu
```

```
                1               5                  10                  15
Thr Leu Ser Leu Thr Cys Thr Val Ser Gly Phe Ser Leu Thr Asn Tyr
                20                  25                  30

Gly Ile His Trp Val Arg Gln Pro Gly Lys Gly Leu Glu Trp Ile
            35                  40                  45

Gly Val Ile Trp Ala Arg Gly Phe Thr Asn Tyr Asn Ser Ala Leu Met
        50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
                100                 105                 110

Thr Leu Val Thr Val Ser Ser
        115

<210> SEQ ID NO 75
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH7.0

<400> SEQUENCE: 75

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
                20                  25                  30

Gly Ile His Trp Val Arg Gln Pro Pro Gly Lys Gly Leu Glu Trp Leu
            35                  40                  45

Gly Val Ile Trp Ala Arg Gly Phe Thr Asn Tyr Asn Ser Ala Leu Met
        50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
                100                 105                 110

Thr Leu Val Thr Val Ser Ser
        115

<210> SEQ ID NO 76
<211> LENGTH: 119
<212> TYPE: PRT
<213> ORGANISM: Homo sapiens
<220> FEATURE:
<221> NAME/KEY: MISC_FEATURE
<223> OTHER INFORMATION: hVH8.0

<400> SEQUENCE: 76

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Ser Asn Tyr
                20                  25                  30

Gly Ile His Trp Val Arg Gln Pro Pro Gly Lys Gly Leu Glu Trp Leu
            35                  40                  45

Gly Val Ile Trp Ala Arg Gly Phe Thr Asn Tyr Asn Ser Ala Leu Met
        50                  55                  60
```

```
Ser Arg Leu Thr Ile Ser Lys Asp Asn Ser Lys Asn Gln Phe Ser Leu
 65                  70                  75                  80

Lys Leu Ser Ser Val Thr Ala Ala Asp Thr Ala Val Tyr Phe Cys Ala
                 85                  90                  95

Arg Ala Asn Asp Gly Val Tyr Tyr Ala Met Asp Tyr Trp Gly Gln Gly
                100                 105                 110

Thr Leu Val Thr Val Ser Ser
            115
```

<210> SEQ ID NO 77
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH9.0
<220> FEATURE:
<221> NAME/KEY: VARIANT
<222> LOCATION: (48)..(48)
<223> OTHER INFORMATION: Xaa at position 48 can be Leu or Ile

<400> SEQUENCE: 77

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Thr Asn Tyr
                 20                  25                  30

Gly Ile His Trp Val Arg Gln Pro Pro Gly Lys Gly Leu Glu Trp Xaa
             35                  40                  45

Gly Val Ile Trp Ala Arg Gly Phe Thr Asn Tyr Asn Ser Ala Leu Met
 50                  55                  60

Ser Arg Leu Thr Ile Ser Val Asp Asn Ser Lys Asn Gln Val Ser Leu
 65                  70                  75                  80

Lys Leu Ser Ser Val Thr Ala Ala Asp Thr Ala Val Tyr Phe Cys Ala
                 85                  90                  95

Arg Ala Asn Asp Gly Val Tyr Tyr Ala Met Asp Tyr Trp Gly Gln Gly
                100                 105                 110

Thr Leu Val Thr Val Ser Ser
            115
```

<210> SEQ ID NO 78
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH10.0

<400> SEQUENCE: 78

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Thr Asn Tyr
                 20                  25                  30

Gly Ile His Trp Val Arg Gln Pro Pro Gly Lys Gly Leu Glu Trp Leu
             35                  40                  45

Gly Val Ile Trp Ala Arg Gly Phe Thr Asn Tyr Asn Ser Ala Leu Met
 50                  55                  60

Ser Arg Leu Thr Ile Ser Lys Asp Thr Ser Lys Asn Gln Val Ser Leu
 65                  70                  75                  80

Lys Leu Ser Ser Val Thr Ala Ala Asp Thr Ala Val Tyr Phe Cys Ala
                 85                  90                  95
```

Arg Ala Asn Asp Gly Val Tyr Tyr Ala Met Asp Tyr Trp Gly Gln Gly
                100                 105                 110

Thr Leu Val Thr Val Ser Ser
        115

<210> SEQ ID NO 79
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH11.0
<220> FEATURE:
<221> NAME/KEY: VARIANT
<222> LOCATION: (48)..(48)
<223> OTHER INFORMATION: Xaa at position 48 can be Leu or Ile

<400> SEQUENCE: 79

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Xaa
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
                100                 105                 110

Thr Leu Val Thr Val Ser Ser
        115

<210> SEQ ID NO 80
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL2.0

<400> SEQUENCE: 80

Gln Phe Val Leu Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 81

<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL3.0

<400> SEQUENCE: 81

Gln Phe Val Leu Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 82
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL4.0

<400> SEQUENCE: 82

Asp Val Val Met Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 83
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL5.0

<400> SEQUENCE: 83

Asp Phe Val Leu Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Trp Ile Tyr

```
                  35                  40                  45
Asp Thr Ser Lys Leu Ala Ser Gly Val Pro Ser Arg Phe Ser Gly Ser
         50                  55                  60
Gly Ser Gly Thr Asp Tyr Thr Phe Thr Ile Ser Ser Leu Glu Ala Glu
 65                  70                  75                  80
Asp Ala Ala Thr Tyr Tyr Cys Gln Gln Trp Thr Thr Asn Pro Leu Thr
                 85                  90                  95
Phe Gly Gln Gly Thr Lys Val Glu Ile Lys
                100                 105

<210> SEQ ID NO 84
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL6.0

<400> SEQUENCE: 84

Gln Phe Val Met Thr Gln Ser Pro Ala Phe Leu Ser Val Thr Pro Gly
  1               5                  10                  15
Glu Lys Val Thr Ile Thr Cys Ser Ala Asn Ser Ser Val Asn Tyr Ile
                 20                  25                  30
His Trp Tyr Gln Gln Lys Pro Asp Gln Ala Pro Lys Lys Trp Ile Tyr
                 35                  40                  45
Asp Thr Ser Lys Leu Ala Ser Gly Val Pro Ser Arg Phe Ser Gly Ser
         50                  55                  60
Gly Ser Gly Thr Asp Tyr Thr Phe Thr Ile Ser Ser Leu Glu Ala Glu
 65                  70                  75                  80
Asp Ala Ala Thr Tyr Tyr Cys Gln Gln Trp Thr Thr Asn Pro Leu Thr
                 85                  90                  95
Phe Gly Gln Gly Thr Lys Val Glu Ile Lys
                100                 105

<210> SEQ ID NO 85
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL7.0

<400> SEQUENCE: 85

Asp Phe Val Met Thr Gln Ser Pro Ala Phe Leu Ser Val Thr Pro Gly
  1               5                  10                  15
Glu Lys Val Thr Ile Thr Cys Ser Ala Asn Ser Ser Val Asn Tyr Ile
                 20                  25                  30
His Trp Tyr Gln Gln Lys Pro Asp Gln Ala Pro Lys Lys Trp Ile Tyr
                 35                  40                  45
Asp Thr Ser Lys Leu Ala Ser Gly Val Pro Ser Arg Phe Ser Gly Ser
         50                  55                  60
Gly Ser Gly Thr Asp Tyr Thr Phe Thr Ile Ser Ser Leu Glu Ala Glu
 65                  70                  75                  80
Asp Ala Ala Thr Tyr Tyr Cys Gln Gln Trp Thr Thr Asn Pro Leu Thr
                 85                  90                  95
Phe Gly Gln Gly Thr Lys Val Glu Ile Lys
                100                 105

<210> SEQ ID NO 86
```

```
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL8.0

<400> SEQUENCE: 86

Gln Phe Val Leu Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 87
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL9.0

<400> SEQUENCE: 87

Gln Phe Val Leu Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Trp Ile Lys
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 88
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL10.0

<400> SEQUENCE: 88

Asp Phe Val Met Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Leu Ile Tyr
```

```
                    35                  40                  45
Asp Thr Ser Lys Leu Ala Ser Gly Val Pro Ser Arg Phe Ser Gly Ser
        50                  55                  60
Gly Ser Gly Thr Asp Tyr Thr Phe Thr Ile Ser Ser Leu Glu Ala Glu
 65                  70                  75                  80
Asp Ala Ala Thr Tyr Tyr Cys Gln Gln Trp Thr Thr Asn Pro Leu Thr
                85                  90                  95
Phe Gly Gln Gly Thr Lys Val Glu Ile Lys
            100                 105

<210> SEQ ID NO 89
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL11.0

<400> SEQUENCE: 89

Asp Phe Val Met Thr Gln Ser Pro Ala Phe Leu Ser Val Thr Pro Gly
 1               5                  10                  15
Glu Lys Val Thr Ile Thr Cys Ser Ala Asn Ser Ser Val Asn Tyr Ile
                20                  25                  30
His Trp Tyr Gln Gln Lys Pro Asp Gln Ala Pro Lys Lys Trp Ile Tyr
            35                  40                  45
Asp Thr Ser Lys Leu Ala Ser Gly Val Pro Ser Arg Phe Ser Gly Ser
        50                  55                  60
Gly Ser Gly Thr Asp Phe Thr Phe Thr Ile Ser Ser Leu Glu Ala Glu
 65                  70                  75                  80
Asp Ala Ala Thr Tyr Tyr Cys Gln Gln Trp Thr Thr Asn Pro Leu Thr
                85                  90                  95
Phe Gly Gln Gly Thr Lys Val Glu Ile Lys
            100                 105

<210> SEQ ID NO 90
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL1.0Q

<400> SEQUENCE: 90

Gln Phe Val Leu Thr Gln Ser Pro Ala Phe Leu Ser Val Thr Pro Gly
 1               5                  10                  15
Glu Lys Val Thr Ile Thr Cys Ser Ala Gln Ser Ser Val Asn Tyr Ile
                20                  25                  30
His Trp Tyr Gln Gln Lys Pro Asp Gln Ala Pro Lys Lys Trp Ile Tyr
            35                  40                  45
Asp Thr Ser Lys Leu Ala Ser Gly Val Pro Ser Arg Phe Ser Gly Ser
        50                  55                  60
Gly Ser Gly Thr Asp Tyr Thr Phe Thr Ile Ser Ser Leu Glu Ala Glu
 65                  70                  75                  80
Asp Ala Ala Thr Tyr Tyr Cys Gln Gln Trp Thr Thr Asn Pro Leu Thr
                85                  90                  95
Phe Gly Gln Gly Thr Lys Val Glu Ile Lys
            100                 105

<210> SEQ ID NO 91
```

```
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL10.0Q

<400> SEQUENCE: 91

Asp Phe Val Met Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Lys Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 92
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL12.0Q

<400> SEQUENCE: 92

Asp Phe Val Met Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Lys Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 93
<211> LENGTH: 222
<212> TYPE: PRT
<213> ORGANISM: Rattus rattus
<220> FEATURE:
<221> NAME/KEY: MISC_FEATURE
<223> OTHER INFORMATION: Rat alpha2 integrin I domain protein

<400> SEQUENCE: 93

Ser Pro Asp Phe Gln Ser Leu Thr Ser Phe Ser Pro Ala Val Gln Asp
1               5                   10                  15

Val Val Val Val Cys Asp Glu Ser Asn Ser Ile Tyr Pro Trp Glu Ala
            20                  25                  30

Val Lys Asn Phe Leu Glu Lys Phe Val Gln Gly Leu Asp Ile Gly Pro
```

```
                    35                  40                  45
Lys Lys Thr Gln Val Ala Leu Ile Gln Tyr Ala Asn Asp Pro Arg Val
 50                  55                  60
Val Phe Asn Leu Thr Thr Tyr Lys Asn Lys Glu Asp Met Val Gln Ala
 65                  70                  75                  80
Thr Ser Glu Thr Arg Gln Tyr Gly Gly Asp Leu Thr Asn Thr Phe Lys
                     85                  90                  95
Ala Ile Gln Phe Ala Arg Asp Ile Ala Tyr Leu Pro Glu Ser Gly Gly
                100                 105                 110
Arg Pro Gly Ala Thr Lys Val Met Val Val Thr Asp Gly Glu Ser
                115                 120                 125
His Asp Gly Ser Lys Leu Gln Thr Val Ile Gln Gln Cys Asn Asp Asp
            130                 135                 140
Glu Ile Leu Arg Phe Gly Ile Ala Val Leu Gly Tyr Leu Asn Arg Asn
145                 150                 155                 160
Ala Leu Asp Thr Lys Asn Leu Ile Lys Glu Ile Lys Ala Ile Ala Ser
                165                 170                 175
Thr Pro Thr Glu Arg Tyr Phe Phe Asn Val Ala Asp Glu Ala Ala Leu
            180                 185                 190
Leu Glu Lys Ala Gly Thr Leu Gly Glu His Ile Phe Ser Ile Glu Gly
                195                 200                 205
Thr Val Gln Gly Gly Asp Asn Phe Gln Met Glu Met Ala Gln
            210                 215                 220

<210> SEQ ID NO 94
<211> LENGTH: 228
<212> TYPE: PRT
<213> ORGANISM: Mus musculus
<220> FEATURE:
<221> NAME/KEY: MISC_FEATURE
<223> OTHER INFORMATION: Mouse alpha2 integrin I domain protein

<400> SEQUENCE: 94

Ser Pro Asp Phe Gln Phe Leu Thr Ser Phe Ser Pro Ala Val Gln Ala
 1                   5                  10                  15
Cys Pro Ser Leu Val Asp Val Val Val Cys Asp Glu Ser Asn Ser
                 20                  25                  30
Ile Tyr Pro Trp Glu Ala Val Lys Asn Phe Leu Val Lys Phe Val Thr
             35                  40                  45
Gly Leu Asp Ile Gly Pro Lys Lys Thr Gln Val Ala Leu Ile Gln Tyr
 50                  55                  60
Ala Asn Glu Pro Arg Ile Ile Phe Asn Leu Asn Asp Phe Glu Thr Lys
 65                  70                  75                  80
Glu Asp Met Val Gln Ala Thr Ser Glu Thr Arg Gln His Gly Gly Asp
                 85                  90                  95
Leu Thr Asn Thr Phe Arg Ala Ile Glu Phe Ala Arg Asp Tyr Ala Tyr
                100                 105                 110
Ser Gln Thr Ser Gly Gly Arg Pro Gly Ala Thr Lys Val Met Val Val
            115                 120                 125
Val Thr Asp Gly Glu Ser His Asp Gly Ser Lys Leu Lys Thr Val Ile
130                 135                 140
Gln Gln Cys Asn Asp Asp Glu Ile Leu Arg Phe Gly Ile Ala Val Leu
145                 150                 155                 160
Gly Tyr Leu Asn Arg Asn Ala Leu Asp Thr Lys Asn Leu Ile Lys Glu
                165                 170                 175
Ile Lys Ala Ile Ala Ser Thr Pro Thr Glu Arg Tyr Phe Phe Asn Val
```

```
            180                 185                 190
Ser Asp Glu Ala Ala Leu Leu Glu Lys Ala Gly Thr Leu Gly Glu Gln
        195                 200                 205

Ile Phe Ser Ile Glu Gly Thr Val Gln Gly Gly Asp Asn Phe Gln Met
        210                 215                 220

Glu Met Ser Gln
225

<210> SEQ ID NO 95
<211> LENGTH: 26
<212> TYPE: DNA
<213> ORGANISM: Homo Sapiens
<220> FEATURE:
<221> NAME/KEY: misc_feature
<223> OTHER INFORMATION: Kappa-F

<400> SEQUENCE: 95
cgaactgtgg ctgcaccatc tgtctt                                            26

<210> SEQ ID NO 96
<211> LENGTH: 41
<212> TYPE: DNA
<213> ORGANISM: Homo Sapiens
<220> FEATURE:
<221> NAME/KEY: misc_feature
<223> OTHER INFORMATION: Kappa-BamHI-R

<400> SEQUENCE: 96
aattcggatc cttactaaca ctctcccctg ttgaagctct t                            41

<210> SEQ ID NO 97
<211> LENGTH: 40
<212> TYPE: DNA
<213> ORGANISM: Homo Sapiens
<220> FEATURE:
<221> NAME/KEY: misc_feature
<223> OTHER INFORMATION: VH12.0-(K71V)-F

<400> SEQUENCE: 97
gcctgaccat cagcgtggac aacagcaaga accaggtgag                              40

<210> SEQ ID NO 98
<211> LENGTH: 40
<212> TYPE: DNA
<213> ORGANISM: Homo Sapiens
<220> FEATURE:
<221> NAME/KEY: misc_feature
<223> OTHER INFORMATION: VH12.0(K71V)-R

<400> SEQUENCE: 98
ctcacctggt tcttgctgtt gtccacgctg atggtcaggc                              40

<210> SEQ ID NO 99
<211> LENGTH: 40
<212> TYPE: DNA
<213> ORGANISM: Homo Sapiens
<220> FEATURE:
<221> NAME/KEY: misc_feature
<223> OTHER INFORMATION: VH13.0-(N73T)-F

<400> SEQUENCE: 99
ctgaccatca gcaaggacac cagcaagaac caggtgagcc                              40

<210> SEQ ID NO 100
<211> LENGTH: 40
<212> TYPE: DNA
```

```
<213> ORGANISM: Homo Sapiens
<220> FEATURE:
<221> NAME/KEY: misc_feature
<223> OTHER INFORMATION: VH13.0-(N73T)R

<400> SEQUENCE: 100
ggctcacctg gttcttgctg gtgtccttgc tgatggtcag                            40

<210> SEQ ID NO 101
<211> LENGTH: 41
<212> TYPE: DNA
<213> ORGANISM: Homo Sapiens
<220> FEATURE:
<221> NAME/KEY: misc_feature
<223> OTHER INFORMATION: VH14.0-(V78F)-F

<400> SEQUENCE: 101
gcaaggacaa cagcaagaac cagtttagcc tgaagctgag c                          41

<210> SEQ ID NO 102
<211> LENGTH: 41
<212> TYPE: DNA
<213> ORGANISM: Homo Sapiens
<220> FEATURE:
<221> NAME/KEY: misc_feature
<223> OTHER INFORMATION: VH14.0 (V78F)-R

<400> SEQUENCE: 102
gctcagcttc aggctaaact ggttcttgct gttgtccttg c                          41

<210> SEQ ID NO 103
<211> LENGTH: 648
<212> TYPE: DNA
<213> ORGANISM: Macaca fascicularis
<220> FEATURE:
<221> NAME/KEY: misc_feature
<223> OTHER INFORMATION: Cynomolgus alpha2 I domain

<400> SEQUENCE: 103
agtcctgatt ttcagctctc agccagcttc tcacctgcaa ctcagccctg cccttccctc      60
atagatgttg tggttgtgtg tgatgaatca aatagtattt atccttggga tgcagtagac     120
aattttttgg aaaaatttgt acaaggcctg gatataggcc ccacaaagac acaggtgggg     180
ttaattcagt atgccaataa tccaagagtt gtgtttaact tgaacacata taaaaccaaa     240
gaagaaatga ttgtagcaac atcccagaca tcccaatatg gtgggaccct cacaaacaca     300
ttcggagcaa ttcaatatgc aagaaaatat gcctattcag cagcttctgg tgggcgacga     360
agtgctacga agtaatggt agttgtaact gacggtgaat cacatgatgg ttcaatgttg      420
aaagctgtga ttgatcaatg caaccatgac aatatactga ggtttggcat agcagttctt     480
gggtacttaa acagaaacgc ccttgatact aaaaatttaa taaagaaat aaaagcgatc      540 gctagtattc caacagaaag atacttttc aatgtgtctg atgaagcagc tctactagaa      600
aaggctggga cattaggaga acaaattttc agcattgaag gtactgtt                  648

<210> SEQ ID NO 104
<211> LENGTH: 648
<212> TYPE: DNA
<213> ORGANISM: Macaca mulatta
<220> FEATURE:
<221> NAME/KEY: misc_feature
<223> OTHER INFORMATION: Rhesus alpha2 I domain

<400> SEQUENCE: 104
agtcctgatt ttcagctctc agccagcttc tcacctgcaa ctcagccctg cccttccctc      60
```

```
atagatgttg tggttgtgtg tgatgaatca aatagtattt atccttggga tgcagtaaag    120
aattttttgg aaaaatttgt acaaggcctg gatataggcc ccacaaagac acaggtgggg    180
ttaattcagt atgccaataa tccaagagtt gtgtttaact tgaacacata taaaaccaaa    240
gaagaaatga ttgtagcaac atcccagaca tcccaatatg gtggggacct cacaaacaca    300
ttcggagcaa ttcaatatgc aagaaaatat gcctattcag cagcttctgg tgggcgacga    360
agtgctacga aagtaatggt agttgtaact gacggtgaat cacatgatgg ttcaatgttg    420
aaagctgtga ttgatcaatg caaccatgac aatatactga ggtttggcat agcagttctt    480
gggtacttaa acagaaacgc ccttgatact aaaaatttaa taaagaaat aaaagcgatc     540 gctagtattc aacagaaaag atactttttc aatgtgtctg atgaagcagc tctactagaa    600
aaggctggga cattaggaga acaaattttc agcattgaag gtactgtt                 648
```

<210> SEQ ID NO 105
<211> LENGTH: 997
<212> TYPE: DNA
<213> ORGANISM: Homo Sapiens
<220> FEATURE:
<221> NAME/KEY: misc_feature
<223> OTHER INFORMATION: IgG4 constant region
<220> FEATURE:
<221> NAME/KEY: CDS
<222> LOCATION: (1)..(978)

<400> SEQUENCE: 105

```
tcc acc aag ggc cca tcc gtc ttc ccc ctg gcg ccc tgc tcc agg agc          48
Ser Thr Lys Gly Pro Ser Val Phe Pro Leu Ala Pro Cys Ser Arg Ser
1               5                   10                  15 acc tcc gag agc aca gcc gcc ctg ggc tgc ctg gtc aag gac tac ttc         96
Thr Ser Glu Ser Thr Ala Ala Leu Gly Cys Leu Val Lys Asp Tyr Phe
            20                  25                  30 ccc gaa ccg gtg acg gtg tcg tgg aac tca ggc gcc ctg acc agc ggc        144
Pro Glu Pro Val Thr Val Ser Trp Asn Ser Gly Ala Leu Thr Ser Gly
        35                  40                  45 gtg cac acc ttc ccg gct gtc cta cag tcc tca gga ctc tac tcc ctc        192
Val His Thr Phe Pro Ala Val Leu Gln Ser Ser Gly Leu Tyr Ser Leu
    50                  55                  60 agc agc gtg gtg acc gtg ccc tcc agc agc ttg ggc acg aag acc tac        240
Ser Ser Val Val Thr Val Pro Ser Ser Ser Leu Gly Thr Lys Thr Tyr
65                  70                  75                  80 acc tgc aac gta gat cac aag ccc agc aac acc aag gtg gac aag aga        288
Thr Cys Asn Val Asp His Lys Pro Ser Asn Thr Lys Val Asp Lys Arg
                85                  90                  95 gtt gag tcc aaa tat ggt ccc cca tgc cca tca tgc cca gca cct gag        336
Val Glu Ser Lys Tyr Gly Pro Pro Cys Pro Ser Cys Pro Ala Pro Glu
            100                 105                 110 ttc ctg ggg gga cca tca gtc ttc ctg ttc ccc cca aaa ccc aag gac        384
Phe Leu Gly Gly Pro Ser Val Phe Leu Phe Pro Pro Lys Pro Lys Asp
        115                 120                 125 act ctc atg atc tcc cgg acc cct gag gtc acg tgc gtg gtg gtg gac        432
Thr Leu Met Ile Ser Arg Thr Pro Glu Val Thr Cys Val Val Val Asp
    130                 135                 140 gtg agc cag gaa gac ccc gag gtc cag ttc aac tgg tac gtg gat ggc        480
Val Ser Gln Glu Asp Pro Glu Val Gln Phe Asn Trp Tyr Val Asp Gly
145                 150                 155                 160 gtg gag gtg cat aat gcc aag aca aag ccg cgg gag gag cag ttc aac        528
Val Glu Val His Asn Ala Lys Thr Lys Pro Arg Glu Glu Gln Phe Asn
                165                 170                 175 agc acg tac cgt gtg gtc agc gtc ctc acc gtc ctg cac cag gac tgg        576
```

```
Ser Thr Tyr Arg Val Val Ser Val Leu Thr Val Leu His Gln Asp Trp
            180                 185                 190 ctg aac ggc aag gag tac aag tgc aag gtc tcc aac aaa ggc ctc ccg       624
Leu Asn Gly Lys Glu Tyr Lys Cys Lys Val Ser Asn Lys Gly Leu Pro
        195                 200                 205 tcc tcc atc gag aaa acc atc tcc aaa gcc aaa ggg cag ccc cga gag       672
Ser Ser Ile Glu Lys Thr Ile Ser Lys Ala Lys Gly Gln Pro Arg Glu
    210                 215                 220 cca cag gtg tac acc ctg ccc cca tcc cag gag gag atg acc aag aac       720
Pro Gln Val Tyr Thr Leu Pro Pro Ser Gln Glu Glu Met Thr Lys Asn
225                 230                 235                 240 cag gtc agc ctg acc tgc ctg gtc aaa ggc ttc tac ccc agc gac atc       768
Gln Val Ser Leu Thr Cys Leu Val Lys Gly Phe Tyr Pro Ser Asp Ile
            245                 250                 255 gcc gtg gag tgg gag agc aat ggg cag ccg gag aac aac tac aag acc       816
Ala Val Glu Trp Glu Ser Asn Gly Gln Pro Glu Asn Asn Tyr Lys Thr
        260                 265                 270 acg cct ccc gtg ctg gac tcc gac ggc tcc ttc ttc ctc tac agc agg       864
Thr Pro Pro Val Leu Asp Ser Asp Gly Ser Phe Phe Leu Tyr Ser Arg
    275                 280                 285 cta acc gtg gac aag agc agg tgg cag gag ggg aat gtc ttc tca tgc       912
Leu Thr Val Asp Lys Ser Arg Trp Gln Glu Gly Asn Val Phe Ser Cys
290                 295                 300 tcc gtg atg cat gag gct ctg cac aac cac tac aca cag aag agc ctc       960
Ser Val Met His Glu Ala Leu His Asn His Tyr Thr Gln Lys Ser Leu
305                 310                 315                 320 tcc ctg tct ctg ggt aaa tgataggatc cgcggccgc                          997
Ser Leu Ser Leu Gly Lys
            325

<210> SEQ ID NO 106
<211> LENGTH: 326
<212> TYPE: PRT
<213> ORGANISM: Homo Sapiens

<400> SEQUENCE: 106

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val Glu Ser Lys Tyr Gly Pro Pro Cys Pro Ser Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

```
Ser Thr Tyr Arg Val Ser Val Leu Thr Val Leu His Gln Asp Trp
            180                 185                 190
Leu Asn Gly Lys Glu Tyr Lys Cys Lys Val Ser Asn Lys Gly Leu Pro
        195                 200                 205
Ser Ser Ile Glu Lys Thr Ile Ser Lys Ala Lys Gly Gln Pro Arg Glu
210                 215                 220
Pro Gln Val Tyr Thr Leu Pro Pro Ser Gln Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Val Leu Asp Ser Asp Gly Ser Phe Phe Leu Tyr Ser Arg
        275                 280                 285
Leu Thr Val Asp Lys Ser Arg Trp Gln Glu Gly Asn Val Phe Ser Cys
290                 295                 300
Ser Val Met His Glu Ala Leu His Asn His Tyr Thr Gln Lys Ser Leu
305                 310                 315                 320
Ser Leu Ser Leu Gly Lys
                325

<210> SEQ ID NO 107
<211> LENGTH: 648
<212> TYPE: DNA
<213> ORGANISM: HOMO SAPIENS
<220> FEATURE:
<221> NAME/KEY: misc_feature
<223> OTHER INFORMATION: Human alpha2 I Domain

<400> SEQUENCE: 107
agtcctgatt ttcagctctc agccagcttc tcacctgcaa ctcagccctg cccttccctc    60
atagatgttg tggtggtgtg tgatgaatca aatagtattt atccttggga tgcagtaaag   120 aatttttgg aaaaatttgt acaaggcctg gatataggcc ccacaaagac acaggtgggg   180
ttaattcagt atgccaataa tccaagagtt gtgtttaact tgaacacata taaaaccaaa   240
gaagaaatga ttgtagcaac atcccagaca tcccaatatg gtggggacct cacaaacaca   300
ttcggagcaa ttcaatatgc aagaaaatat gcctattcag cagcttctgg tgggcgacga   360
agtgctacga aagtaatggt agttgtaact gacggtgaat cacatgatgg ttcaatgttg   420
aaagctgtga ttgatcaatg caaccatgac aatatactga ggtttggcat agcagttctt   480
gggtacttaa acagaaacgc ccttgatact aaaaatttaa taaagaaat aaaagcgatc   540 gctagtattc caacagaaag atacttttc aatgtgtctg atgaagcagc tctactagaa   600
aaggctggga cattaggaga acaaattttc agcattgaag gtactgtt               648

<210> SEQ ID NO 108
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL12.0

<400> SEQUENCE: 108

Asp Phe Val Met Thr Gln Ser Pro Ala Phe Leu Ser Val Thr Pro Gly
1               5                   10                  15
Glu Lys Val Thr Ile Thr Cys Ser Ala Asn Ser Ser Val Asn Tyr Ile
            20                  25                  30
```

```
His Trp Tyr Gln Gln Lys Pro Asp Gln Ala Pro Lys Lys Leu Ile Tyr
         35                  40                  45

Asp Thr Ser Lys Leu Ala Ser Gly Val Pro Ser Arg Phe Ser Gly Ser
         50                  55                  60

Gly Ser Gly Thr Asp Phe Thr Phe Thr Ile Ser Ser Leu Glu Ala Glu
 65              70                  75                  80

Asp Ala Ala Thr Tyr Tyr Cys Gln Gln Trp Thr Thr Asn Pro Leu Thr
                 85                  90                  95

Phe Gly Gln Gly Thr Lys Val Glu Ile Lys
            100                 105

<210> SEQ ID NO 109
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH12.0
<220> FEATURE:
<221> NAME/KEY: VARIANT
<222> LOCATION: (48)..(48)
<223> OTHER INFORMATION: Xaa at position 48 can be Leu or Ile

<400> SEQUENCE: 109

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Asn Tyr
             20                  25                  30

Gly Ile His Trp Ile Arg Gln Pro Pro Gly Lys Gly Leu Glu Trp Xaa
         35                  40                  45

Gly Val Ile Trp Ala Arg Gly Phe Thr Asn Tyr Asn Ser Ala Leu Met
     50                  55                  60

Ser Arg Leu Thr Ile Ser Lys Asp Asn Ser Lys Asn Gln Val Ser Leu
 65              70                  75                  80

Lys Leu Ser Ser Val Thr Ala Ala Asp Thr Ala Val Tyr Tyr Cys Ala
                 85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 110
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH13.0

<400> SEQUENCE: 110

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Asn Tyr
             20                  25                  30

Gly Ile His Trp Val Arg Gln Pro Pro Gly Lys Gly Leu Glu Trp Ile
         35                  40                  45

Gly Val Ile Trp Ala Arg Gly Phe Thr Asn Tyr Asn Ser Ala Leu Met
     50                  55                  60

Ser Arg Val Thr Ile Ser Lys Asp Asn Ser Lys Asn Gln Val Ser Leu
 65              70                  75                  80
```

```
Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 111
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH14.0
<220> FEATURE:
<221> NAME/KEY: VARIANT
<222> LOCATION: (48)..(48)
<223> OTHER INFORMATION: Xaa at position 48 can be Leu or Ile

<400> SEQUENCE: 111

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Xaa
        35                  40                  45

Gly Val Ile Trp Ala Arg Gly Phe Thr Asn Tyr Asn Ser Ala Leu Met
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 112
<211> LENGTH: 10
<212> TYPE: PRT
<213> ORGANISM: Homo Sapiens
<220> FEATURE:
<221> NAME/KEY: MISC_FEATURE
<223> OTHER INFORMATION: LCDR1 [N26Q]

<400> SEQUENCE: 112

Ser Ala Gln Ser Ser Val Asn Tyr Ile His
1               5                   10

<210> SEQ ID NO 113
<211> LENGTH: 681
<212> TYPE: DNA
<213> ORGANISM: Rattus rattus
<220> FEATURE:
<221> NAME/KEY: misc_feature
<223> OTHER INFORMATION: Rat alpha 2 I domain

<400> SEQUENCE: 113
agtccagact ttcagtcgtt gacaagcttc tcacctgcag ttcaagcttg cccttccctc      60
gtagatgtcg tagttgtctg tgatgaatca aacagtattt atccctggga agcagtaaag    120
aatttttggg aaaagtttgt gcaaggcctg gatataggac ctaaaaagac acaggtggcg    180
ttaattcaat atgccaacga cccaagagtt gtctttaact tgaccactta caaaaacaaa    240
```

```
gaagatatgg ttcaggccac atccgagacg cgccagtatg gtggggacct cacaaacacc    300
ttcaaggcta tccaatttgc aagagacatt gcttatttac cggagtctgg cgggcgccca    360
ggtgctacaa aagtcatggt agttgtgact gatggggaat cccatgatgg gtcgaagctg    420
caaactgtga tccagcaatg caatgatgac gagatactga ggtttggcat agcggttctt    480
ggatatttaa acagaaatgc tcttgatact aaaaatctaa tcaaagaaat taaagcaatc    540
gctagcactc caacggagag gtactttttc aatgtggccg atgaggcggc tcttctggag    600
aaagctggca ctctagggga gcacatattc agcattgaag gcactgttca aggaggagac    660
aacttccaga tggaaatggc a                                              681
```

```
<210> SEQ ID NO 114
<211> LENGTH: 648
<212> TYPE: DNA
<213> ORGANISM: Mus musculus
<220> FEATURE:
<221> NAME/KEY: misc_feature
<223> OTHER INFORMATION: Mouse alpha 2 I domain clone

<400> SEQUENCE: 114
```

```
agtccagact ttcagttctt gaccagcttt tcacctgcag ttcaggcttg cccttccctc     60
gtggatgttg tagttgtatg tgatgaatca aacagtattt atccttggga agcagtaaag    120 aacttttgg taaagtttgt gacaggcctg gatataggac ctaaaagac acaggtggcg     180 ttaattcaat atgccaatga gccgagaatt atatttaact tgaacgattt cgaaaccaaa    240
gaggatatgg tccaggccac atctgagacg cgccaacatg gtgggaccct cacaaacacc    300
ttcagagcta tcgaattcgc aagagactac gcttattcac agacttctgg cgggcgcccg    360
ggtgctacaa aagtcatggt agttgtgacc gatggcgagt cccatgatgg gtcgaagctg    420
aaaactgtga tccagcaatg caatgatgac gagatactga ggttcggcat agcagttctt    480
gggtatttaa acagaaatgc tcttgatact aaaaatttaa tcaaagaaat aaaagcaatt    540
gctagtactc caaccgagag atactttttc aatgtggccg acgaagcggc tcttctggag    600
aaggctggaa ctctagggga gcaaatattc agcattgaag gcactgtt                 648
```

```
<210> SEQ ID NO 115
<211> LENGTH: 6
<212> TYPE: DNA
<213> ORGANISM: Homo sapiens
<220> FEATURE:
<221> NAME/KEY: misc_feature
<223> OTHER INFORMATION: Exemplary upstream sequence from the start of
      gene transcription
<220> FEATURE:
<221> NAME/KEY: misc_feature
<222> LOCATION: (2)..(2)
<223> OTHER INFORMATION: n is a, c, g, or t

<400> SEQUENCE: 115 cncaat                                                                 6
```

```
<210> SEQ ID NO 116
<211> LENGTH: 6
<212> TYPE: DNA
<213> ORGANISM: Homo sapiens
<220> FEATURE:
<221> NAME/KEY: misc_feature
<223> OTHER INFORMATION: Exemplary sequence at  3' end of gene

<400> SEQUENCE: 116 aataaa                                                                 6
```

```
<210> SEQ ID NO 117
<211> LENGTH: 31
<212> TYPE: DNA
<213> ORGANISM: Homo Sapiens
<220> FEATURE:
<221> NAME/KEY: misc_feature
<223> OTHER INFORMATION: halphaI F

<400> SEQUENCE: 117
ggggatccag tcctgaattt tcagctctca g                              31

<210> SEQ ID NO 118
<211> LENGTH: 27
<212> TYPE: DNA
<213> ORGANISM: Homo Sapiens
<220> FEATURE:
<221> NAME/KEY: misc_feature
<223> OTHER INFORMATION: halphaI R

<400> SEQUENCE: 118
gggaattcaa cagtaccttc aatgctg                                   27

<210> SEQ ID NO 119
<211> LENGTH: 19
<212> TYPE: DNA
<213> ORGANISM: Homo sapiens
<220> FEATURE:
<221> NAME/KEY: misc_feature
<223> OTHER INFORMATION: Human I domain forward primer

<400> SEQUENCE: 119
ggggatccag tcctgattt                                            19

<210> SEQ ID NO 120
<211> LENGTH: 18
<212> TYPE: DNA
<213> ORGANISM: Homo sapiens
<220> FEATURE:
<221> NAME/KEY: misc_feature
<223> OTHER INFORMATION: Human I domain reverse primer

<400> SEQUENCE: 120
ggaattcaac agtaccctt                                            18

<210> SEQ ID NO 121
<211> LENGTH: 29
<212> TYPE: DNA
<213> ORGANISM: Homo Sapiens
<220> FEATURE:
<221> NAME/KEY: misc_feature
<223> OTHER INFORMATION: malphaI F

<400> SEQUENCE: 121
ggggatccag tccagacttt cagttcttg                                 29

<210> SEQ ID NO 122
<211> LENGTH: 28
<212> TYPE: DNA
<213> ORGANISM: Homo Sapiens
<220> FEATURE:
<221> NAME/KEY: misc_feature
<223> OTHER INFORMATION: malphaI R

<400> SEQUENCE: 122
tgggaattca acagtgcctt caatgctg                                  28
```

<210> SEQ ID NO 123
<211> LENGTH: 31
<212> TYPE: DNA
<213> ORGANISM: Homo Sapiens
<220> FEATURE:
<221> NAME/KEY: misc_feature
<223> OTHER INFORMATION: ralphaI F

<400> SEQUENCE: 123
ggggatccag tccagacttt cagtcgttga c                                31

<210> SEQ ID NO 124
<211> LENGTH: 31
<212> TYPE: DNA
<213> ORGANISM: Homo Sapiens
<220> FEATURE:
<221> NAME/KEY: misc_feature
<223> OTHER INFORMATION: ralphaI R

<400> SEQUENCE: 124
tgggaattct gccatttcca tctggaagtt g                                31

<210> SEQ ID NO 125
<211> LENGTH: 34
<212> TYPE: DNA
<213> ORGANISM: Homo Sapiens
<220> FEATURE:
<221> NAME/KEY: misc_feature
<223> OTHER INFORMATION: halphaI I21V F

<400> SEQUENCE: 125
cagccctgcc cttccctcgt agatgttgtg gttg                             34

<210> SEQ ID NO 126
<211> LENGTH: 34
<212> TYPE: DNA
<213> ORGANISM: Homo Sapiens
<220> FEATURE:
<221> NAME/KEY: misc_feature
<223> OTHER INFORMATION: halphaI I21V R

<400> SEQUENCE: 126
caaccacaac atctacgagg gaagggcagg gctg                             34

<210> SEQ ID NO 127
<211> LENGTH: 33
<212> TYPE: DNA
<213> ORGANISM: Homo Sapiens
<220> FEATURE:
<221> NAME/KEY: misc_feature
<223> OTHER INFORMATION: halphaI E44V F

<400> SEQUENCE: 127
cagtaaagaa tttttggta aaatttgtca agg                               33

<210> SEQ ID NO 128
<211> LENGTH: 33
<212> TYPE: DNA
<213> ORGANISM: Homo Sapiens
<220> FEATURE:
<221> NAME/KEY: misc_feature
<223> OTHER INFORMATION: halphaI E44V R

<400> SEQUENCE: 128
ccttgacaaa ttttaccaaa aaattcttta ctg                              33

<210> SEQ ID NO 129
<211> LENGTH: 35

```
<212> TYPE: DNA
<213> ORGANISM: Homo Sapiens
<220> FEATURE:
<221> NAME/KEY: misc_feature
<223> OTHER INFORMATION: halphaI Q48T F

<400> SEQUENCE: 129
ttttggaaaa atttgtaaca ggcctggata taggc                                35

<210> SEQ ID NO 130
<211> LENGTH: 35
<212> TYPE: DNA
<213> ORGANISM: Homo Sapiens
<220> FEATURE:
<221> NAME/KEY: misc_feature
<223> OTHER INFORMATION: halphaI Q48T R

<400> SEQUENCE: 130
gcctatatcc aggcctgtta caaatttttc cgggg                                35

<210> SEQ ID NO 131
<211> LENGTH: 33
<212> TYPE: DNA
<213> ORGANISM: Homo Sapiens
<220> FEATURE:
<221> NAME/KEY: misc_feature
<223> OTHER INFORMATION: halphaI N67E F

<400> SEQUENCE: 131
cagtatgcca atgagccaag agttgtgttt aac                                  33

<210> SEQ ID NO 132
<211> LENGTH: 33
<212> TYPE: DNA
<213> ORGANISM: Homo Sapiens
<220> FEATURE:
<221> NAME/KEY: misc_feature
<223> OTHER INFORMATION: halphaI N67E R

<400> SEQUENCE: 132
gttaaacaca actcttggct cattggcata ctg                                  33

<210> SEQ ID NO 133
<211> LENGTH: 34
<212> TYPE: DNA
<213> ORGANISM: homo Sapiens
<220> FEATURE:
<221> NAME/KEY: misc_feature
<223> OTHER INFORMATION: halphaI V70I F

<400> SEQUENCE: 133
tgccaataat ccaagaattg tgtttaactt gaac                                 34

<210> SEQ ID NO 134
<211> LENGTH: 33
<212> TYPE: DNA
<213> ORGANISM: Homo Sapiens
<220> FEATURE:
<221> NAME/KEY: misc_feature
<223> OTHER INFORMATION: halphaI V70I R

<400> SEQUENCE: 134
gttcaagtta acacaattct tggattattg gca                                  33

<210> SEQ ID NO 135
<211> LENGTH: 34
<212> TYPE: DNA
<213> ORGANISM: Homo Sapiens
```

```
<220> FEATURE:
<221> NAME/KEY: misc_feature
<223> OTHER INFORMATION: halphaI V71I F

<400> SEQUENCE: 135
ccaataatcc aagagttatc tttaacttga acac                                    34

<210> SEQ ID NO 136
<211> LENGTH: 34
<212> TYPE: DNA
<213> ORGANISM: Homo Sapiens
<220> FEATURE:
<221> NAME/KEY: misc_feature
<223> OTHER INFORMATION: halphaI V71I R

<400> SEQUENCE: 136
gtgttcaagt taaagataac tcttggatta ttgg                                    34

<210> SEQ ID NO 137
<211> LENGTH: 33
<212> TYPE: DNA
<213> ORGANISM: Homo Sapiens
<220> FEATURE:
<221> NAME/KEY: misc_feature
<223> OTHER INFORMATION: halphaI T76D F

<400> SEQUENCE: 137
gtgtttaact tgaacgacta taaaaccaaa gaa                                     33

<210> SEQ ID NO 138
<211> LENGTH: 33
<212> TYPE: DNA
<213> ORGANISM: Homo Sapiens
<220> FEATURE:
<221> NAME/KEY: misc_feature
<223> OTHER INFORMATION: haplhaI T76D R

<400> SEQUENCE: 138
ttctttggtt ttatagtcgt tcaagttaaa cac                                     33

<210> SEQ ID NO 139
<211> LENGTH: 33
<212> TYPE: DNA
<213> ORGANISM: Homo Sapiens
<220> FEATURE:
<221> NAME/KEY: misc_feature
<223> OTHER INFORMATION: halphaI Y77F F

<400> SEQUENCE: 139
tttaacttga acacatttaa aaccaaagaa gaa                                     33

<210> SEQ ID NO 140
<211> LENGTH: 33
<212> TYPE: DNA
<213> ORGANISM: Homo Sapiens
<220> FEATURE:
<221> NAME/KEY: misc_feature
<223> OTHER INFORMATION: halphaI Y77F R

<400> SEQUENCE: 140
ttcttctttg gttttaaatg tgttcaagtt aaa                                     33

<210> SEQ ID NO 141
<211> LENGTH: 33
<212> TYPE: DNA
<213> ORGANISM: Homo Sapiens
<220> FEATURE:
<221> NAME/KEY: misc_feature
```

```
<223> OTHER INFORMATION: halphaI K78E F

<400> SEQUENCE: 141
aacttgaaca catatgaaac caaagaagaa atg                              33

<210> SEQ ID NO 142
<211> LENGTH: 33
<212> TYPE: DNA
<213> ORGANISM: Homo Sapiens
<220> FEATURE:
<221> NAME/KEY: misc_feature
<223> OTHER INFORMATION: halphaI K78E R

<400> SEQUENCE: 142
catttcttct ttggtttcat atgtgttcaa gtt                              33

<210> SEQ ID NO 143
<211> LENGTH: 33
<212> TYPE: DNA
<213> ORGANISM: Homo Sapiens
<220> FEATURE:
<221> NAME/KEY: misc_feature
<223> OTHER INFORMATION: halphaI Y93H F

<400> SEQUENCE: 143
tcccagacat cccaacatgg tggggacctc aca                              33

<210> SEQ ID NO 144
<211> LENGTH: 33
<212> TYPE: DNA
<213> ORGANISM: Homo Sapiens
<220> FEATURE:
<221> NAME/KEY: misc_feature
<223> OTHER INFORMATION: halphaI Y93H R

<400> SEQUENCE: 144
tgtgaggtcc ccaccatgtt gggatgtctg gga                              33

<210> SEQ ID NO 145
<211> LENGTH: 39
<212> TYPE: DNA
<213> ORGANISM: Homo Sapiens
<220> FEATURE:
<221> NAME/KEY: misc_feature
<223> OTHER INFORMATION: halphaI Y93F F

<400> SEQUENCE: 145
acatgggaga catcccaatt tggtggggac ctcacaaac                        39

<210> SEQ ID NO 146
<211> LENGTH: 39
<212> TYPE: DNA
<213> ORGANISM: Homo Sapiens
<220> FEATURE:
<221> NAME/KEY: misc_feature
<223> OTHER INFORMATION: halphaI Y93F R

<400> SEQUENCE: 146
gtttgtgagg tccccaccaa attgggatgt ctcccatgt                        39

<210> SEQ ID NO 147
<211> LENGTH: 33
<212> TYPE: DNA
<213> ORGANISM: Homo Sapiens
<220> FEATURE:
<221> NAME/KEY: misc_feature
<223> OTHER INFORMATION: halphaI Q105E F
```

<400> SEQUENCE: 147
ttcggagcaa ttgaatatgc aagaaaatat gcc                33

<210> SEQ ID NO 148
<211> LENGTH: 33
<212> TYPE: DNA
<213> ORGANISM: Homo Sapiens
<220> FEATURE:
<221> NAME/KEY: misc_feature
<223> OTHER INFORMATION: halphaI Q105E R

<400> SEQUENCE: 148
ggcatatttt cttgcatatt caattgctcc gaa                33

<210> SEQ ID NO 149
<211> LENGTH: 39
<212> TYPE: DNA
<213> ORGANISM: Homo Sapiens
<220> FEATURE:
<221> NAME/KEY: misc_feature
<223> OTHER INFORMATION: halphaI A114Q F

<400> SEQUENCE: 149
aaatatgcct attcacaagc ttctggtggg cgacgaagt          39

<210> SEQ ID NO 150
<211> LENGTH: 39
<212> TYPE: DNA
<213> ORGANISM: Homo Sapiens
<220> FEATURE:
<221> NAME/KEY: misc_feature
<223> OTHER INFORMATION: halphaI A114Q R

<400> SEQUENCE: 150
acttcgtcgc ccaccagaag cttgtgaata ggcatattt          39

<210> SEQ ID NO 151
<211> LENGTH: 39
<212> TYPE: DNA
<213> ORGANISM: Homo Sapiens
<220> FEATURE:
<221> NAME/KEY: misc_feature
<223> OTHER INFORMATION: halphaI A115T F

<400> SEQUENCE: 151
aaatatgcct attcagcaac ttctggtggg cgacgaagt          39

<210> SEQ ID NO 152
<211> LENGTH: 39
<212> TYPE: DNA
<213> ORGANISM: Homo Sapiens
<220> FEATURE:
<221> NAME/KEY: misc_feature
<223> OTHER INFORMATION: halphaI A115T R

<400> SEQUENCE: 152
acttcgtcgc ccaccagaag ttgctgaata ggcatattt          39

<210> SEQ ID NO 153
<211> LENGTH: 39
<212> TYPE: DNA
<213> ORGANISM: Homo Sapiens
<220> FEATURE:
<221> NAME/KEY: misc_feature
<223> OTHER INFORMATION: halphaI A115Q F

<400> SEQUENCE: 153

-continued aaatatgcct attcagcaca gtctggtggg cgacgaagt        39

<210> SEQ ID NO 154
<211> LENGTH: 39
<212> TYPE: DNA
<213> ORGANISM: Homo Sapiens
<220> FEATURE:
<221> NAME/KEY: misc_feature
<223> OTHER INFORMATION: halphaI A115Q R

<400> SEQUENCE: 154
acttcgtcgc ccaccagact gtgctgaata ggcatattt        39

<210> SEQ ID NO 155
<211> LENGTH: 39
<212> TYPE: DNA
<213> ORGANISM: Homo Sapiens
<220> FEATURE:
<221> NAME/KEY: misc_feature
<223> OTHER INFORMATION: halphaI R165D F

<400> SEQUENCE: 155
gttcttgggt acttaaacga caacgcccct tgatactaaa        39

<210> SEQ ID NO 156
<211> LENGTH: 39
<212> TYPE: DNA
<213> ORGANISM: Homo Sapiens
<220> FEATURE:
<221> NAME/KEY: misc_feature
<223> OTHER INFORMATION: halphaI R165D R

<400> SEQUENCE: 156
tttagtatca agggcgttgt cgtttaagta cccaagaac        39

<210> SEQ ID NO 157
<211> LENGTH: 39
<212> TYPE: DNA
<213> ORGANISM: Homo Sapiens
<220> FEATURE:
<221> NAME/KEY: misc_feature
<223> OTHER INFORMATION: halphaI N166D F

<400> SEQUENCE: 157
cttgggtact aaacaggga cgcccttgat actaaaaat        39

<210> SEQ ID NO 158
<211> LENGTH: 39
<212> TYPE: DNA
<213> ORGANISM: Homo Sapiens
<220> FEATURE:
<221> NAME/KEY: misc_feature
<223> OTHER INFORMATION: halphaI N166D R

<400> SEQUENCE: 158 attttagta tcaagggcgt ccctgtttaa gtacccaag        39

<210> SEQ ID NO 159
<211> LENGTH: 40
<212> TYPE: DNA
<213> ORGANISM: Homo Sapiens
<220> FEATURE:
<221> NAME/KEY: misc_feature
<223> OTHER INFORMATION: halphaI E195W F

<400> SEQUENCE: 159
ttcaatgtgt ctgattgggc agctctacta gaaaaggctg        40

```
<210> SEQ ID NO 160
<211> LENGTH: 40
<212> TYPE: DNA
<213> ORGANISM: Homo Sapiens
<220> FEATURE:
<221> NAME/KEY: misc_feature
<223> OTHER INFORMATION: halphaI E195W R

<400> SEQUENCE: 160
cagccttttc tagtagagct gcccaatcag acacattgaa                              40

<210> SEQ ID NO 161
<211> LENGTH: 38
<212> TYPE: DNA
<213> ORGANISM: Homo Sapiens
<220> FEATURE:
<221> NAME/KEY: misc_feature
<223> OTHER INFORMATION: halphaI K40D F

<400> SEQUENCE: 161
atccttggga tgcagtagac aattttttgg aaaaattt                                38

<210> SEQ ID NO 162
<211> LENGTH: 38
<212> TYPE: DNA
<213> ORGANISM: Homo Sapiens
<220> FEATURE:
<221> NAME/KEY: misc_feature
<223> OTHER INFORMATION: halphaI K40D R

<400> SEQUENCE: 162 aaattttttcc aaaaaattgt ctactgcatc ccaaggat                               38

<210> SEQ ID NO 163
<211> LENGTH: 39
<212> TYPE: DNA
<213> ORGANISM: Homo Sapiens
<220> FEATURE:
<221> NAME/KEY: misc_feature
<223> OTHER INFORMATION: halphaI R69D F

<400> SEQUENCE: 163
cagtatgcca ataatccaga cgttgtgttt aacttgaac                               39

<210> SEQ ID NO 164
<211> LENGTH: 39
<212> TYPE: DNA
<213> ORGANISM: Homo Sapiens
<220> FEATURE:
<221> NAME/KEY: misc_feature
<223> OTHER INFORMATION: halphaI R69D R

<400> SEQUENCE: 164
gttcaagtta aacacaacgt ctggattatt ggcatactg                               39

<210> SEQ ID NO 165
<211> LENGTH: 36
<212> TYPE: DNA
<213> ORGANISM: Homo Sapiens
<220> FEATURE:
<221> NAME/KEY: misc_feature
<223> OTHER INFORMATION: halphaI N73D F

<400> SEQUENCE: 165
aatccaagag ttgtgtttga cttgaacaca tataaa                                  36

<210> SEQ ID NO 166
```

-continued

```
<211> LENGTH: 36
<212> TYPE: DNA
<213> ORGANISM: Homo Sapiens
<220> FEATURE:
<221> NAME/KEY: misc_feature
<223> OTHER INFORMATION: halphaI N73D R

<400> SEQUENCE: 166
tttatatgtg ttcaagtcaa acacaactct tggatt                                 36

<210> SEQ ID NO 167
<211> LENGTH: 39
<212> TYPE: DNA
<213> ORGANISM: Homo Sapiens
<220> FEATURE:
<221> NAME/KEY: misc_feature
<223> OTHER INFORMATION: halphaI Q89H F

<400> SEQUENCE: 167
atgattgtag caacatccca cacatcccaa tatggtggg                              39

<210> SEQ ID NO 168
<211> LENGTH: 39
<212> TYPE: DNA
<213> ORGANISM: Homo Sapiens
<220> FEATURE:
<221> NAME/KEY: misc_feature
<223> OTHER INFORMATION: halphaI Q89H R

<400> SEQUENCE: 168
atgattgtag caacatccca cacatcccaa tatggtggg                              39

<210> SEQ ID NO 169
<211> LENGTH: 40
<212> TYPE: DNA
<213> ORGANISM: Homo Sapiens
<220> FEATURE:
<221> NAME/KEY: misc_feature
<223> OTHER INFORMATION: malphaI H93Y F

<400> SEQUENCE: 169
cacatctgag acgcgccaat atggtgggga cctcacaaac                             40

<210> SEQ ID NO 170
<211> LENGTH: 40
<212> TYPE: DNA
<213> ORGANISM: Homo Sapiens
<220> FEATURE:
<221> NAME/KEY: misc_feature
<223> OTHER INFORMATION: malphaI H93Y R

<400> SEQUENCE: 170
gtttgtgagg tccccaccat attggcgcgt ctcagatgtg                             40

<210> SEQ ID NO 171
<211> LENGTH: 216
<212> TYPE: PRT
<213> ORGANISM: Macaca fascicularis
<220> FEATURE:
<221> NAME/KEY: MISC_FEATURE
<223> OTHER INFORMATION: Cynomologus

<400> SEQUENCE: 171

Ser Pro Asp Phe Gln Leu Ser Ala Ser Phe Ser Pro Ala Thr Gln Pro
1               5                   10                  15
Cys Pro Ser Leu Ile Asp Val Val Val Cys Asp Glu Ser Asn Ser
            20                  25                  30
```

```
Ile Tyr Pro Trp Asp Ala Val Asp Asn Phe Leu Glu Lys Phe Val Gln
             35                  40                  45

Gly Leu Asp Ile Gly Pro Thr Lys Thr Gln Val Gly Leu Ile Gln Tyr
 50                      55                  60

Ala Asn Asn Pro Arg Val Val Phe Asn Leu Asn Thr Tyr Lys Thr Lys
 65                  70                  75                  80

Glu Glu Met Ile Val Ala Thr Ser Gln Thr Ser Gln Tyr Gly Gly Asp
                 85                  90                  95

Leu Thr Asn Thr Phe Gly Ala Ile Gln Tyr Ala Arg Lys Tyr Ala Tyr
            100                 105                 110

Ser Ala Ala Ser Gly Gly Arg Arg Ser Ala Thr Lys Val Met Val Val
            115                 120                 125

Val Thr Asp Gly Glu Ser His Asp Gly Ser Met Leu Lys Ala Val Ile
130                 135                 140

Asp Gln Cys Asn His Asp Asn Ile Leu Arg Phe Gly Ile Ala Val Leu
145                 150                 155                 160

Gly Tyr Leu Asn Arg Asn Ala Leu Asp Thr Lys Asn Leu Ile Lys Glu
                165                 170                 175

Ile Lys Ala Ile Ala Ser Ile Pro Thr Glu Arg Tyr Phe Phe Asn Val
            180                 185                 190

Ser Asp Glu Ala Ala Leu Leu Glu Lys Ala Gly Thr Leu Gly Glu Gln
            195                 200                 205

Ile Phe Ser Ile Glu Gly Thr Val
            210                 215

<210> SEQ ID NO 172
<211> LENGTH: 216
<212> TYPE: PRT
<213> ORGANISM: Macaca mulatta
<220> FEATURE:
<221> NAME/KEY: MISC_FEATURE
<223> OTHER INFORMATION: Rhesus

<400> SEQUENCE: 172

Ser Pro Asp Phe Gln Leu Ser Ala Ser Phe Ser Pro Ala Thr Gln Pro
 1               5                  10                  15

Cys Pro Ser Leu Ile Asp Val Val Val Cys Asp Glu Ser Asn Ser
             20                  25                  30

Ile Tyr Pro Trp Asp Ala Val Lys Asn Phe Leu Glu Lys Phe Val Gln
             35                  40                  45

Gly Leu Asp Ile Gly Pro Thr Lys Thr Gln Val Gly Leu Ile Gln Tyr
 50                      55                  60

Ala Asn Asn Pro Arg Val Val Phe Asn Leu Asn Thr Tyr Lys Thr Lys
 65                  70                  75                  80

Glu Glu Met Ile Val Ala Thr Ser Gln Thr Ser Gln Tyr Gly Gly Asp
                 85                  90                  95

Leu Thr Asn Thr Phe Gly Ala Ile Gln Tyr Ala Arg Lys Tyr Ala Tyr
            100                 105                 110

Ser Ala Ala Ser Gly Gly Arg Arg Ser Ala Thr Lys Val Met Val Val
            115                 120                 125

Val Thr Asp Gly Glu Ser His Asp Gly Ser Met Leu Lys Ala Val Ile
130                 135                 140

Asp Gln Cys Asn His Asp Asn Ile Leu Arg Phe Gly Ile Ala Val Leu
145                 150                 155                 160

Gly Tyr Leu Asn Arg Asn Ala Leu Asp Thr Lys Asn Leu Ile Lys Glu
                165                 170                 175
```

```
Ile Lys Ala Ile Ala Ser Ile Pro Thr Glu Arg Tyr Phe Phe Asn Val
            180                 185                 190
Ser Asp Glu Ala Ala Leu Leu Glu Lys Ala Gly Thr Leu Gly Glu Gln
                195                 200                 205
Ile Phe Ser Ile Glu Gly Thr Val
            210                 215

<210> SEQ ID NO 173
<211> LENGTH: 1435
<212> TYPE: DNA
<213> ORGANISM: Homo Sapiens
<220> FEATURE:
<221> NAME/KEY: misc_feature
<223> OTHER INFORMATION: hvH14.0 IgG4 Heavy Chain
<220> FEATURE:
<221> NAME/KEY: CDS
<222> LOCATION: (22)..(1416)

<400> SEQUENCE: 173
```

| | | | | | | | | | | | | | | | | | |
|---|---|---|---|---|---|---|---|---|---|---|---|---|---|---|---|---|---|
| tctcgagaag | cttccaccat | g | gag | aca | gac | aca | ctc | ctg | cta | tgg | gta | ctg | | | | | 51 |
| | | | Glu | Thr | Asp | Thr | Leu | Leu | Leu | Trp | Val | Leu | | | | | |
| | | | 1 | | | | 5 | | | | | 10 | | | | | |
| ctg | ctc | tgg | gtt | cca | ggt | tcc | act | gga | cag | gtg | cag | ttg | cag | gag | tca | | 99 |
| Leu | Leu | Trp | Val | Pro | Gly | Ser | Thr | Gly | Gln | Val | Gln | Leu | Gln | Glu | Ser | | |
| | | | | 15 | | | | | 20 | | | | | 25 | | | |
| ggc | cct | ggc | ctg | gtg | aag | ccc | agc | gag | acc | ctg | agc | ctg | acc | tgt | acc | | 147 |
| Gly | Pro | Gly | Leu | Val | Lys | Pro | Ser | Glu | Thr | Leu | Ser | Leu | Thr | Cys | Thr | | |
| | | | 30 | | | | | 35 | | | | | 40 | | | | |
| gtc | tct | gga | ttt | agc | tta | acc | aac | tat | ggc | atc | cac | tgg | ata | cgc | cag | | 195 |
| Val | Ser | Gly | Phe | Ser | Leu | Thr | Asn | Tyr | Gly | Ile | His | Trp | Ile | Arg | Gln | | |
| | | | | 45 | | | | | 50 | | | | | 55 | | | |
| cct | cca | ggc | aag | ggc | ctg | gag | tgg | ctg | ggc | gtg | ata | tgg | gct | cgc | ggc | | 243 |
| Pro | Pro | Gly | Lys | Gly | Leu | Glu | Trp | Leu | Gly | Val | Ile | Trp | Ala | Arg | Gly | | |
| | | | 60 | | | | | 65 | | | | | 70 | | | | |
| ttc | aca | aac | tat | aac | agc | gct | ctc | atg | tcc | cgc | gtg | acc | atc | agc | aag | | 291 |
| Phe | Thr | Asn | Tyr | Asn | Ser | Ala | Leu | Met | Ser | Arg | Val | Thr | Ile | Ser | Lys | | |
| 75 | | | | | 80 | | | | | 85 | | | | | 90 | | |
| gac | aac | agc | aag | aac | cag | gtg | agc | ctg | aag | ctg | agc | agc | gtg | acc | gcc | | 339 |
| Asp | Asn | Ser | Lys | Asn | Gln | Val | Ser | Leu | Lys | Leu | Ser | Ser | Val | Thr | Ala | | |
| | | | | 95 | | | | | 100 | | | | | 105 | | | |
| gcg | gac | acc | gcc | gtg | tac | tac | tgc | gcc | aga | gcc | aac | gac | ggg | gtc | tac | | 387 |
| Ala | Asp | Thr | Ala | Val | Tyr | Tyr | Cys | Ala | Arg | Ala | Asn | Asp | Gly | Val | Tyr | | |
| | | | 110 | | | | | 115 | | | | | 120 | | | | |
| tat | gcc | atg | gac | tac | tgg | ggc | cag | gga | acc | ctg | gtc | acc | gtc | agc | tca | | 435 |
| Tyr | Ala | Met | Asp | Tyr | Trp | Gly | Gln | Gly | Thr | Leu | Val | Thr | Val | Ser | Ser | | |
| | | | 125 | | | | | 130 | | | | | 135 | | | | |
| gcg | tcc | acc | aag | ggc | cca | tcc | gtc | ttc | ccc | ctg | gcg | ccc | tgc | tcc | agg | | 483 |
| Ala | Ser | Thr | Lys | Gly | Pro | Ser | Val | Phe | Pro | Leu | Ala | Pro | Cys | Ser | Arg | | |
| | | | 140 | | | | | 145 | | | | | 150 | | | | |
| agc | acc | tcc | gag | agc | aca | gcc | gcc | ctg | ggc | tgc | ctg | gtc | aag | gac | tac | | 531 |
| Ser | Thr | Ser | Glu | Ser | Thr | Ala | Ala | Leu | Gly | Cys | Leu | Val | Lys | Asp | Tyr | | |
| 155 | | | | | 160 | | | | | 165 | | | | | 170 | | |
| ttc | ccc | gaa | ccg | gtg | acg | gtg | tcg | tgg | aac | tca | ggc | gcc | ctg | acc | agc | | 579 |
| Phe | Pro | Glu | Pro | Val | Thr | Val | Ser | Trp | Asn | Ser | Gly | Ala | Leu | Thr | Ser | | |
| | | | | 175 | | | | | 180 | | | | | 185 | | | |
| ggc | gtg | cac | acc | ttc | ccg | gct | gtc | cta | cag | tcc | tca | gga | ctc | tac | tcc | | 627 |
| Gly | Val | His | Thr | Phe | Pro | Ala | Val | Leu | Gln | Ser | Ser | Gly | Leu | Tyr | Ser | | |
| | | | 190 | | | | | 195 | | | | | 200 | | | | |
| ctc | agc | agc | gtg | gtg | acc | gtg | ccc | tcc | agc | agc | ttg | ggc | acg | aag | acc | | 675 |
| Leu | Ser | Ser | Val | Val | Thr | Val | Pro | Ser | Ser | Ser | Leu | Gly | Thr | Lys | Thr | | |
| | | | 205 | | | | | 210 | | | | | 215 | | | | |
| tac | acc | tgc | aac | gta | gat | cac | aag | ccc | agc | aac | acc | aag | gtg | gac | aag | | 723 |

```
Tyr Thr Cys Asn Val Asp His Lys Pro Ser Asn Thr Lys Val Asp Lys
        220                 225                 230 aga gtt gag tcc aaa tat ggt ccc cca tgc cca tca tgc cca gca cct    771
Arg Val Glu Ser Lys Tyr Gly Pro Pro Cys Pro Ser Cys Pro Ala Pro
235                 240                 245                 250 gag ttc ctg ggg gga cca tca gtc ttc ctg ttc ccc cca aaa ccc aag    819
Glu Phe Leu Gly Gly Pro Ser Val Phe Leu Phe Pro Pro Lys Pro Lys
            255                 260                 265 gac act ctc atg atc tcc cgg acc cct gag gtc acg tgc gtg gtg gtg    867
Asp Thr Leu Met Ile Ser Arg Thr Pro Glu Val Thr Cys Val Val Val
                270                 275                 280 gac gtg agc cag gaa gac ccc gag gtc cag ttc aac tgg tac gtg gat    915
Asp Val Ser Gln Glu Asp Pro Glu Val Gln Phe Asn Trp Tyr Val Asp
            285                 290                 295 ggc gtg gag gtg cat aat gcc aag aca aag ccg cgg gag gag cag ttc    963
Gly Val Glu Val His Asn Ala Lys Thr Lys Pro Arg Glu Glu Gln Phe
300                 305                 310 aac agc acg tac cgt gtg gtc agc gtc ctc acc gtc ctg cac cag gac   1011
Asn Ser Thr Tyr Arg Val Val Ser Val Leu Thr Val Leu His Gln Asp
315                 320                 325                 330 tgg ctg aac ggc aag gag tac aag tgc aag gtc tcc aac aaa ggc ctc   1059
Trp Leu Asn Gly Lys Glu Tyr Lys Cys Lys Val Ser Asn Lys Gly Leu
                335                 340                 345 ccg tcc tcc atc gag aaa acc atc tcc aaa gcc aaa ggg cag ccc cga   1107
Pro Ser Ser Ile Glu Lys Thr Ile Ser Lys Ala Lys Gly Gln Pro Arg
            350                 355                 360 gag cca cag gtg tac acc ctg ccc cca tcc cag gag gag atg acc aag   1155
Glu Pro Gln Val Tyr Thr Leu Pro Pro Ser Gln Glu Glu Met Thr Lys
                365                 370                 375 aac cag gtc agc ctg acc tgc ctg gtc aaa ggc ttc tac ccc agc gac   1203
Asn Gln Val Ser Leu Thr Cys Leu Val Lys Gly Phe Tyr Pro Ser Asp
            380                 385                 390 atc gcc gtg gag tgg gag agc aat ggg cag ccg gag aac aac tac aag   1251
Ile Ala Val Glu Trp Glu Ser Asn Gly Gln Pro Glu Asn Asn Tyr Lys
395                 400                 405                 410 acc acg cct ccc gtg ctg gac tcc gac ggc tcc ttc ttc ctc tac agc   1299
Thr Thr Pro Pro Val Leu Asp Ser Asp Gly Ser Phe Phe Leu Tyr Ser
                415                 420                 425 agg cta acc gtg gac aag agc agg tgg cag gag ggg aat gtc ttc tca   1347
Arg Leu Thr Val Asp Lys Ser Arg Trp Gln Glu Gly Asn Val Phe Ser
            430                 435                 440 tgc tcc gtg atg cat gag gct ctg cac aac cac tac aca cag aag agc   1395
Cys Ser Val Met His Glu Ala Leu His Asn His Tyr Thr Gln Lys Ser
                445                 450                 455 ctc tcc ctg tct ctg ggt aaa tgataggatc cgcggccgc                  1435
Leu Ser Leu Ser Leu Gly Lys
    460                 465

<210> SEQ ID NO 174
<211> LENGTH: 465
<212> TYPE: PRT
<213> ORGANISM: Homo Sapiens

<400> SEQUENCE: 174

Glu Thr Asp Thr Leu Leu Leu Trp Val Leu Leu Leu Trp Val Pro Gly
1               5                   10                  15

Ser Thr Gly Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45
```

```
Thr Asn Tyr Gly Ile His Trp Ile Arg Gln Pro Gly Lys Gly Leu
    50                  55                  60

Glu Trp Leu Gly Val Ile Trp Ala Arg Gly Phe Thr Asn Tyr Asn Ser
65                  70                  75                  80

Ala Leu Met Ser Arg Val Thr Ile Ser Lys Asp Asn Ser Lys Asn Gln
                85                  90                  95

Val Ser Leu Lys Leu Ser Ser Val Thr Ala Ala Asp Thr Ala Val Tyr
                100                 105                 110

Tyr Cys Ala Arg Ala Asn Asp Gly Val Tyr Tyr Ala Met Asp Tyr Trp
            115                 120                 125

Gly Gln Gly Thr Leu Val Thr Val Ser Ser Ala Ser Thr Lys Gly Pro
        130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Ser Leu Gly Thr Lys Thr Tyr Thr Cys Asn Val Asp
        210                 215                 220

His Lys Pro Ser Asn Thr Lys Val Asp Lys Arg Val Glu Ser Lys Tyr
225                 230                 235                 240

Gly Pro Pro Cys Pro Ser Cys Pro Ala Pro Glu Phe Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser Gln Glu Asp
            275                 280                 285

Pro Glu Val Gln Phe Asn Trp Tyr Val Asp Gly Val Glu Val His Asn
        290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
                340                 345                 350

Thr Ile Ser Lys Ala Lys Gly Gln Pro Arg Glu Pro Gln Val Tyr Thr
            355                 360                 365

Leu Pro Pro Ser Gln Glu Glu Met Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
                420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
        450                 455                 460

Lys
465
```

<210> SEQ ID NO 175
<211> LENGTH: 1435
<212> TYPE: DNA
<213> ORGANISM: Homo Sapiens
<220> FEATURE:
<221> NAME/KEY: misc_feature
<223> OTHER INFORMATION: hvH12.0 IgG4 Heavy Chain
<220> FEATURE:
<221> NAME/KEY: CDS
<222> LOCATION: (22)..(1416)

<400> SEQUENCE: 175

```
tctcgagaag cttccaccat g gag aca gac aca ctc ctg cta tgg gta ctg      51
                        Glu Thr Asp Thr Leu Leu Leu Trp Val Leu
                         1               5                   10 ctg ctc tgg gtt cca ggt tcc act gga cag gtg cag ttg cag gag tca      99
Leu Leu Trp Val Pro Gly Ser Thr Gly Gln Val Gln Leu Gln Glu Ser
             15                  20                  25 ggc cct ggc ctg gtg aag ccc agc gag acc ctg agc ctg acc tgt acc     147
Gly Pro Gly Leu Val Lys Pro Ser Glu Thr Leu Ser Leu Thr Cys Thr
         30                  35                  40 gtc tct gga ttt agc tta acc aac tat ggc atc cac tgg ata cgc cag     195
Val Ser Gly Phe Ser Leu Thr Asn Tyr Gly Ile His Trp Ile Arg Gln
     45                  50                  55 cct cca ggc aag ggc ctg gag tgg ctg ggc gtg ata tgg gct cgc ggc     243
Pro Pro Gly Lys Gly Leu Glu Trp Leu Gly Val Ile Trp Ala Arg Gly
 60                  65                  70 ttc aca aac tat aac agc gct ctc atg tcc cgc ctg acc atc agc aag     291
Phe Thr Asn Tyr Asn Ser Ala Leu Met Ser Arg Leu Thr Ile Ser Lys
75                  80                  85                  90 gac aac agc aag aac cag gtg agc ctg aag ctg agc agc gtg acc gcc     339
Asp Asn Ser Lys Asn Gln Val Ser Leu Lys Leu Ser Ser Val Thr Ala
                 95                 100                 105 gcg gac acc gcc gtg tac tac tgc gcc aga gcc aac gac ggg gtc tac     387
Ala Asp Thr Ala Val Tyr Tyr Cys Ala Arg Ala Asn Asp Gly Val Tyr
             110                 115                 120 tat gcc atg gac tac tgg ggc cag gga acc ctg gtc acc gtc agc tca     435
Tyr Ala Met Asp Tyr Trp Gly Gln Gly Thr Leu Val Thr Val Ser Ser
         125                 130                 135 gcg tcc acc aag ggc cca tcc gtc ttc ccc ctg gcg ccc tgc tcc agg     483
Ala Ser Thr Lys Gly Pro Ser Val Phe Pro Leu Ala Pro Cys Ser Arg
     140                 145                 150 agc acc tcc gag agc aca gcc gcc ctg ggc tgc ctg gtc aag gac tac     531
Ser Thr Ser Glu Ser Thr Ala Ala Leu Gly Cys Leu Val Lys Asp Tyr
155                 160                 165                 170 ttc ccc gaa ccg gtg acg gtg tcg tgg aac tca ggc gcc ctg acc agc     579
Phe Pro Glu Pro Val Thr Val Ser Trp Asn Ser Gly Ala Leu Thr Ser
                 175                 180                 185 ggc gtg cac acc ttc ccg gct gtc cta cag tcc tca gga ctc tac tcc     627
Gly Val His Thr Phe Pro Ala Val Leu Gln Ser Ser Gly Leu Tyr Ser
             190                 195                 200 ctc agc agc gtg gtg acc gtg ccc tcc agc agc ttg ggc acg aag acc     675
Leu Ser Ser Val Val Thr Val Pro Ser Ser Ser Leu Gly Thr Lys Thr
         205                 210                 215 tac acc tgc aac gta gat cac aag ccc agc aac acc aag gtg gac aag     723
Tyr Thr Cys Asn Val Asp His Lys Pro Ser Asn Thr Lys Val Asp Lys
     220                 225                 230 aga gtt gag tcc aaa tat ggt ccc cca tgc cca tca tgc cca gca cct     771
Arg Val Glu Ser Lys Tyr Gly Pro Pro Cys Pro Ser Cys Pro Ala Pro
235                 240                 245                 250 gag ttc ctg ggg gga cca tca gtc ttc ctg ttc ccc cca aaa ccc aag     819
Glu Phe Leu Gly Gly Pro Ser Val Phe Leu Phe Pro Pro Lys Pro Lys
```

```
Glu Phe Leu Gly Gly Pro Ser Val Phe Leu Phe Pro Pro Lys Pro Lys
                255                 260                 265 gac act ctc atg atc tcc cgg acc cct gag gtc acg tgc gtg gtg gtg      867
Asp Thr Leu Met Ile Ser Arg Thr Pro Glu Val Thr Cys Val Val Val
            270                 275                 280 gac gtg agc cag gaa gac ccc gag gtc cag ttc aac tgg tac gtg gat      915
Asp Val Ser Gln Glu Asp Pro Glu Val Gln Phe Asn Trp Tyr Val Asp
        285                 290                 295 ggc gtg gag gtg cat aat gcc aag aca aag ccg cgg gag gag cag ttc      963
Gly Val Glu Val His Asn Ala Lys Thr Lys Pro Arg Glu Glu Gln Phe
    300                 305                 310 aac agc acg tac cgt gtg gtc agc gtc ctc acc gtc ctg cac cag gac     1011
Asn Ser Thr Tyr Arg Val Val Ser Val Leu Thr Val Leu His Gln Asp
315                 320                 325                 330 tgg ctg aac ggc aag gag tac aag tgc aag gtc tcc aac aaa ggc ctc     1059
Trp Leu Asn Gly Lys Glu Tyr Lys Cys Lys Val Ser Asn Lys Gly Leu
                335                 340                 345 ccg tcc tcc atc gag aaa acc atc tcc aaa gcc aaa ggg cag ccc cga     1107
Pro Ser Ser Ile Glu Lys Thr Ile Ser Lys Ala Lys Gly Gln Pro Arg
            350                 355                 360 gag cca cag gtg tac acc ctg ccc cca tcc cag gag gag atg acc aag     1155
Glu Pro Gln Val Tyr Thr Leu Pro Pro Ser Gln Glu Glu Met Thr Lys
        365                 370                 375 aac cag gtc agc ctg acc tgc ctg gtc aaa ggc ttc tac ccc agc gac     1203
Asn Gln Val Ser Leu Thr Cys Leu Val Lys Gly Phe Tyr Pro Ser Asp
    380                 385                 390 atc gcc gtg gag tgg gag agc aat ggg cag ccg gag aac aac tac aag     1251
Ile Ala Val Glu Trp Glu Ser Asn Gly Gln Pro Glu Asn Asn Tyr Lys
395                 400                 405                 410 acc acg cct ccc gtg ctg gac tcc gac ggc tcc ttc ttc ctc tac agc     1299
Thr Thr Pro Pro Val Leu Asp Ser Asp Gly Ser Phe Phe Leu Tyr Ser
                415                 420                 425 agg cta acc gtg gac aag agc agg tgg cag gag ggg aat gtc ttc tca     1347
Arg Leu Thr Val Asp Lys Ser Arg Trp Gln Glu Gly Asn Val Phe Ser
            430                 435                 440 tgc tcc gtg atg cat gag gct ctg cac aac cac tac aca cag aag agc     1395
Cys Ser Val Met His Glu Ala Leu His Asn His Tyr Thr Gln Lys Ser
        445                 450                 455 ctc tcc ctg tct ctg ggt aaa tgataggatc cgcggccgc                    1435
Leu Ser Leu Ser Leu Gly Lys
    460                 465

<210> SEQ ID NO 176
<211> LENGTH: 465
<212> TYPE: PRT
<213> ORGANISM: Homo Sapiens

<400> SEQUENCE: 176

Glu Thr Asp Thr Leu Leu Leu Trp Val Leu Leu Leu Trp Val Pro Gly
1               5                   10                  15

Ser Thr Gly Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Thr Asn Tyr Gly Ile His Trp Ile Arg Gln Pro Pro Gly Lys Gly Leu
    50                  55                  60

Glu Trp Leu Gly Val Ile Trp Ala Arg Gly Phe Thr Asn Tyr Asn Ser
65                  70                  75                  80

Ala Leu Met Ser Arg Leu Thr Ile Ser Lys Asp Asn Ser Lys Asn Gln
                85                  90                  95
```

```
Val Ser Leu Lys Leu Ser Ser Val Thr Ala Asp Thr Ala Val Tyr
            100                 105                 110
Tyr Cys Ala Arg Ala Asn Asp Gly Val Tyr Tyr Ala Met Asp Tyr Trp
        115                 120                 125
Gly Gln Gly Thr Leu Val Thr Val Ser Ser Ala Ser Thr Lys Gly Pro
    130                 135                 140
Ser Val Phe Pro Leu Ala Pro Cys Ser Arg Ser Thr Ser Glu Ser Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
        195                 200                 205
Val Pro Ser Ser Ser Leu Gly Thr Lys Thr Tyr Thr Cys Asn Val Asp
    210                 215                 220
His Lys Pro Ser Asn Thr Lys Val Asp Lys Arg Val Glu Ser Lys Tyr
225                 230                 235                 240
Gly Pro Pro Cys Pro Ser Cys Pro Ala Pro Glu Phe Leu Gly Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser Gln Glu Asp
        275                 280                 285
Pro Glu Val Gln Phe Asn Trp Tyr Val Asp Gly Val Glu Val His Asn
    290                 295                 300
Ala Lys Thr Lys Pro Arg Glu Glu Gln Phe Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Gly Leu Pro Ser Ser Ile Glu Lys
            340                 345                 350
Thr Ile Ser Lys Ala Lys Gly Gln Pro Arg Glu Pro Gln Val Tyr Thr
        355                 360                 365
Leu Pro Pro Ser Gln Glu Glu Met Thr Lys Asn Gln Val Ser Leu Thr
    370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Arg Leu Thr Val Asp Lys
            420                 425                 430
Ser Arg Trp Gln Glu Gly Asn Val Phe Ser Cys Ser Val Met His Glu
        435                 440                 445
Ala Leu His Asn His Tyr Thr Gln Lys Ser Leu Ser Leu Ser Leu Gly
    450                 455                 460
Lys
465

<210> SEQ ID NO 177
<211> LENGTH: 744
<212> TYPE: DNA
<213> ORGANISM: Homo Sapiens
<220> FEATURE:
<221> NAME/KEY: misc_feature
```

<223> OTHER INFORMATION: VL10.0Q light chain
<220> FEATURE:
<221> NAME/KEY: CDS
<222> LOCATION: (22)..(720)

<400> SEQUENCE: 177

```
ctatctcgag aagcttccac c atg gag aca gac aca ctc ctg cta tgg gta        51
                        Met Glu Thr Asp Thr Leu Leu Leu Trp Val
                         1               5                  10 ctg ctg ctc tgg gtt cca ggt tcc act gga gac ttc gtg atg acc cag        99
Leu Leu Leu Trp Val Pro Gly Ser Thr Gly Asp Phe Val Met Thr Gln
             15                  20                  25 tct cca gca ttc ctg agc gtg acc ccc ggc gag aag gtg acc atc acc       147
Ser Pro Ala Phe Leu Ser Val Thr Pro Gly Glu Lys Val Thr Ile Thr
                 30                  35                  40 tgc agc gcc caa tca agc gtg aac tac att cac tgg tac cag cag aag       195
Cys Ser Ala Gln Ser Ser Val Asn Tyr Ile His Trp Tyr Gln Gln Lys
             45                  50                  55 ccc gac cag gcc ccc aag aaa ttg atc tat gac act tcc aag ctg gcc       243
Pro Asp Gln Ala Pro Lys Lys Leu Ile Tyr Asp Thr Ser Lys Leu Ala
 60                  65                  70 agc ggc gtg ccc agc cgc ttc agc ggc agc ggc agc ggc acc gac tac       291
Ser Gly Val Pro Ser Arg Phe Ser Gly Ser Gly Ser Gly Thr Asp Tyr
 75                  80                  85                  90 acc ttc acc atc agc agc ctg gag gcc gag gac gct gcc acc tat tac       339
Thr Phe Thr Ile Ser Ser Leu Glu Ala Glu Asp Ala Ala Thr Tyr Tyr
                 95                 100                 105 tgc cag cag tgg acc act aac cca ctg acc ttc ggc cag ggc acc aag       387
Cys Gln Gln Trp Thr Thr Asn Pro Leu Thr Phe Gly Gln Gly Thr Lys
             110                 115                 120 gtc gaa atc aaa cga act gtg gct gca cca tct gtc ttc atc ttc ccg       435
Val Glu Ile Lys Arg Thr Val Ala Ala Pro Ser Val Phe Ile Phe Pro
                 125                 130                 135 cca tct gat gag cag ttg aaa tct gga act gcc tct gtt gtg tgc ctg       483
Pro Ser Asp Glu Gln Leu Lys Ser Gly Thr Ala Ser Val Val Cys Leu
             140                 145                 150 ctg aat aac ttc tat ccc aga gag gcc aaa gta cag tgg aag gtg gat       531
Leu Asn Asn Phe Tyr Pro Arg Glu Ala Lys Val Gln Trp Lys Val Asp
155                 160                 165                 170 aac gcc ctc caa tcg ggt aac tcc cag gag agt gtc aca gag cag gac       579
Asn Ala Leu Gln Ser Gly Asn Ser Gln Glu Ser Val Thr Glu Gln Asp
                 175                 180                 185 agc aag gac agc acc tac agc ctc agc agc acc ctg acg ctg agc aaa       627
Ser Lys Asp Ser Thr Tyr Ser Leu Ser Ser Thr Leu Thr Leu Ser Lys
             190                 195                 200 gca gac tac gag aaa cac aaa gtc tac gcc tgc gaa gtc acc cat cag       675
Ala Asp Tyr Glu Lys His Lys Val Tyr Ala Cys Glu Val Thr His Gln
                 205                 210                 215 ggc ctg agc tcg ccc gtc aca aag agc ttc aac agg gga gag tgt           720
Gly Leu Ser Ser Pro Val Thr Lys Ser Phe Asn Arg Gly Glu Cys
             220                 225                 230 tgataggatc cgcggccgca tagg                                            744
```

<210> SEQ ID NO 178
<211> LENGTH: 233
<212> TYPE: PRT
<213> ORGANISM: Homo Sapiens

<400> SEQUENCE: 178

```
Met Glu Thr Asp Thr Leu Leu Leu Trp Val Leu Leu Leu Trp Val Pro
 1               5                  10                  15
```

```
Gly Ser Thr Gly Asp Phe Val Met Thr Gln Ser Pro Ala Phe Leu Ser
            20                  25                  30

Val Thr Pro Gly Glu Lys Val Thr Ile Thr Cys Ser Ala Gln Ser Ser
        35                  40                  45

Val Asn Tyr Ile His Trp Tyr Gln Gln Lys Pro Asp Gln Ala Pro Lys
50                  55                  60

Lys Leu Ile Tyr Asp Thr Ser Lys Leu Ala Ser Gly Val Pro Ser Arg
65                  70                  75                  80

Phe Ser Gly Ser Gly Ser Gly Thr Asp Tyr Thr Phe Thr Ile Ser Ser
                85                  90                  95

Leu Glu Ala Glu Asp Ala Ala Thr Tyr Tyr Cys Gln Gln Trp Thr Thr
            100                 105                 110

Asn Pro Leu Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 179
<211> LENGTH: 1460
<212> TYPE: DNA
<213> ORGANISM: Homo Sapiens
<220> FEATURE:
<221> NAME/KEY: misc_feature
<223> OTHER INFORMATION: h2206-VH14 IgG1 Heavy Chain (DANS); Positions
      -24 to -5 is the leader sequence; Position -4 to -1 are extra
      amino acids; DANS at positions -4 to -1 is preferably deleted
<220> FEATURE:
<221> NAME/KEY: CDS
<222> LOCATION: (22)..(1440)
<220> FEATURE:
<221> NAME/KEY: mat_peptide
<222> LOCATION: (94)..(1440)

<400> SEQUENCE: 179
ataggctagc ctcgagccac c atg gag aca gac aca ctc ctg cta tgg gta        51
                         Met Glu Thr Asp Thr Leu Leu Leu Trp Val
                                 -20                     -15 ctg ctg ctc tgg gtt cca ggt tcc act gga gac gcg aat tca cag gtg       99
Leu Leu Leu Trp Val Pro Gly Ser Thr Gly Asp Ala Asn Ser Gln Val
        -10                  -5                  -1  1 cag ttg cag gag tca ggc cct ggc ctg gtg aag ccc agc gag acc ctg      147
Gln Leu Gln Glu Ser Gly Pro Gly Leu Val Lys Pro Ser Glu Thr Leu
        5                   10                  15 agc ctg acc tgt acc gtc tct gga ttt agc tta acc aac tat ggc atc      195
Ser Leu Thr Cys Thr Val Ser Gly Phe Ser Leu Thr Asn Tyr Gly Ile
    20                  25                  30 cac tgg ata cgc cag cct cca ggc aag ggc ctg gag tgg ctg ggc gtg      243
His Trp Ile Arg Gln Pro Pro Gly Lys Gly Leu Glu Trp Leu Gly Val
35                  40                  45                  50
```

|   |   |   |   |   |   |   |   |   |   |   |   |   |   |   |   |      |
|---|---|---|---|---|---|---|---|---|---|---|---|---|---|---|---|------|
| ata | tgg | gct | cgc | ggc | ttc | aca | aac | tat | aac | agc | gct | ctc | atg | tcc | cgc | 291 |
| Ile | Trp | Ala | Arg | Gly | Phe | Thr | Asn | Tyr | Asn | Ser | Ala | Leu | Met | Ser | Arg |    |
|    |    |    | 55 |    |    |    |    | 60 |    |    |    |    |    | 65 |    |    |

|   |   |   |   |   |   |   |   |   |   |   |   |   |   |   |   |      |
|---|---|---|---|---|---|---|---|---|---|---|---|---|---|---|---|------|
| gtg | acc | atc | agc | aag | gac | aac | agc | aag | aac | cag | gtg | agc | ctg | aag | ctg | 339 |
| Val | Thr | Ile | Ser | Lys | Asp | Asn | Ser | Lys | Asn | Gln | Val | Ser | Leu | Lys | Leu |    |
|    |    | 70 |    |    |    |    | 75 |    |    |    |    | 80 |    |    |    |    |

|   |   |   |   |   |   |   |   |   |   |   |   |   |   |   |   |      |
|---|---|---|---|---|---|---|---|---|---|---|---|---|---|---|---|------|
| agc | agc | gtg | acc | gcc | gcg | gac | acc | gcc | gtg | tac | tac | tgc | gcc | aga | gcc | 387 |
| Ser | Ser | Val | Thr | Ala | Ala | Asp | Thr | Ala | Val | Tyr | Tyr | Cys | Ala | Arg | Ala |    |
|    |    |    | 85 |    |    |    |    | 90 |    |    |    |    | 95 |    |    |    |

|   |   |   |   |   |   |   |   |   |   |   |   |   |   |   |   |      |
|---|---|---|---|---|---|---|---|---|---|---|---|---|---|---|---|------|
| aac | gac | ggg | gtc | tac | tat | gcc | atg | gac | tac | tgg | ggc | cag | gga | acc | ctg | 435 |
| Asn | Asp | Gly | Val | Tyr | Tyr | Ala | Met | Asp | Tyr | Trp | Gly | Gln | Gly | Thr | Leu |    |
|    |    | 100 |    |    |    |    | 105 |    |    |    |    | 110 |    |    |    |    |

|   |   |   |   |   |   |   |   |   |   |   |   |   |   |   |   |      |
|---|---|---|---|---|---|---|---|---|---|---|---|---|---|---|---|------|
| gtc | acc | gtc | agc | tca | gcg | tcg | acc | aag | ggc | cca | tcg | gtc | ttc | ccc | ctg | 483 |
| Val | Thr | Val | Ser | Ser | Ala | Ser | Thr | Lys | Gly | Pro | Ser | Val | Phe | Pro | Leu |    |
| 115 |    |    |    |    | 120 |    |    |    |    | 125 |    |    |    |    | 130 |    |

|   |   |   |   |   |   |   |   |   |   |   |   |   |   |   |   |      |
|---|---|---|---|---|---|---|---|---|---|---|---|---|---|---|---|------|
| gca | ccc | tcc | tcc | aag | agc | acc | tct | ggg | ggc | aca | gcg | gcc | ctg | ggc | tgc | 531 |
| Ala | Pro | Ser | Ser | Lys | Ser | Thr | Ser | Gly | Gly | Thr | Ala | Ala | Leu | Gly | Cys |    |
|    |    |    |    | 135 |    |    |    |    | 140 |    |    |    |    | 145 |    |    |

|   |   |   |   |   |   |   |   |   |   |   |   |   |   |   |   |      |
|---|---|---|---|---|---|---|---|---|---|---|---|---|---|---|---|------|
| ctg | gtc | aag | gac | tac | ttc | ccc | gaa | ccg | gtg | acg | gtg | tca | tgg | aac | tca | 579 |
| Leu | Val | Lys | Asp | Tyr | Phe | Pro | Glu | Pro | Val | Thr | Val | Ser | Trp | Asn | Ser |    |
|    |    |    | 150 |    |    |    |    | 155 |    |    |    |    | 160 |    |    |    |

|   |   |   |   |   |   |   |   |   |   |   |   |   |   |   |   |      |
|---|---|---|---|---|---|---|---|---|---|---|---|---|---|---|---|------|
| ggc | gcc | ctg | acc | agc | ggc | gtg | cac | acc | ttc | ccg | gct | gtc | cta | cag | tcc | 627 |
| Gly | Ala | Leu | Thr | Ser | Gly | Val | His | Thr | Phe | Pro | Ala | Val | Leu | Gln | Ser |    |
|    |    | 165 |    |    |    |    | 170 |    |    |    |    | 175 |    |    |    |    |

|   |   |   |   |   |   |   |   |   |   |   |   |   |   |   |   |      |
|---|---|---|---|---|---|---|---|---|---|---|---|---|---|---|---|------|
| tca | gga | ctc | tac | tcc | ctc | agc | agc | gtg | gtg | acc | gtg | ccc | tcc | agc | agc | 675 |
| Ser | Gly | Leu | Tyr | Ser | Leu | Ser | Ser | Val | Val | Thr | Val | Pro | Ser | Ser | Ser |    |
|    | 180 |    |    |    |    | 185 |    |    |    |    | 190 |    |    |    |    |    |

|   |   |   |   |   |   |   |   |   |   |   |   |   |   |   |   |      |
|---|---|---|---|---|---|---|---|---|---|---|---|---|---|---|---|------|
| ttg | ggc | acc | cag | acc | tac | atc | tgc | aac | gtg | aat | cac | aag | ccc | agc | aac | 723 |
| Leu | Gly | Thr | Gln | Thr | Tyr | Ile | Cys | Asn | Val | Asn | His | Lys | Pro | Ser | Asn |    |
| 195 |    |    |    |    | 200 |    |    |    |    | 205 |    |    |    |    | 210 |    |

|   |   |   |   |   |   |   |   |   |   |   |   |   |   |   |   |      |
|---|---|---|---|---|---|---|---|---|---|---|---|---|---|---|---|------|
| acc | aag | gtg | gac | aag | aaa | gtt | gag | ccc | aaa | tct | tgt | gac | aaa | act | cac | 771 |
| Thr | Lys | Val | Asp | Lys | Lys | Val | Glu | Pro | Lys | Ser | Cys | Asp | Lys | Thr | His |    |
|    |    |    | 215 |    |    |    |    | 220 |    |    |    |    | 225 |    |    |    |

|   |   |   |   |   |   |   |   |   |   |   |   |   |   |   |   |      |
|---|---|---|---|---|---|---|---|---|---|---|---|---|---|---|---|------|
| aca | tgc | cca | ccg | tgc | cca | gca | cct | gaa | ctc | ctg | ggg | gga | ccg | tca | gtc | 819 |
| Thr | Cys | Pro | Pro | Cys | Pro | Ala | Pro | Glu | Leu | Leu | Gly | Gly | Pro | Ser | Val |    |
|    |    | 230 |    |    |    |    | 235 |    |    |    |    | 240 |    |    |    |    |

|   |   |   |   |   |   |   |   |   |   |   |   |   |   |   |   |      |
|---|---|---|---|---|---|---|---|---|---|---|---|---|---|---|---|------|
| ttc | ctc | ttc | ccc | cca | aaa | ccc | aag | gac | acc | ctc | atg | atc | tcc | cgg | acc | 867 |
| Phe | Leu | Phe | Pro | Pro | Lys | Pro | Lys | Asp | Thr | Leu | Met | Ile | Ser | Arg | Thr |    |
|    |    | 245 |    |    |    |    | 250 |    |    |    |    | 255 |    |    |    |    |

|   |   |   |   |   |   |   |   |   |   |   |   |   |   |   |   |      |
|---|---|---|---|---|---|---|---|---|---|---|---|---|---|---|---|------|
| cct | gag | gtc | aca | tgc | gtg | gtg | gtg | gac | gtg | agc | cac | gaa | gac | cct | gag | 915 |
| Pro | Glu | Val | Thr | Cys | Val | Val | Val | Asp | Val | Ser | His | Glu | Asp | Pro | Glu |    |
|    | 260 |    |    |    |    | 265 |    |    |    |    | 270 |    |    |    |    |    |

|   |   |   |   |   |   |   |   |   |   |   |   |   |   |   |   |      |
|---|---|---|---|---|---|---|---|---|---|---|---|---|---|---|---|------|
| gtc | aag | ttc | aac | tgg | tac | gtg | gac | ggc | gtg | gag | gtg | cat | aat | gcc | aag | 963 |
| Val | Lys | Phe | Asn | Trp | Tyr | Val | Asp | Gly | Val | Glu | Val | His | Asn | Ala | Lys |    |
| 275 |    |    |    |    | 280 |    |    |    |    | 285 |    |    |    |    | 290 |    |

|   |   |   |   |   |   |   |   |   |   |   |   |   |   |   |   |      |
|---|---|---|---|---|---|---|---|---|---|---|---|---|---|---|---|------|
| aca | aag | ccg | cgg | gag | gag | cag | tac | aac | agc | acg | tac | cgt | gtg | gtc | agc | 1011 |
| Thr | Lys | Pro | Arg | Glu | Glu | Gln | Tyr | Asn | Ser | Thr | Tyr | Arg | Val | Val | Ser |    |
|    |    |    | 295 |    |    |    |    | 300 |    |    |    |    | 305 |    |    |    |

|   |   |   |   |   |   |   |   |   |   |   |   |   |   |   |   |      |
|---|---|---|---|---|---|---|---|---|---|---|---|---|---|---|---|------|
| gtc | ctc | acc | gtc | ctg | cac | cag | gac | tgg | ctg | aat | ggc | aag | gag | tac | aag | 1059 |
| Val | Leu | Thr | Val | Leu | His | Gln | Asp | Trp | Leu | Asn | Gly | Lys | Glu | Tyr | Lys |    |
|    |    |    | 310 |    |    |    |    | 315 |    |    |    |    | 320 |    |    |    |

|   |   |   |   |   |   |   |   |   |   |   |   |   |   |   |   |      |
|---|---|---|---|---|---|---|---|---|---|---|---|---|---|---|---|------|
| tgc | aag | gtc | tcc | aac | aaa | gcc | ctc | cca | gcc | ccc | atc | gag | aaa | acc | atc | 1107 |
| Cys | Lys | Val | Ser | Asn | Lys | Ala | Leu | Pro | Ala | Pro | Ile | Glu | Lys | Thr | Ile |    |
|    |    | 325 |    |    |    |    | 330 |    |    |    |    | 335 |    |    |    |    |

|   |   |   |   |   |   |   |   |   |   |   |   |   |   |   |   |      |
|---|---|---|---|---|---|---|---|---|---|---|---|---|---|---|---|------|
| tcc | aaa | gcc | aaa | ggg | cag | ccc | cga | gaa | cca | cag | gtg | tac | acc | ctg | ccc | 1155 |
| Ser | Lys | Ala | Lys | Gly | Gln | Pro | Arg | Glu | Pro | Gln | Val | Tyr | Thr | Leu | Pro |    |
|    | 340 |    |    |    |    | 345 |    |    |    |    | 350 |    |    |    |    |    |

|   |   |   |   |   |   |   |   |   |   |   |   |   |   |   |   |      |
|---|---|---|---|---|---|---|---|---|---|---|---|---|---|---|---|------|
| cca | tcc | cgg | gat | gag | ctg | acc | aag | aac | cag | gtc | agc | ctg | acc | tgc | ctg | 1203 |
| Pro | Ser | Arg | Asp | Glu | Leu | Thr | Lys | Asn | Gln | Val | Ser | Leu | Thr | Cys | Leu |    |
| 355 |    |    |    |    | 360 |    |    |    |    | 365 |    |    |    |    | 370 |    |

-continued

```
gtc aaa ggc ttc tat ccc agc gac atc gcc gtg gag tgg gag agc aat    1251
Val Lys Gly Phe Tyr Pro Ser Asp Ile Ala Val Glu Trp Glu Ser Asn
            375                 380                 385 ggg cag ccg gag aac aac tac aag acc acg cct ccc gtg ctg gac tcc    1299
Gly Gln Pro Glu Asn Asn Tyr Lys Thr Thr Pro Pro Val Leu Asp Ser
390                 395                 400 gac ggc tcc ttc ttc ctc tac agc aag ctc acc gtg gac aag agc agg    1347
Asp Gly Ser Phe Phe Leu Tyr Ser Lys Leu Thr Val Asp Lys Ser Arg
        405                 410                 415 tgg cag cag ggg aac gtc ttc tca tgc tcc gtg atg cat gag gct ctg    1395
Trp Gln Gln Gly Asn Val Phe Ser Cys Ser Val Met His Glu Ala Leu
    420                 425                 430 cac aac cac tac acg cag aag agc ctc tcc ctg tct ccg ggt aaa        1440
His Asn His Tyr Thr Gln Lys Ser Leu Ser Leu Ser Pro Gly Lys
435                 440                 445 tgataagcgg ccgcttccct                                              1460

<210> SEQ ID NO 180
<211> LENGTH: 473
<212> TYPE: PRT
<213> ORGANISM: Homo Sapiens

<400> SEQUENCE: 180

Met Glu Thr Asp Thr Leu Leu Leu Trp Val Leu Leu Leu Trp Val Pro
            -20                 -15                 -10

Gly Ser Thr Gly Asp Ala Asn Ser Gln Val Gln Leu Gln Glu Ser Gly
        -5                  -1  1               5

Pro Gly Leu Val Lys Pro Ser Glu Thr Leu Ser Leu Thr Cys Thr Val
    10                  15                  20

Ser Gly Phe Ser Leu Thr Asn Tyr Gly Ile His Trp Ile Arg Gln Pro
25                  30                  35                  40

Pro Gly Lys Gly Leu Glu Trp Leu Gly Val Ile Trp Ala Arg Gly Phe
                45                  50                  55

Thr Asn Tyr Asn Ser Ala Leu Met Ser Arg Val Thr Ile Ser Lys Asp
            60                  65                  70

Asn Ser Lys Asn Gln Val Ser Leu Lys Leu Ser Ser Val Thr Ala Ala
        75                  80                  85

Asp Thr Ala Val Tyr Tyr Cys Ala Arg Ala Asn Asp Gly Val Tyr Tyr
    90                  95                  100

Ala Met Asp Tyr Trp Gly Gln Gly Thr Leu Val Thr Val Ser Ser Ala
105                 110                 115                 120

Ser Thr Lys Gly Pro Ser Val Phe Pro Leu Ala Pro Ser Ser Lys Ser
                125                 130                 135

Thr Ser Gly Gly Thr Ala Ala Leu Gly Cys Leu Val Lys Asp Tyr Phe
            140                 145                 150

Pro Glu Pro Val Thr Val Ser Trp Asn Ser Gly Ala Leu Thr Ser Gly
        155                 160                 165

Val His Thr Phe Pro Ala Val Leu Gln Ser Ser Gly Leu Tyr Ser Leu
    170                 175                 180

Ser Ser Val Val Thr Val Pro Ser Ser Ser Leu Gly Thr Gln Thr Tyr
185                 190                 195                 200

Ile Cys Asn Val Asn His Lys Pro Ser Asn Thr Lys Val Asp Lys Lys
                205                 210                 215

Val Glu Pro Lys Ser Cys Asp Lys Thr His Thr Cys Pro Pro Cys Pro
            220                 225                 230

Ala Pro Glu Leu Leu Gly Gly Pro Ser Val Phe Leu Phe Pro Pro Lys
```

```
                  235                 240                 245
Pro Lys Asp Thr Leu Met Ile Ser Arg Thr Pro Glu Val Thr Cys Val
250                 255                 260

Val Val Asp Val Ser His Glu Asp Pro Glu Val Lys Phe Asn Trp Tyr
265                 270                 275                 280

Val Asp Gly Val Glu Val His Asn Ala Lys Thr Lys Pro Arg Glu Glu
                285                 290                 295

Gln Tyr Asn Ser Thr Tyr Arg Val Val Ser Val Leu Thr Val Leu His
            300                 305                 310

Gln Asp Trp Leu Asn Gly Lys Glu Tyr Lys Cys Lys Val Ser Asn Lys
        315                 320                 325

Ala Leu Pro Ala Pro Ile Glu Lys Thr Ile Ser Lys Ala Lys Gly Gln
    330                 335                 340

Pro Arg Glu Pro Gln Val Tyr Thr Leu Pro Pro Ser Arg Asp Glu Leu
345                 350                 355                 360

Thr Lys Asn Gln Val Ser Leu Thr Cys Leu Val Lys Gly Phe Tyr Pro
                365                 370                 375

Ser Asp Ile Ala Val Glu Trp Glu Ser Asn Gly Gln Pro Glu Asn Asn
            380                 385                 390

Tyr Lys Thr Thr Pro Pro Val Leu Asp Ser Asp Gly Ser Phe Phe Leu
        395                 400                 405

Tyr Ser Lys Leu Thr Val Asp Lys Ser Arg Trp Gln Gln Gly Asn Val
    410                 415                 420

Phe Ser Cys Ser Val Met His Glu Ala Leu His Asn His Tyr Thr Gln
425                 430                 435                 440

Lys Ser Leu Ser Leu Ser Pro Gly Lys
                445

<210> SEQ ID NO 181
<211> LENGTH: 469
<212> TYPE: PRT
<213> ORGANISM: Homo Sapiens
<220> FEATURE:
<221> NAME/KEY: MISC_FEATURE
<223> OTHER INFORMATION: hVH14.0 IgG1 Heavy Chain [DANS-Deleted]

<400> SEQUENCE: 181

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Glu Thr Leu Ser Leu Thr Cys Thr Val Ser Gly Phe Ser
        35                  40                  45

Leu Thr Asn Tyr Gly Ile His Trp Ile Arg Gln Pro Pro Gly Lys Gly
    50                  55                  60

Leu Glu Trp Leu Gly Val Ile Trp Ala Arg Gly Phe Thr Asn Tyr Asn
65                  70                  75                  80

Ser Ala Leu Met Ser Arg Val Thr Ile Ser Lys Asp Asn Ser Lys Asn
                85                  90                  95

Gln Val Ser Leu Lys Leu Ser Ser Val Thr Ala Ala Asp Thr Ala Val
            100                 105                 110

Tyr Tyr Cys Ala Arg Ala Asn Asp Gly Val Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
```

```
                145                 150                 155                 160
Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
                210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Lys Phe Asn Trp Tyr Val Asp Gly Val
                290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Asp Glu Leu Thr Lys Asn Gln
                370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
                450                 455                 460

Leu Ser Pro Gly Lys
465

<210> SEQ ID NO 182
<211> LENGTH: 469
<212> TYPE: PRT
<213> ORGANISM: Homo Sapiens
<220> FEATURE:
<221> NAME/KEY: MISC_FEATURE
<223> OTHER INFORMATION: hVH12.0 IgG1 Heavy Chain [DANS-deleted]

<400> SEQUENCE: 182

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
                20                  25                  30

Lys Pro Ser Glu Thr Leu Ser Leu Thr Cys Thr Val Ser Gly Phe Ser
```

-continued

```
                35                  40                  45
Leu Thr Asn Tyr Gly Ile His Trp Ile Arg Gln Pro Pro Lys Gly
 50                  55                  60

Leu Glu Trp Leu Gly Val Ile Trp Ala Arg Gly Phe Thr Asn Tyr Asn
 65                  70                  75                  80

Ser Ala Leu Met Ser Arg Leu Thr Ile Ser Lys Asp Asn Ser Lys Asn
                 85                  90                  95

Gln Val Ser Leu Lys Leu Ser Ser Val Thr Ala Ala Asp Thr Ala Val
                100                 105                 110

Tyr Tyr Cys Ala Arg Ala Asn Asp Gly Val Tyr Ala Met Asp Tyr
                115                 120                 125

Trp Gly Gln Gly Thr Leu Val Thr Val Ser Ser Ala Ser Thr Lys Gly
                130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
                210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Lys Phe Asn Trp Tyr Val Asp Gly Val
                290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Asp Glu Leu Thr Lys Asn Gln
                370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
                450                 455                 460
```

```
Leu Ser Pro Gly Lys
465

<210> SEQ ID NO 183
<211> LENGTH: 24
<212> TYPE: PRT
<213> ORGANISM: Homo sapiens

<400> SEQUENCE: 183

His Asn Ser Ser Ser Trp Tyr Gly Arg Tyr Phe Asp Tyr Trp Gly Gln
1               5                   10                  15

Gly Thr Leu Val Thr Val Ser Ser
            20

<210> SEQ ID NO 184
<211> LENGTH: 19
<212> TYPE: PRT
<213> ORGANISM: Homo sapiens

<400> SEQUENCE: 184

Glu Glu Gly Asn Thr Leu Pro Trp Thr Phe Gly Gln Gly Thr Lys Val
1               5                   10                  15

Glu Ile Lys

<210> SEQ ID NO 185
<211> LENGTH: 119
<212> TYPE: PRT
<213> ORGANISM: Artificial sequence
<220> FEATURE:
<223> OTHER INFORMATION: Synthesized: humanized VH region
<220> FEATURE:
<221> NAME/KEY: VARIANT
<222> LOCATION: (30)..(30)
<223> OTHER INFORMATION: Xaa at position 30 can be Thr or Ile
<220> FEATURE:
<221> NAME/KEY: VARIANT
<222> LOCATION: (31)..(31)
<223> OTHER INFORMATION: Xaa at position 31 can be Asn or Ser
<220> FEATURE:
<221> NAME/KEY: VARIANT
<222> LOCATION: (37)..(37)
<223> OTHER INFORMATION: Xaa at position 37 can be Val or Ile
<220> FEATURE:
<221> NAME/KEY: VARIANT
<222> LOCATION: (48)..(48)
<223> OTHER INFORMATION: Xaa at position 48 can be Leu or Ile
<220> FEATURE:
<221> NAME/KEY: VARIANT
<222> LOCATION: (67)..(67)
<223> OTHER INFORMATION: Xaa at position 67 can be Val or Leu
<220> FEATURE:
<221> NAME/KEY: VARIANT
<222> LOCATION: (71)..(71)
<223> OTHER INFORMATION: Xaa at position 71 can be Lys or Val
<220> FEATURE:
<221> NAME/KEY: VARIANT
<222> LOCATION: (73)..(73)
<223> OTHER INFORMATION: Xaa at position 73 can be Asn or Thr
<220> FEATURE:
<221> NAME/KEY: VARIANT
<222> LOCATION: (78)..(78)
<223> OTHER INFORMATION: Xaa at position 78 can be Val or Phe
<220> FEATURE:
<221> NAME/KEY: VARIANT
<222> LOCATION: (94)..(94)
<223> OTHER INFORMATION: Xaa at position 94 can be Phe or Tyr

<400> SEQUENCE: 185

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Xaa Xaa Tyr
```

```
                20                  25                  30
Gly Ile His Trp Xaa Arg Gln Pro Pro Gly Lys Gly Leu Glu Trp Xaa
            35                  40                  45

Gly Val Ile Trp Ala Arg Gly Phe Thr Asn Tyr Asn Ser Ala Leu Met
        50                  55                  60

Ser Arg Xaa Thr Ile Ser Xaa Asp Xaa Ser Lys Asn Gln Xaa Ser Leu
65                  70                  75                  80

Lys Leu Ser Ser Val Thr Ala Ala Asp Thr Ala Val Tyr Xaa Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 186
<211> LENGTH: 106
<212> TYPE: PRT
<213> ORGANISM: Artificial sequence
<220> FEATURE:
<223> OTHER INFORMATION: Synthesized: humanized VL region
<220> FEATURE:
<221> NAME/KEY: VARIANT
<222> LOCATION: (1)..(1)
<223> OTHER INFORMATION: Xaa at position 1 can be Gln or Asp
<220> FEATURE:
<221> NAME/KEY: VARIANT
<222> LOCATION: (2)..(2)
<223> OTHER INFORMATION: Xaa at position 2 can be Phe or Val
<220> FEATURE:
<221> NAME/KEY: VARIANT
<222> LOCATION: (4)..(4)
<223> OTHER INFORMATION: Xaa at position 4 can be Leu or Met
<220> FEATURE:
<221> NAME/KEY: VARIANT
<222> LOCATION: (45)..(45)
<223> OTHER INFORMATION: Xaa at position 45 can be Lys or Leu
<220> FEATURE:
<221> NAME/KEY: VARIANT
<222> LOCATION: (46)..(46)
<223> OTHER INFORMATION: Xaa at position 46 can be Trp or Leu
<220> FEATURE:
<221> NAME/KEY: VARIANT
<222> LOCATION: (48)..(48)
<223> OTHER INFORMATION: Xaa at position 48 can be Tyr or Lys
<220> FEATURE:
<221> NAME/KEY: VARIANT
<222> LOCATION: (70)..(70)
<223> OTHER INFORMATION: Xaa at position 70 can be Tyr or Phe

<400> SEQUENCE: 186

Xaa Xaa Val Xaa Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Xaa Xaa Ile Xaa
        35                  40                  45

Asp Thr Ser Lys Leu Ala Ser Gly Val Pro Ser Arg Phe Ser Gly Ser
    50                  55                  60

Gly Ser Gly Thr Asp Xaa Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105
```

What is claimed is:

1. A humanized anti-α2 integrin antibody comprising:
    (i) a heavy chain variable region comprising: a heavy chain complementarity determining region 1 (HCDR1) having the amino acid sequence GFSLTNYGIH (SEQ ID NO: 1), a heavy chain complementarity determining region 2 (HCDR2) having the amino acid sequence VIWARGFTNYNSALMS (SEQ ID NO: 2), and a heavy chain complementarity determining region 3 (HCDR3) having the amino acid sequence ANDGVYYAMDY (SEQ ID NO: 3); and
    (ii) a light chain variable region comprising: a light chain complementarity determining region 1 (LCDR1) having the amino acid sequence SAQSSVNYIH (SEQ ID NO:112), a light chain complementarity determining region 2 (LCDR2) having the amino acid sequence DTSKLAS (SEQ ID NO: 5), and a light chain complementarity determining region 3 (LCDR3) having the amino acid sequence QQWTTNPLT (SEQ ID NO: 6).

2. The humanized anti-α2 integrin antibody of claim 1, further comprising a variable heavy chain comprising a FW4 region having the amino acid sequence WGQGTLVTVSS (SEQ ID NO:13).

3. The humanized anti-α2 integrin antibody of claim 1 further comprising a variable light chain FW4 region having the amino acids sequence FGQGTKVEIK of SEQ ID NO:38.

4. The humanized anti-α2 integrin antibody of claim 1, wherein the antibody comprises a heavy chain variable region having the amino acid sequence of SEQ ID NO: 109.

5. The humanized anti-α2 integrin antibody of claim 1, wherein the antibody comprises a light chain variable region having the amino acid sequence of SEQ ID NO: 91.

6. The humanized anti-α2 integrin antibody of claim 1, wherein the antibody comprises a heavy chain variable region having the amino acid sequence of SEQ ID NO: 109 and a light chain variable region having the amino acid sequence of SEQ ID NO: 91.

7. The humanized anti-α2 integrin antibody of claim 1, wherein the light chain complementarity determining region 1 (LCDR1) has the amino acid sequence SAQSSVNYIH (SEQ ID NO: 112).

8. The humanized anti-α2 integrin antibody of claim 1, wherein the antibody comprises a constant region.

9. The humanized anti-α2 integrin antibody of claim 8, wherein the constant region is γ1.

10. The humanized anti-α2 integrin antibody of claim 8, wherein the constant region is γ4.

11. The humanized anti-α2 integrin antibody of claim 1, wherein the antibody recognizes the I domain of human α2 integrin.

12. The humanized anti-α2 integrin antibody of claim 1, wherein the antibody binds α2⊕1 integrin.

13. The humanized anti-α2 integrin antibody of claim 1, which is a full length antibody.

14. The humanized anti-α2 integrin antibody of claim 1, bound to a detectable label.

15. The humanized anti-α2 integrin antibody of claim 1, immobilized on solid phase.

16. The humanized anti-α2 integrin antibody of claim 1, wherein the antibody inhibits binding of α2 or α2β1 integrin to an α2β1 integrin ligand.

17. The humanized anti-α2 integrin antibody of claim 16, wherein the α2β1 integrin ligand is selected from the group consisting of collagen, laminin, Echovirus-1, decorin, E-cadherin, matrix metalloproteinase I (MMP-I), endorepellin, collectin and C1q complement protein.

18. A kit comprising the humanized anti-α2 integrin antibody of claim 1 and instructions for its use to detect α2 or α2β1 integrin protein.

19. A pharmaceutical composition comprising a humanized anti-α2 integrin antibody comprising:
    (i) a heavy chain variable region comprising: a heavy chain complementarity determining region 1 (HCDR1) having the amino acid sequence GFSLTNYGIH (SEQ ID NO:1), a heavy chain complementarity determining region 2 (HCDR2) having the amino acid sequence VIWARGFTNYNSALMS (SEQ ID NO: 2), and a heavy chain complementarity determining region 3 (HCDR3) having the amino acid sequence ANDGVYYAMDY (SEQ ID NO: 3); and
    (ii) a light chain variable region comprising: a light chain complementarity determining region 1 (LCDR1) having the amino acid sequence SAQSSVNYIH (SEQ ID NO: 112), a light chain complementarity determining region 2 (LCDR2) having the amino acid sequence DTSKLAS (SEQ ID NO: 5), and a light chain complementarity determining region 3 (LCDR3) having the amino acid sequence QQWTTNPLT (SEQ ID NO: 6), and a pharmaceutically acceptable carrier.

20. The pharmaceutical composition of claim 19, wherein the antibody further comprises a FW4 region comprising the amino acid sequence WGQGTLVTVSS (SEQ ID NO: 13).

21. The pharmaceutical composition of claim 19, wherein the antibody further comprises a FW4 region comprising the amino acids sequence FGQGTKVEIK (SEQ ID NO: 38).

22. The pharmaceutical composition of claim 19, wherein the antibody comprises a heavy chain variable region having the amino acid sequence of SEQ ID NO: 109.

23. The pharmaceutical composition of claim 19, wherein the antibody comprises a light chain variable region having the amino acid sequence of SEQ ID NO: 91.

24. The pharmaceutical composition of claim 19, wherein the antibody comprises a heavy chain variable region having the amino acid sequence of SEQ 11) NO: 109 and a light chain variable region having the amino acid sequence of SEQ ID NO: 91.

25. The pharmaceutical composition of claim 19, wherein the light chain complementarity determining region 1 (LCDR1) has the amino acid sequence SAQSSVNYIH (SEQ ID NO: 112).

26. The pharmaceutical composition of claim 19, wherein the antibody comprises a constant region.

27. The pharmaceutical composition of claim 26, wherein the constant region is γ1.

28. The pharmaceutical composition of claim 26, wherein the constant region is γ4.

29. The pharmaceutical composition of claim 19, wherein the antibody recognizes the I domain of human α2 integrin.

30. The pharmaceutical composition of claim 19, wherein the antibody binds α2β1 integrin.

31. The pharmaceutical composition of claim 19, wherein the antibody is a full length antibody.

32. The pharmaceutical composition of claim 19, wherein the antibody is bound to a detectable label.

33. The pharmaceutical composition of claim 19, wherein the antibody is immobilized on solid phase.

34. The pharmaceutical composition of claim 19, wherein the antibody inhibits binding of α2 or α2β1 integrin to an α2β1 integrin ligand.

35. The pharmaceutical composition of claim 34, wherein the α2β1 integrin ligand is selected from the group consisting of collagen, laminin, Echovirus-1, decorin, E-cadherin, matrix metalloproteinase I (MMP-I), endorepellin, collectin and C1q complement protein.

36. A kit comprising the pharmaceutical composition of claim 19 and instructions for its use to detect α2 or α2β1 integrin protein.

* * * * *